United States Patent
Long

(10) Patent No.: US 10,590,108 B2
(45) Date of Patent: Mar. 17, 2020

(54) BENZIMIDAZOLES FOR USE IN THE TREATMENT OF CANCER AND INFLAMMATORY DISEASES

(71) Applicant: CAPELLA THERAPEUTICS, INC., San Diego, CA (US)

(72) Inventor: Yun Long, San Diego, CA (US)

(73) Assignee: CAPELLA THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/761,995

(22) PCT Filed: Sep. 22, 2016

(86) PCT No.: PCT/US2016/053059
§ 371 (c)(1),
(2) Date: Aug. 17, 2018

(87) PCT Pub. No.: WO2017/053537
PCT Pub. Date: Mar. 30, 2017

(65) Prior Publication Data
US 2018/0273511 A1  Sep. 27, 2018

Related U.S. Application Data

(60) Provisional application No. 62/222,699, filed on Sep. 23, 2015, provisional application No. 62/222,709, filed on Sep. 23, 2015.

(51) Int. Cl.
*C07D 401/14* (2006.01)
*C07D 405/14* (2006.01)
*A61P 35/00* (2006.01)

(52) U.S. Cl.
CPC ............ *C07D 401/14* (2013.01); *A61P 35/00* (2018.01); *C07D 405/14* (2013.01)

(58) Field of Classification Search
CPC .......................... C07D 409/14; C07D 401/14
See application file for complete search history.

(56) References Cited

U.S. PATENT DOCUMENTS

| | | | |
|---|---|---|---|
| 8,461,328 B2 | 6/2013 | Babu et al. | |
| 10,005,765 B2 * | 6/2018 | Long | C07D 401/14 |
| 10,202,398 B2 * | 2/2019 | Long | C07D 487/04 |
| 2013/0217668 A1 | 8/2013 | Bode et al. | |

FOREIGN PATENT DOCUMENTS

| | | |
|---|---|---|
| CN | 104447765 A | 3/2015 |
| WO | 2011099832 A2 | 8/2011 |
| WO | 2012018668 A1 | 2/2012 |
| WO | 2013074518 A1 | 5/2013 |
| WO | 2013074594 A1 | 5/2013 |
| WO | 2013170159 A1 | 11/2013 |
| WO | 2013184757 A1 | 12/2013 |
| WO | 2013184766 A1 | 12/2013 |
| WO | 2013186229 A1 | 12/2013 |
| WO | 2014001464 A1 | 1/2014 |
| WO | 2014036016 A1 | 6/2014 |
| WO | 2015134210 A1 | 9/2015 |
| WO | 2015143148 A1 | 9/2015 |
| WO | 2015143161 A1 | 9/2015 |

OTHER PUBLICATIONS

Cao et al. CAS: 169:357443, 2015.*
Berge et al., "Pharmaceutical salts," J. Pharm. Sci. 1977, 66, 1-19.
Bose et al., "Activating HER2 mutations in HER2 gene amplification negative breast cancer," Cancer Discov. 2013, 3, 224-237.
Ciardiello et al., "EGFR antagonists in cancer treatment," N. Engl. J. Med. 2008, 358, 1160-1174.
Dadiboyena and Nefzi, "Parallel Synthesis of Structurally Diverse Aminobenzimidazole Tethered Sultams and Benzothiazepinones," Tetrahedron Letters 2012, 53, 6897-6900.
Gradishar, "HER2 therapy—an abundance of riches," N. Engl. J. Med. 2012, 366, 176-178.
Hudis, "Trastuzumab—mechanism of action and use in clinical practice," N. Engl. J. Med. 2007, 357, 39-51.
Hynes et al., "ERBB receptors and cancer: the complexity of targeted inhibitors," Nat. Rev. Cancer 2005, 5, 341-354.
Langer, "Epidermal growth factor receptor inhibition in mutation-positive non-small-cell lung cancer: Is afatinib better or simply newer?" J. Clin. Oncol. 2013, 31, 3303-3306.
Lewis et al., "The discovery and optimization of a novel class of potent, selective, and orally bioavailable anaplastic lymphoma kinase (ALK) inhibitors with potential utility for the treatment of cancer," J. Med. Chem. 2012, 55, 6523-6540.

(Continued)

Primary Examiner — Rei Tsang Shiao
(74) Attorney, Agent, or Firm — Jones Day

(57) ABSTRACT

Provided herein are methods for treating, preventing, or ameliorating one or more symptoms of a condition, disorder, or disease mediated by a lipid kinase or a protein kinase with benzimidazoles, for example, of Formula I or II, and pharmaceutical compositions thereof. Also provided herein are benzimidazoles, and pharmaceutical compositions thereof; and methods of their use for treating, preventing, or ameliorating one or more symptoms of a proliferative disease.

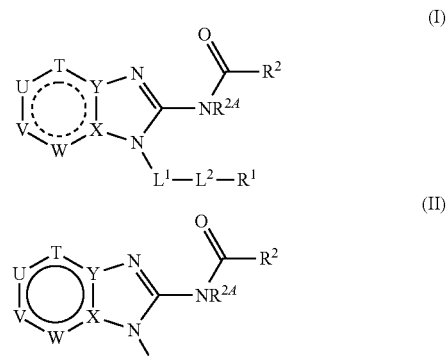

22 Claims, No Drawings

(56) References Cited

OTHER PUBLICATIONS

Nicholson et al., "EGFR and cancer prognosis," Eur. J. Cancer 2001, 37, S9-15.
Sharma et al., "Epidermal growth factor receptor mutations in lung cancer," Nat. Rev. Cancer 2007, 7, 169-181.
Shih et al., "Analysis of Somatic Mutations in Cancer: Molecular Mechanisms of Activation in the ErbB Family of Receptor Tyrosine Kinases," Cancers 2011, 3, 1195-1231.
Slamon et al., "Human breast cancer: correlation of relapse and survival with amplification of the HER-2/neu oncogene," Science 1987, 235, 177-182.
Vyas et al., "Design of novel anaplastic lymphoma kinase (ALK) inhibitors based on predictive 3D QSAR models using different alignment strategies," Med. Chem. Res. 2014, 23, 603-617.
Yarden et al., "Untangling the ErbB signalling network," Nat. Rev. Mol. Cell. Biol. 2001, 2, 127-137.
Zhang and Chang, "Somatic mutations of the epidermal growth factor receptor and non-small-cell lung cancer," J. Med. Genet. 2007, 44, 166-172.

\* cited by examiner

BENZIMIDAZOLES FOR USE IN THE TREATMENT OF CANCER AND INFLAMMATORY DISEASES

CROSS REFERENCE TO RELATED APPLICATIONS

This application is a National Stage of International Application No. PCT/US2016/053059, filed Sep. 22, 2016; which claims the benefit of U.S. Provisional Application Nos. 62/222,699 and 62/222,709, both filed Sep. 23, 2015; the disclosure of each of which is incorporated by reference in its entirety.

FIELD

Provided herein are methods for treating, preventing, or ameliorating one or more symptoms of a condition, disorder, or disease mediated by a lipid kinase or a protein kinase with benzimidazoles and pharmaceutical compositions thereof. Also provided herein are benzimidazoles, and pharmaceutical compositions thereof; and methods of their use for treating, preventing, or ameliorating one or more symptoms of a proliferative disease.

BACKGROUND

In the human receptor tyrosine kinase superfamily, the ERBB family comprises four members: ERBB1 (epidermal growth factor receptor or EGFR), ERBB2 (HER2), ERBB3 (HER3), and ERBB4 (HER4). The ERBB receptors share an overall similar structure with a ligand-binding ectodomain, a single transmembrane domain, and an intracellular kinase domain, which is active in ERBB1, HER2 and ERBB4, but defective in ERBB3. A diverse array of ligands has been identified for the ectodomains of ERBB1, ERBB3, and ERBB4, but not HER2. Ligand binding induces conformational change in receptors to form homo- and hetero-dimerization. Without ligand binding, the extracellular domain of HER2 is already fixed in a conformation that resembles the other ligand-activated ERBB members, making it a preferred dimerization partner for other ligand-bound ERBBs. The dimerized receptors activate the intrinsic kinase activity, leading to phosphorylation of tyrosines at cytoplasmic tails. The ERBB receptors differ in kinase potency, phosphorylation sites, and substrate specificity. The phosphorylated tyrosines serve as the docking sites to recruit downstream effectors and activate multiple cascades of intracellular signaling pathways, including the anti-apoptotic/survival PI3K/AKT and the mitogenic RAS/RAF/MEK/ERK pathways. In normal cells, the activity of ERBB receptors is under tight control to regulate various cellular processes, such as growth, proliferation, development and differentiation, survival and apoptosis, cell shape and adhesion, migration, and angiogenesis. Yarden et al., *Nat. Rev. Mol. Cell. Biol.* 2001, 2, 127-137; Hynes et al., *Nat. Rev. Cancer* 2005, 5, 341-354.

As a major proliferation and survival engine for cells, constitutive activation of ERBB receptors, particularly ERBB1 and HER2, is oncogenic and can be a strong driver for tumorigenesis in cultured cells and animal models. In addition, the activated receptors accelerate cancer development by promoting tumor angiogenesis and metastasis. Persistent activation can result from overexpression of the receptors, production of excessive ligands, or generation of activating mutations in the ectodomains and kinase domains of the receptors. Yarden et al., *Nat. Rev. Mol. Cell. Biol.* 2001, 2, 127-137. In humans, genetic alterations in ERBB genes and other genes that lead to similar deregulation of ERBB receptors are frequently identified in majority of carcinomas, such as lung, breast, colon, prostate, brain, head and neck, oesophagus, ovary, cervix, bladder, stomach, and endometrium cancer. The aberrant activation of ERBB receptors is in general an adverse prognostic indicator for higher recurrence rate and shorter survival time. Nicholson et al., *Eur. J. Cancer* 2001, 37, 9-15; Slamon et al., *Science* 1997, 235, 177-182.

Given the compelling association of activation of ERBB receptors with human cancers, ERBB1 and HER2 are among the kinase targets for drug development, aiming to tame signaling transduction pathways for cancer treatment. To reverse the abnormal activity of ERBB receptors in tumors, monoclonal antibodies targeting the extracellular domains of ERBB1 and HER2 and small molecule chemicals inhibiting the intracellular kinase domains have been developed.

The monoclonal antibody drugs attack the ERBB receptors with high specificity and attenuate ERBB-mediated signaling by prevention of ligand binding and receptor dimerization, elimination receptors from cell surface through endocytosis, inhibition of shedding of extracellular domain, and activation of immune system. Hudis, *N. Engl. J. Med.* 2007, 357, 39-51. Cetuximab and panitumumab, two anti-ERBB1 antibodies, have shown improvement in response rate and the rate of progression-free survival in the treatment of metastatic colon cancer either as monotherapy or in combination with chemotherapies. In addition, cetuximab has also been approved for the treatment of locally advanced, unresectable or metastatic squamous cell carcinoma of the head and neck. Ciardiello et al., *N. Engl. J. Med.* 2008, 358, 1160-1174. Anti-HER2 antibody trastuzumab binds to the domain IV of the HER2 receptor at the juxtamembrane position. In clinical development, trastuzumab has demonstrated increased overall survival rate in early- and metastatic-stage breast cancer patients with tumors showing IHC 3+HER2 overexpression or FISH gene amplification ratio of at least 2.0. Using the same criteria for patient selection, pertuzumab, which binds to a distinct epitope at the domain II of the HER2 receptor, has been found to further increase the complete response rate by addition to trastuzumab and docetaxel regimen as a neoadjuvant treatment for patients with locally advanced, early-stage breast cancer. Gradishar, *N. Engl. J. Med.* 2012, 366, 176-178.

Development of small-molecule ERBB1 kinase inhibitors (ERBB1Is) has become an evolving paradigm for using cancer genomics to guide targeted drug development and treatment. Gefinitib and erlotinib, the first two ERBB1I drugs, are reversible ATP mimetic inhibitors that bind to the wild-type ERBB1 catalytic domain to inhibit tyrosine kinase activity. In unselected patients of non-small cell lung cancer (NSCLC) or pancreatic cancer, only erlotinib has demonstrated clinical benefit by modestly increasing overall survival. Ciardiello et al., *N. Engl. J. Med.* 2008, 358, 1160-1174. In a subset of NSCLC patients that harbor activating mutations within ERBB1 tyrosine kinase domain, both gefitinib and erlotinib treatments are highly sensitive and can achieve lasting efficacy as monotherapy. These drug-responding mutations are mostly in-frame deletions nested around Leu-Arg-Glu-Ala from position 747 to 750 in ERBB1 exon 19, or a leucine to arginine substitution at position 858 (L858R) in exon 21.

However, the initial response to erlotinib or gefitinib relapses in 10-14 months by developing resistant mutations in tumors. Among them, a T790M gate-keeper point mutation in the exon 20 of ERBB1, which poses a steric interference to drug binding, is found in over 50% of acquired resistant tumors. To overcome the resistance from T790M mutation and confer sustained ERBB1 inhibition, the second-generation ERBB1Is have been developed, some of them are irreversible ERBB1 and HER2 dual inhibitors. The irreversible compounds overcome the kinase binding hindrance from T790M mutation by better fitting into the mutated binding pocket and forming covalent bond with the protein amino acid residues. Additionally, irreversible ERBB1Is appear to cause slower acquired resistance to the treatment than reversible inhibitors. Sharma et al., *Nat. Rev. Cancer* 2007, 7. 169-181.

In preclinical testing, afatinib, a second-generation ERBB1I, inhibited the growth of NSCLC HCC827 cells, which harbor the sensitive exon 19 deletion, and is 50-fold more potent than erlotinib in inhibition of growth of NSCLC H1975 cells, which has a T790M mutation in-cis with the L858R mutation. However, afatinib also inhibits A431 cells, whose growth is driven by a wild-type ERBB1, 100-fold more potent than H1975. The difference in potencies portends that, in cancer patients, the compound could inhibit wild-type ERBB1 completely before it reaches sufficient blood level for pharmacological effect on T790M mutant ERBB1. Since wild-type ERBB1 inhibition has been reported to cause dose-limiting toxicity in virtually all previously ERBB1I drugs, the preferential inhibition of wild-type ERBB1 over resistant mutant pose a potential challenge for afatinib to achieve high enough dose for T790M mutant inhibition. Consistent with the preclinical discovery, clinical development has found afatinib only showed equivalent efficacy to erlotinib or gefitinib in patients with sensitive mutations, but failed to demonstrate statistically meaningful superiority to erlotinib and gefitinib in treating patients with acquired T790M resistant mutation even at the maximum tolerated dose. Langer, *J. Clin. Oncol.* 2013, 31, 3303-3330. Thus, there is a clear and unmet need to develop effective therapeutics for treating a proliferative disease, especially drug-resistant cancer.

SUMMARY OF THE DISCLOSURE

Provided herein is a method for treating, preventing, or ameliorating one or more symptoms of a condition, disorder, or disease mediated by a BMX, BTK, PIK3C, PIK3D, ITK, TEC, or TXK kinase in a subject, comprising administering to the subject a therapeutically effective amount of a compound of Formula I:

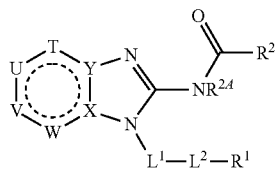
(I)

or a single enantiomer, a racemic mixture, a mixture of diastereomers, or an isotopic variant thereof; or a pharmaceutically acceptable salt, solvate, or prodrug thereof; wherein:

$R^1$ is $-C(O)CR^{1e}=CR^{1f}CR^{1g}$,

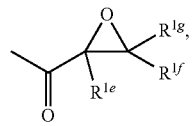

$-N^{1a}C(O)CR^{1e}=CR^{1f}CR^{1g}$,

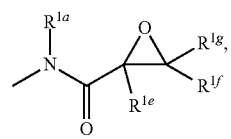

$-S(O)CR^{1e}=CR^{1f}CR^{1g}$,

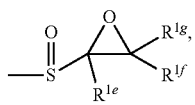

$-S(O_2)CR^{1e}=CR^{1f}CR^{1g}$,

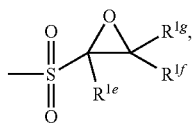

$-NR^{1a}S(O)CR^{1e}=CR^{1f}CR^{1g}$,

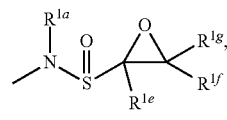

$-NR^{1a}S(O_2)CR^{1e}=CR^{1f}CR^{1g}$, or

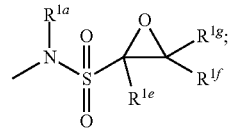

$R^2$ is $C_{3-10}$ cycloalkyl, $C_{6-14}$ aryl, $C_{7-15}$ aralkyl, heteroaryl, or heterocyclyl;

$R^{2A}$ is hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; $L^1$ is a bond, $-O-$, $-S-$, $-N(R^{1A})-$, or $-C(R^{1A}R^{1B})-$, wherein each $R^{1A}$ and $R^{1B}$ is independently hydrogen, halo, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl;

$L^2$ is $C_{3-10}$ cycloalkylene, $C_{6-14}$ arylene, $C_{7-15}$ aralkylene, heteroarylene, or heterocyclylene;

T is a bond, $-O-$, $-S-$, $-N=$, $-N(R^4)-$, $-C(R^4)=$, or $-C(R^4)_2-$;

U is a bond, $-O-$, $-S-$, $-N=$, $-N(R^5)-$, $-C(R^5)=$, or $-C(R^5)_2-$;

V is a bond, —O—, —S—, —N=, —N(R$^6$)—, —C(R$^6$)=, or —C(R$^6$)$_2$—;

W is a bond, —O—, —S—, —N=, —N(R$^7$)—, —C(R$^7$)=, or —C(R$^7$)$_2$—;

X and Y are each independently C or N;

each R$^4$, R$^5$, R$^6$, and R$^7$ is independently (a) hydrogen, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

each R$^{1a}$, R$^{1b}$, R$^{1c}$, and R$^{1d}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl; and each R$^{1e}$, R$^{1f}$, and R$^{1g}$ is independently hydrogen, halo, C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl;

with the proviso that no more than one of T, U, V, and W is a bond; and wherein each alkyl, alkenyl, alkynyl, cycloalkyl, cycloalkylene, aryl, arylene, aralkyl, aralkylene, heteroaryl, heteroarylene, heterocyclyl, and heterocyclylene is optionally substituted with one or more, in one embodiment, one, two, three, or four, substituents Q, where each Q is independently selected from (a) oxo, cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each of which is further optionally substituted with one or more, in one embodiment, one, two, three, or four, substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OP(O)(OR$^a$)$_2$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each of which is optionally substituted with one or more, in one embodiment, one, two, three, or four, substituents Q$^a$; or (iii) R$^b$ and R$^c$ together with the N atom to which they are attached form heterocyclyl, optionally substituted with one or more, in one embodiment, one, two, three, or four, substituents Q$^a$;

wherein each Q$^a$ is independently selected from the group consisting of (a) oxo, cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl; and (c) —C(O)R$^f$, —C(O)OR$^f$, —C(O)NR$^g$R$^h$, —C(NR$^f$)NR$^g$R$^h$, —OR$^f$, —OC(O)R$^f$, —OC(O)OR$^f$, —OC(O)NR$^g$R$^h$, —OC(=NR$^f$)NR$^g$R$^h$, —OP(O)(OR$^f$)$_2$, —OS(O)R$^f$, —OS(O)$_2$R$^f$, —OS(O)NR$^g$R$^h$, —OS(O)$_2$NR$^g$R$^h$, —NR$^g$R$^h$, —NR$^f$C(O)R$^k$, —NR$^f$C(O)OR$^k$, —NR$^f$C(O)NR$^g$R$^h$, —NR$^f$C(=NR$^k$)NR$^g$R$^h$, —NR$^f$S(O)R$^k$, —NR$^f$S(O)$_2$R$^k$, —NR$^f$S(O)NR$^g$R$^h$, —NR$^f$S(O)$_2$NR$^g$R$^h$, —SR$^f$, —S(O)R$^f$, —S(O)$_2$R$^f$, —S(O)NR$^g$R$^h$, and —S(O)$_2$NR$^g$R$^h$; wherein each R$^f$, R$^g$, R$^h$, and R$^k$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or (iii) R$^g$ and R$^h$ together with the N atom to which they are attached form heterocyclyl.

Also provided herein is a compound of Formula XIXa:

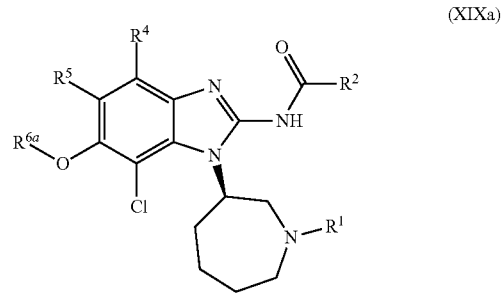

(XIXa)

or a single enantiomer, a racemic mixture, a mixture of diastereomers, or an isotopic variant thereof; or a pharmaceutically acceptable salt, solvate, or prodrug thereof; wherein R$^{6a}$ is —C(O)OR$^{1a}$ or —C(O)NR$^{1b}$R$^{1c}$; and R$^1$, R$^2$, R$^4$, R$^5$, R$^{1a}$, R$^{1b}$, and R$^{1c}$ are each as defined herein.

Additionally, provided herein is a compound of Formula XXII:

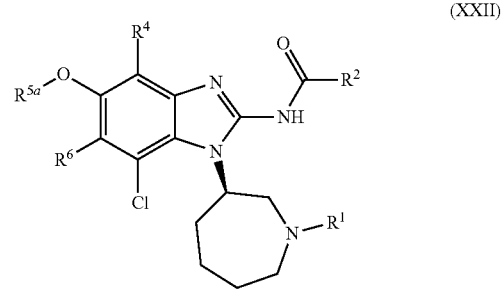

(XXII)

or a single enantiomer, a racemic mixture, a mixture of diastereomers, or an isotopic variant thereof; or a pharmaceutically acceptable salt, solvate, or prodrug thereof; wherein R$^{5a}$ is —C(O)OR$^{1a}$ or —C(O)NR$^{1b}$R$^{1c}$; and R$^1$, R$^2$, R$^4$, and R$^6$, R$^{1a}$, R$^{1b}$, and R$^{1c}$ are each as defined herein.

Furthermore, provided herein is a compound of Formula XXV:

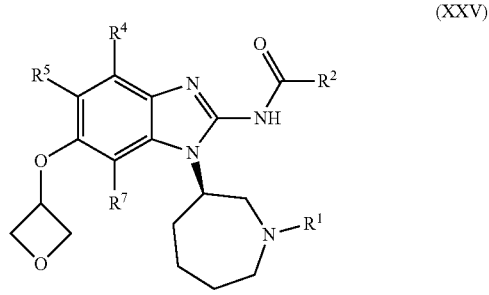

(XXV)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, and $R^7$ are each as defined herein.

Provided herein is a compound of Formula XXVI:

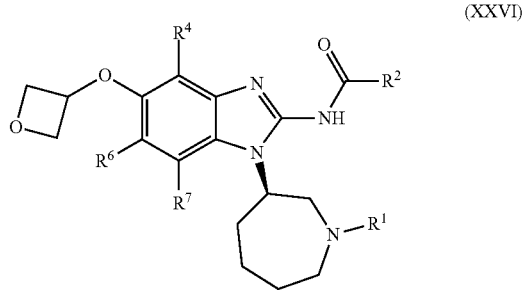

(XXVI)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^6$, and $R^7$ are each as defined herein.

Provided herein is a compound of Formula XXVII:

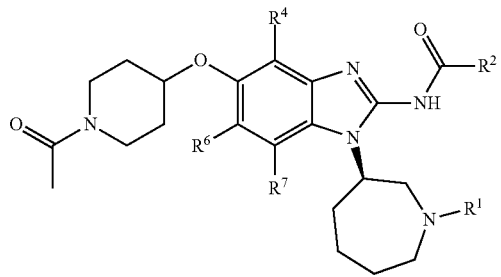

(XXVII)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^6$, and $R^7$ are each as defined herein.

Provided herein is a method for treating, preventing, or ameliorating one or more symptoms of a condition, disorder, or disease mediated by a BMX, BTK, PIK3C, PIK3D, ITK, TEC, or TXK kinase in a subject, comprising administering to the subject a therapeutically effective amount of a compound of Formula II:

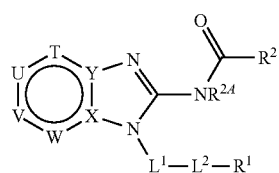

(II)

or a single enantiomer, a racemic mixture, a mixture of diastereomers, or an isotopic variant thereof; or a pharmaceutically acceptable salt, solvate, or prodrug thereof; wherein:

T is a bond, —O—, —S—, —N=, —N($R^4$)—, or —C($R^4$)=;

U is a bond, —O—, —S—, —N=, —N($R^5$)—, or —C($R^5$)=;

V is a bond, —O—, —S—, —N=, —N($R^6$)—, or —C($R^6$)=;

W is a bond, —O—, —S—, —N=, —N($R^7$)—, or —C($R^7$)=;

$R^4$, $R^5$, $R^6$, and $R^7$ are each defined herein; or $R^4$ and $R^5$, $R^5$ and $R^6$, or $R^6$ and $R^7$ are linked together to form $C_{3-7}$ cycloalkyl, $C_{6-14}$ aryl, heteroaryl, or heterocyclyl, each of which is optionally substituted with one or more substituents Q; and $R^1$, $R^2$, $R^{2A}$, $L^1$, $L^2$, Q, X, and Y are each as defined herein.

Provided herein is a compound of Formula VIII-A:

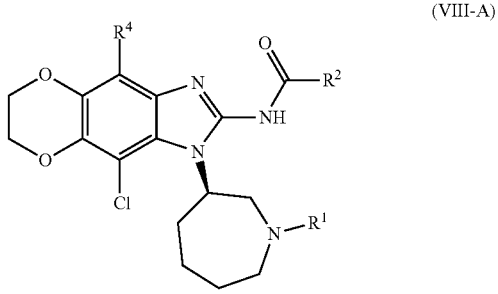

(VIII-A)

or a single enantiomer, a racemic mixture, a mixture of diastereomers, or an isotopic variant thereof; or a pharmaceutically acceptable salt, solvate, or prodrug thereof; wherein $R^1$, $R^2$, and $R^4$ are each as defined herein.

Provided herein is a compound of Formula IX-A:

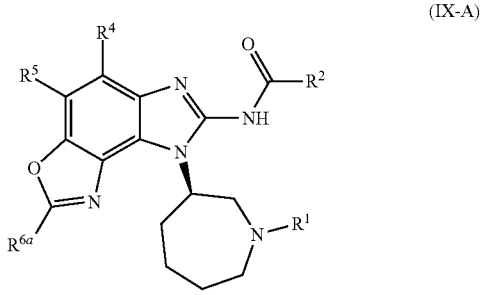

(IX-A)

or a single enantiomer, a racemic mixture, a mixture of diastereomers, or an isotopic variant thereof; or a pharmaceutically acceptable salt, solvate, or prodrug thereof; wherein:

$R^{6a}$ is (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2$ $R^d$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; and $R^1$, $R^2$, $R^4$, $R^5$, $R^{1a}$, $R^{1b}$, $R^{1c}$, $R^{1d}$, and Q are each as defined herein.

Provided herein is a compound of Formula X-A:

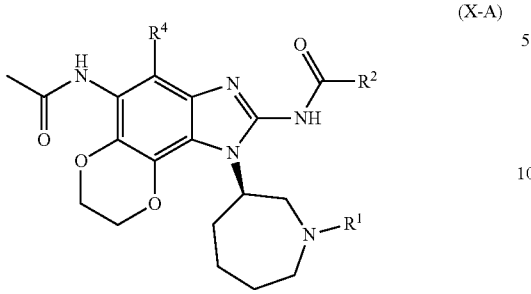

(X-A)

or a single enantiomer, a racemic mixture, a mixture of diastereomers, or an isotopic variant thereof; or a pharmaceutically acceptable salt, solvate, or prodrug thereof; wherein $R^1$, $R^2$, and $R^4$ are each as defined herein.

Provided herein are pharmaceutical compositions comprising a compound disclosed herein, e.g., a compound of Formula XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof; and optionally a pharmaceutically acceptable excipient or carrier.

Provided herein is a method for treating, preventing, or ameliorating one or more symptoms of a proliferative disease in a subject, comprising administering to the subject a compound disclosed herein, e.g., a compound of Formula XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

Provided herein is a method for treating, preventing, or ameliorating one or more symptoms of an ERBB-mediated condition, disorder, or disease in a subject, comprising administering to the subject a compound disclosed herein, e.g., a compound of Formula XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

Provided herein is a method of inhibiting the growth of a cell, comprising contacting the cell with a compound provided herein, e.g., a compound of Formula XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

Provided herein is a method for modulating the activity of a tyrosine kinase, in one embodiment, an ERBB kinase, comprising contacting the ERBB kinase with a compound disclosed herein, e.g., a compound of Formula XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

Provided herein is a method for treating, preventing, or ameliorating one or more symptoms of a condition, disorder, or disease mediated by a BMX, BTK, PIK3C, PIK3D, ITK, TEC, or TXK kinase in a subject, comprising administering to the subject a therapeutically effective amount of a compound, e.g., a compound of Formula I or II, or a single enantiomer, a racemic mixture, a mixture of diastereomers, or an isotopic variant thereof; or a pharmaceutically acceptable salt, solvate, or prodrug thereof.

DETAILED DESCRIPTION

To facilitate understanding of the disclosure set forth herein, a number of terms are defined below.

Generally, the nomenclature used herein and the laboratory procedures in biology, biochemistry, medicinal chemistry, organic chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "tumor," "neoplasm," and "neoplastic disorder or disease" are used interchangeably herein and are meant to refer to unwanted cell proliferation of one or more subset of cells in a multicellular organism resulting in harm (i.e., discomfort or decreased life expectancy) to the multicellular organisms. In certain embodiments, a tumor can be benign (non-invasive) or malignant (invasive).

The term "cancer" is meant to refer to a malignant neoplasm, which is characterized by uncontrolled cell proliferation where cells have lost their normal regulatory controls that would otherwise govern the rate of cell growth. These unregulated, dividing cells can spread throughout the body and invade normal tissues in a process referred to as "metastasis."

The term "subject" refers to an animal, including, but not limited to, a primate (e.g., human), cow, pig, sheep, goat, horse, dog, cat, rabbit, rat, and mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a condition, disorder, or disease, or one or more of the symptoms associated with the condition, disorder, or disease; or alleviating or eradicating the cause(s) of the condition, disorder, or disease itself.

The terms "prevent," "preventing," and "prevention" are meant to include a method of delaying and/or precluding the onset of a condition, disorder, or disease, and/or its attendant symptoms; barring a subject from acquiring a condition, disorder, or disease; or reducing a subject's risk of acquiring a condition, disorder, or disease.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The term "therapeutically effective amount" are meant to include the amount of a compound that, when administered, is sufficient to prevent development of, or alleviate to some extent, one or more of the symptoms of the condition, disorder, or disease being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "IC$_{50}$" or "EC$_{50}$" refers an amount, concentration, or dosage of a compound that is required for 50% inhibition of a maximal response in an assay that measures such a response.

The term "GC$_{50}$" refers an amount, concentration, or dosage of a compound that is required to reduce the viability of cells treated with the compound by 50%, in comparison with cells untreated with the compound.

The term "CC$_{50}$" refers an amount, concentration, or dosage of a compound that results in 50% reduction of the viability of a host. In certain embodiments, the CC$_{50}$ of a compound is the amount, concentration, or dosage of the compound that is required to reduce the viability of cells treated with the compound by 50%, in comparison with cells untreated with the compound. The term "relapsed" refers to a situation where a subject, who has had a remission of cancer after therapy has a return of cancer cells.

The term "refractory or resistant" refers to a circumstance where a subject, even after intensive treatment, has residual cancer cells in his body.

The term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2012; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "ERBB" or "ERBB kinase" refers to a tyrosine kinase of the ERBB family or a variant thereof, including, but not limited to, ERBB1 (EGFR or HER1), ERBB2 (HER2/c-neu), ERBB3 (HER3), and ERBB4 (HER4). ERBB variants include proteins substantially homologous to a native ERBB kinase, i.e., proteins having one or more naturally or non-naturally occurring amino acid deletions, insertions or substitutions (e.g., ERBB derivatives, homologs, and fragments), as compared to the amino acid sequence of a native ERBB. The amino acid sequence of an ERBB variant is at least about 80% identical, at least about 90% identical, or at least about 95% identical to a native ERBB.

The terms "ERBB-mediated condition, disorder or disease" and "a condition, disorder, or disease mediated by ERBB" refer to a condition, disorder, or disease characterized by abnormal or dysregulated, e.g., greater than normal, ERBB activity. Abnormal ERBB kinase functional activity might arise as the result of ERBB kinase overexpression in cells, expression of the ERBB kinase in cells which normally do not express ERBB, or dysregulation due to constitutive activation, caused, for example, by a mutation in ERBB. An ERBB-mediated condition, disorder, or disease may be completely or partially mediated by inappropriate ERBB activity. In particular, an ERBB-mediated condition, disorder, or disease is one in which modulation of an ERBB activity results in some effect on the underlying condition, disorder, or disease, e.g., an ERBB inhibitor results in some improvement in at least some of patients being treated.

The term "alkyl" refers to a linear or branched saturated monovalent hydrocarbon radical, wherein the alkyl may optionally be substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkylene" refers to a linear or branched saturated divalent hydrocarbon radical, wherein the alkylene may optionally be substituted with one or more substituents Q as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms).

The term "heteroalkylene" refers to a linear or branched saturated divalent hydrocarbon radical that contains one or more heteroatoms in the hydrocarbon chain, each of which is independently selected from O, S, and N. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1}$-6 and branched $C_{3-6}$ heteroalkylene groups are also referred as "lower heteroalkylene." Examples of heteroalkylene groups include, but are not limited to, —$CH_2O$—, —$CH_2OCH_2$—, —$CH_2CH_2O$—, —$CH_2NH$—, —$CH_2NHCH_2$—, —$CH_2CH_2NH$—, —$CH_2S$—, —$CH_2SCH_2$—, and —$CH_2CH_2S$—. In certain embodiments, heteroalkylene may also be optionally substituted with one or more substituents Q as described herein.

The term "alkenyl" refers to a linear or branched monovalent hydrocarbon radical, which contains one or more, in one embodiment, one, two, three, four, or five, in another embodiment, one or two, carbon-carbon double bond(s). The alkenyl may be optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more, in one embodiment, one, two, three, four, or five, in another embodiment, one or two, carbon-carbon double bond(s). The alkenylene may be optionally substituted with one or more substituents Q as described herein. The term "alkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "heteroalkenylene" refers to a linear or branched divalent hydrocarbon radical, which contains one or more, in one embodiment, one, two, three, four, or five, in another embodiment, one or two, carbon-carbon double bond(s), and which contains one or more heteroatoms in the hydrocarbon chain, each of which is independently selected from O, S, and N. The heteroalkenylene may be optionally substituted with one or more substituents Q as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of heteroalkenylene groups include, but are not limited to, —CH═CHO—, —CH═CHOCH_2—, —CH═CHCH_2O—, —CH═CHS—, —CH═CHSCH_2—, —CH═CHCH_2S—, or —CH═CHCH_2NH—.

The term "alkynyl" refers to a linear or branched monovalent hydrocarbon radical, which contains one or more, in one embodiment, one, two, three, four, or five, in another embodiment, one or two, carbon-carbon triple bond(s). The alkynyl may be optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 4 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms. Examples of alkynyl groups include, but are not limited to, ethynyl (—C≡CH), propynyl (including all isomeric forms, e.g., 1-propynyl (—C≡CCH_3) and propargyl (—CH_2C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "alkynylene" refers to a linear or branched divalent hydrocarbon radical, which contains one or more, in one embodiment, one, two, three, four, or five, in another embodiment, one or two, carbon-carbon triple bond(s). The alkynylene may be optionally substituted with one or more substituents Q as described herein. For example, $C_{2-6}$ alkynylene refers to a linear unsaturated divalent hydrocarbon radical of 2 to 6 carbon atoms or a branched unsaturated divalent hydrocarbon radical of 4 to 6 carbon atoms. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 4 to 20 ($C_{4-20}$), 4 to 15 ($C_{4-15}$), 4 to 10 ($C_{4-10}$), or 4 to 6 ($C_{4-6}$) carbon atoms.

Examples of alkynylene groups include, but are not limited to, ethynylene, propynylene (including all isomeric forms, e.g., 1-propynylene and propargylene), butynylene (including all isomeric forms, e.g., 1-butyn-1-ylene and 2-butyn-1-ylene), pentynylene (including all isomeric forms, e.g., 1-pentyn-1-ylene and 1-methyl-2-butyn-1-ylene), and hexynylene (including all isomeric forms, e.g., 1-hexyn-1-ylene).

The term "cycloalkyl" refers to a cyclic monovalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "cycloalkylene" refers to a cyclic divalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene (e.g., 1,1-cyclopropylene and 1,2-cyclopropylene), cyclobutylene (e.g., 1,1-cyclobutylene, 1,2-cyclobutylene, or 1,3-cyclobutylene), cyclopentylene (e.g., 1,1-cyclopentylene, 1,2-cyclopentylene, or 1,3-cyclopentylene), cyclohexylene (e.g., 1,1-cyclohexylene, 1,2-cyclohexylene, 1,3-cyclohexylene, or 1,4-cyclohexylene), cycloheptylene (e.g., 1,1-cycloheptylene, 1,2-cycloheptylene, 1,3-cycloheptylene, or 1,4-cycloheptylene), decalinylene, and adamantylene.

The term "aryl" refers to a monovalent monocyclic aromatic hydrocarbon radical or monovalent polycyclic aromatic hydrocarbon radical that contains at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted with one or more substituents Q as described herein.

The term "arylene" refers to a divalent monocyclic aromatic hydrocarbon radical or divalent polycyclic aromatic hydrocarbon radical that contains at least one aromatic hydrocarbon ring. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which may be saturated, partially unsaturated, or aromatic, for example, dihydronaphthylene, indenylene, indanylene, or tetrahydronaphthylene (tetralinylene). In certain embodiments, arylene may be optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, aralkyl are optionally substituted with one or more substituents Q as described herein.

The term "heteroaryl" refers to a monovalent monocyclic aromatic group or monovalent polycyclic aromatic group that contains at least one aromatic ring, wherein at least one aromatic ring contains one or more heteroatoms in the ring, each of which is independently selected from O, S, and N. Heteroaryl groups are bonded to the rest of a molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted with one or more substituents Q as described herein.

The term "heteroarylene" refers to a divalent monocyclic aromatic group or divalent polycyclic aromatic group that contains at least one aromatic ring, wherein at least one aromatic ring contains one or more heteroatoms in the ring, each of which is independently selected from O, S, and N. A heteroarylene group has at least one linkage to the rest of a molecule via its aromatic ring(s). Each ring of a heteroarylene group can contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzotriazolylene, benzoxazolylene, furopyridylene, imidazopyridinylene, imidazothiazolylene, indolizinylene, indolylene, indazolylene, isobenzofuranylene, isobenzothienylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroarylene groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. In certain embodiments, heteroarylene may also be optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted with one or more substituents Q as described herein.

The term "heterocyclylene" refers to a divalent monocyclic non-aromatic ring system or divalent polycyclic ring system that contains at least one non-aromatic ring, wherein one or more of the non-aromatic ring atoms are heteroatoms independently selected from O, S, and N; and the remaining ring atoms are carbon atoms. Heterocyclylene groups are bonded to the rest of a molecule through the non-aromatic ring. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclylene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. In certain embodiments, heterocyclic may also be optionally substituted with one or more substituents Q as described herein.

The term "halogen", "halide" or "halo" refers to fluorine, chlorine, bromine, and/or iodine.

The term "optionally substituted" is intended to mean that a group or substituent, such as an alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, or heterocyclylene group, may be substituted with one or more, in one embodiment, one, two, three, or four, substituents Q, each of which is independently selected from, e.g., (a) oxo (=O), cyano (—CN), halo, and nitro (—NO$_2$); (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OP(O)(OR$^a$)$_2$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) R$^b$ and R$^c$ together with the N atom to which they are attached form heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^f$, —C(O)OR$^f$, —C(O)NR$^g$R$^h$, —C(NR$^f$)NR$^g$R$^h$, —OR$^f$, —OC(O)R$^f$, —OC(O)OR$^f$, —OC(O)NR$^g$R$^h$, —OC(=NR$^f$)NR$^g$R$^h$, —OP(O)(OR$^f$)$_2$, —OS(O)R$^f$, —OS(O)$_2$R$^f$, —OS(O)NR$^g$R$^h$, —OS(O)$_2$NR$^g$R$^h$, —NR$^g$R$^h$, —NR$^f$C(O)R$^k$, —NR$^f$C(O)OR$^k$, —NR$^f$C(O)NR$^g$R$^h$, —NR$^f$C(=NR$^k$)NR$^g$R$^h$, —NR$^f$S(O)R$^k$, —NR$^f$S(O)$_2$R$^k$, —NR$^f$S(O)NR$^g$R$^h$, —NR$^f$S(O)$_2$NR$^g$R$^h$, —SR$^f$, —S(O)R$^f$, —S(O)$_2$R$^f$, —S(O)NR$^g$R$^h$, and —S(O)$_2$NR$^g$R$^h$; wherein each R$^f$, R$^g$, R$^h$, and R$^k$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^g$ and R$^h$ together with the N atom to which they are attached form heterocyclyl.

The terms "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^1$H), deuterium ($^2$H), tritium (3H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, for example, or any carbon can be $^{13}$C, as example, or any nitrogen can be $^{15}$N, as example, and any oxygen can be $^{18}$O, where feasible according to the judgment of one of skill. In certain embodiments, an "isotopic variant" of a compound contains unnatural proportions of deuterium.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "a single enantiomer, a racemic mixture, a mixture of diastereomers, or an isotopic variant thereof; or a pharmaceutically acceptable salt, solvate, or prodrug thereof" has the same meaning as the phrase "(i) a single enantiomer, a racemic mixture, a mixture of diastereomers, or an isotopic variant of the compound referenced therein; (ii) a pharmaceutically acceptable salt, solvate, or prodrug of the compound referenced therein; or (iii) a pharmaceutically acceptable salt, solvate, or prodrug of a single enantiomer, a racemic mixture, a mixture of diastereomers, or an isotopic variant of the compound referenced therein."

As used herein, the abbreviations for any protective groups, amino acids and other compounds, are, unless indicated otherwise, in accord with their common usage or recognized abbreviations including abbreviations found in *J. Org. Chem.* 2007, 72, 23A-24A or abbreviations established by the IUPAC-IUB Commission on Biochemical Nomenclature (*Biochem.* 1972, 11, 942-944).

Compounds

In one embodiment, provided herein is a compound of Formula I:

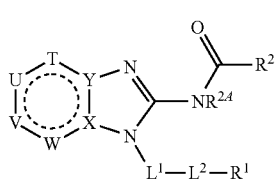

(I)

or a single enantiomer, a racemic mixture, a mixture of diastereomers, or an isotopic variant thereof; or a pharmaceutically acceptable salt, solvate, or prodrug thereof; wherein R$^1$, R$^2$, R$^{2A}$, L$^1$, L$^2$, T, U, V, W, X, and Y are each as defined herein.

In another embodiment, provided herein is a compound of Formula II:

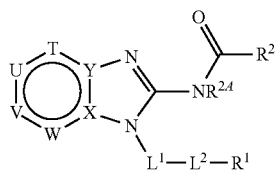
(II)

or a single enantiomer, a racemic mixture, a mixture of diastereomers, or an isotopic variant thereof; or a pharmaceutically acceptable salt, solvate, or prodrug thereof; wherein $R^1$, $R^2$, $R^{2A}$, $L^1$, $L^2$, T, U, V, W, X, and Y are each as defined herein.

In yet another embodiment, provided herein is a compound of Formula III:

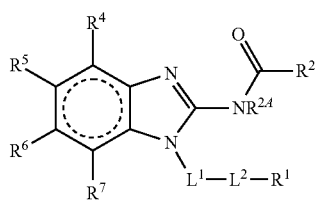
(III)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^6$, $R^7$, $R^{2A}$, $L^1$, and $L^2$ are each as defined herein.

In yet another embodiment, provided herein is a compound of Formula IV:

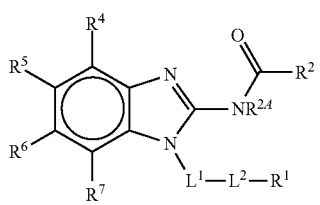
(IV)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^6$, $R^7$, $R^{2A}$, $L^1$, and $L^2$ are each as defined herein.

In yet another embodiment, provided herein is a compound of Formula V:

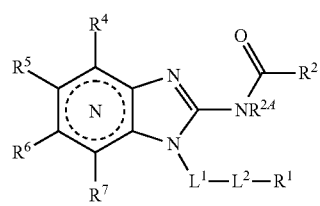
(V)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^6$, $R^7$, $R^{2A}$, $L^1$, and $L^2$ are each as defined herein, and the symbol

represents that the 6-membered ring contains one N atom in the ring.

In yet another embodiment, provided herein is a compound of Formula VI:

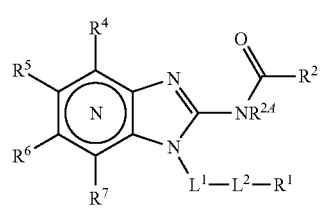
(VI)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^6$, $R^7$, $R^{2A}$, $L^1$, and $L^2$ are each as defined herein; and the symbol

represents that the 6-membered ring contains one N atom in the ring.

In yet another embodiment, provided herein is a compound of Formula VII:

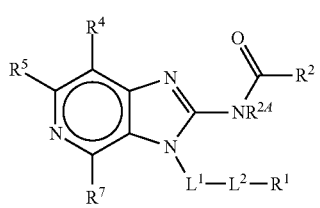
(VII)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^7$, $R^{2A}$, $L^1$, and $L^2$ are each as defined herein.

In yet another embodiment, provided herein is a compound of Formula VIII:

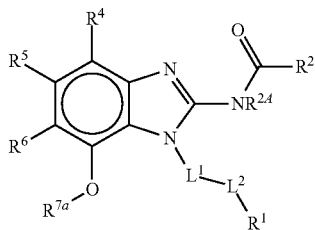

(VIII)

or a single enantiomer, a racemic mixture, a mixture of diastereomers, or an isotopic variant thereof; or a pharmaceutically acceptable salt, solvate, or prodrug thereof; wherein:

$R^{7a}$ is (i) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (ii) —C(O)$R^{1a}$, —C(O)O$R^{1a}$, —C(O)N$R^{1b}R^{1c}$, —C(N$R^{1a}$)N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$, or —S(O)$_2$N$R^{1b}R^{1c}$; and $R^1$, $R^2$, $R^4$, $R^5$, $R^6$, $R^{2A}$, $R^{1a}$, $R^{1b}$, $R^{1c}$, $R^{1d}$, $L^1$, $L^2$, and Q are each as defined herein.

In yet another embodiment, provided herein is a compound of Formula IX:

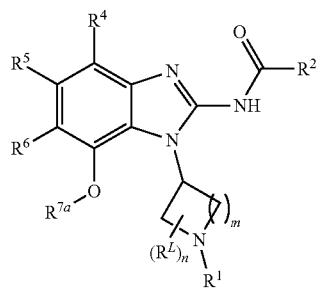

(IX)

or a single enantiomer, a racemic mixture, a mixture of diastereomers, or an isotopic variant thereof; or a pharmaceutically acceptable salt, solvate, or prodrug thereof; wherein:

m is an integer of 0, 1, 2, 3, 4, 5, 6, 7, 8, 9, or 10;

n is an integer of 0, 1, 2, 3, 4, 5, or 6;

each $R^L$ is independently (i) hydrogen; or (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (iii) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2R^{1a}$, —S(O)N$R^{1b}R^{1c}$ or —S(O)$_2$N$R^{1b}R^{1c}$; or two $R^L$ together, when there are two or more $R^L$ attached to the same ring, are linked together to form (i) a bond, —O—, —N$R^N$—, or —S—; or (ii) $C_{1-6}$ alkylene, $C_{1-6}$ heteroalkylene, $C_{2-6}$ alkenylene, or $C_{2-6}$ heteroalkenylene, each of which is optionally substituted with one or more substituents Q;

$R^N$ is (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more substituents Q; (c) —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^d$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; and $R^1$, $R^2$, $R^4$, $R^5$, $R^6$, $R^{1a}$, $R^{1b}$, $R^{1c}$, $R^{1d}$, $R^{7a}$, and Q are each as defined herein.

In yet another embodiment, provided herein is a compound of Formula X:

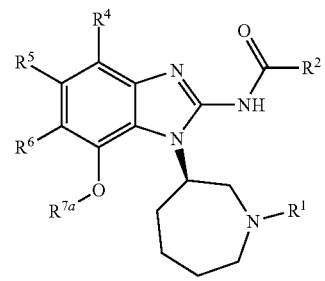

(X)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^6$, and $R^{7a}$ are each as defined herein.

In yet another embodiment, provided herein is a compound of Formula XI:

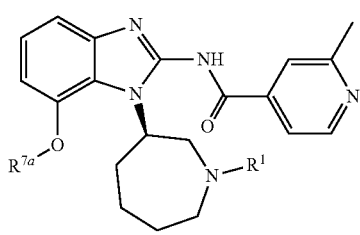

(XI)

or an isotopic variant thereof; or a pharmaceutically acceptable salt, solvate, or prodrug thereof; wherein $R^1$ and $R^{7a}$ are each as defined herein.

In one embodiment, provided herein is a compound of Formula XIa:

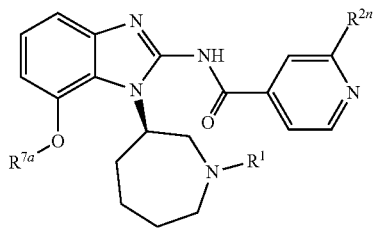

(XIa)

or a single enantiomer, a racemic mixture, a mixture of diastereomers, or an isotopic variant thereof; or a pharmaceutically acceptable salt, solvate, or prodrug thereof; wherein $R^{2n}$ is $C_{1-6}$ alkyl optionally substituted with one or more substituents Q or —$OR^{1a}$, and $R^1$, $R^{1a}$, $R^{7a}$, and Q are each as defined herein; in one embodiment, $R^{2n}$ is methyl, monofluoromethyl, difluoromethyl, trifluoromethyl, —OH, or —$OCH_3$.

In certain embodiments, in Formula VIII, IX, X, XI, or XIa, $R^{7a}$ is:

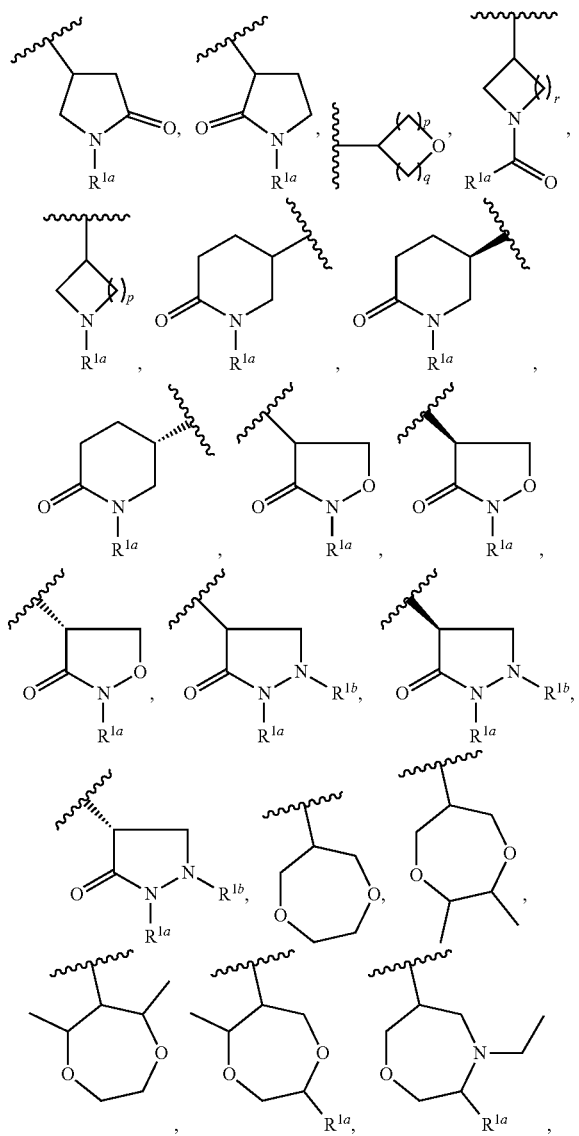

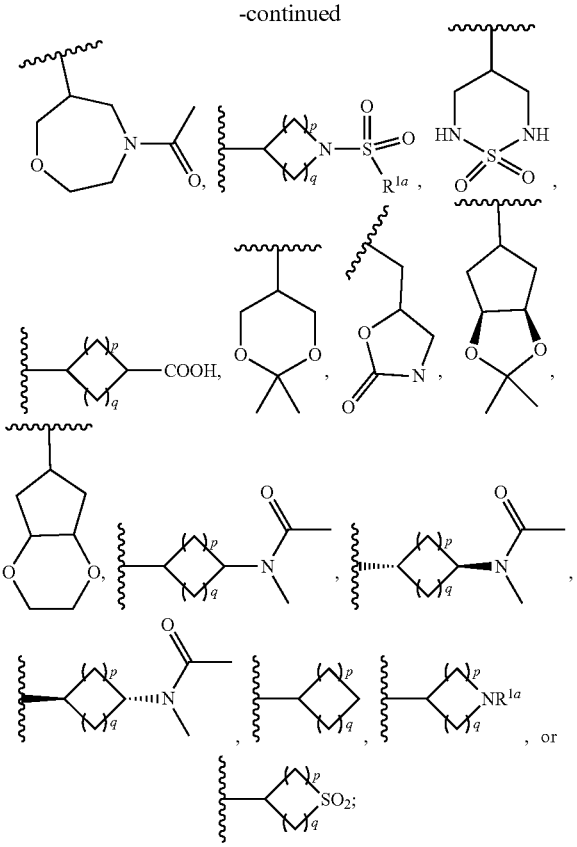

wherein:

each $R^{1a}$ and $R^{1b}$ is as defined herein; in one embodiment, $R^{1a}$ is hydrogen, methyl, ethyl, difluoromethyl, or trifluoromethyl; in another embodiment, $R^{1b}$ is hydrogen, methyl, methyl, ethyl, difluoromethyl, trifluoromethyl, 2-hydroxyethyl, or ethenyl;

p and q are each independently an integer of 0, 1, or 3, with the proviso that the total of p and q is no less than 1;

each r is independently an integer of 0, 1, 2, 3, 4, 5, or 6.

In certain embodiments, in Formula VIII, IX, X, XI, or XIa, $R^{7a}$ is piperidin-4-yl, 1-methyl-piperidin-4-yl, 1-ethyl-piperidin-4-yl, 1-(2,2,2-trifluoroethyl)-piperidin-4-yl, 1-isopropyl-piperidin-4-yl, 1-cyclopropyl-piperidin-4-yl, 1-acetyl-piperidin-4-yl, tetrahydro-2H-pyran-4-yl, or 1,1-dioxo-tetrahydro-2H-thiopyran-4-yl.

In another embodiment, provided herein is a compound of Formula XIb:

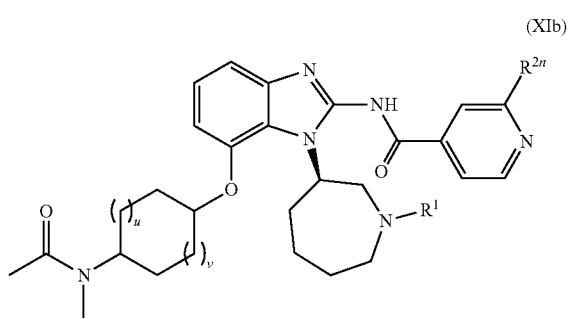

(XIb)

or a single enantiomer, a racemic mixture, a mixture of diastereomers, or an isotopic variant thereof; or a pharmaceutically acceptable salt, solvate, or prodrug thereof, wherein u and v are each independently an integer of 0, 1, 2, or 3; and $R^1$ and $R^{2n}$ are each as defined herein.

In yet another embodiment, provided herein is a compound of Formula XIc:

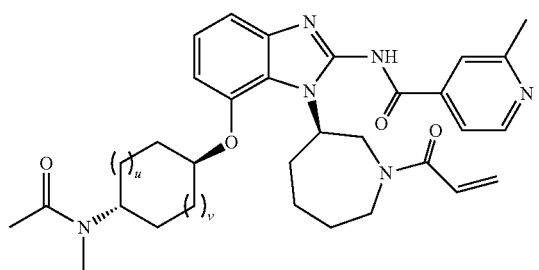
(XIc)

or an isotopic variant thereof; or a pharmaceutically acceptable salt, solvate, or prodrug thereof; wherein u and v are each as defined herein.

In yet another embodiment, provided herein is a compound of Formula XId:

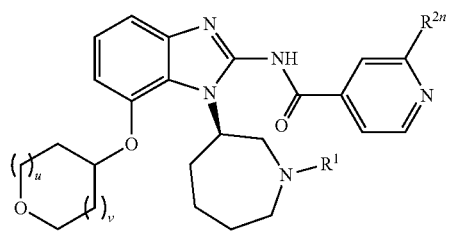
(XId)

or a single enantiomer, a racemic mixture, a mixture of diastereomers, or an isotopic variant thereof; or a pharmaceutically acceptable salt, solvate, or prodrug thereof; wherein $R^1$, $R^{2n}$, u, and v are each as defined herein.

In yet another embodiment, provided herein is a compound of Formula XIe:

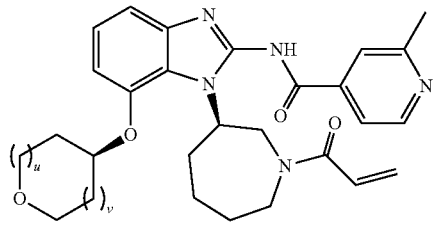
(XIe)

or an isotopic variant thereof; or a pharmaceutically acceptable salt, solvate, or prodrug thereof; wherein u and v are each as defined herein.

In yet another embodiment, provided herein is a compound of Formula XIf:

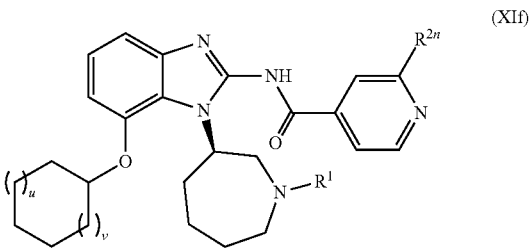
(XIf)

or a single enantiomer, a racemic mixture, a mixture of diastereomers, or an isotopic variant thereof; or a pharmaceutically acceptable salt, solvate, or prodrug thereof; wherein $R^1$, $R^{2n}$, u, and v are each as defined herein.

In yet another embodiment, provided herein is a compound of Formula XIg:

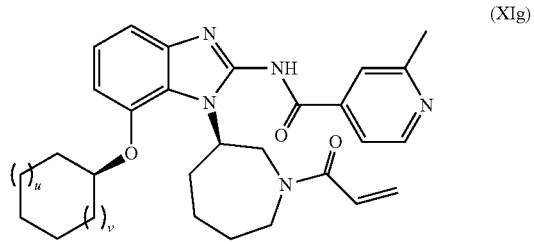
(XIg)

or an isotopic variant thereof; or a pharmaceutically acceptable salt, solvate, or prodrug thereof; wherein u and v are each as defined herein.

In yet another embodiment, provided herein is a compound of Formula XIh:

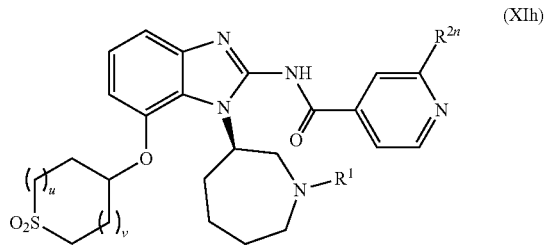
(XIh)

or a single enantiomer, a racemic mixture, a mixture of diastereomers, or an isotopic variant thereof; or a pharmaceutically acceptable salt, solvate, or prodrug thereof; wherein $R^1$, $R^{2n}$, u, and v are each as defined herein.

In still another embodiment, provided herein is a compound of Formula XIi:

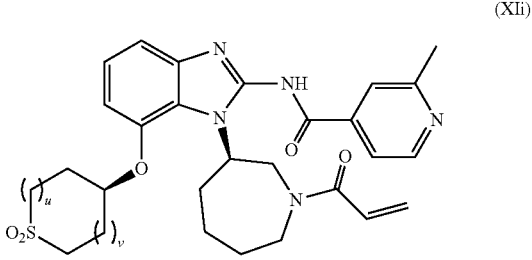
(XIi)

or an isotopic variant thereof; or a pharmaceutically acceptable salt, solvate, or prodrug thereof; wherein u and v are each as defined herein.

In yet another embodiment, provided herein is a compound of Formula XII:

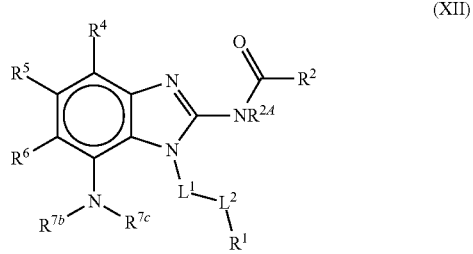

(XII)

or a single enantiomer, a racemic mixture, a mixture of diastereomers, or an isotopic variant thereof; or a pharmaceutically acceptable salt, solvate, or prodrug thereof; wherein:

$R^{7b}$ is (i) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (ii) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

$R^{7c}$ is (i) hydrogen; or (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (iii) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; or $R^{7b}$ and $R^{7c}$ together with the N atom to which they are attached form heterocyclyl, optionally substituted with one or more substituents Q; and $R^1$, $R^2$, $R^4$, $R^5$, $R^6$, $R^{2A}$, $R^{1a}$, $R^{1b}$, $R^{1c}$, $R^{1d}$, $L^1$, $L^2$, and Q are each as defined herein.

In yet another embodiment, provided herein is a compound of Formula XIII:

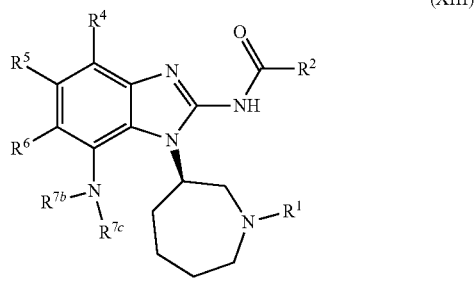

(XIII)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^6$, $R^{7b}$, and $R^{7c}$ are each as defined herein.

In yet another embodiment, provided herein is a compound of Formula XIV:

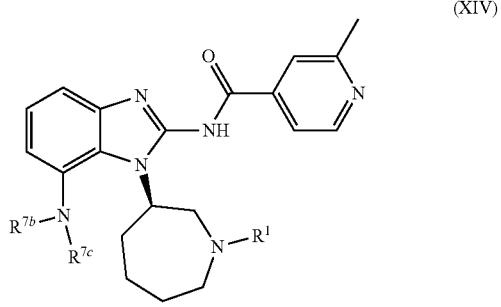

(XIV)

or an isotopic variant thereof; or a pharmaceutically acceptable salt, solvate, or prodrug thereof; wherein $R^1$, $R^{7b}$, and $R^{7c}$ are each as defined herein.

In one embodiment, provided herein is a compound of Formula XIVa:

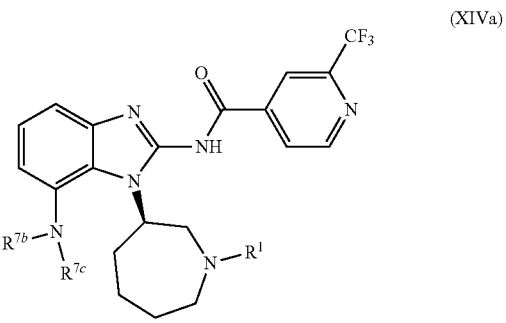

(XIVa)

or an isotopic variant thereof; or a pharmaceutically acceptable salt, solvate, or prodrug thereof; wherein $R^1$, $R^{7b}$, and $R^{7c}$ are each as defined herein.

In certain embodiments, in Formula XII, XIII, XIV, or XIVa, $R^{7b}$ is:

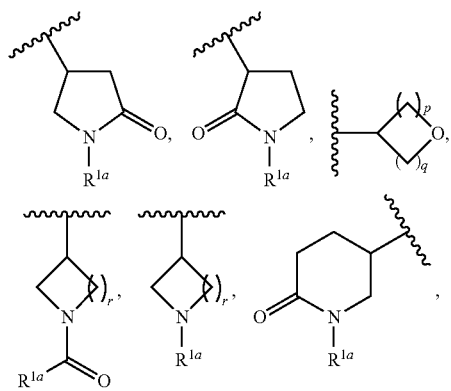

-continued

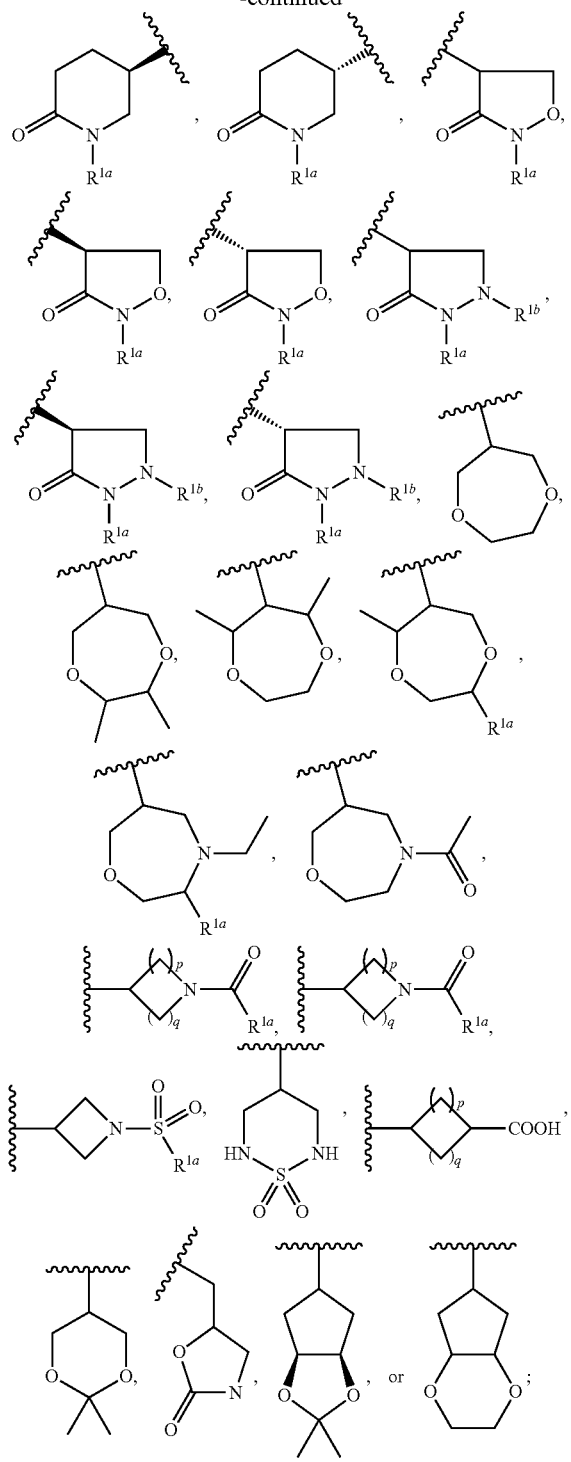

In certain embodiments, in Formula XII, XIII, XIV, or XIVa, $R^{7c}$ is hydrogen, methyl, ethyl, difluoromethyl, or trifluoromethyl.

In certain embodiment, in Formula XII, XIII, XIV, or XIVa, the moiety $-NR^{7a}R^{7b}$ is:

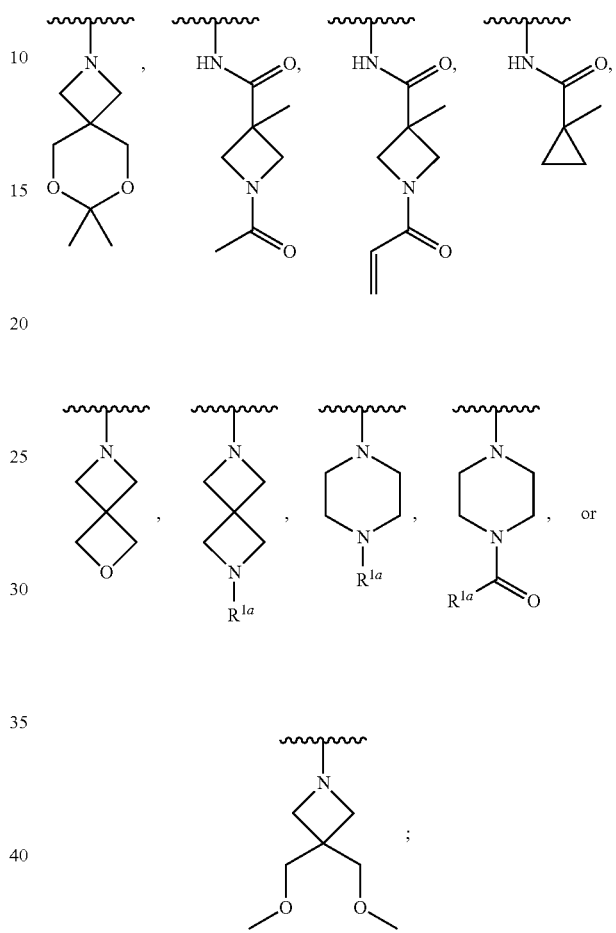

wherein each $R^{1a}$ is as defined herein; in one embodiment, $R^{1a}$ is hydrogen, methyl, ethyl, difluoromethyl, or trifluoromethyl.

In yet another embodiment, provided herein is a compound of Formula XV:

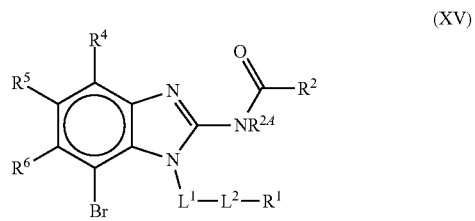

(XV)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^6$, $R^{2A}$, $L^1$, and $L^2$ are each as defined herein.

wherein:
each $R^{1a}$ and $R^{1b}$ is as defined herein; in one embodiment, $R^{1a}$ is hydrogen, methyl, ethyl, difluoromethyl, or trifluoromethyl; in another embodiment, $R^{1b}$ is hydrogen, methyl, methyl, ethyl, difluoromethyl, trifluoromethyl, 2-hydroxyethyl, or ethenyl;
each p and q is independently an integer of 0, 1, 2, or 3, with the proviso that the total of p and q is no less than 1; and
each r is independently an integer of 0, 1, 2, 3, 4, 5, or 6.

In yet another embodiment, provided herein is a compound of Formula XVI:

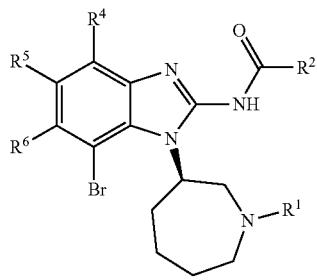

(XVI)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, and $R^6$ are each as defined herein.

In yet another embodiment, provided herein is a compound of Formula XVII:

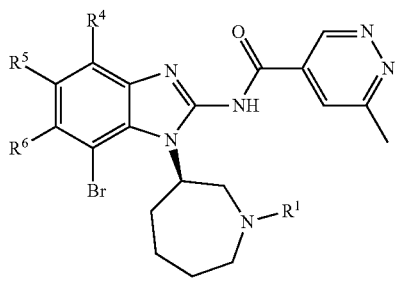

(XVII)

or a single enantiomer, a racemic mixture, a mixture of diastereomers, or an isotopic variant thereof; or a pharmaceutically acceptable salt, solvate, or prodrug thereof; wherein $R^1$, $R^4$, $R^5$, and $R^6$ are each as defined herein.

In one embodiment, provided herein is a compound of Formula XVIIa:

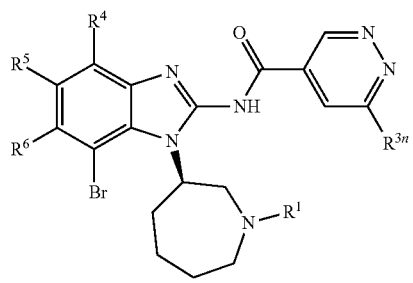

(XVIIa)

or a single enantiomer, a racemic mixture, a mixture of diastereomers, or an isotopic variant thereof; or a pharmaceutically acceptable salt, solvate, or prodrug thereof, wherein
$R^{3n}$ is $C_{1-6}$ alkyl optionally substituted with one or more substituents Q or —$OR^{1a}$, and $R^1$, $R^4$, $R^5$, $R^6$, $R^{1a}$, and Q are each as defined herein; in one embodiment, $R^{3n}$ is methyl, monofluoromethyl, difluoromethyl, trifluoromethyl, —OH, or —$OCH_3$.

In yet another embodiment, provided herein is a compound of Formula XVIII:

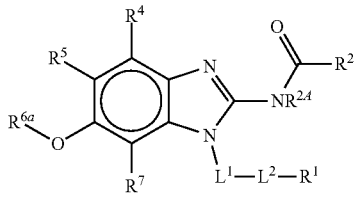

(XVIII)

or a single enantiomer, a racemic mixture, a mixture of diastereomers, or an isotopic variant thereof; or a pharmaceutically acceptable salt, solvate, or prodrug thereof; wherein:
$R^{6a}$ is (i) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (ii) —$C(O)R^{1a}$, —$C(O)OR^{1a}$, —$C(O)NR^{1b}R^{1c}$, —$C(NR^{1a})NR^{1b}R^{1c}$, —$NR^{1b}R^{1c}$, —$NR^{1a}C(O)R^{1d}$, —$NR^{1a}C(O)OR^{1d}$, —$NR^{1a}C(O)NR^{1b}R^{1c}$, —$NR^{1a}C(=NR^{1d})NR^{1b}R^{1c}$, —$NR^{1a}S(O)R^{1d}$, —$NR^{1a}S(O)_2R^{1d}$, —$NR^{1a}S(O)NR^{1b}R^{1c}$, —$NR^{1a}S(O)_2NR^{1b}R^{1c}$, —$S(O)R^{1a}$, —$S(O)_2R^{1a}$, —$S(O)NR^{1b}R^{1c}$, or —$S(O)_2NR^{1b}R^{1c}$; and
$R^1$, $R^2$, $R^4$, $R^5$, $R^7$, $R^{2A}$, $R^{1a}$, $R^{1b}$, $R^{1c}$, $R^{1d}$, $L^1$, $L^2$, and Q are each as defined herein.

In yet another embodiment, provided herein is a compound of Formula XIX:

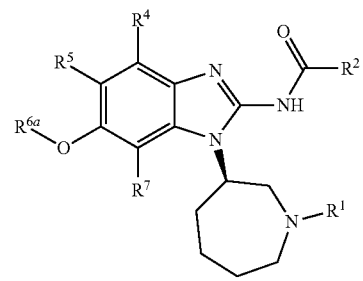

(XIX)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^{6a}$, and $R^7$ are each as defined herein.

In one embodiment, provided herein is a compound of Formula XIXa:

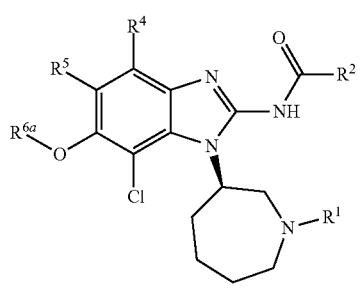

(XIXa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, and $R^{6a}$ are each as defined herein.

In yet another embodiment, provided herein is a compound of Formula XX:

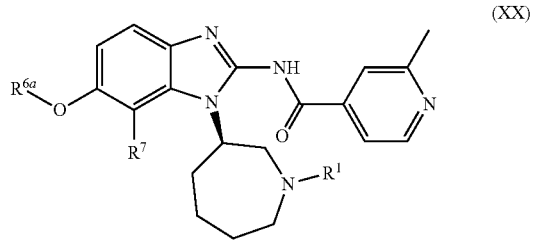

(XX)

or an isotopic variant thereof; or a pharmaceutically acceptable salt, solvate, or prodrug thereof; wherein $R^1$, $R^7$, and $R^{6a}$ are each as defined herein; in one embodiment, $R^7$ is methyl, difluoromethyl, trifluoromethyl, or $-OR^{1a}$, where $R^{1a}$ is as defined herein.

In one embodiment, provided herein is a compound of Formula XXa:

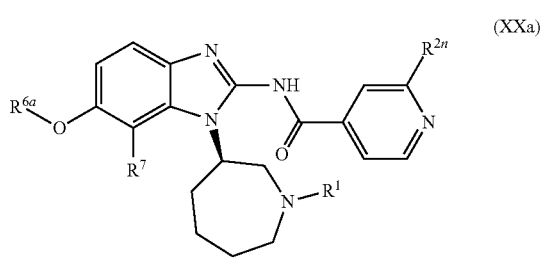

(XXa)

or a single enantiomer, a racemic mixture, a mixture of diastereomers, or an isotopic variant thereof; or a pharmaceutically acceptable salt, solvate, or prodrug thereof; wherein $R^{2n}$ is $C_{1-6}$ alkyl optionally substituted with one or more substituents Q or $-OR^{1a}$, and $R^1$, $R^7$, $R^{1a}$, $R^{6a}$, and Q are each as defined herein; in one embodiment, $R^7$ is chloro, methyl, monofluoromethyl, difluoromethyl, trifluoromethyl, or $-OR^{1a}$, where $R^{1a}$ is as defined herein; in another embodiment, $R^{2n}$ is methyl, monofluoromethyl, difluoromethyl, trifluoromethyl, $-OH$, or $-OCH_3$.

In certain embodiments, in Formula XVIII, XIX, XIXa, XX, or XXa, $R^{6a}$ is:

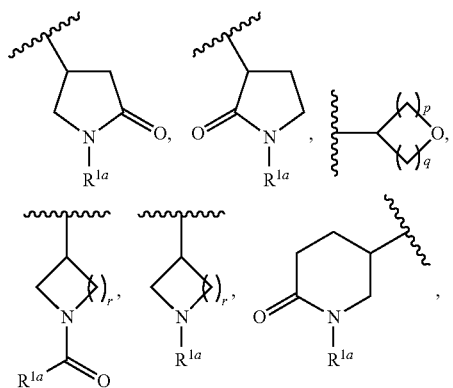

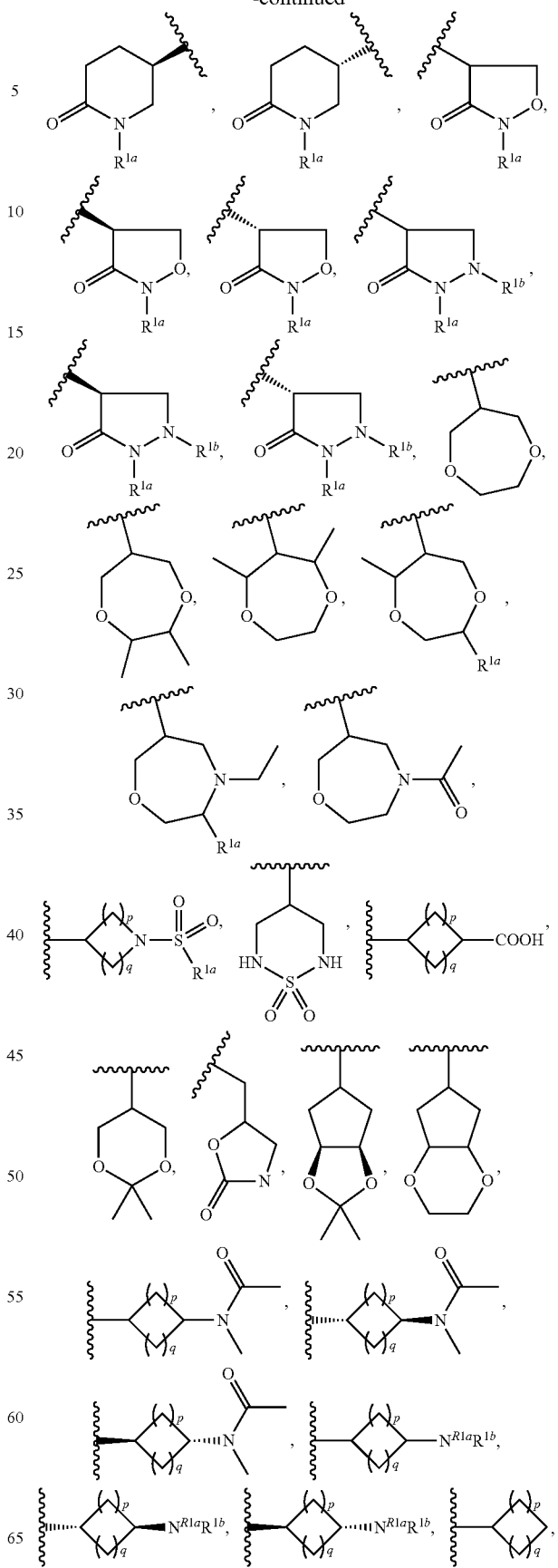

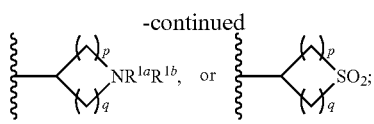

wherein $R^{1a}$, $R^{1b}$, p, q, and r are each as defined herein.

In certain embodiments, in Formula XVIII, XIX, XIXa, XX, or XXa, $R^{6a}$ is cyclopropyl, oxetan-3-yl, tetrahydrofuran-3-yl, (R)-tetrahydrofuran-3-yl, (S)-tetrahydrofuran-3-yl, 2-oxo-pyrrolidin-3-yl, tetrahydro-2H-pyran-4-yl, 1-ethyl-piperidin-4-yl, 1-dioxo-tetrahydro-2H-thiopyran-4-yl, 1-ethyl-piperidine-4-yl, or pyrimidin-4-yl.

In certain embodiments, in Formula XVIII, XIX, XIXa, XX, or XXa, $R^{6a}$ is —C(O)$R^{1a}$, —C(O)O$R^{1a}$, —C(O)N$R^{1b}R^{1c}$, —C(N$R^{1a}$)N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; wherein $R^{1a}$, $R^{1b}$, $R^{1c}$, and $R^{1d}$ are each as defined herein.

In certain embodiments, in Formula XVIII, XIX, XIXa, XX, or XXa, $R^{6a}$ is —C(O)O$R^{1a}$ or —C(O)N$R^{1b}R^{1c}$; wherein $R^{1a}$, $R^{1b}$, and $R^{1c}$ are each as defined herein.

In certain embodiments, in Formula XVIII, XIX, XIXa, XX, or XXa, $R^{6a}$ is —C(O)O$R^{1a}$; wherein $R^{1a}$ is as defined herein. In certain embodiments, in Formula XVIII, XIX, XIXa, XX, or XXa, $R^{6a}$ is —C(O)O$R^{1a}$; wherein $R^{1a}$ is $C_{1-6}$ alkyl, $C_{3-10}$ cycloalkyl, or heterocyclyl, each of which is optionally substituted with one or more substituents Q. In certain embodiments, in Formula XVIII, XIX, XIXa, XX, or XXa, $R^{6a}$ is —C(O)O$R^{1a}$; wherein $R^{1a}$ is methyl, isopropyl, cyclobutyl, cyclopentyl, cyclohexyl, oxetanyl, tetrahydrofuryl, or tetrahydro-2H-pyranyl, each of which is optionally substituted with one or more substituents Q.

In certain embodiments, in Formula XVIII, XIX, XIXa, XX, or XXa, $R^{6a}$ is —C(O)N$R^{1b}R^{1c}$; and $R^{1b}$ and $R^{1c}$ are each as defined herein. In certain embodiments, in Formula XVIII, XIX, XIXa, XX, or XXa, $R^{6a}$ is —C(O)N$R^{1b}R^{1c}$; and $R^{1b}$ and $R^{1c}$ are each independently $C_{1-6}$ alkyl, which is optionally substituted with one or more substituents Q; or $R^{1b}$ and $R^{1c}$ together with the N atom to which they are attached form heterocyclyl, which is optionally substituted with one or more substituents Q. In certain embodiments, in Formula XVIII, XIX, XIXa, XX, or XXa, $R^{6a}$ is —C(O)N$R^{1b}R^{1c}$; and $R^{1b}$ and $R^{1c}$ are each independently methyl or isopropyl, each of which is optionally substituted with one or more substituents Q; or $R^{1b}$ and $R^{1c}$ together with the N atom to which they are attached form aziridinyl, azetidinyl, pyrrolidinyl, morpholinyl, piperidinyl, piperazinyl, or 1,1-dioxo-thiomorpholinyl, each of which is optionally substituted with one or more substituents Q.

In certain embodiments, in Formula XVIII, XIX, XIXa, XX, or XXa, $R^{6a}$ is methoxycarbonyl, isopropoxycarbonyl, cyclobutoxycarbonyl, cyclopentoxycarbonyl, cyclohexoxycarbonyl, oxetan-3-oxycarbonyl, tetrahydrofuran-3-oxycarbonyl, tetrahydro-2H-pyran-4-oxycarbonyl, N,N-dimethylaminecarbonyl, N-methyl-N-isopropylaminecarbonyl, aziridin-1-ylcarbonyl, azetidin-1-ylcarbonyl, pyrrolidin-1-ylcarbonyl, 3-fluoro-pyrrolidin-1-ylcarbonyl, 3-methoxy-pyrrolidin-1-ylcarbonyl, 3,3-difluoro-pyrrolidin-1-ylcarbonyl, morpholin-4-ylcarbonyl, 4-isopropyl-piperazin-1-ylcarbonyl, 4-cyclopropyl-piperazin-1-ylcarbonyl, 4-acetyl-piperazin-1-ylcarbonyl, or 1,1-dioxo-thiomorpholin-4-ylcarbonyl.

In another embodiment, provided herein is a compound of Formula XXb:

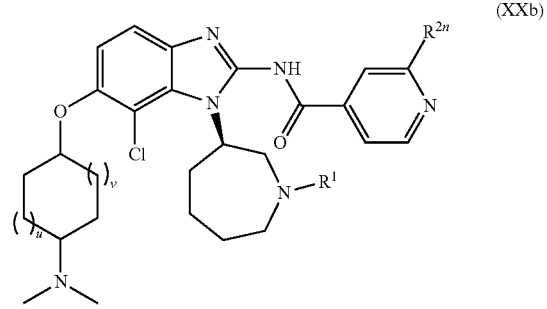

(XXb)

or a single enantiomer, a racemic mixture, a mixture of diastereomers, or an isotopic variant thereof; or a pharmaceutically acceptable salt, solvate, or prodrug thereof; wherein $R^1$, $R^{2n}$, u, and v are each as defined herein.

In yet another embodiment, provided herein is a compound of Formula XXc:

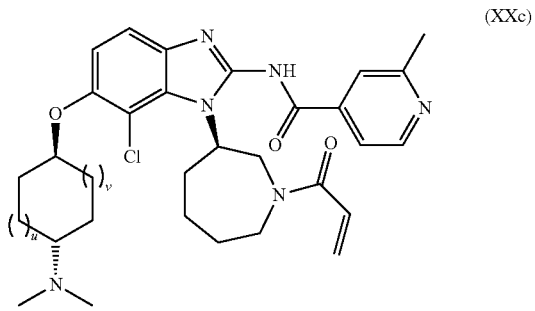

(XXc)

or an isotopic variant thereof; or a pharmaceutically acceptable salt, solvate, or prodrug thereof; wherein u and v are each as defined herein.

In yet another embodiment, provided herein is a compound of Formula XXd:

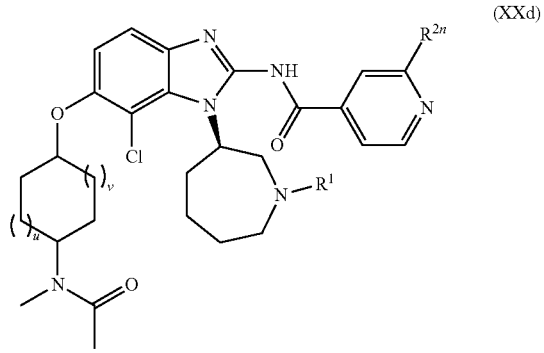

(XXd)

or a single enantiomer, a racemic mixture, a mixture of diastereomers, or an isotopic variant thereof; or a pharmaceutically acceptable salt, solvate, or prodrug thereof; wherein $R^1$, $R^{2n}$, u, and v are each as defined herein.

In yet another embodiment, provided herein is a compound of Formula XXe:

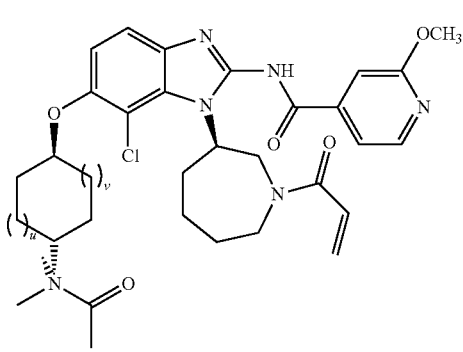

(XXe)

or an isotopic variant thereof; or a pharmaceutically acceptable salt, solvate, or prodrug thereof; wherein u and v are each as defined herein.

In yet another embodiment, provided herein is a compound of Formula XXf:

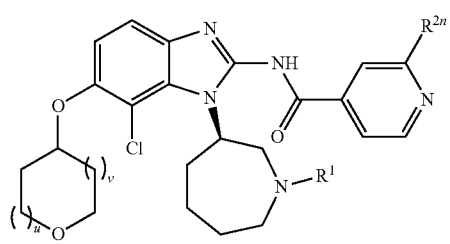

(XXf)

or a single enantiomer, a racemic mixture, a mixture of diastereomers, or an isotopic variant thereof; or a pharmaceutically acceptable salt, solvate, or prodrug thereof; wherein $R^1$, $R^{2n}$, u, and v are each as defined herein.

In yet another embodiment, provided herein is a compound of Formula XXg:

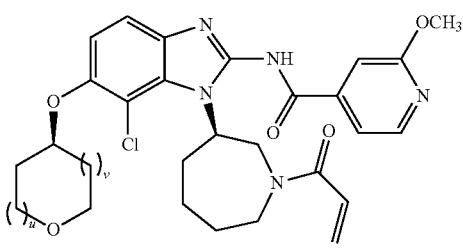

(XXg)

or an isotopic variant thereof; or a pharmaceutically acceptable salt, solvate, or prodrug thereof; wherein u and v are each as defined herein.

In yet another embodiment, provided herein is a compound of Formula XXh:

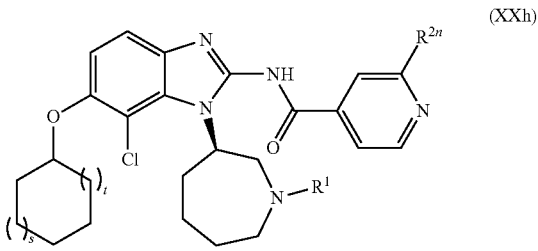

(XXh)

or a single enantiomer, a racemic mixture, a mixture of diastereomers, or an isotopic variant thereof; or a pharmaceutically acceptable salt, solvate, or prodrug thereof; wherein $R^1$, $R^{2n}$, u, and v are each as defined herein.

In yet another embodiment, provided herein is a compound of Formula XXi:

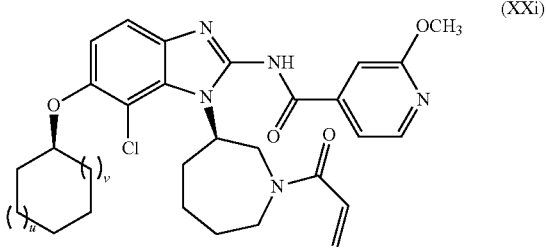

(XXi)

or an isotopic variant thereof; or a pharmaceutically acceptable salt, solvate, or prodrug thereof; wherein u and v are each as defined herein.

In yet another embodiment, provided herein is a compound of Formula XXj:

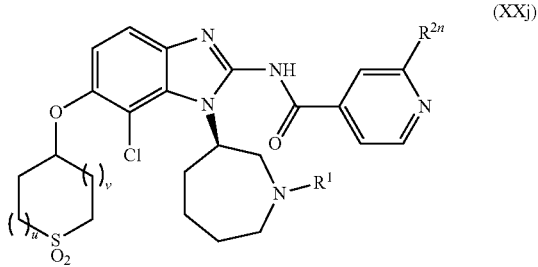

(XXj)

or a single enantiomer, a racemic mixture, a mixture of diastereomers, or an isotopic variant thereof; or a pharmaceutically acceptable salt, solvate, or prodrug thereof; wherein $R^1$, $R^{2n}$, u, and v are each as defined herein.

In yet another embodiment, provided herein is a compound of Formula XXk:

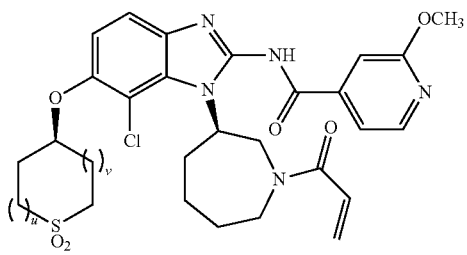

(XXk)

or an isotopic variant thereof; or a pharmaceutically acceptable salt, solvate, or prodrug thereof; wherein u and v are each as defined herein.

In still another embodiment, provided herein is a compound of Formula XX1:

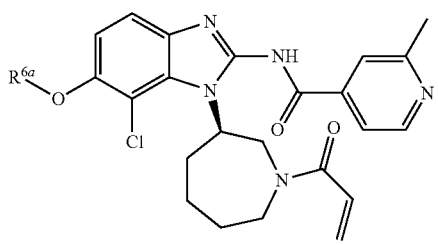

(XX1)

or a single enantiomer, a racemic mixture, a mixture of diastereomers, or an isotopic variant thereof; or a pharmaceutically acceptable salt, solvate, or prodrug thereof; wherein $R^{6a}$ is methoxycarbonyl, isopropoxycarbonyl, cyclobutoxycarbonyl, cyclopentoxycarbonyl, cyclohexoxycarbonyl, oxetan-3-oxycarbonyl, tetrahydrofuran-3-oxycarbonyl, tetrahydro-2H-pyran-4-oxycarbonyl, N,N-dimethylaminecarbonyl, N-methyl-N-isopropylaminecarbonyl, aziridin-1-ylcarbonyl, azetidin-1-ylcarbonyl, pyrrolidin-1-ylcarbonyl, 3-fluoro-pyrrolidin-1-ylcarbonyl, 3-methoxy-pyrrolidin-1-ylcarbonyl, 3,3-difluoro-pyrrolidin-1-ylcarbonyl, morpholin-4-ylcarbonyl, 4-isopropyl-piperazin-1-ylcarbonyl, 4-cyclopropyl-piperazin-1-ylcarbonyl, 4-acetyl-piperazin-1-ylcarbonyl, or 1,1-dioxo-thiomorpholin-4-ylcarbonyl.

In yet another embodiment, provided herein is a compound of Formula XXI:

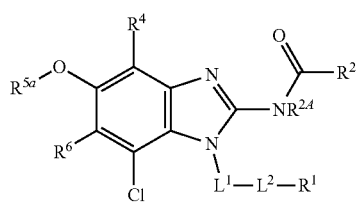

(XXI)

or a single enantiomer, a racemic mixture, a mixture of diastereomers, or an isotopic variant thereof; or a pharmaceutically acceptable salt, solvate, or prodrug thereof; wherein $R^{5a}$ is (i) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (ii) —C(O)$R^{1a}$, —C(O)O$R^{1a}$, —C(O)N$R^{1b}R^{1c}$, —C(N$R^{1a}$)N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2$ $R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; and $R^1$, $R^2$, $R^4$, $R^6$, $R^{2A}$, $R^{1a}$, $R^{1b}$, $R^{1c}$, $R^{1d}$, $L^1$, $L^2$, and Q are each as defined herein.

In yet another embodiment, provided herein is a compound of Formula XXII:

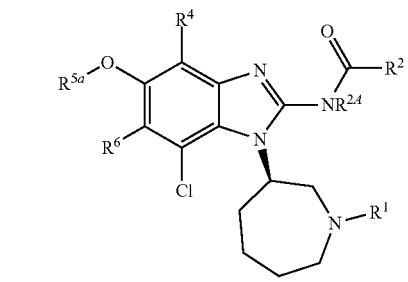

(XXII)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^6$, and $R^{5a}$ are each as defined herein.

In yet another embodiment, provided herein is a compound of Formula XXIII:

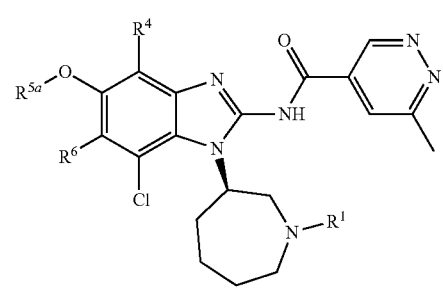

(XXIII)

or a single enantiomer, a racemic mixture, a mixture of diastereomers, or an isotopic variant thereof; or a pharmaceutically acceptable salt, solvate, or prodrug thereof; wherein $R^1$, $R^4$, $R^6$, and $R^{5a}$ are each as defined herein.

In yet another embodiment, provided herein is a compound of Formula XXIV:

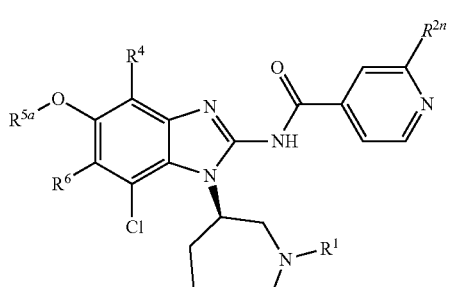

(XXIV)

or a single enantiomer, a racemic mixture, a mixture of diastereomers, or an isotopic variant thereof; or a pharmaceutically acceptable salt, solvate, or prodrug thereof; wherein $R^1$, $R^4$, $R^6$, $R^{2n}$, and $R^{5a}$ are each as defined herein.

In certain embodiments, in any of Formulae XXI to XXIV, $R^{5a}$ is:

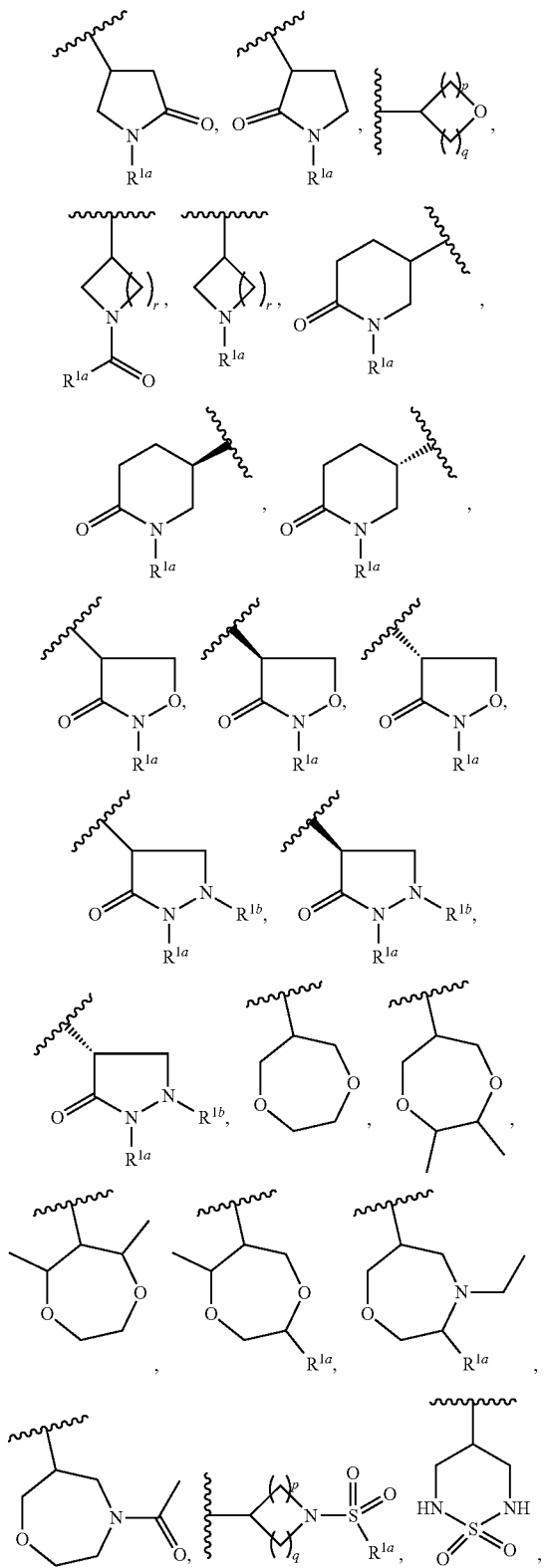

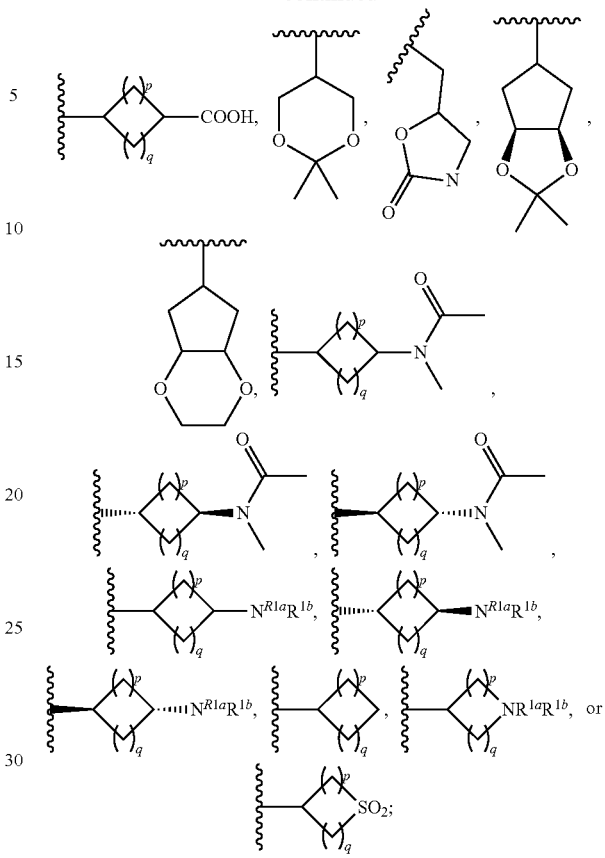

wherein $R^{1a}$, $R^{1b}$, p, q, and r are each as defined herein.

In certain embodiments, in any of Formulae XXI to XXIV, $R^{5a}$ is oxetan-3-yl, tetrahydro-2H-pyran-4-yl, 1-ethyl-piperidin-4-yl, or 1-acetyl-piperidin-4-yl.

In certain embodiments, in any of Formulae XXI to XXIV, $R^{5a}$ is —C(O)$R^{1a}$, —C(O)O$R^{1a}$, —C(O)N$R^{1b}R^{1c}$, —C(N$R^a$)N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$; wherein $R^{1a}$, $R^{1b}$, $R^{1c}$, and $R^{1d}$ are each as defined herein. In certain embodiments, in any of Formulae XXI to XXIV, $R^{5a}$ is —C(O)O$R^1$a or —C(O)N$R^{1b}R^{1c}$; wherein $R^{1a}$, $R^{1b}$, and $R^{1c}$ are each as defined herein.

In certain embodiments, in any of Formulae XXI to XXIV, $R^{5a}$ is —C(O)O$R^{1a}$; wherein $R^{1a}$ is as defined herein. In certain embodiments, in any of Formulae XXI to XXIV, $R^{5a}$ is —C(O)O$R^{1a}$; wherein $R^{1a}$ is $C_{1-6}$ alkyl, $C_{3-10}$ cycloalkyl, or heterocyclyl, each of which is optionally substituted with one or more substituents Q. In certain embodiments, in any of Formulae XXI to XXIV, $R^{5a}$ is —C(O)O$R^{1a}$; wherein $R^{1a}$ is methyl, isopropyl, cyclobutyl, cyclopentyl, cyclohexyl, oxetanyl, tetrahydrofuryl, or tetrahydro-2H-pyranyl, each of which is optionally substituted with one or more substituents Q.

In certain embodiments, in any of Formulae XXI to XXIV, $R^{5a}$ is —C(O)N$R^{1b}R^{1c}$; and $R^{1b}$ and $R^{1c}$ are each as defined herein. In certain embodiments, in any of Formulae XXI to XXIV, $R^{5a}$ is —C(O)N$R^{1b}R^{1c}$; and $R^{1b}$ and $R^{1c}$ are each independently $C_{1-6}$ alkyl, which is optionally substituted with one or more substituents Q; or $R^{1b}$ and $R^{1c}$ together with the N atom to which they are attached form heterocyclyl, which is optionally substituted with one or more substituents Q. In certain embodiments, in any of Formulae XXI to XXIV, $R^{5a}$ is —C(O)NR$^{1b}$R$^{1c}$; and R$^{1b}$ and R$^{1c}$ are each independently methyl or isopropyl, each of which is optionally substituted with one or more substituents Q; or R$^{1b}$ and R$^{1c}$ together with the N atom to which they are attached form aziridinyl, azetidinyl, pyrrolidinyl, morpholinyl, piperidinyl, piperazinyl, or 1,1-dioxo-thiomorpholinyl, each of which is optionally substituted with one or more substituents Q.

In certain embodiments, in any of Formulae XXI to XXIV, $R^{5a}$ is methoxycarbonyl, isopropoxycarbonyl, cyclobutoxycarbonyl, cyclopentoxycarbonyl, cyclohexoxycarbonyl, oxetan-3-oxycarbonyl, tetrahydrofuran-3-oxycarbonyl, tetrahydro-2H-pyran-4-oxycarbonyl, N,N-dimethylaminecarbonyl, N-methyl-N-isopropylaminecarbonyl, aziridin-1-ylcarbonyl, azetidin-1-ylcarbonyl, pyrrolidin-1-ylcarbonyl, 3-fluoro-pyrrolidin-1-ylcarbonyl, 3-methoxy-pyrrolidin-1-ylcarbonyl, 3,3-difluoro-pyrrolidin-1-ylcarbonyl, morpholin-4-ylcarbonyl, 4-isopropyl-piperazin-1-ylcarbonyl, 4-cyclopropyl-piperazin-1-ylcarbonyl, 4-acetyl-piperazin-1-ylcarbonyl, or 1,1-dioxo-thiomorpholin-4-ylcarbonyl.

In one embodiment, provided herein is a compound of Formula XXIVa:

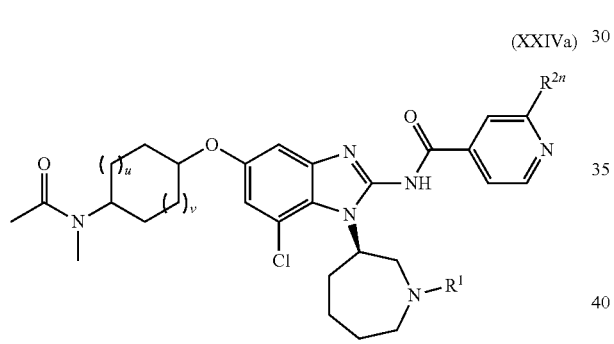

(XXIVa)

or a single enantiomer, a racemic mixture, a mixture of diastereomers, or an isotopic variant thereof; or a pharmaceutically acceptable salt, solvate, or prodrug thereof; wherein R$^1$, R$^{2n}$, u, and v are each as defined herein.

In another embodiment, provided herein is a compound of Formula XXIVb:

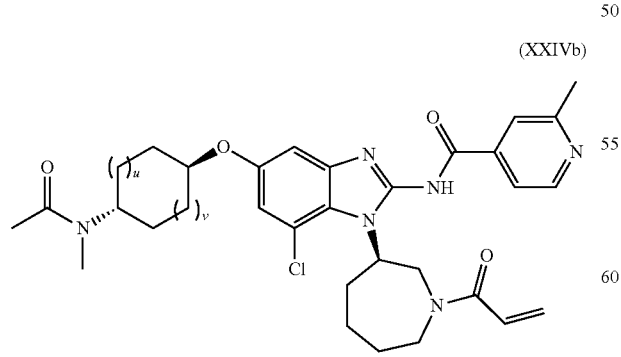

(XXIVb)

or an isotopic variant thereof; or a pharmaceutically acceptable salt, solvate, or prodrug thereof; wherein u and v are each as defined herein.

In yet another embodiment, provided herein is a compound of Formula XXIVc:

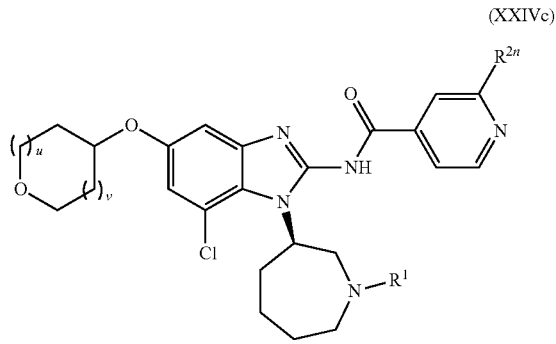

(XXIVc)

or a single enantiomer, a racemic mixture, a mixture of diastereomers, or an isotopic variant thereof; or a pharmaceutically acceptable salt, solvate, or prodrug thereof; wherein R$^1$, R$^{2n}$, u, and v are each as defined herein.

In yet another embodiment, provided herein is a compound of Formula XXIVd:

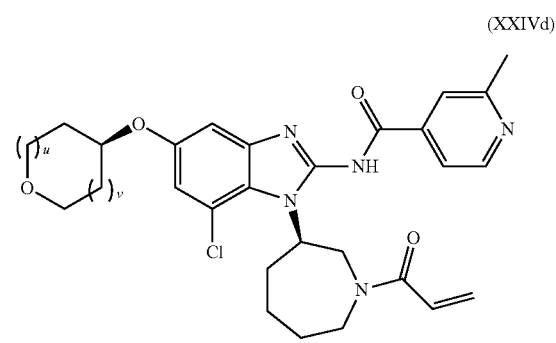

(XXIVd)

or an isotopic variant thereof; or a pharmaceutically acceptable salt, solvate, or prodrug thereof; wherein u and v are each as defined herein.

In yet another embodiment, provided herein is a compound of Formula XXIVe:

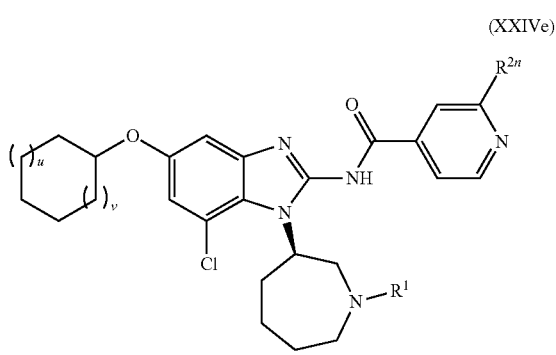

(XXIVe)

or a single enantiomer, a racemic mixture, a mixture of diastereomers, or an isotopic variant thereof; or a pharmaceutically acceptable salt, solvate, or prodrug thereof; wherein R$^1$, R$^{2n}$, u, and v are each as defined herein.

In yet another embodiment, provided herein is a compound of Formula XXIVf:

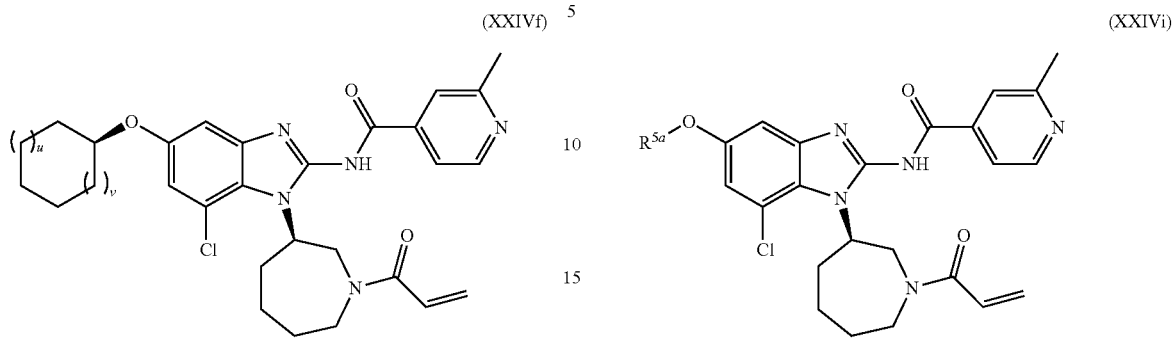

(XXIVf)

or an isotopic variant thereof; or a pharmaceutically acceptable salt, solvate, or prodrug thereof; wherein u and v are each as defined herein.

In yet another embodiment, provided herein is a compound of Formula

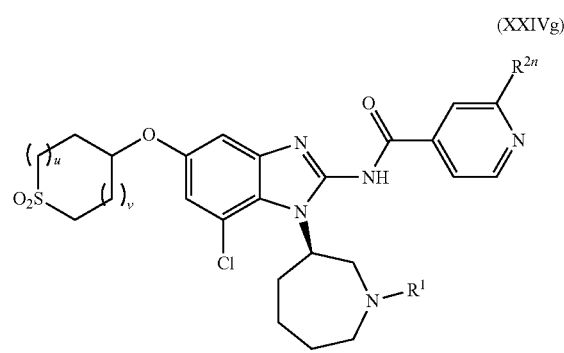

(XXIVg)

or a single enantiomer, a racemic mixture, a mixture of diastereomers, or an isotopic variant thereof; or a pharmaceutically acceptable salt, solvate, or prodrug thereof; wherein $R^1$, $R^{2n}$, u, and v are each as defined herein.

In yet another embodiment, provided herein is a compound of Formula XXIVh:

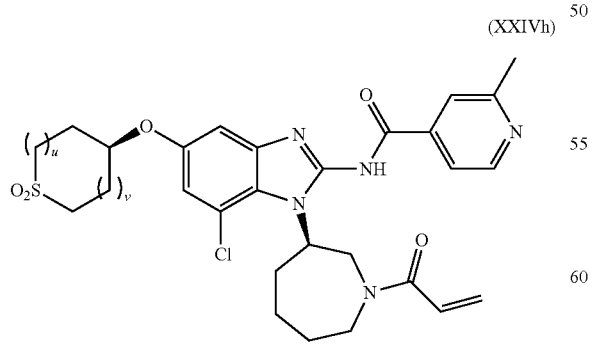

(XXIVh)

or an isotopic variant thereof; or a pharmaceutically acceptable salt, solvate, or prodrug thereof; wherein u and v are each as defined herein.

In still another embodiment, provided herein is a compound of Formula XXIVi:

(XXIVi)

or a single enantiomer, a racemic mixture, a mixture of diastereomers, or an isotopic variant thereof; or a pharmaceutically acceptable salt, solvate, or prodrug thereof; wherein $R^{5a}$ is:

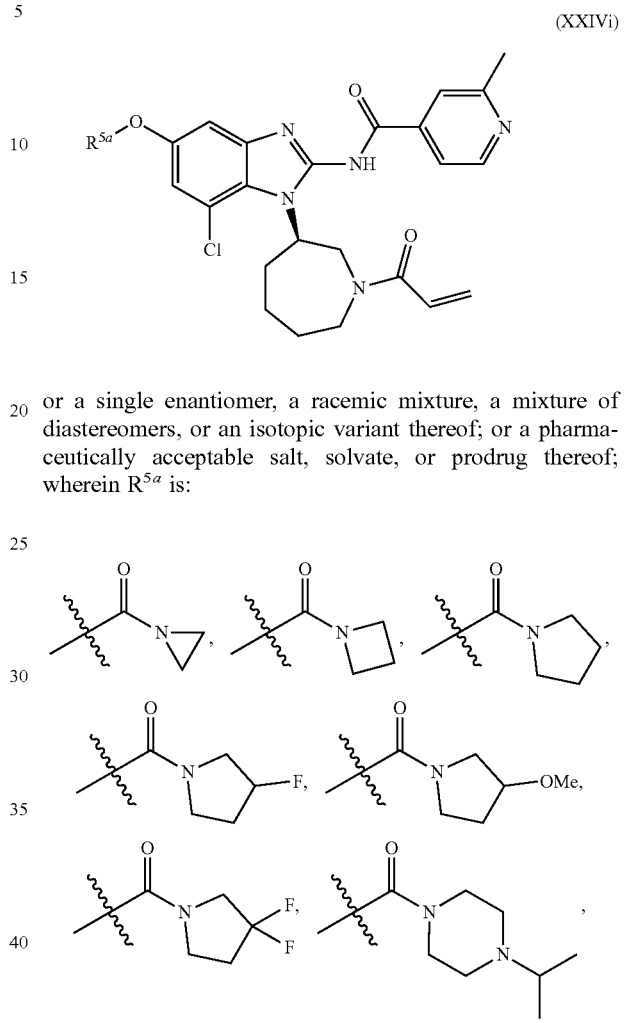

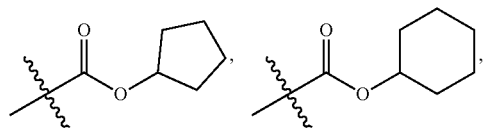

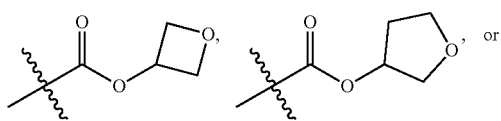

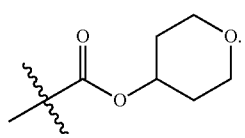

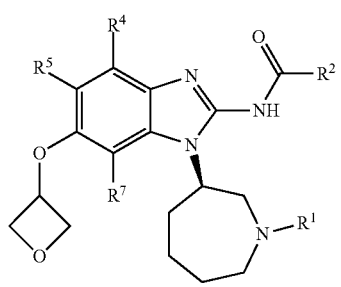

In yet another embodiment, provided herein is a compound of Formula XXV:

(XXV)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, and $R^7$ are each as defined herein.

In one embodiment, provided herein is a compound of Formula XXVa:

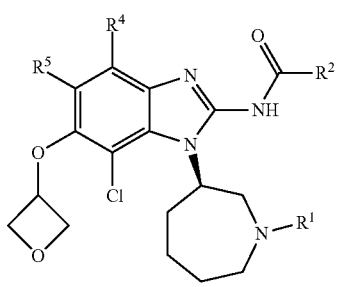

(XXVa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, and $R^5$ are each as defined herein.

In another embodiment, provided herein is a compound of Formula XXVb:

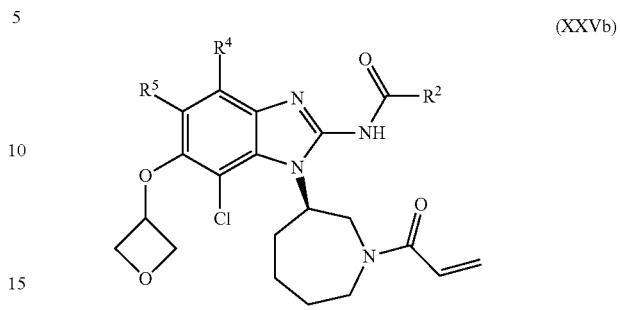

(XXVb)

or a single enantiomer, a racemic mixture, a mixture of diastereomers, or an isotopic variant thereof; or a pharmaceutically acceptable salt, solvate, or prodrug thereof; wherein $R^2$, $R^4$, and $R^5$ are each as defined herein.

In one embodiment, in Formula XXV, XXVa, or XXVb, $R^4$ and $R^5$ are both hydrogen. In another embodiment, in Formula XXV, XXVa, or XXVb, $R^2$ is monocyclic heteroaryl or bicyclic heteroaryl, each optionally substituted with one or more substituents Q as defined herein. In yet another embodiment, in Formula XXV, XXVa, or XXVb, $R^2$ is monocyclic heteroaryl, substituted with one or more substituents Q as defined herein. In still another embodiment, in Formula XXV, XXVa, or XXVb, $R^2$ is bicyclic heteroaryl, optionally substituted with one or more substituents Q as defined herein.

In one embodiment, in Formula XXV, XXVa, or XXVb, $R^4$ and $R^5$ are both hydrogen; and $R^2$ is monocyclic heteroaryl or bicyclic heteroaryl, each optionally substituted with one or more substituents Q as defined herein. In another embodiment, in Formula XXV, XXVa, or XXVb, $R^4$ and $R^5$ are both hydrogen; $R^2$ is monocyclic heteroaryl, substituted with one or more substituents Q as defined herein. In still another embodiment, in Formula XXV, XXVa, or XXVb, $R^4$ and $R^5$ are both hydrogen; $R^2$ is bicyclic heteroaryl, optionally substituted with one or more substituents Q as defined herein.

In yet another embodiment, provided herein is a compound of Formula XXVI:

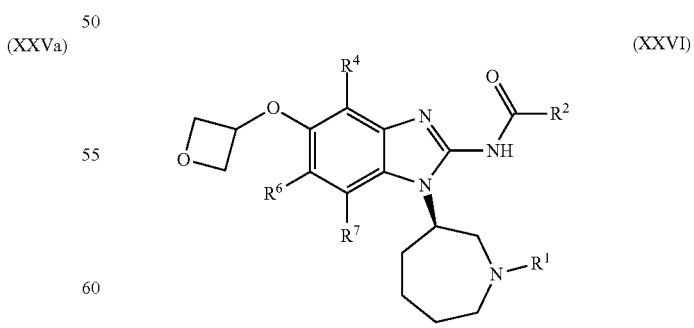

(XXVI)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^6$, and $R^7$ are each as defined herein.

In one embodiment, provided herein is a compound of Formula XXVIa:

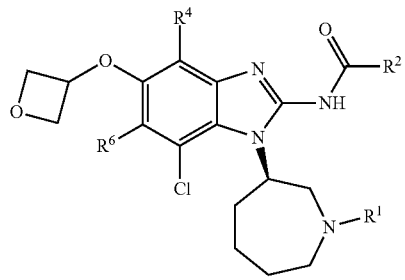

(XXVIa)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, and $R^6$ are each as defined herein.

In another embodiment, provided herein is a compound of Formula XXVIb:

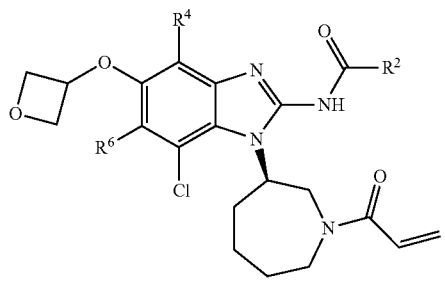

(XXVIb)

or a single enantiomer, a racemic mixture, a mixture of diastereomers, or an isotopic variant thereof; or a pharmaceutically acceptable salt, solvate, or prodrug thereof; wherein $R^2$, $R^4$, and $R^6$ are each as defined herein.

In one embodiment, in Formula XXVI, XXVIa, or XXVIb, $R^4$ and $R^6$ are both hydrogen. In another embodiment, in Formula XXVI, XXVIa, or XXVIb, $R^2$ is monocyclic heteroaryl or bicyclic heteroaryl, each optionally substituted with one or more substituents Q as defined herein. In yet another embodiment, in Formula XXVI, XXVIa, or XXVIb, $R^2$ is monocyclic heteroaryl, substituted with one or more substituents Q as defined herein. In still another embodiment, in Formula XXVI, XXVIa, or XXVIb, $R^2$ is bicyclic heteroaryl, optionally substituted with one or more substituents Q as defined herein.

In one embodiment, in Formula XXVI, XXVIa, or XXVIb, $R^4$ and $R^6$ are both hydrogen; and $R^2$ is monocyclic heteroaryl or bicyclic heteroaryl, each optionally substituted with one or more substituents Q as defined herein. In another embodiment, in Formula XXVI, XXVIa, or XXVIb, $R^4$ and $R^6$ are both hydrogen; $R^2$ is monocyclic heteroaryl, substituted with one or more substituents Q as defined herein. In still another embodiment, in Formula XXVI, XXVIa, or XXVIb, $R^4$ and $R^6$ are both hydrogen; $R^2$ is bicyclic heteroaryl, optionally substituted with one or more substituents Q as defined herein.

In still another embodiment, provided herein is a compound of Formula XXVII:

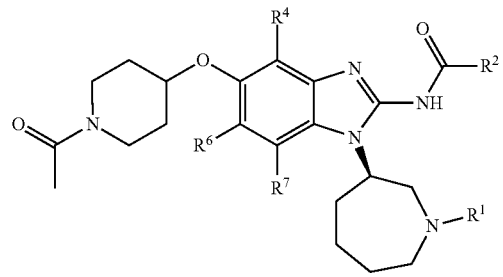

(XXVII)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^6$, and $R^7$ are each as defined herein.

In one embodiment, provided herein is a compound of Formula XXVIIa:

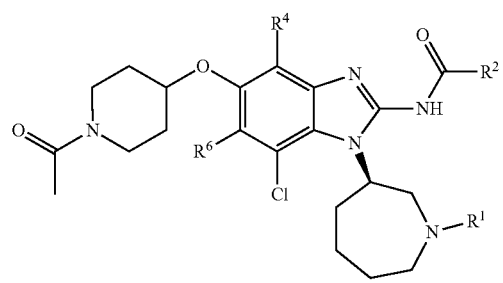

(XXVII)

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, and $R^6$ are each as defined herein.

In another embodiment, provided herein is a compound of Formula XXVIIb:

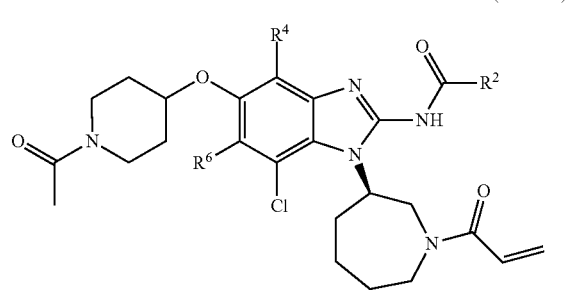

(XXVIIb)

or a single enantiomer, a racemic mixture, a mixture of diastereomers, or an isotopic variant thereof; or a pharmaceutically acceptable salt, solvate, or prodrug thereof; wherein $R^2$, $R^4$, and $R^6$ are each as defined herein.

In one embodiment, in Formula XXVII, XXVIIa, or XXVIIb, $R^4$ and $R^6$ are both hydrogen. In another embodiment, in Formula XXVII, XXVIIa, or XXVIIb, $R^2$ is monocyclic heteroaryl or bicyclic heteroaryl, each optionally substituted with one or more substituents Q as defined herein. In yet another embodiment, in Formula XXVII, XXVIIa, or XXVIIb, R² is monocyclic heteroaryl, substituted with one or more substituents Q as defined herein. In still another embodiment, in Formula XXVII, XXVIIa, or XXVIIb, R² is bicyclic heteroaryl, optionally substituted with one or more substituents Q as defined herein.

In one embodiment, in Formula XXVII, XXVIIa, or XXVIIb, R⁴ and R⁶ are both hydrogen; and R² is monocyclic heteroaryl or bicyclic heteroaryl, each optionally substituted with one or more substituents Q as defined herein. In another embodiment, in Formula XXVII, XXVIIa, or XXVIIb, R⁴ and R⁶ are both hydrogen; R² is monocyclic heteroaryl, substituted with one or more substituents Q as defined herein. In still another embodiment, in Formula XXVII, XXVIIa, or XXVIIb, R⁴ and R⁶ are both hydrogen; R² is bicyclic heteroaryl, optionally substituted with one or more substituents Q as defined herein.

In one embodiment, provided herein is a compound of Formula IV:

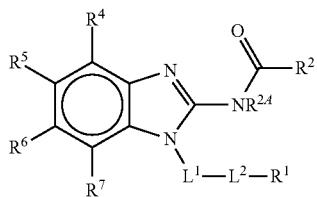
(IV)

or a single enantiomer, a racemic mixture, a mixture of diastereomers, or an isotopic variant thereof; or a pharmaceutically acceptable salt, solvate, or prodrug thereof; wherein R¹, R², R⁴, R⁵, R⁶, R⁷, R²ᴬ, L¹, and L² are each as defined herein; and one of the pairs, R⁴ and R⁵, R⁵ and R⁶, and R⁶ and R⁷, are linked together to form C₃₋₇ cycloalkyl, C₆₋₁₄ aryl, heteroaryl, or heterocyclyl, each of which is optionally substituted with one or more substituents Q as defined herein.

In yet another embodiment, provided herein is a compound of Formula VI:

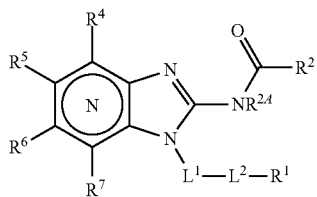
(VI)

or a single enantiomer, a racemic mixture, a mixture of diastereomers, or an isotopic variant thereof; or a pharmaceutically acceptable salt, solvate, or prodrug thereof; wherein R¹, R², R⁴, R⁵, R⁶, R⁷, R²ᴬ, L¹, and L² are each as defined herein; one of the pairs, R⁴ and R⁵, R⁵ and R⁶, and R⁶ and R⁷, are linked together to form C₃₋₇ cycloalkyl, C₆₋₁₄ aryl, heteroaryl, or heterocyclyl, each of which is optionally substituted with one or more substituents Q as defined herein; and the symbol

represents that the 6-membered ring contains one N atom in the ring.

In yet another embodiment, provided herein is a compound of Formula IV-A:

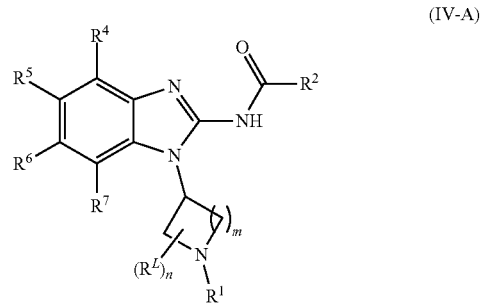
(IV-A)

or a single enantiomer, a racemic mixture, a mixture of diastereomers, or an isotopic variant thereof; or a pharmaceutically acceptable salt, solvate, or prodrug thereof; wherein:

m is an integer of 0, 1, 2, 3, 4, 5, 6, 7, 8, 9, or 10;

n is an integer of 0, 1, 2, 3, 4, 5, or 6;

each $R^L$ is independently (i) hydrogen; or (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (iii) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)₂R$^{1a}$, —OS(O)NR$^{1b}$R$^{1c}$, —OS(O)₂NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)₂R$^{1d}$, —NR$^{1a}$S(O)NR$^{1b}$R$^{1c}$, —NR$^{1a}$S(O)₂NR$^{1b}$R$^{1c}$, —SR$^{1a}$, —S(O)R$^{1a}$, —S(O)₂R$^{1a}$, —S(O)NR$^{1b}$R$^{1c}$, or —S(O)₂NR$^{1b}$R$^{1c}$; or two $R^L$ together, when there are two or more $R^L$ attached to the same ring, are linked together to form (i) a bond, —O—, —NR$^N$—, or —S—; or (ii) $C_{1-6}$ alkylene, $C_{1-6}$ heteroalkylene, $C_{2-6}$ alkenylene, or $C_{2-6}$ heteroalkenylene, each of which is optionally substituted with one or more substituents Q;

$R^N$ is (a) hydrogen; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more substituents Q; (c) —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)₂R$^{1a}$, —OS(O)NR$^{1b}$R$^{1c}$, —OS(O)₂NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)₂R$^{1d}$, —NR$^{1a}$S(O)NR$^{1b}$R$^{1C}$, —NR$^{1a}$S(O)₂NR$^{1b}$R$^{1c}$, —S(O)R$^{1a}$, —S(O)₂R$^{1a}$, —S(O)NR$^{1b}$R$^{1c}$, or —S(O)₂NR$^{1b}$R$^{1c}$; and R¹, R², R⁴, R⁵, R⁶, R⁷, R$^{1a}$, R$^{1b}$, R$^{1c}$, R$^{1d}$, and Q is as defined herein; and one of the pairs, R⁴ and R⁵, R⁵ and R⁶, and R⁶ and R⁷, are linked together to form $C_{3-7}$ cycloalkyl, $C_{6-14}$ aryl, heteroaryl, or heterocyclyl, each of which is optionally substituted with one or more substituents Q as defined herein.

In yet another embodiment, provided herein is a compound of Formula V-A:

(V-A)

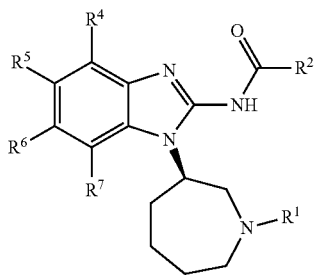

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^6$, and $R^7$ are each as defined herein; and one of the pairs, $R^4$ and $R^5$, $R^5$ and $R^6$, and $R^6$ and $R^7$, are linked together to form $C_{3-7}$ cycloalkyl, $C_{6-14}$ aryl, heteroaryl, or heterocyclyl, each of which is optionally substituted with one or more substituents Q as defined herein.

In yet another embodiment, provided herein is a compound of Formula VI-A:

(VI-A)

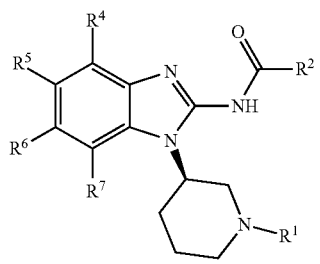

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^6$, and $R^7$ are each as defined herein; and one of the pairs, $R^4$ and $R^5$, $R^5$ and $R^6$, and $R^6$ and $R^7$, are linked together to form $C_{3-7}$ cycloalkyl, $C_{6-14}$ aryl, heteroaryl, or heterocyclyl, each of which is optionally substituted with one or more substituents Q as defined herein.

In yet another embodiment, provided herein is a compound of Formula VII-A:

(VII-A)

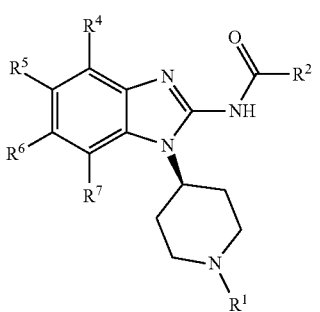

or a single enantiomer, a racemic mixture, a mixture of diastereomers, or an isotopic variant thereof; or a pharmaceutically acceptable salt, solvate, or prodrug thereof; wherein $R^1$, $R^2$, $R^4$, $R^5$, $R^6$, and $R^7$ are each as defined herein; and one of the pairs, $R^4$ and $R^5$, $R^5$ and $R^6$, and $R^6$ and $R^7$, are linked together to form $C_{3-7}$ cycloalkyl, $C_{6-14}$ aryl, heteroaryl, or heterocyclyl, each of which is optionally substituted with one or more substituents Q as defined herein.

In certain embodiments, in Formula II, IV, VI, IV-A, V-A, VI-A, or VII-A, $R^5$ and $R^6$ are linked together to form $C_{3-7}$ cycloalkyl, $C_{6-14}$ aryl, heteroaryl, or heterocyclyl, each of which is optionally substituted with one or more substituents Q. In certain embodiments, in Formula II, IV, VI, IV-A, V-A, VI-A, or VII-A, $R^5$ and $R^6$ are linked together to form heterocyclyl, optionally substituted with one or more substituents Q.

In certain embodiments, in Formula II, IV, VI, IV-A, V-A, VI-A, or VII-A, $R^5$ and $R^6$ are linked together to form heterocyclyl selected from:

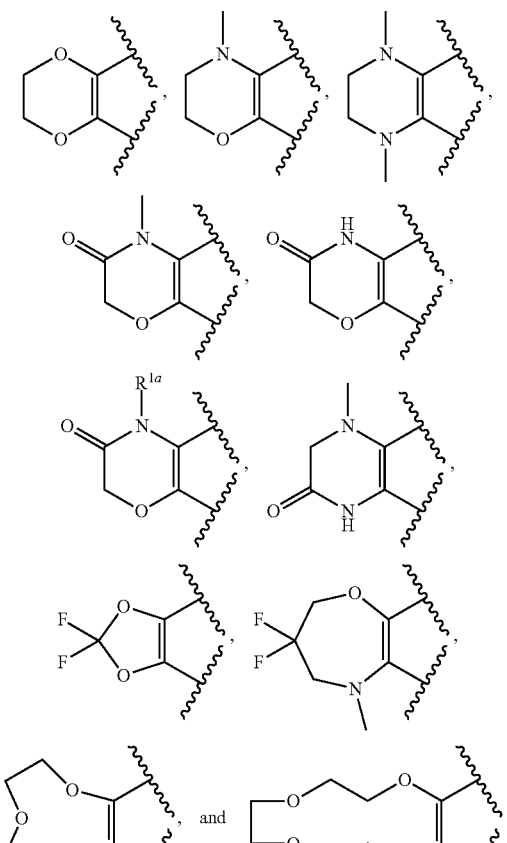

wherein $R^{1a}$ is as defined herein; and when the heterocyclyl group is not symmetric, the heterocyclyl group can then be attached to the rest of the compound in either direction unless specified.

In certain embodiments, in Formula II, IV, VI, IV-A, V-A, VI-A, or VII-A, $R^5$ and $R^6$ are linked together to form heterocyclyl selected from:

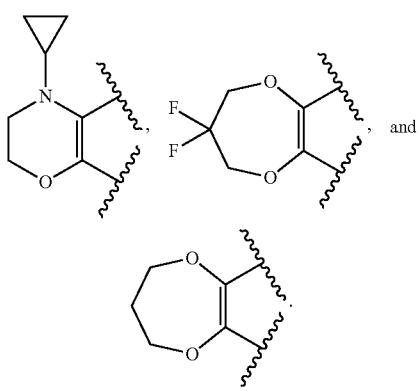

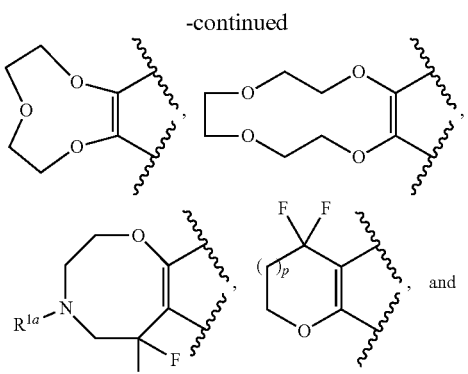

In certain embodiments, in Formula II, IV, VI, IV-A, V-A, VI-A, or VII-A, $R^6$ and $R^7$ are linked together to form $C_{3-7}$ cycloalkyl, $C_{6-14}$ aryl, heteroaryl, or heterocyclyl, each of which is optionally substituted with one or more substituents Q. In certain embodiments, in Formula II, IV, VI, IV-A, V-A, VI-A, or VII-A, $R^6$ and $R^7$ are linked together to form heterocyclyl, optionally substituted with one or more substituents Q.

In certain embodiments, in Formula II, IV, VI, IV-A, V-A, VI-A, or VII-A, $R^6$ and $R^7$ are linked together to form heterocyclyl selected from:

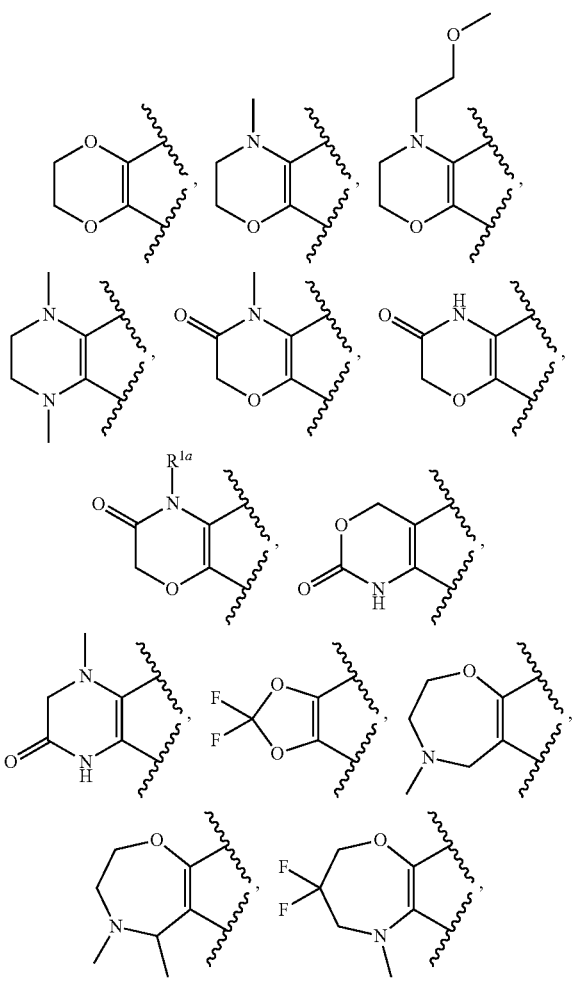

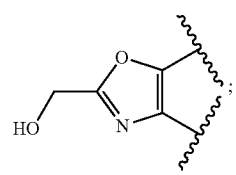

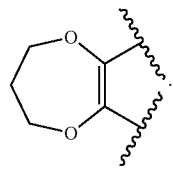

wherein p is an integer of 1, 2, 3, 4, 5, or 6; $R^{1a}$ is as defined herein; and when the heterocyclyl group is not symmetric, the heterocyclyl group can then be attached to the rest of the compound in either directions unless specified.

In certain embodiments, in Formula II, IV, VI, IV-A, V-A, VI-A, or VII-A, $R^6$ and $R^7$ are linked together to form heterocyclyl selected from:

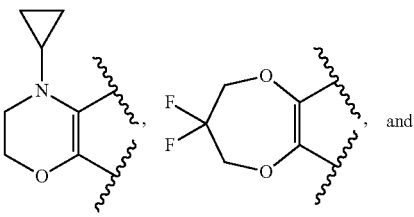

In one embodiment, provided herein is a compound having the formula selected from:

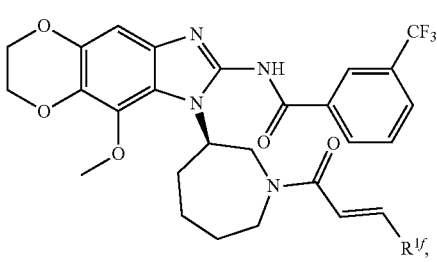

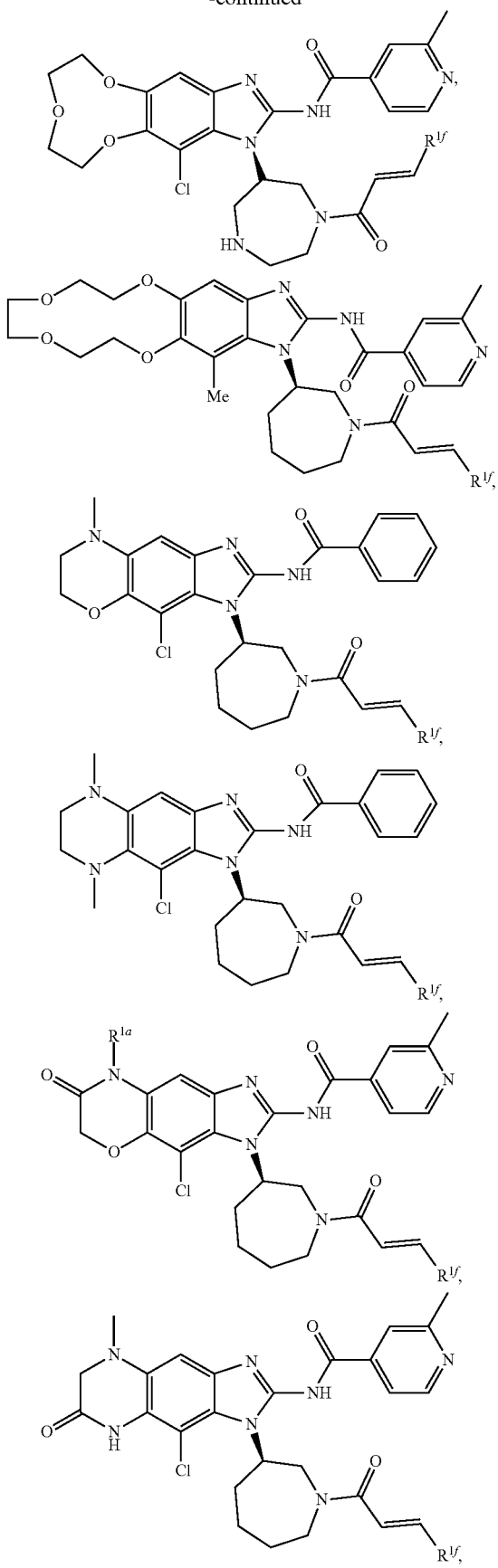

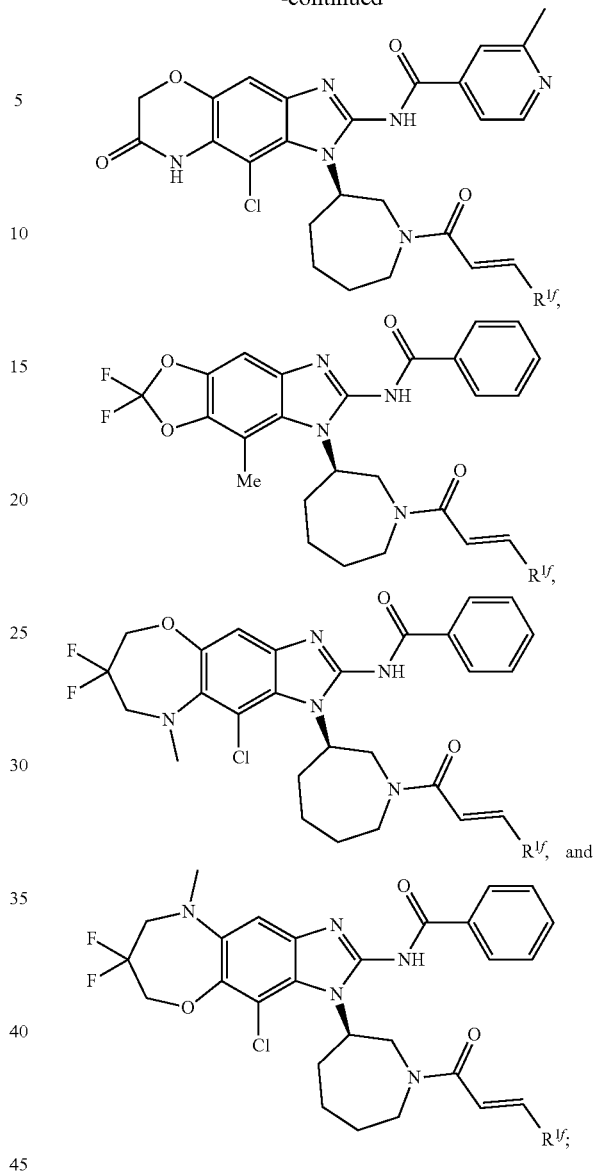

and single enantiomers, racemic mixtures, mixtures of diastereomers, and isotopic variants thereof; and pharmaceutically acceptable salts, solvates, and prodrugs thereof; wherein $R^{1a}$ and $R^{1f}$ are each as defined herein, in one embodiment, $R^{1a}$ is hydrogen or methyl, in another embodiment, $R^{1f}$ is hydrogen, dimethylaminomethyl, pyrrolidin-1-ylmethyl, or piperidin-1-ylmethyl.

In another embodiment, provided herein is a compound having the formula selected from:

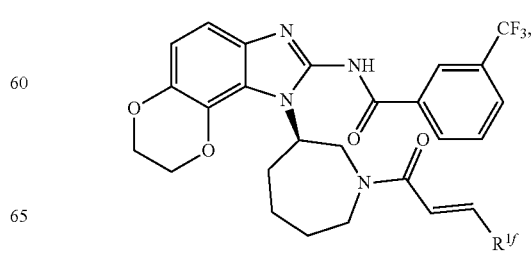

-continued
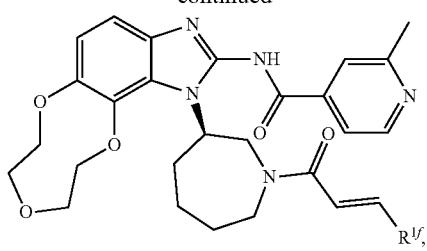
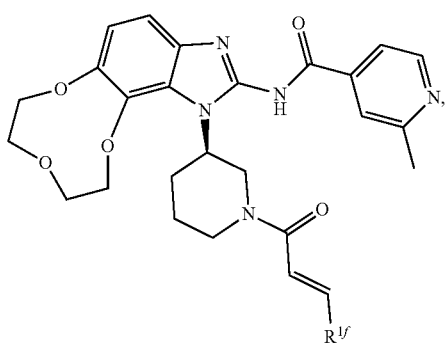
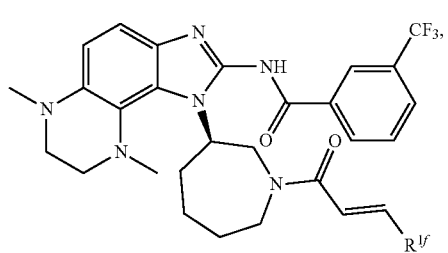
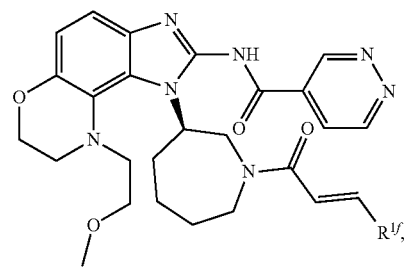
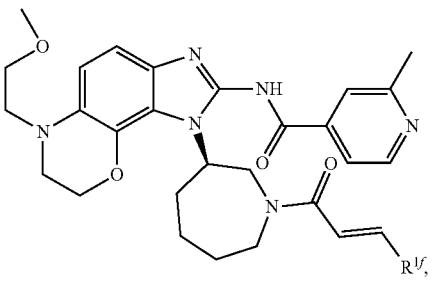
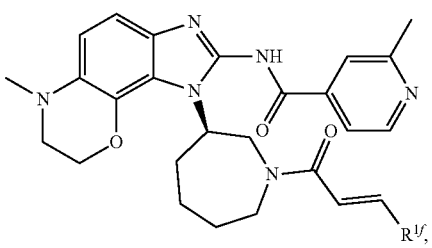
-continued
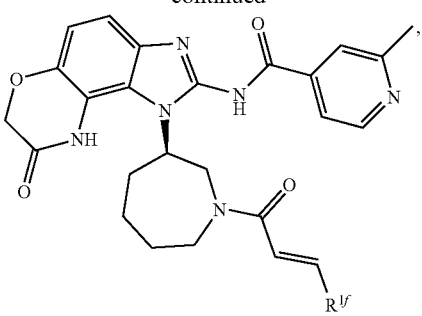
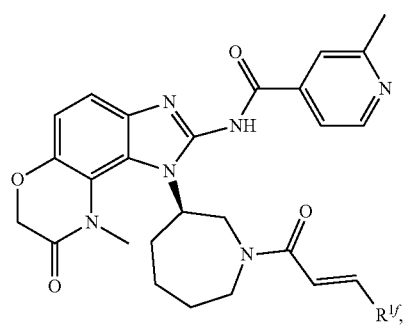
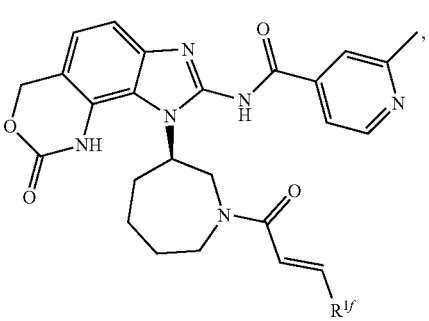
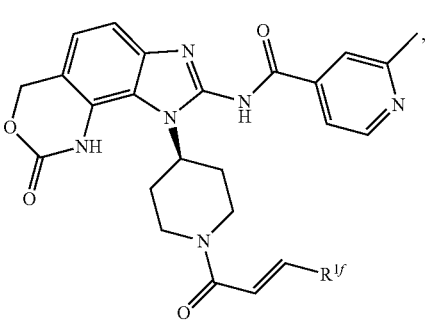
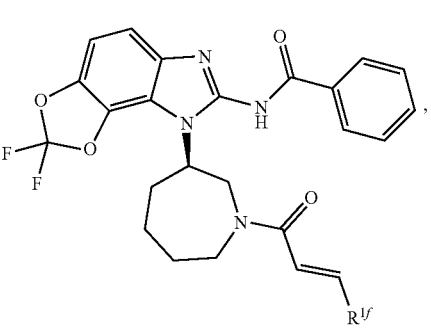

63

-continued

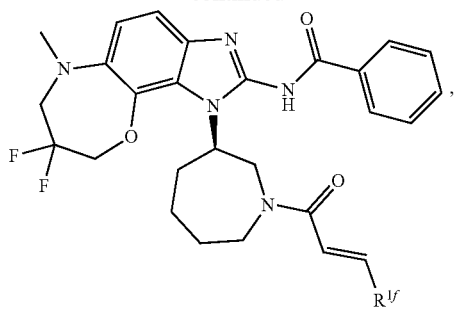

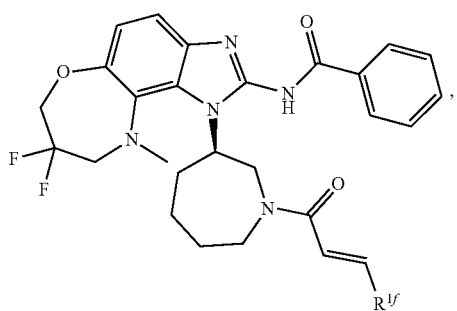

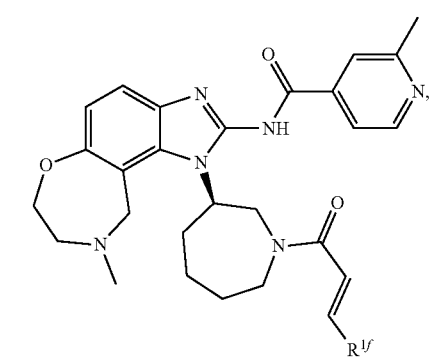

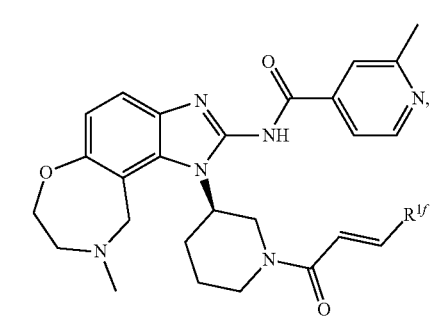

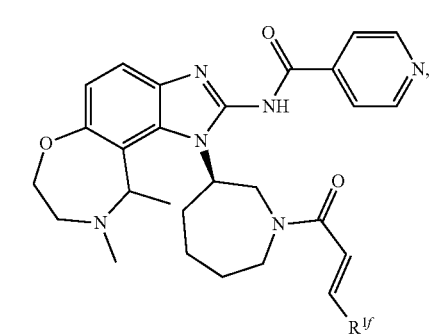

64

-continued

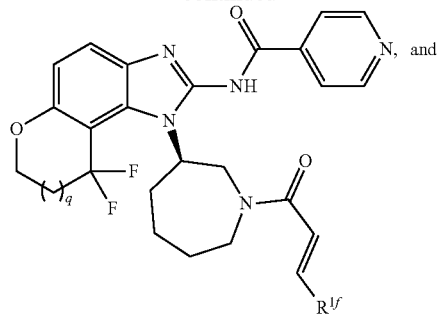

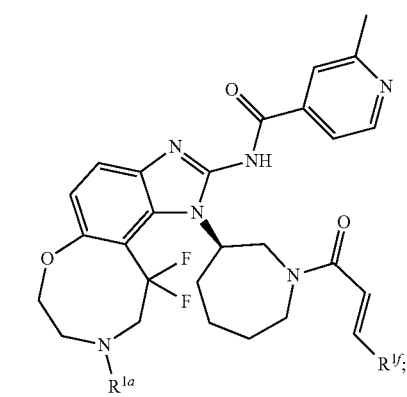

and single enantiomers, racemic mixtures, mixtures of diastereomers, and isotopic variants thereof; and pharmaceutically acceptable salts, solvates, and prodrugs thereof; wherein q is an integer of 1, 2, 3, 4, 5, or 6; and $R^{1a}$ and $R^{1f}$ are each as defined herein, in one embodiment, $R^{1a}$ is hydrogen or methyl, in another embodiment, $R^{1f}$ is hydrogen, dimethylaminomethyl, pyrrolidin-1-ylmethyl, or piperidin-1-ylmethyl.

In yet another embodiment, provided herein is a compound of Formula VIII-A:

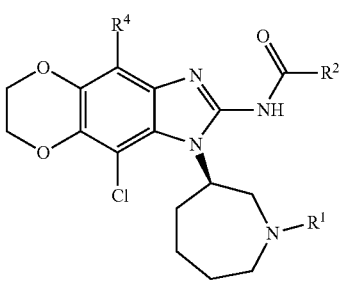

(VIII-A)

or a single enantiomer, a racemic mixture, a mixture of diastereomers, or an isotopic variant thereof; or a pharmaceutically acceptable salt, solvate, or prodrug thereof; wherein $R^1$, $R^2$, and $R^4$ are each as defined herein.

In one embodiment, provided herein is a compound of Formula VIIIa-A:

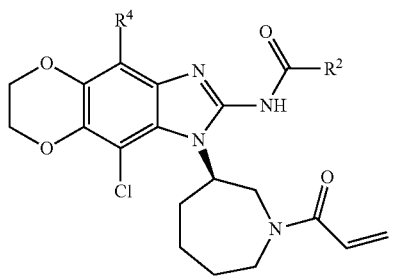

(VIIIa-A)

or a single enantiomer, a racemic mixture, a mixture of diastereomers, or an isotopic variant thereof; or a pharmaceutically acceptable salt, solvate, or prodrug thereof; wherein $R^2$ and $R^4$ are each as defined herein.

In yet another embodiment, provided herein is a compound of Formula IX-A:

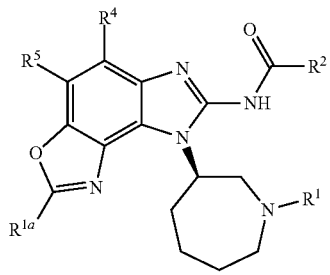

(IX-A)

or a single enantiomer, a racemic mixture, a mixture of diastereomers, or an isotopic variant thereof; or a pharmaceutically acceptable salt, solvate, or prodrug thereof; wherein $R^{6a}$ is (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q; or (c) —C(O)$R^{1a}$, —C(O)O$R^{1a}$, —C(O)N$R^{1b}R^{1c}$, —C(N$R^{1a}$)N$R^{1b}R^{1c}$, —O$R^{1a}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2$$R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2$$R^{1d}$, —N$R^{1a}$S(O)N$R^{1b}R^{1c}$, —N$R^{1a}$S(O)$_2$N$R^{1b}R^{1c}$, —S$R^{1a}$, —S(O)$R^{1a}$, —S(O)$_2$$R^{1a}$, —S(O)N$R^{1b}R^{1c}$, or —S(O)$_2$N$R^{1b}R^{1c}$; and $R^1$, $R^2$, $R^4$, $R^5$, and Q are each as defined herein.

In one embodiment, provided herein is a compound of Formula IXa-A:

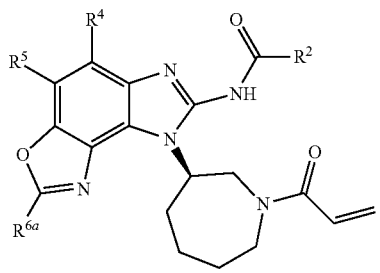

(IXa-A)

or a single enantiomer, a racemic mixture, a mixture of diastereomers, or an isotopic variant thereof; or a pharmaceutically acceptable salt, solvate, or prodrug thereof; wherein $R^2$, $R^4$, $R^5$, and $R^{6a}$ are each as defined herein.

In one embodiment, in Formula IX-A or IXa-A, $R^{6a}$ is (a) hydrogen; or (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more substituents Q. In another embodiment, in Formula IX-A or IXa-A, $R^{6a}$ is $C_{1-6}$ alkyl, optionally substituted with one or more substituents Q.

In still another embodiment, provided herein is a compound of Formula X-A:

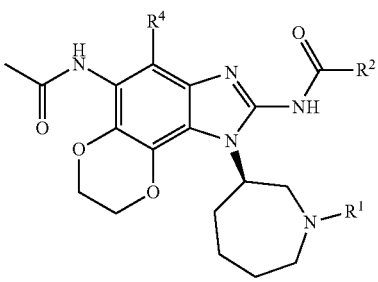

(X-A)

or a single enantiomer, a racemic mixture, a mixture of diastereomers, or an isotopic variant thereof; or a pharmaceutically acceptable salt, solvate, or prodrug thereof; wherein $R^1$, $R^2$, and $R^4$ are each as defined herein.

In one embodiment, provided herein is a compound of Formula Xa-A:

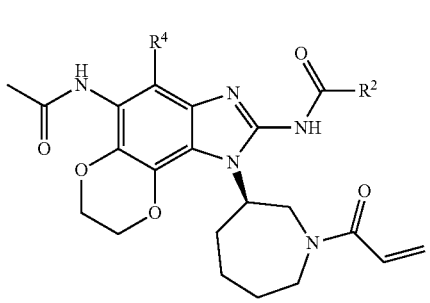

(Xa-A)

or a single enantiomer, a racemic mixture, a mixture of diastereomers, or an isotopic variant thereof; or a pharmaceutically acceptable salt, solvate, or prodrug thereof; wherein $R^2$ and $R^4$ are each as defined herein.

The groups, $R^1$, $R^2$, $R^4$, $R^5$, $R^6$, $R^7$, $R^{2n}$, $R^{3n}$, $R^{5a}$, $R^{6a}$, $R^{7a}$, $R^{7b}$, $R^{7c}$, $L^1$, $L^2$, T, U, V, W, X, Y, Z, m, n, p, q, r, u and v in formulae described herein, including Formulae I to XXVII, XIa to XIi, XIVa, XVIIa, XIXa, XXa to XXI, XXIVa to XXIVi, XXVa, XXVb, XXVIa, XXVIb, XXVIIa, XXVIIb, XXVIIIa, XXVIIIb, IV-A to X-A, and VIIIa-A to Xa-A are further defined herein. All combinations of the embodiments provided herein for such groups are within the scope of this disclosure.

In certain embodiments, $R^1$ is —C(O)C$R^{1e}$=C$R^{1f}$$R^{1g}$, wherein $R^{1e}$, $R^f$, and $R^{1g}$ are each as defined herein. In certain embodiments, $R^1$ is

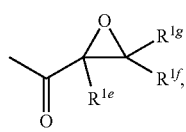

wherein $R^{1e}$, $R^{1f}$ and $R^{1g}$ are each as defined herein. In certain embodiments, $R^1$ is $-N^{1a}C(O)CR^{1e}=CR^{1f}CR^{1g}$, wherein $R^{1a}$, $R^{1e}$, $R^{1f}$, and $R^{1g}$ are each as defined herein. In certain embodiments, $R^1$ is

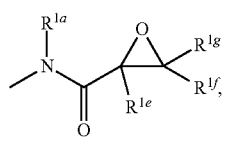

wherein $R^{1a}$, $R^{1e}$, $R^{1f}$ and $R^{1g}$ are each as defined herein. In certain embodiments, $R^1$ is $-S(O)CR^{1e}=CR^{1f}CR^{1g}$, wherein $R^{1e}$, $R^{1f}$, and $R^{1g}$ are each as defined herein. In certain embodiments, $R^1$ is

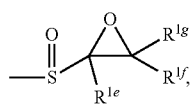

wherein $R^{1e}$, $R^{1f}$, and $R^{1g}$ are each as defined herein. In certain embodiments, $R^1$ is $-NR^{1a}S(O)CR^{1e}=CR^{1f}CR^{1g}$, wherein $R^{1a}$, $R^{1e}$, $R^{1f}$, and $R^{1g}$ are each as defined herein. In certain embodiments, $R^1$ is

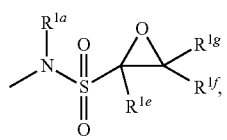

wherein $R^{1a}$, $R^{1e}$, $R^{1f}$, and $R^{1g}$ are each as defined herein. In certain embodiments, $R^1$ is certain embodiments, $R^1$ is $-NR^{1a}S(O_2)CR^{1e}=CR^{1f}CR^{1g}$, wherein $R^{1a}$, $R^{1e}$, $R^{1f}$, and $R^{1g}$ are each as defined herein. In certain embodiments, $R^1$ is

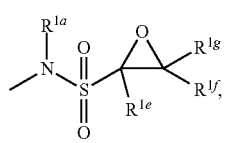

wherein $R^{1a}$, $R^{1e}$, $R^{1f}$, and $R^{1g}$ are each as defined herein. In certain embodiments, $R^{1a}$, $R^{1e}$, $R^{1f}$, and $R^{1g}$ are all hydrogen.

In certain embodiments, $R^1$ is selected from:

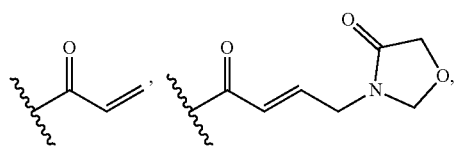

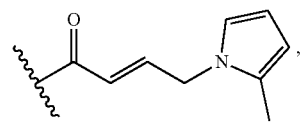

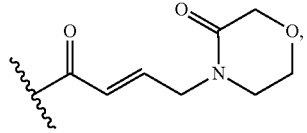

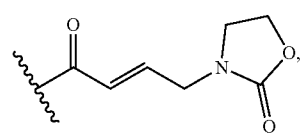

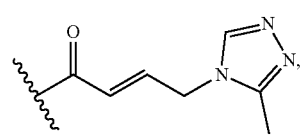

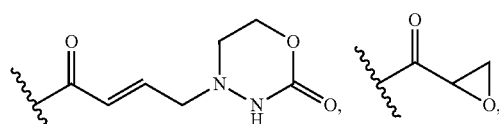

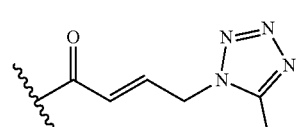

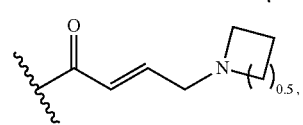

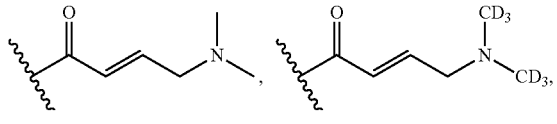

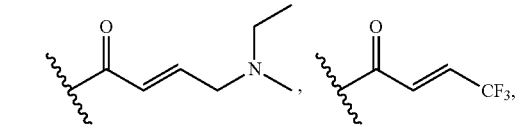

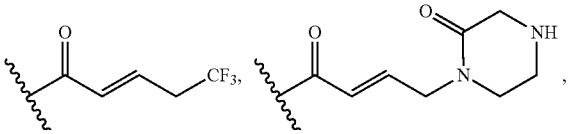

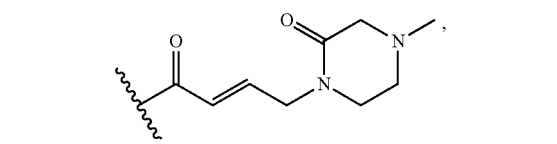

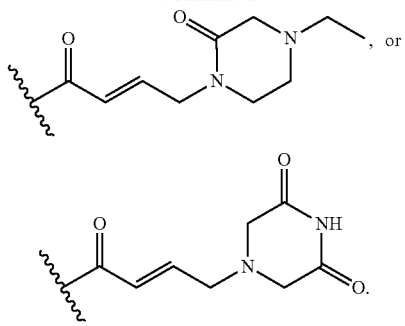

In certain embodiments, $R^1$ is selected from:

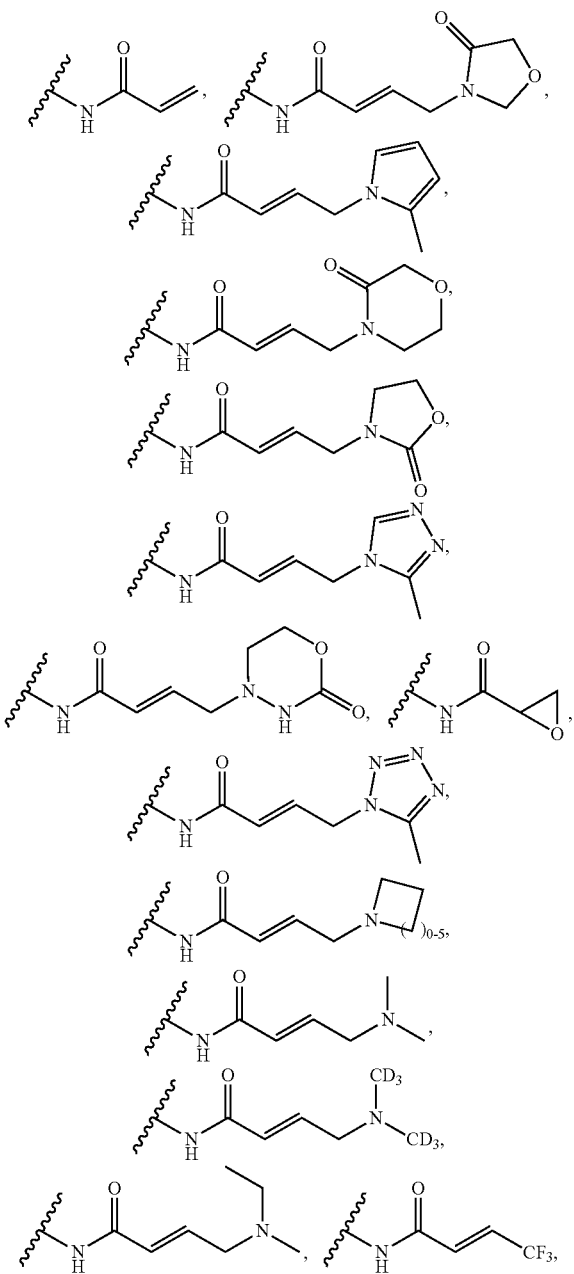

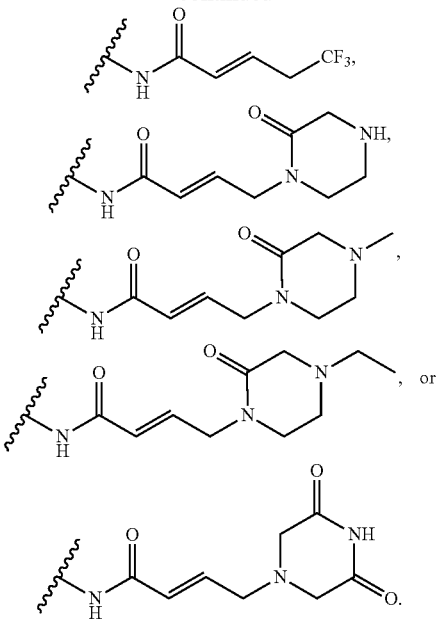

In certain embodiments, $R^2$ is $C_{3-7}$ cycloalkyl, optionally substituted with one or more substituents Q. In certain embodiments, $R^2$ is $C_{6-14}$ aryl, optionally substituted with one or more substituents Q. In certain embodiments, $R^2$ is 6- to 10-membered monocyclic or bicyclic aryl, optionally substituted with one or more substituents Q. In certain embodiments, $R^2$ is phenyl, optionally substituted with one or more substituents Q. In certain embodiments, $R^2$ is phenyl or methyl-phenyl. In certain embodiments, $R^2$ is phenyl, 3-methyl-phenyl, or 4-((2-(methylcarbamoyl)pyridin-4-yl)oxy)phenyl. In certain embodiments, $R^2$ is $C_{7-15}$ aralkyl, optionally substituted with one or more substituents Q. In certain embodiments, $R^2$ is heteroaryl, optionally substituted with one or more substituents Q. In certain embodiments, $R^2$ is 5- to 10-membered heteroaryl, optionally substituted with one or more substituents Q. In certain embodiments, $R^2$ is 5- to 10-membered heteroaryl comprising 1 to 4 heteroatoms selected from N, O, and S, which is optionally substituted with one or more substituents Q. In certain embodiments, $R^2$ is monocyclic heteroaryl, optionally substituted with one or more substituents Q. In certain embodiments, $R^2$ is 5-membered heteroaryl, optionally substituted with one or more substituents Q. In certain embodiments, $R^2$ is 6-membered heteroaryl, optionally substituted with one or more substituents Q. In certain embodiments, $R^2$ is pyridinyl or pyridazinyl, optionally substituted with one or more substituents Q. In certain embodiments, $R^2$ is hydroxy-pyridinyl, methoxy-pyridinyl, methyl-pyridinyl, difluoromethyl-pyridinyl, trifluoromethyl-pyridinyl, methylaminocarbonyl-pyridinyl, or methyl-pyridazinyl. In certain embodiments, $R^2$ is 2-hydroxy-pyridin-4-yl, 2-methoxy-pyridin-4-yl, 2-methyl-pyridin-4-yl, 2-monofluoromethyl-pyridin-4-yl, 2-difluoromethyl-pyridin-4-yl, 2-trifluoromethyl-pyridin-4-yl, 2-methylaminocarbonyl-pyridin-4-yl, or 3-methyl-pyridazin-5-yl. In certain embodiments, $R^2$ is bicyclic heteroaryl, optionally substituted with one or more substituents Q. In certain embodiments, $R^2$ is 5,6-fused heteroaryl, optionally substituted with one or more substituents Q. In certain embodiments, $R^2$ is benzo[c][1,2,5]oxodiazolyl, benzo[c][1,2,5]thiodiazolyl, imidazo[1,5-a]pyridinyl, imidazo[1,2-a]pyridinyl, or triazolo[4,3-a]pyridinyl, each optionally substituted with one or more substituents Q. In certain embodiments, $R^2$ is benzo[c][1,2,5]oxodiazol-5-yl, benzo[c][1,2,5]thiodiazol-5-yl, imidazo[1,5-a]pyridin-7-yl, imidazo[1,2-a]pyridin-7-yl, or triazolo[4,3-a]pyridine-7-yl, each optionally substituted with one or more substituents Q. In certain embodiments, $R^2$ is heterocyclyl, optionally substituted with one or more substituents Q. In certain embodiments, $R^2$ is 4- to 12-membered monocyclic or bicyclic heterocyclyl comprising 1 to 4 heteroatoms selected from N, O, and S, which is optionally substituted with one or more substituents Q.

In certain embodiments, $R^4$ is hydrogen. In certain embodiments, $R^4$ is cyano. In certain embodiments, $R^4$ is halo. In certain embodiments, $R^4$ is fluoro, chloro, bromo, or iodo. In certain embodiments, $R^4$ is nitro. In certain embodiments, $R^4$ is $C_{1-6}$ alkyl, optionally substituted with one or more substituents Q. In certain embodiments, $R^4$ is $C_{2-6}$ alkenyl, optionally substituted with one or more substituents Q. In certain embodiments, $R^4$ is $C_{2-6}$ alkynyl, optionally substituted with one or more substituents Q. In certain embodiments, $R^4$ is $C_{3-7}$ cycloalkyl, optionally substituted with one or more substituents Q. In certain embodiments, $R^4$ is $C_{6-14}$ aryl, optionally substituted with one or more substituents Q. In certain embodiments, $R^4$ is $C_{7-15}$ aralkyl, optionally substituted with one or more substituents Q. In certain embodiments, $R^4$ is heteroaryl, optionally substituted with one or more substituents Q. In certain embodiments, $R^4$ is heterocyclyl, optionally substituted with one or more substituents Q.

In certain embodiments, $R^4$ is —C(O)$R^{1a}$, where $R^{1a}$ is as defined herein. In certain embodiments, $R^4$ is —C(O)O$R^{1a}$, where $R^{1a}$ is as defined herein. In certain embodiments, $R^4$ is —C(O)N$R^{1b}R^{1c}$, where $R^{1b}$ and $R^{1c}$ are each as defined herein. In certain embodiments, $R^4$ is —C(N$R^{1a}$)N$R^{1b}R^{1c}$, where $R^{1a}$, $R^{1b}$, and $R^{1c}$ are each as defined herein. In certain embodiments, $R^4$ is —O$R^{1a}$, where $R^{1a}$ is as defined herein. In certain embodiments, $R^4$ is —OC(O)$R^{1a}$, where $R^{1a}$ is as defined herein. In certain embodiments, $R^4$ is —OC(O)O$R^{1a}$, where $R^{1a}$ is as defined herein. In certain embodiments, $R^4$ is —OC(O)N$R^{1b}R^{1c}$, where $R^{1b}$ and $R^{1c}$ are each as defined herein. In certain embodiments, $R^4$ is —OC(=N$R^{1a}$)N$R^{1b}R^{1c}$, where $R^{1a}$, $R^{1b}$, and $R^{1c}$ are each as defined herein. In certain embodiments, $R^4$ is —OS(O)$R^{1a}$, where $R^{1a}$ is as defined herein. In certain embodiments, $R^4$ is —OS(O)$_2R^{1a}$, where $R^{1a}$ is as defined herein. In certain embodiments, $R^4$ is —OS(O)N$R^{1b}R^{1c}$, where $R^{1b}$ and $R^{1c}$ are each as defined herein. In certain embodiments, $R^4$ is —OS(O)$_2$N$R^{1b}R^{1c}$, where $R^{1b}$ and $R^{1c}$ are each as defined herein. In certain embodiments, $R^4$ is —N$R^{1b}R^{1c}$, where $R^{1b}$ and $R^{1c}$ are each as defined herein. In certain embodiments, $R^4$ is —N$R^{1a}$C(O)$R^{1d}$, where $R^{1a}$ and $R^{1d}$ are each as defined herein. In certain embodiments, $R^4$ is —N$R^{1a}$C(O)O$R^{1d}$, where $R^{1a}$ and $R^{1d}$ are each as defined herein. In certain embodiments, $R^4$ is —N$R^{1a}$C(O)N$R^{1b}R^{1c}$, where $R^{1a}$, $R^{1b}$, and $R^{1c}$ are each as defined herein. In certain embodiments, $R^4$ is —N$R^{1a}$C(=N$R^{1d}$)N$R^{1b}R^{1c}$, where $R^{1a}$, $R^{1b}$, $R^{1c}$, and $R^{1d}$ are each as defined herein. In certain embodiments, $R^4$ is —N$R^{1a}$S(O)$R^{1d}$, where $R^{1a}$ and $R^{1d}$ are each as defined herein. In certain embodiments, $R^4$ is —N$R^{1a}$S(O)$_2R^{1d}$, where $R^{1a}$ and $R^{1d}$ are each as defined herein. In certain embodiments, $R^4$ is —N$R^{1a}$S(O)N$R^{1b}R^{1c}$, where $R^{1a}$, $R^{1b}$, and $R^{1c}$ are each as defined herein. In certain embodiments, $R^4$ is —N$R^a$S(O)$_2$N$R^{1b}R^{1c}$, where $R^{1a}$, $R^{1b}$, and $R^{1c}$ are each as defined herein. In certain embodiments, $R^4$ is —S$R^{1a}$, where $R^{1a}$ is as defined herein. In certain embodiments, $R^4$ is —S(O)$R^{1a}$, where $R^{1a}$ is as defined herein. In certain embodiments, $R^4$ is —S(O)$_2R^{1a}$, where $R^{1a}$ is as defined herein. In certain embodiments, $R^4$ is —S(O)N$R^{1b}R^{1c}$, where $R^{1b}$ and $R^{1c}$ are each as defined herein. In certain embodiments, $R^4$ is —S(O)$_2$N$R^{1b}R^{1c}$, where $R^{1b}$ and $R^{1c}$ are each as defined herein. In certain embodiments, two $R^4$ are linked together to form =O.

In certain embodiments, $R^5$ is hydrogen. In certain embodiments, $R^5$ is cyano. In certain embodiments, $R^5$ is halo. In certain embodiments, $R^5$ is fluoro, chloro, bromo, or iodo. In certain embodiments, $R^5$ is nitro. In certain embodiments, $R^5$ is $C_{1-6}$ alkyl, optionally substituted with one or more substituents Q. In certain embodiments, $R^5$ is $C_{2-6}$ alkenyl, optionally substituted with one or more substituents Q. In certain embodiments, $R^5$ is $C_{2-6}$ alkynyl, optionally substituted with one or more substituents Q. In certain embodiments, $R^5$ is $C_{3-7}$ cycloalkyl, optionally substituted with one or more substituents Q. In certain embodiments, $R^5$ is $C_{6-14}$ aryl, optionally substituted with one or more substituents Q. In certain embodiments, $R^5$ is $C_{7-15}$ aralkyl, optionally substituted with one or more substituents Q. In certain embodiments, $R^5$ is heteroaryl, optionally substituted with one or more substituents Q. In certain embodiments, $R^5$ is heterocyclyl, optionally substituted with one or more substituents Q. In certain embodiments, $R^5$ is piperazinyl, optionally substituted with one or more substituents Q. In certain embodiments, $R^5$ is 4-acetylpiperazinyl.

In certain embodiments, $R^5$ is —C(O)$R^{1a}$, where $R^{1a}$ is as defined herein. In certain embodiments, $R^5$ is —C(O)O$R^a$, where $R^{1a}$ is as defined herein. In certain embodiments, $R^5$ is —C(O)N$R^{1b}R^{1c}$, where $R^{1b}$ and $R^{1c}$ are each as defined herein. In certain embodiments, $R^5$ is —C(N$R^{1a}$)N$R^{1b}R^{1c}$, where $R^{1a}$, $R^{1b}$, and $R^{1c}$ are each as defined herein. In certain embodiments, $R^5$ is —O$R^{1a}$, where $R^{1a}$ is as defined herein. In certain embodiments, $R^5$ is —O$C_{1-6}$ alkyl, optionally substituted with one or more substituents Q. In certain embodiments, $R^5$ is —OCH$_3$, optionally substituted with one or more substituents Q. In certain embodiments, $R^5$ is trifluoromethoxy. In certain embodiments, $R^5$ is —O-heterocyclyl, optionally substituted with one or more substituents Q. In certain embodiments, $R^5$ is —O— oxetanyl, —O-tetrahydro-2H-pyranyl, or —O-piperidyl, each optionally substituted with one or more substituents Q. In certain embodiments, $R^6$ is oxetan-3-yloxy, optionally substituted with one or more substituents Q. In certain embodiments, $R^6$ is tetrahydro-2H-pyran-4-yl)oxy, optionally substituted with one or more substituents Q. In certain embodiments, $R^5$ is piperid-4-yloxy, optionally substituted with one or more substituents Q. In certain embodiments, $R^5$ is 1-ethyl-piperid-4-yloxy or 1-acetyl-piperid-4-yloxy. In certain embodiments, $R^5$ is —OC(O)$R^{1a}$, where $R^{1a}$ is as defined herein. In certain embodiments, $R^5$ is —OC(O)O$R^{1a}$, where $R^{1a}$ is as defined herein. In certain embodiments, $R^5$ is —OC(O)N$R^{1b}R^{1c}$, where $R^{1b}$ and $R^{1c}$ are each as defined herein. In certain embodiments, $R^5$ is —OC(=N$R^1$a)N$R^{1b}R^{1c}$, where $R^{1a}$, $R^{1b}$, and $R^{1c}$ are each as defined herein. In certain embodiments, $R^5$ is —OS(O)$R^{1a}$, where $R^{1a}$ is as defined herein. In certain embodiments, $R^5$ is —OS(O)$_2R^{1a}$, where $R^{1a}$ is as defined herein. In certain embodiments, $R^5$ is —OS(O)N$R^{1b}R^{1c}$, where $R^{1b}$ and $R^{1c}$ are each as defined herein. In certain embodiments, $R^5$ is —OS(O)$_2$N$R^{1b}R^{1c}$, where $R^{1b}$ and $R^{1c}$ are each as defined herein. In certain embodiments, $R^5$ is —N$R^{1b}$, $R^{1c}$, where $R^{1b}$ and $R^{1c}$ are each as defined herein. In certain embodiments, $R^5$ is —N$R^{1a}$C(O)$R^{1d}$, where $R^{1a}$ and $R^{1d}$ are each as defined herein. In certain embodiments, $R^5$ is —NHC(O)—$C_{1-6}$ alkyl, optionally substituted with one or more substituents Q. In certain embodiments, $R^5$ is —NHC(O)-methyl, optionally substituted with one or more substituents Q. In certain embodiments, $R^5$ is acetamido. In certain embodiments, $R^5$ is —$NR^{1a}C(O)OR^d$, where $R^{1a}$ and $R^{1d}$ are each as defined herein. In certain embodiments, $R^5$ is —$NR^{1a}C(O)NR^{1b}R^{1c}$, where $R^{1a}$, $R^{1b}$, and $R^{1c}$ are each as defined herein. In certain embodiments, $R^5$ is —$NR^{1a}C(=NR^{1d})NR^{1b}R^{1c}$, where $R^{1a}$, $R^{1b}$, $R^{1c}$, and $R^{1d}$ are each as defined herein. In certain embodiments, $R^5$ is —$NR^{1a}S(O)R^{1d}$, where $R^{1a}$ and $R^{1d}$ are each as defined herein. In certain embodiments, $R^5$ is —$NR^{1a}S(O)_2R^{1d}$, where $R^{1a}$ and $R^{1d}$ are each defined herein. In certain embodiments, $R^5$ is —$NR^{1a}S(O)NR^{1b}R^{1c}$, where $R^{1a}$, $R^{1b}$, and $R^{1c}$ are each as defined herein. In certain embodiments, $R^5$ is —$NR^{1a}S(O)_2NR^{1b}R^{1c}$, where $R^{1a}$, $R^{1b}$, and $R^{1c}$ are each as defined herein. In certain embodiments, $R^5$ is —$SR^{1a}$, where $R^{1a}$ is as defined herein. In certain embodiments, $R^5$ is —$S(O)R^{1a}$, where $R^{1a}$ is as defined herein. In certain embodiments, $R^5$ is —$S(O)_2R^{1a}$, where $R^{1a}$ is as defined herein. In certain embodiments, $R^5$ is —$S(O)NR^{1b}R^{1c}$, where $R^{1b}$ and $R^{1c}$ are each as defined herein. In certain embodiments, $R^5$ is —$S(O)_2NR^{1b}R^{1c}$, where $R^{1b}$ and $R^{1c}$ are each as defined herein. In certain embodiments, two $R^5$ are linked together to form =O.

In certain embodiments, $R^6$ is hydrogen. In certain embodiments, $R^6$ is cyano. In certain embodiments, $R^6$ is halo. In certain embodiments, $R^6$ is fluoro, chloro, bromo, or iodo. In certain embodiments, $R^6$ is nitro. In certain embodiments, $R^6$ is $C_{1-6}$ alkyl, optionally substituted with one or more substituents Q. In certain embodiments, $R^6$ is $C_{2-6}$ alkenyl, optionally substituted with one or more substituents Q. In certain embodiments, $R^6$ is $C_{2-6}$ alkynyl, optionally substituted with one or more substituents Q. In certain embodiments, $R^6$ is $C_{3-7}$ cycloalkyl, optionally substituted with one or more substituents Q. In certain embodiments, $R^6$ is $C_{6-14}$ aryl, optionally substituted with one or more substituents Q. In certain embodiments, $R^6$ is $C_{7-15}$ aralkyl, optionally substituted with one or more substituents Q. In certain embodiments, $R^6$ is heteroaryl, optionally substituted with one or more substituents Q. In certain embodiments, $R^6$ is heterocyclyl, optionally substituted with one or more substituents Q.

In certain embodiments, $R^6$ is —$C(O)R^{1a}$, where $R^{1a}$ is as defined herein. In certain embodiments, $R^6$ is —$C(O)OR^{1a}$, where $R^{1a}$ is as defined herein. In certain embodiments, $R^6$ is —$C(O)NR^{1b}R^{1c}$, where $R^{1b}$ and $R^{1c}$ are each as defined herein. In certain embodiments, $R^6$ is —$C(NR^{1a})NR^{1b}R^{1c}$, where $R^{1a}$, $R^{1b}$, and $R^{1c}$ are each as defined herein. In certain embodiments, $R^6$ is —$OR^{1a}$, where $R^{1a}$ is as defined herein. In certain embodiments, $R^6$ is —O—$C_{1-6}$ alkyl, optionally substituted with one or more substituents Q. In certain embodiments, $R^6$ is —O-ethyl, optionally substituted with one or more substituents Q. In certain embodiments, $R^6$ is 2-methoxy-ethoxy. In certain embodiments, $R^6$ is —O—heterocyclyl, optionally substituted with one or more substituents Q. In certain embodiments, $R^6$ is —O-oxetanyl or —O-piperidyl, each optionally substituted with one or more substituents Q. In certain embodiments, $R^6$ is oxetan-3-yloxy, optionally substituted with one or more substituents Q. In certain embodiments, $R^6$ is piperid-4-yloxy, optionally substituted with one or more substituents Q. In certain embodiments, $R^6$ is 1-ethyl-piperid-4-yloxy. In certain embodiments, $R^6$ is —$OC(O)R^{1a}$, where $R^{1a}$ is as defined herein. In certain embodiments, $R^6$ is —$OC(O)OR^{1a}$, where $R^{1a}$ is as defined herein. In certain embodiments, $R^6$ is —$OC(O)NR^{1b}R^{1c}$, where $R^{1b}$ and $R^{1c}$ are each as defined herein. In certain embodiments, $R^6$ is —$OC(=NR^a)NR^{1b}R^{1c}$, where $R^{1a}$, $R^{1b}$, and $R^{1c}$ are each as defined herein. In certain embodiments, $R^6$ is —$OS(O)R^{1a}$, where $R^{1a}$ is as defined herein. In certain embodiments, $R^6$ is —$OS(O)_2R^{1a}$, where $R^{1a}$ is as defined herein. In certain embodiments, $R^6$ is —$OS(O)NR^{1b}R^{1c}$ where $R^{1b}$ and $R^{1c}$ are each as defined herein. In certain embodiments, $R^6$ is —$OS(O)_2NR^{1b}R^{1c}$, where $R^{1b}$ and $R^{1c}$ are each as defined herein. In certain embodiments, $R^6$ is —$NR^{1b}R^{1c}$, where $R^{1b}$ and $R^{1c}$ are each as defined herein. In certain embodiments, $R^6$ is —$NR^{1a}C(O)R^{1d}$, where $R^{1a}$ and $R^{1d}$ are each as defined herein. In certain embodiments, $R^6$ is —$NR^{1a}C(O)OR^{1d}$, where $R^{1a}$ and $R^{1d}$ are each as defined herein. In certain embodiments, $R^6$ is —$NR^{1a}C(O)NR^{1b}R^{1c}$, where $R^{1a}$, $R^{1b}$, and $R^{1c}$ are each as defined herein. In certain embodiments, $R^6$ is —$NR^{1a}C(=NR^{1d})NR^{1b}R^{1c}$, where $R^{1a}$, $R^{1b}$, $R^{1c}$, and $R^{1d}$ are each as defined herein. In certain embodiments, $R^6$ is —$NR^{1a}S(O)R^{1d}$, where $R^{1a}$ and $R^{1d}$ are each as defined herein. In certain embodiments, $R^6$ is —$NR^{1a}S(O)_2R^{1d}$, where $R^{1a}$ and $R^{1d}$ are each defined herein. In certain embodiments, $R^6$ is —$NR^{1a}S(O)NR^{1b}R^{1c}$, where $R^{1a}$, $R^{1b}$, and $R^{1c}$ are each as defined herein. In certain embodiments, $R^6$ is —$NR^{1a}S(O)_2NR^{1b}R^{1c}$, where $R^{1a}$, $R^{1b}$, and $R^{1c}$ are each as defined herein. In certain embodiments, $R^6$ is —$SR^{1a}$, where $R^{1a}$ is as defined herein. In certain embodiments, $R^6$ is —$S(O)R^{1a}$, where $R^{1a}$ is as defined herein. In certain embodiments, $R^6$ is —$S(O)_2R^{1a}$, where $R^{1a}$ is as defined herein. In certain embodiments, $R^6$ is —$S(O)NR^{1b}R^{1c}$, where $R^{1b}$ and $R^{1c}$ are each as defined herein. In certain embodiments, $R^6$ is —$S(O)_2NR^{1b}R^{1c}$, where $R^{1b}$ and $R^{1c}$ are each as defined herein. In certain embodiments, two $R^6$ are linked together to form =O.

In certain embodiments, $R^7$ is hydrogen. In certain embodiments, $R^7$ is cyano. In certain embodiments, $R^7$ is halo. In certain embodiments, $R^7$ is fluoro, chloro, bromo, or iodo. In certain embodiments, $R^7$ is chloro. In certain embodiments, $R^7$ is bromo. In certain embodiments, $R^7$ is nitro. In certain embodiments, $R^7$ is $C_{1-6}$ alkyl, optionally substituted with one or more substituents Q. In certain embodiments, $R^7$ is $C_{2-6}$ alkenyl, optionally substituted with one or more substituents Q. In certain embodiments, $R^7$ is $C_{2-6}$ alkynyl, optionally substituted with one or more substituents Q. In certain embodiments, $R^7$ is $C_{3-7}$ cycloalkyl, optionally substituted with one or more substituents Q. In certain embodiments, $R^7$ is $C_{6-14}$ aryl, optionally substituted with one or more substituents Q. In certain embodiments, $R^7$ is $C_{7-15}$ aralkyl, optionally substituted with one or more substituents Q. In certain embodiments, $R^7$ is heteroaryl, optionally substituted with one or more substituents Q. In certain embodiments, $R^7$ is heterocyclyl, optionally substituted with one or more substituents Q.

In certain embodiments, $R^7$ is —$C(O)R^{1a}$, where $R^{1a}$ is as defined herein. In certain embodiments, $R^7$ is —$C(O)OR^{1a}$, where $R^{1a}$ is as defined herein. In certain embodiments, $R^7$ is —$C(O)NR^{1b}R^{1c}$, where $R^{1b}$ and $R^{1c}$ are each as defined herein. In certain embodiments, $R^7$ is —$C(NR^{1a})NR^{1b}R^{1c}$, where $R^{1a}$, $R^{1b}$, and $R^{1c}$ are each as defined herein. In certain embodiments, $R^7$ is —$OR^{1a}$, where $R^{1a}$ is as defined herein. In certain embodiments, $R^7$ is —O—$C_{1-6}$ alkyl, optionally substituted with one or more substituents Q. In certain embodiments, $R^7$ is —O-ethyl, optionally substituted with one or more substituents Q. In certain embodiments, $R^7$ is 2-methoxy-ethoxy. In certain embodiments, $R^7$ is —O—heterocyclyl, optionally substituted with one or more substituents Q. In certain embodiments, $R^7$ is —O-tetrahydro-2H-pyranyl or —O-piperidyl, each optionally substituted with one or more substituents Q. In certain embodiments, $R^7$ is tetrahydro-2H-pyran-4-yl)oxy, optionally substituted with one or more substituents Q. In certain embodiments, $R^7$ is piperid-4-yloxy, optionally substituted with one or more substituents Q. In certain embodiments, $R^7$ is 1-ethyl-piperid-4-yloxy, 1-acetyl-piperid-4-yloxy, or 1-acryloyl-piperid-4-yloxy. In certain embodiments, $R^7$ is —OC(O)$R^{1a}$, where $R^{1a}$ is as defined herein. In certain embodiments, $R^7$ is —OC(O)O$R^{1a}$, where $R^{1a}$ is as defined herein. In certain embodiments, $R^7$ is —OC(O)N$R^{1b}R^{1c}$, where $R^{1b}$ and $R^{1c}$ are each as defined herein. In certain embodiments, $R^7$ is —OC(=N$R^{1a}$)N$R^{1b}R^{1c}$, where $R^{1a}$, $R^{1b}$, and $R^{1c}$ are each as defined herein. In certain embodiments, $R^7$ is —OS(O)$R^{1a}$, where $R^{1a}$ is as defined herein. In certain embodiments, $R^7$ is —OS(O)$_2R^{1a}$, where $R^{1a}$ is as defined herein. In certain embodiments, $R^7$ is —OS(O)N$R^{1b}R^{1c}$, where $R^{1b}$ and $R^{1c}$ are each as defined herein. In certain embodiments, $R^7$ is —OS(O)$_2$N$R^{1b}R^{1c}$, where $R^{1b}$ and $R^{1c}$ are each as defined herein. In certain embodiments, $R^7$ is —N$R^{1b}R^{1c}$, where $R^{1b}$ and $R^{1c}$ are each as defined herein. In certain embodiments, $R^7$ is —N$R^{1a}$C(O)$R^{1d}$, where $R^{1a}$ and $R^{1d}$ are each as defined herein. In certain embodiments, $R^7$ is —N$R^a$C(O)O$R^{1d}$, where $R^{1a}$ and $R^{1d}$ are each as defined herein. In certain embodiments, $R^7$ is —N$R^{1a}$C(O)N$R^{1b}R^{1c}$, where $R^{1a}$, $R^{1b}$, and $R^{1c}$ are each as defined herein. In certain embodiments, $R^7$ is —N$R^{1a}$C(=N$R^{1d}$)N$R^{1b}R^{1c}$, where $R^{1a}$, $R^{1b}$, $R^{1c}$, and $R^{1d}$ are each as defined herein. In certain embodiments, $R^7$ is —N$R^{1a}$S(O)$R^{1d}$, where $R^{1a}$ and $R^{1d}$ are each as defined herein. In certain embodiments, $R^7$ is —N$R^{1a}$S(O)$_2R^{1d}$, where $R^{1a}$ and $R^{1d}$ are each defined herein. In certain embodiments, $R^7$ is —N$R^{1a}$S(O)N$R^{1b}R^{1c}$, where $R^{1a}$, $R^{1b}$, and $R^{1c}$ are each as defined herein. In certain embodiments, $R^7$ is —N$R^{1a}$S(O)$_2$N$R^{1b}R^{1c}$, where $R^{1a}$, $R^{1b}$, and $R^{1c}$ are each as defined herein. In certain embodiments, $R^7$ is —S$R^{1a}$, where $R^{1a}$ is as defined herein. In certain embodiments, $R^7$ is —S(O)$R^{1a}$, where $R^{1a}$ is as defined herein. In certain embodiments, $R^7$ is —S(O)$_2R^{1a}$, where $R^{1a}$ is as defined herein. In certain embodiments, $R^7$ is —S(O)N$R^{1b}R^{1c}$, where $R^{1b}$ and $R^{1c}$ are each as defined herein. In certain embodiments, $R^7$ is —S(O)$_2$N$R^{1b}R^{1c}$, where $R^{1b}$ and $R^{1c}$ are each as defined herein. In certain embodiments, two $R^7$ are linked together to form =O.

In certain embodiments, one of the pairs, $R^4$ and $R^5$, $R^5$ and $R^6$, and $R^6$ and $R^7$, are linked together to form $C_{3-7}$ cycloalkyl, $C_{6-14}$ aryl, heteroaryl, or heterocyclyl, each of which is optionally substituted with one or more substituents Q.

In certain embodiments, $R^4$ and $R^5$ are linked together to form $C_{3-7}$ cycloalkyl, $C_{6-14}$ aryl, heteroaryl, or heterocyclyl, each of which is optionally substituted with one or more substituents Q. In certain embodiments, $R^4$ and $R^5$ are linked together to form $C_{3-7}$ cycloalkyl, optionally substituted with one or more substituents Q. In certain embodiments, $R^4$ and $R^5$ are linked together to form $C_{6-14}$ aryl, optionally substituted with one or more substituents Q. In certain embodiments, $R^4$ and $R^5$ are linked together to form heteroaryl, optionally substituted with one or more substituents Q. In certain embodiments, $R^4$ and $R^5$ are linked together to form heterocyclyl, optionally substituted with one or more substituents Q.

In certain embodiments, $R^4$ and $R^5$ are linked together to form heterocyclyl selected from:

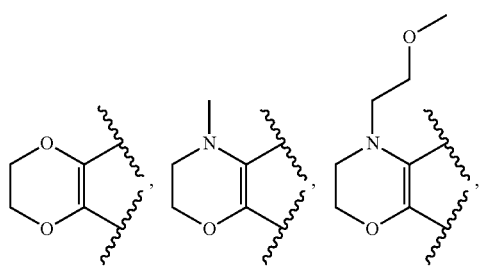

-continued

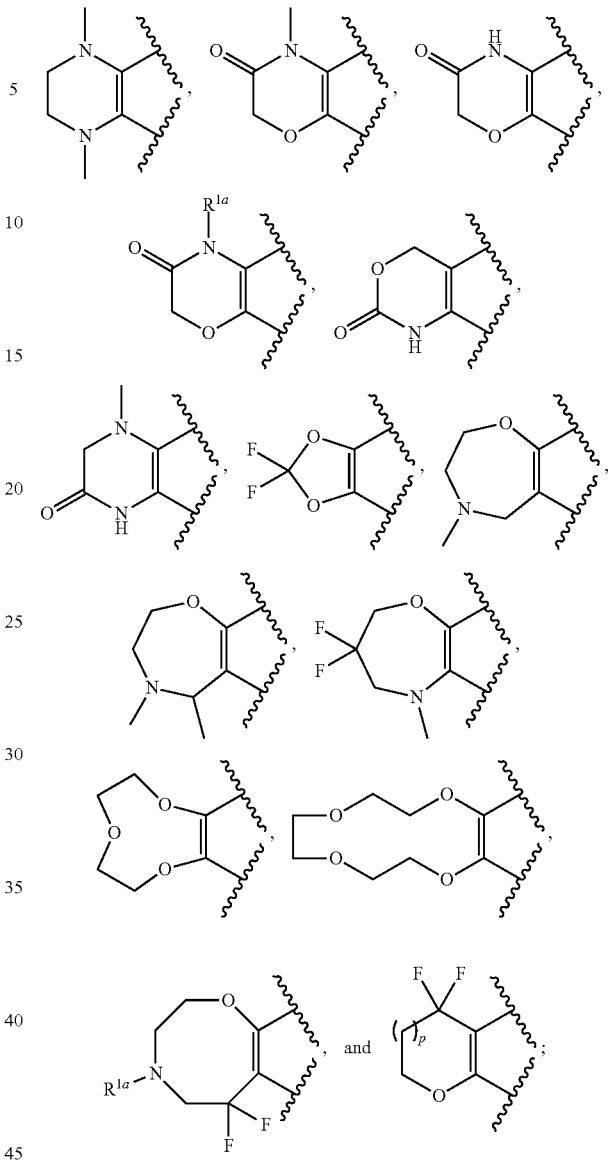

wherein p is an integer of 1, 2, 3, 4, 5, or 6; $R^{1a}$ is as defined herein; and when the heterocyclyl group is not symmetric, the heterocyclyl group can then be attached to the rest of the compound in either directions unless specified.

In certain embodiments, $R^5$ and $R^6$ are linked together to form $C_{3-7}$ cycloalkyl, $C_{6-14}$ aryl, heteroaryl, or heterocyclyl, each of which is optionally substituted with one or more substituents Q. In certain embodiments, $R^5$ and $R^6$ are linked together to form $C_{3-7}$ cycloalkyl, optionally substituted with one or more substituents Q. In certain embodiments, $R^5$ and $R^6$ are linked together to form $C_{6-14}$ aryl, optionally substituted with one or more substituents Q. In certain embodiments, $R^5$ and $R^6$ are linked together to form heteroaryl, optionally substituted with one or more substituents Q. In certain embodiments, $R^5$ and $R^6$ are linked together to form heterocyclyl, optionally substituted with one or more substituents Q.

In certain embodiments, $R^5$ and $R^6$ are linked together to form heterocyclyl selected from:

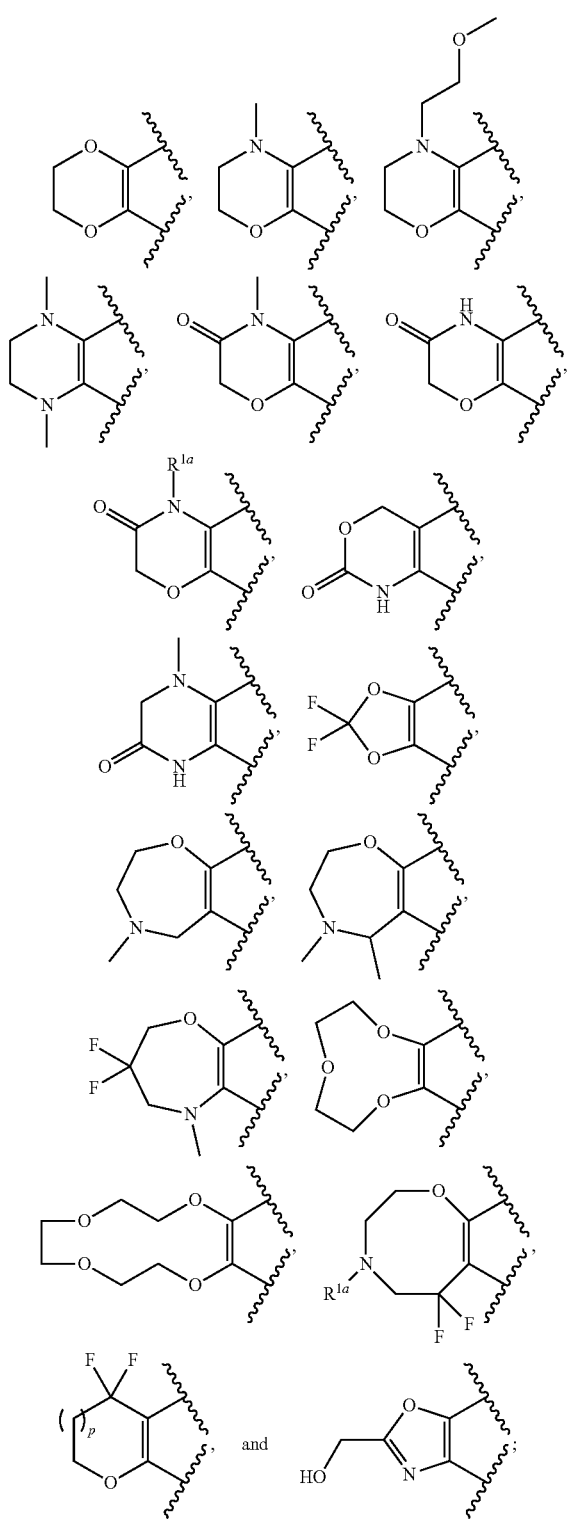

wherein p is an integer of 1, 2, 3, 4, 5, or 6; $R^{1a}$ is as defined herein; and when the heterocyclyl group is not symmetric, the heterocyclyl group can then be attached to the rest of the compound in either directions unless specified.

In certain embodiments, $R^6$ and $R^7$ are linked together to form $C_{3-7}$ cycloalkyl, $C_{6-14}$ aryl, heteroaryl, or heterocyclyl, each of which is optionally substituted with one or more substituents Q. In certain embodiments, $R^6$ and $R^7$ are linked together to form $C_{3-7}$ cycloalkyl, optionally substituted with one or more substituents Q. In certain embodiments, $R^6$ and $R^7$ are linked together to form $C_{6-14}$ aryl, optionally substituted with one or more substituents Q. In certain embodiments, $R^6$ and $R^7$ are linked together to form heteroaryl, optionally substituted with one or more substituents Q. In certain embodiments, $R^6$ and $R^7$ are linked together to form heterocyclyl, optionally substituted with one or more substituents Q.

In certain embodiments, $R^6$ and $R^7$ are linked together to form heteroaryl or heterocyclyl selected from:

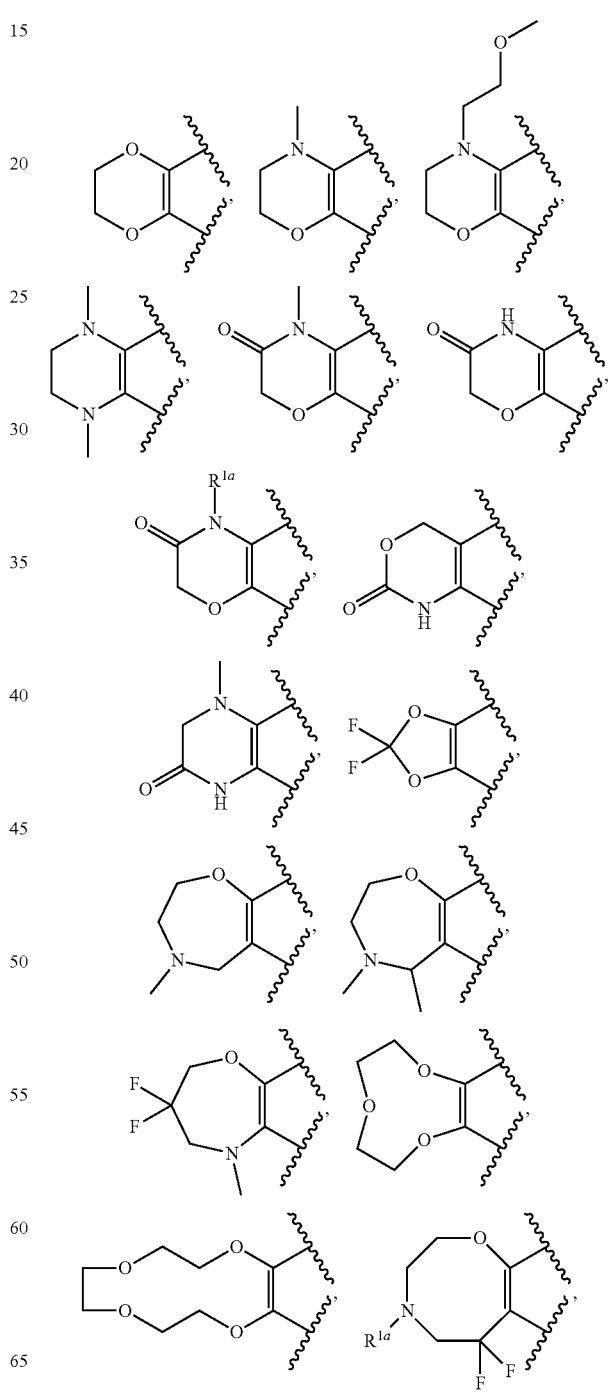

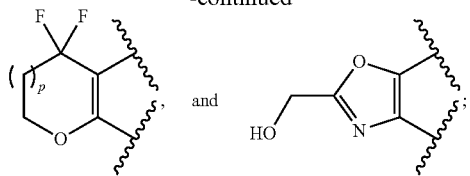

wherein p is an integer of 1, 2, 3, 4, 5, or 6; $R^{1a}$ is as defined herein; and when the heterocyclyl group is not symmetric, the heterocyclyl group can then be attached to the rest of the compound in either directions unless specified.

In certain embodiments, $R^{2A}$ is hydrogen. In certain embodiments, $R^{2A}$ is $C_{1-6}$ alkyl, optionally substituted with one or more substituents Q. In certain embodiments, $R^{2A}$ is methyl or ethyl, each optionally substituted with one or more substituents Q. In certain embodiments, $R^{2A}$ is $C_{2-6}$ alkenyl, optionally substituted with one or more substituents Q. In certain embodiments, $R^{2A}$ is $C_{2-6}$ alkynyl, optionally substituted with one or more substituents Q. In certain embodiments, $R^{2A}$ is $C_{3-7}$ cycloalkyl, optionally substituted with one or more substituents Q. In certain embodiments, $R^{2A}$ is $C_{6-14}$ aryl, optionally substituted with one or more substituents Q. In certain embodiments, $R^{2A}$ is $C_{7-15}$ aralkyl, optionally substituted with one or more substituents Q. In certain embodiments, $R^{2A}$ is heteroaryl, optionally substituted with one or more substituents Q. In certain embodiments, $R^{2A}$ is heterocyclyl, optionally substituted with one or more substituents Q.

In certain embodiments, $R^{2n}$ is $C_{1-6}$ alkyl, optionally substituted with one or more substituents Q. In certain embodiments, $R^{2n}$ is methyl or ethyl, each optionally substituted with one or more substituents Q. In certain embodiments, $R^{2n}$ is methyl, monofluoromethyl, difluoromethyl, or trifluoromethyl. In certain embodiments, $R^{2n}$ is —$OR^{1a}$, where $R^{1a}$ is as defined herein. In certain embodiments, $R^{2n}$ is —OH. In certain embodiments, $R^{2n}$ is —O—$C_{1-6}$ alkyl, optionally substituted with one or more substituents Q. In certain embodiments, $R^{2n}$ is methoxy.

In certain embodiments, $R^{3n}$ is $C_{1-6}$ alkyl, optionally substituted with one or more substituents Q. In certain embodiments, $R^{3n}$ is methyl or ethyl, each optionally substituted with one or more substituents Q. In certain embodiments, $R^{3n}$ is methyl, monofluoromethyl, difluoromethyl, or trifluoromethyl. In certain embodiments, $R^{3n}$ is —$OR^{1a}$, where $R^{1a}$ is as defined herein. In certain embodiments, $R^{3n}$ is —OH. In certain embodiments, $R^{3n}$ is —O—$C_{1-6}$ alkyl, optionally substituted with one or more substituents Q. In certain embodiments, $R^{3n}$ is methoxy.

In certain embodiments, $R^{5a}$ is $C_{1-6}$ alkyl, optionally substituted with one or more substituents Q. In certain embodiments, $R^{5a}$ is methyl or ethyl, each optionally substituted with one or more substituents Q. In certain embodiments, $R^{5a}$ is trifluoromethyl or 2-methoxyethyl. In certain embodiments, $R^{5a}$ is $C_{2-6}$ alkenyl, optionally substituted with one or more substituents Q. In certain embodiments, $R^{5a}$ is $C_{2-6}$ alkynyl, optionally substituted with one or more substituents Q. In certain embodiments, $R^{5a}$ is $C_{3-7}$ cycloalkyl, optionally substituted with one or more substituents Q. In certain embodiments, $R^{5a}$ is $C_{6-14}$ aryl, optionally substituted with one or more substituents Q. In certain embodiments, $R^{5a}$ is $C_{7-15}$ aralkyl, optionally substituted with one or more substituents Q. In certain embodiments, $R^{5a}$ is heteroaryl, optionally substituted with one or more substituents Q. In certain embodiments, $R^{5a}$ is heterocyclyl, optionally substituted with one or more substituents Q. In certain embodiments, $R^{5a}$ is oxetanyl, tetrahydro-2H-pyranyl, piperidyl, or piperazinyl, each optionally substituted with one or more substituents Q. In certain embodiments, $R^{5a}$ is oxetan-3-yl, tetrahydro-2H-pyran-4-yl, piperid-4-yl, or piperazine-1-yl, each optionally substituted with one or more substituents Q. In certain embodiments, $R^{5a}$ is 1-ethyl-piperid-4-yl, 1-acetyl-piperid-4-yl, or 4-acetyl-piperazine-1-yl.

In certain embodiments, $R^{6a}$ is $C_{1-6}$ alkyl, optionally substituted with one or more substituents Q. In certain embodiments, $R^{6a}$ is methyl or ethyl, each optionally substituted with one or more substituents Q. In certain embodiments, $R^{6a}$ is trifluoromethyl or 2-methoxyethyl. In certain embodiments, $R^{6a}$ is $C_{2-6}$ alkenyl, optionally substituted with one or more substituents Q. In certain embodiments, $R^{6a}$ is $C_{2-6}$ alkynyl, optionally substituted with one or more substituents Q. In certain embodiments, $R^{6a}$ is $C_{3-7}$ cycloalkyl, optionally substituted with one or more substituents Q. In certain embodiments, $R^{6a}$ is cyclopropanyl, optionally substituted with one or more substituents Q. In certain embodiments, $R^{6a}$ is $C_{6-14}$ aryl, optionally substituted with one or more substituents Q. In certain embodiments, $R^{6a}$ is $C_{7-15}$ aralkyl, optionally substituted with one or more substituents Q. In certain embodiments, $R^{6a}$ is heteroaryl, optionally substituted with one or more substituents Q. In certain embodiments, $R^{6a}$ is heterocyclyl, optionally substituted with one or more substituents Q. In certain embodiments, $R^{6a}$ is oxetanyl, tetrahydrofuranyl, 2-oxopyrrolidinyl, tetrahydro-2H-pyranyl, 1,1-dioxo-tetrahydro-2H-thiopyranyl, or piperidyl, each optionally substituted with one or more substituents Q. In certain embodiments, $R^{6a}$ is oxetan-3-yl, tetrahydrofuran-3-yl, 2-oxo-pyrrolidin-3-yl, tetrahydro-2H-pyran-4-yl, 1,1-dioxo-tetrahydro-2H-thiopyran-4-yl, or piperid-4-yl, each optionally substituted with one or more substituents Q. In certain embodiments, $R^{6a}$ is oxetan-3-yl, tetrahydrofuran-3-yl, 2-oxo-pyrrolidin-3-yl, tetrahydro-2H-pyran-4-yl, 1,1-dioxo-tetrahydro-2H-thiopyran-4-yl, or 1-ethyl-piperid-4-yl.

In certain embodiments, $R^{6a}$ is —$C(O)R^{1a}$, where $R^{1a}$ is as defined herein. In certain embodiments, $R^{6a}$ is —$C(O)OR^{1a}$, where $R^{1a}$ is as defined herein. In certain embodiments, $R^{6a}$ is —$C(O)NR^{1b}R^{1c}$, where $R^{1b}$ and $R^{1c}$ are each as defined herein. In certain embodiments, $R^{6a}$ is —$C(NR^{a})NR^{1b}R^{1c}$, where $R^{1a}$, $R^{1b}$, and $R^{1c}$ are each as defined herein. In certain embodiments, $R^{6a}$ is —$NR^{1b}R^{1c}$, where $R^{1b}$ and $R^{1c}$ are each as defined herein. In certain embodiments, $R^{6a}$ is —$NR^{1a}C(O)R^{1d}$, where $R^{1a}$ and $R^{1d}$ are each as defined herein. In certain embodiments, $R^{6a}$ is —$NR^{1a}C(O)OR^{1d}$, where $R^{1a}$ and $R^{1d}$ are each as defined herein. In certain embodiments, $R^{6a}$ is —$NR^{1a}C(O)NR^{1b}R^{1c}$, where $R^{1a}$, $R^{1b}$, and $R^{1c}$ are each as defined herein. In certain embodiments, $R^{6a}$ is —$NR^{1a}C(=NR^{1d})NR^{1b}R^{1c}$, where $R^{1a}$, $R^{1b}$, $R^{1c}$, and $R^{1d}$ are each as defined herein. In certain embodiments, $R^{6a}$ is —$NR^{1a}S(O)R^{1d}$, where $R^{1a}$ and $R^{1d}$ are each as defined herein. In certain embodiments, $R^{6a}$ is —$NR^{1a}S(O)_2R^{1d}$, where $R^{1a}$ and $R^{1d}$ are each defined herein. In certain embodiments, $R^{6a}$ is —$NR^{1a}S(O)NR^{1b}R^{1c}$, where $R^{1a}$, $R^{1b}$, and $R^{1c}$ are each as defined herein. In certain embodiments, $R^{6a}$ is —$NR^{a}S(O)_2NR^{1b}R^{1c}$, where $R^{1a}$, $R^{1b}$, and $R^{1c}$ are each as defined herein. In certain embodiments, $R^{6a}$ is —$S(O)R^{1a}$, where $R^{1a}$ is as defined herein. In certain embodiments, $R^{6a}$ is —$S(O)_2R^{1a}$, where $R^{1a}$ is as defined herein. In certain embodiments, $R^{6a}$ is —$S(O)NR^{1b}R^{1c}$, where $R^{1b}$ and $R^{1c}$ are each as defined herein. In certain embodiments, $R^{6a}$ is —$S(O)_2NR^{1b}R^{1c}$, where $R^{1b}$ and $R^{1c}$ are each as defined herein.

In certain embodiments, $R^{7a}$ is $C_{4-6}$ alkyl, optionally substituted with one or more substituents Q. In certain embodiments, $R^{7a}$ is $C_{2-6}$ alkenyl, optionally substituted with one or more substituents Q. In certain embodiments, $R^{7a}$ is $C_{2-6}$ alkynyl, optionally substituted with one or more substituents Q. In certain embodiments, $R^{7a}$ is $C_{3-7}$ cycloalkyl, optionally substituted with one or more substituents Q. In certain embodiments, $R^{7a}$ is $C_{6-14}$ aryl, optionally substituted with one or more substituents Q. In certain embodiments, $R^{7a}$ is $C_{7-15}$ aralkyl, optionally substituted with one or more substituents Q. In certain embodiments, $R^{7a}$ is heteroaryl, optionally substituted with one or more substituents Q. In certain embodiments, $R^{7a}$ is heterocyclyl, optionally substituted with one or more substituents Q. In certain embodiments, $R^{7a}$ is tetrahydro-2H-pyranyl, 1,1-dioxo-tetrahydro-2H-thiopyranyl, or piperidyl, each optionally substituted with one or more substituents Q. In certain embodiments, $R^{7a}$ is tetrahydro-2H-pyran-4-yl, 1,1-dioxo-tetrahydro-2H-thiopyran-4-yl, or piperid-4-yl, each optionally substituted with one or more substituents Q. In certain embodiments, $R^{7a}$ is tetrahydro-2H-pyran-4-yl, 1,1-dioxo-tetrahydro-2H-thiopyran-4-yl, piperid-4-yl, 1-methyl-piperid-4-yl, 1-ethyl-piperid-4-yl, 1-(2,2,2-trifluoromethyl)-piperid-4-yl, 1-isopropyl-piperid-4-yl, 1-cyclopropyl-piperid-4-yl, or 1-acetyl-piperid-4-yl.

In certain embodiments, $R^{7b}$ is $C_{4-6}$ alkyl, optionally substituted with one or more substituents Q. In certain embodiments, $R^{7b}$ is $C_{2-6}$ alkenyl, optionally substituted with one or more substituents Q. In certain embodiments, $R^{7b}$ is $C_{2-6}$ alkynyl, optionally substituted with one or more substituents Q. In certain embodiments, $R^{7b}$ is $C_{3-7}$ cycloalkyl, optionally substituted with one or more substituents Q. In certain embodiments, $R^{7b}$ is $C_{6-14}$ aryl, optionally substituted with one or more substituents Q. In certain embodiments, $R^{7b}$ is $C_{7-15}$ aralkyl, optionally substituted with one or more substituents Q. In certain embodiments, $R^{7b}$ is heteroaryl, optionally substituted with one or more substituents Q. In certain embodiments, $R^{7b}$ is heterocyclyl, optionally substituted with one or more substituents Q.

In certain embodiments, $R^{7c}$ is hydrogen. In certain embodiments, $R^{7c}$ is $C_{4-6}$ alkyl, optionally substituted with one or more substituents Q. In certain embodiments, $R^{7c}$ is $C_{2-6}$ alkenyl, optionally substituted with one or more substituents Q. In certain embodiments, $R^{7c}$ is $C_{2-6}$ alkynyl, optionally substituted with one or more substituents Q. In certain embodiments, $R^{7c}$ is $C_{3-7}$ cycloalkyl, optionally substituted with one or more substituents Q. In certain embodiments, $R^{7c}$ is $C_{6-14}$ aryl, optionally substituted with one or more substituents Q. In certain embodiments, $R^{7c}$ is $C_{7-15}$ aralkyl, optionally substituted with one or more substituents Q. In certain embodiments, $R^{7c}$ is heteroaryl, optionally substituted with one or more substituents Q. In certain embodiments, $R^{7c}$ is heterocyclyl, optionally substituted with one or more substituents Q.

In certain embodiments, $R^{7b}$ and $R^{7c}$ together with the N atom to which they are attached form heterocyclyl, optionally substituted with one or more substituents Q.

In certain embodiments, $L^1$ is a bond. In certain embodiments, $L^1$ is —O—. In certain embodiments, L is —S—. In certain embodiments, $L^1$ is —N($R^{1A}$)—, wherein $R^{1A}$ is as defined herein. In certain embodiments, $L^1$ is —N($R^{1A}$)—, wherein $R^{1A}$ is hydrogen or methyl. In certain embodiments, $L^1$ is —C($R^{1A}R^{1B}$)—, wherein $R^{1A}$ and $R^{1B}$ are each as defined herein. In certain embodiments, $L^1$ is —CH$_2$—.

In certain embodiments, $L^2$ is $C_{3-10}$ cycloalkylene, optionally substituted with one or more substituents Q. In certain embodiments, $L^2$ is $C_{6-14}$ arylene, optionally substituted with one or more substituents Q. In certain embodiments, $L^2$ is $C_{7-15}$ aralkylene, optionally substituted with one or more substituents Q. In certain embodiments, $L^2$ is heteroarylene, optionally substituted with one or more substituents Q. In certain embodiments, $L^2$ is heterocyclylene, optionally substituted with one or more substituents Q.

In certain embodiments, $L^2$ is:

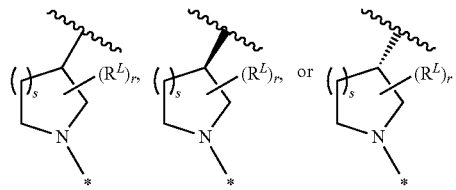

wherein s is an integer of 0, 1, 2, 3, 4, 5, 6, 7, 8, 9, or 10; and $R^L$ and r are each as defined herein.

In certain embodiments, $L^2$ is

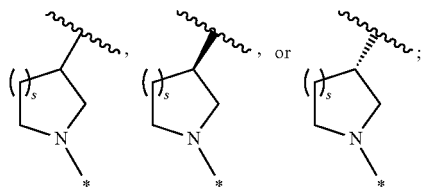

wherein s is as defined herein.

In certain embodiments, $L^2$ is

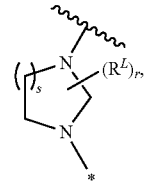

wherein $R^L$, r, and s are each as defined herein.

In certain embodiments, $L^2$ is

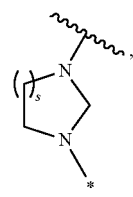

wherein s is as defined herein.

In certain embodiments, $L^2$ is

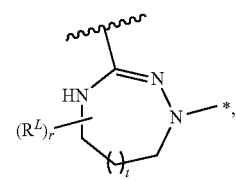

wherein t is an integer of 0, 1, 2, 3, 4, 5, or 6; and $R^L$ and r are each as defined herein.

In certain embodiments, $L^2$ is
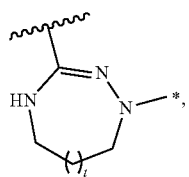
wherein t is as defined herein.
In certain embodiments, $L^2$ is
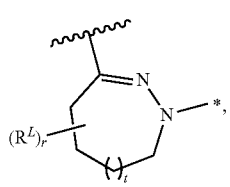
wherein $R^L$, r, and t are each as defined herein.
In certain embodiments, $L^2$ is
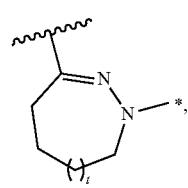
wherein t is as defined herein.
In certain embodiments, $L^1$-$L^2$ is:
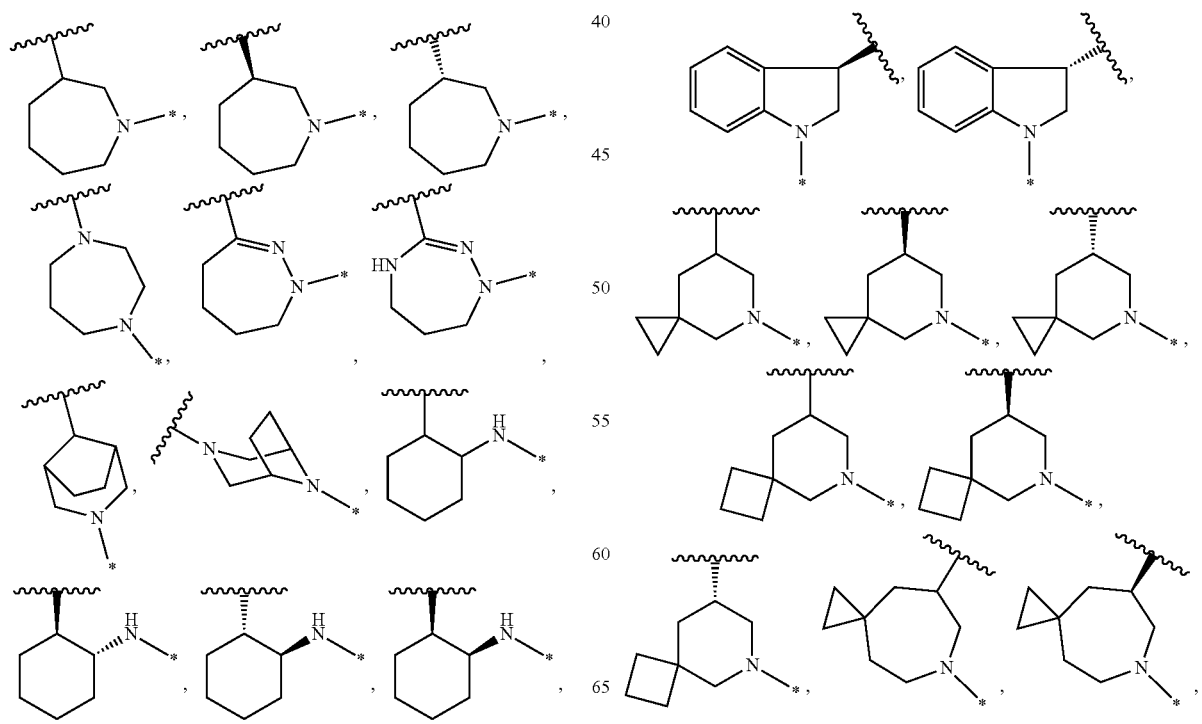

-continued

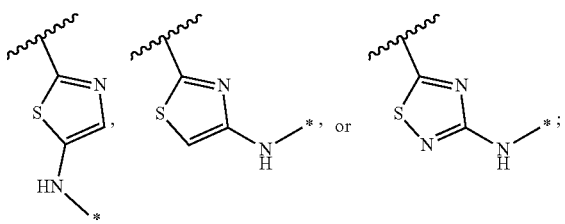

wherein the symbol

represents that the 6-membered ring contains one to three N atoms in the ring, and each sulfur is optionally oxidized as sulfoxide or sulfone.

In certain embodiments, $L^1$-$L^2$ is:

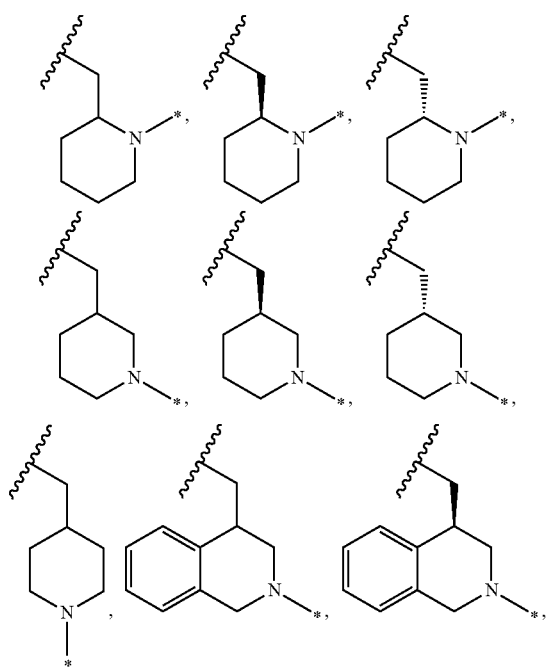

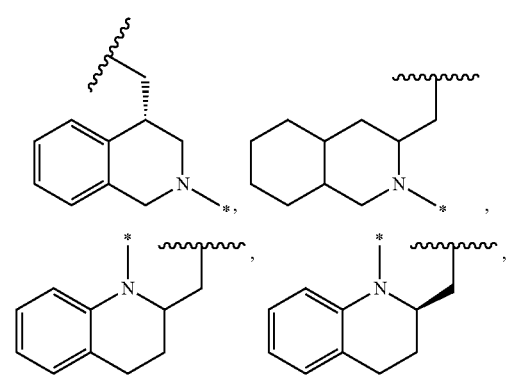

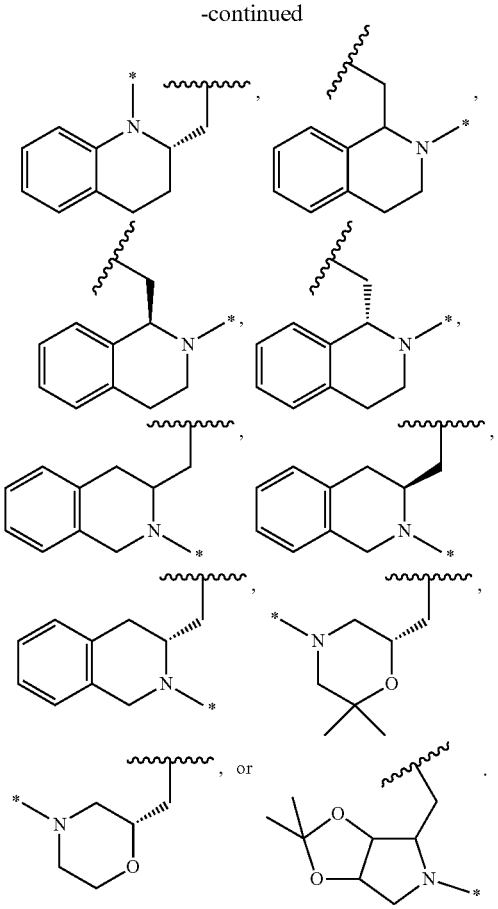

In certain embodiments, T is a bond. In certain embodiments, T is —O—. In certain embodiments, T is —S—. In certain embodiments, T is —N=. In certain embodiments, T is —N($R^4$)—, wherein $R^4$ is as defined herein. In certain embodiments, T is —C($R^4$)=, wherein $R^4$ is as defined herein. In certain embodiments, T is —C($R^4$)$_2$—, wherein $R^4$ is as defined herein.

In certain embodiments, U is a bond. In certain embodiments, U is —O—. In certain embodiments, U is —S—. In certain embodiments, U is —N=. In certain embodiments, U is —N($R^5$)—, wherein $R^5$ is as defined herein. In certain embodiments, U is —C($R^5$)=, wherein $R^5$ is as defined herein. In certain embodiments, U is —C($R^5$)$_2$—, wherein $R^5$ is as defined herein.

In certain embodiments, V is a bond. In certain embodiments, V is —O—. In certain embodiments, V is —S—. In certain embodiments, V is —N=. In certain embodiments, V is —N($R^6$)—, wherein $R^6$ is as defined herein. In certain embodiments, V is —C($R^6$)=, wherein $R^6$ is as defined herein. In certain embodiments, V is —C($R^6$)$_2$—, wherein $R^6$ is as defined herein.

In certain embodiments, W is a bond. In certain embodiments, W is —O—. In certain embodiments, W is —S—. In certain embodiments, W is —N=. In certain embodiments, W is —N($R^7$)—, wherein $R^7$ is as defined herein. In certain embodiments, W is —C($R^7$)=, wherein $R^7$ is as defined herein. In certain embodiments, W is —C($R^7$)$_2$—, wherein $R^7$ is as defined herein.

In certain embodiments, X is C. In certain embodiments, X is N.

In certain embodiments, Y is C. In certain embodiments, Y is N.

In certain embodiments, m is 0. In certain embodiments, m is 1. In certain embodiments, m is 2. In certain embodiments, m is 3. In certain embodiments, m is 4. In certain embodiments, m is 5. In certain embodiments, m is 6. In certain embodiments, m is 7. In certain embodiments, m is 8. In certain embodiments, m is 9. In certain embodiments, m is 10.

In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6.

In certain embodiments, p is 0. In certain embodiments, p is 1. In certain embodiments, p is 2. In certain embodiments, p is 3. In certain embodiments, p is 4. In certain embodiments, p is 5. In certain embodiments, p is 6.

In certain embodiments, q is 0. In certain embodiments, q is 1. In certain embodiments, q is 2. In certain embodiments, q is 3. In certain embodiments, q is 4. In certain embodiments, q is 5. In certain embodiments, q is 6.

In certain embodiments, r is 0. In certain embodiments, r is 1. In certain embodiments, r is 2. In certain embodiments, r is 3. In certain embodiments, r is 4. In certain embodiments, r is 5. In certain embodiments, r is 6.

In certain embodiments, u is 0. In certain embodiments, u is 1. In certain embodiments, u is 2. In certain embodiments, u is 3.

In certain embodiments, v is 0. In certain embodiments, v is 1. In certain embodiments, v is 2. In certain embodiments, v is 3.

In one embodiment, provided herein is a compound selected from the group consisting of:

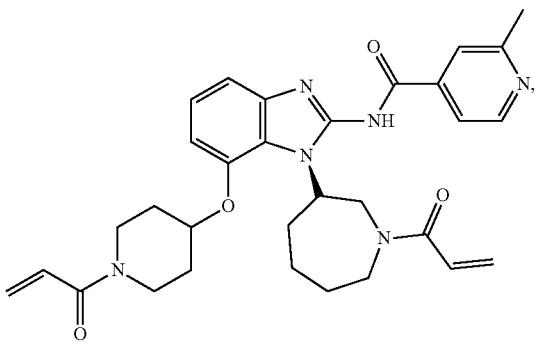

A1

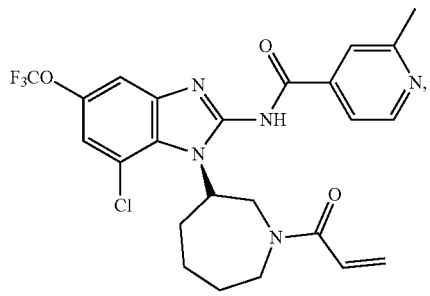

A2

-continued

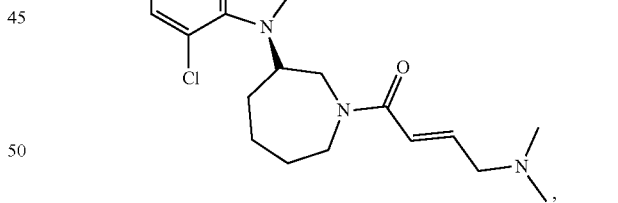

A3

A4

A5

A6

91
-continued
A7
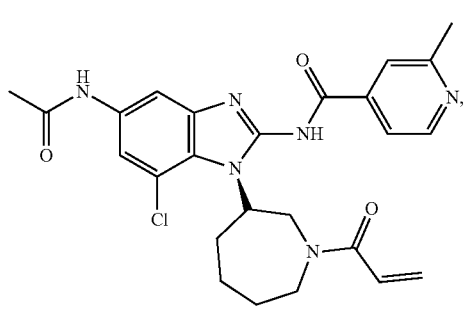
A8
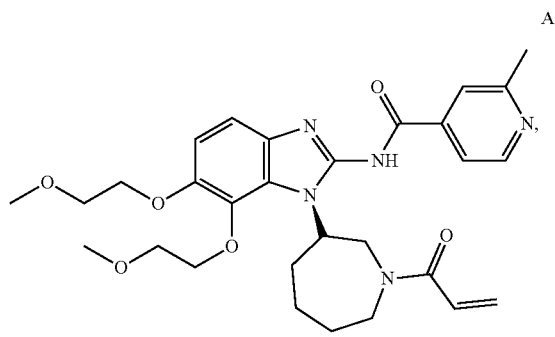
A9
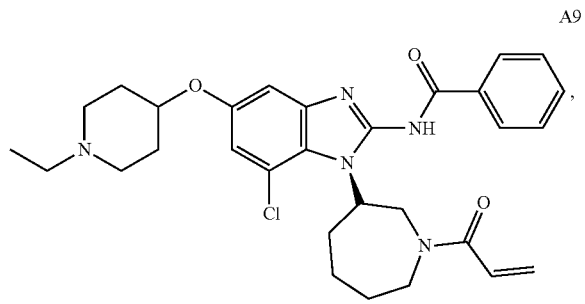
A10
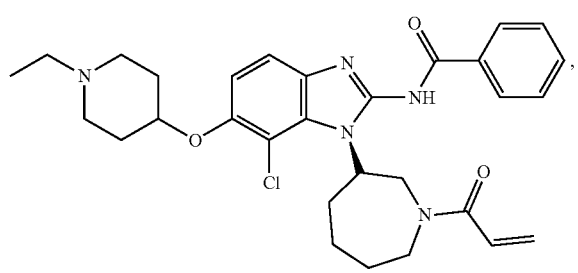
A11
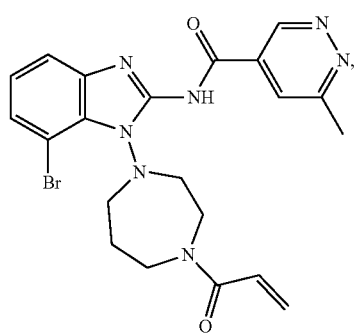
92
-continued
A12
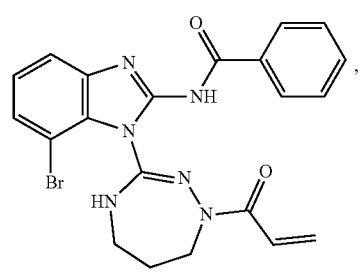
A13
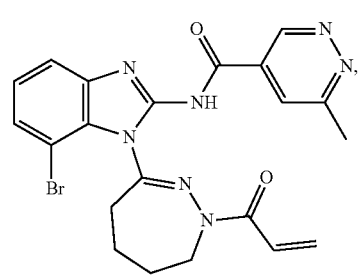
A14
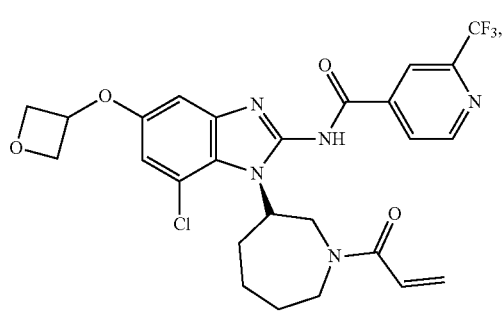
A15
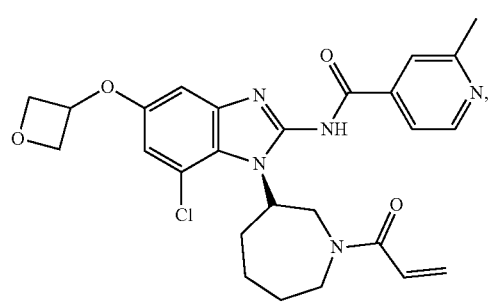
A16
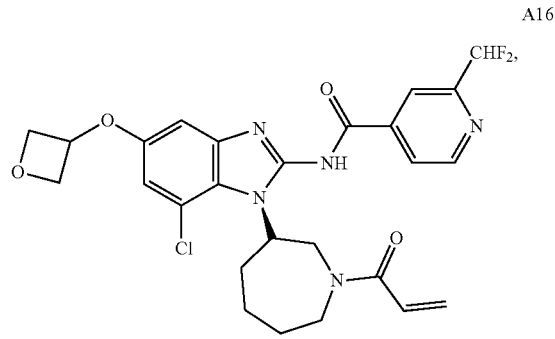

A17
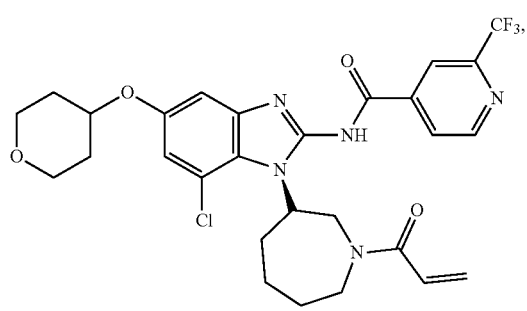
A18
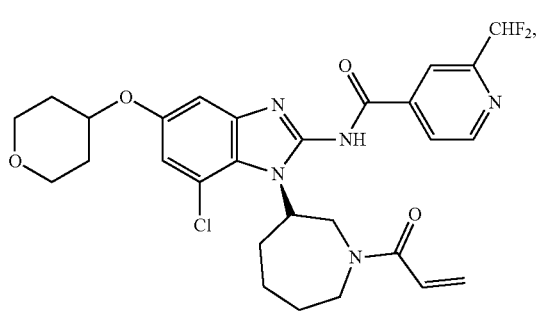
A19
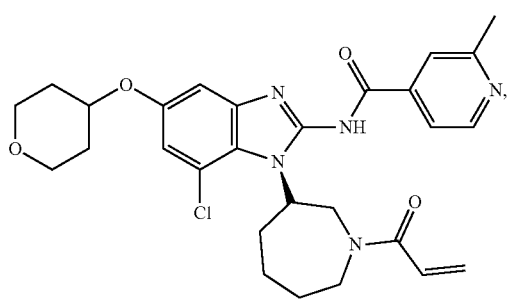
A20
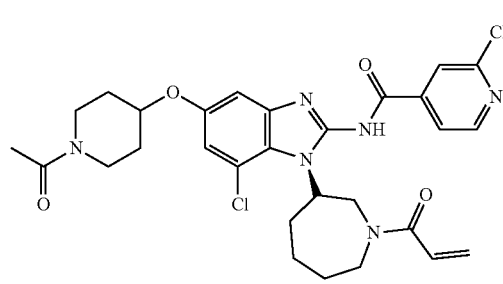
A21
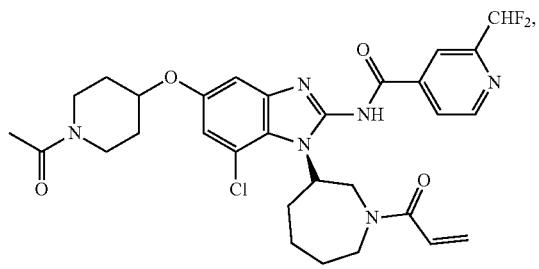
A22
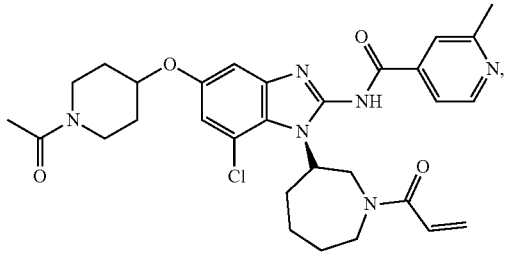
A23
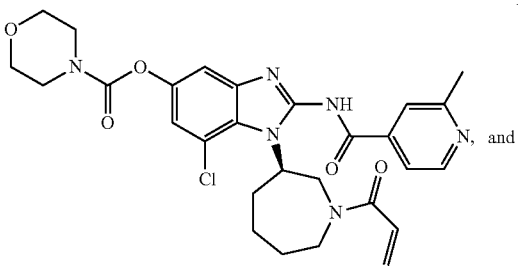
A24
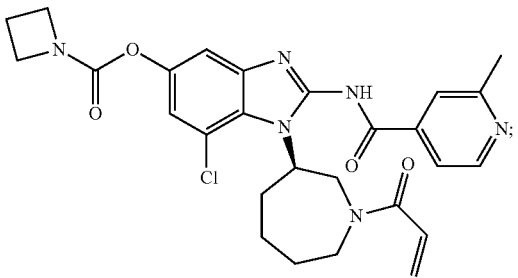
and isotopic variants thereof; and pharmaceutically acceptable salts, solvates, and prodrugs thereof.
In another embodiment, provided herein is a compound selected from the group consisting of:
C1
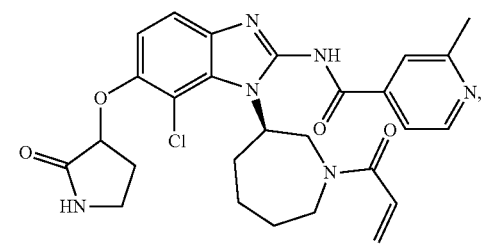
C2
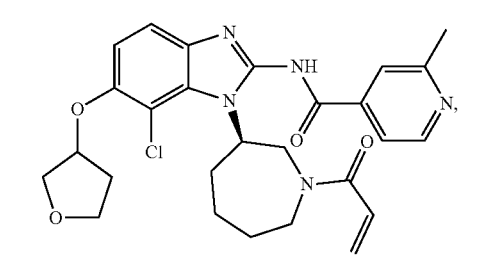

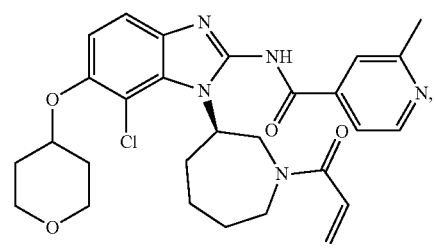
C3
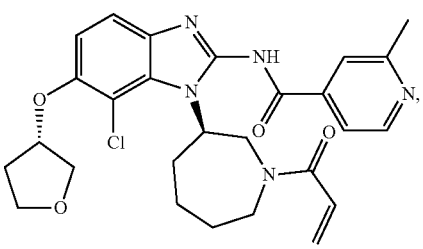
C9
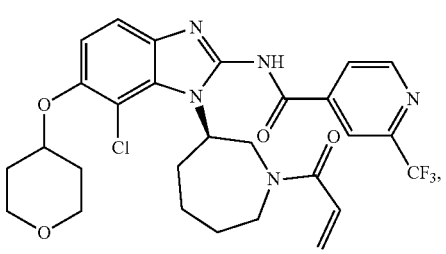
C4
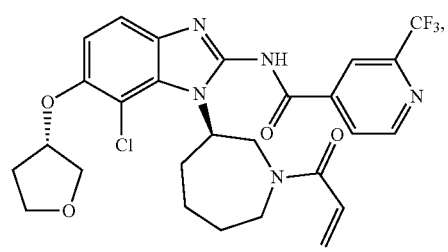
C10
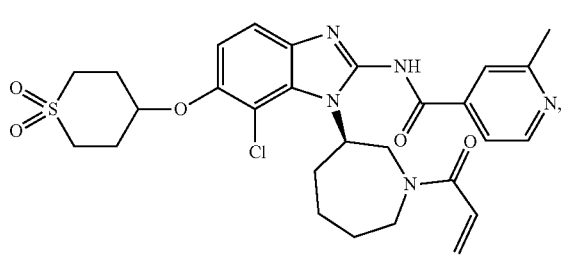
C5
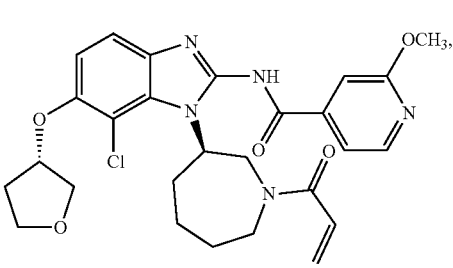
C11
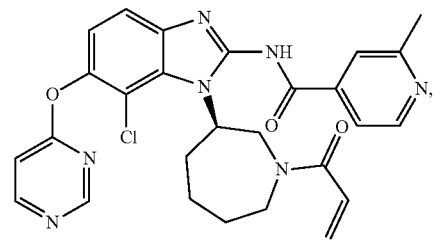
C6
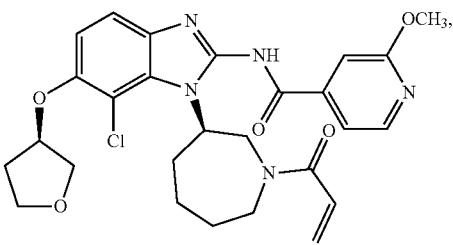
C12
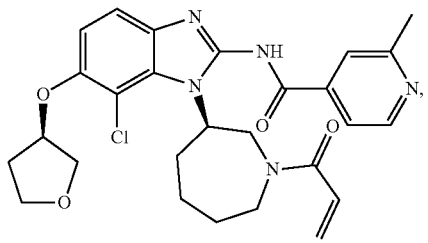
C7
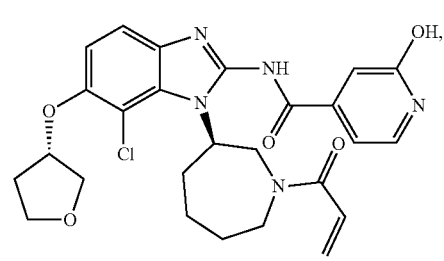
C13
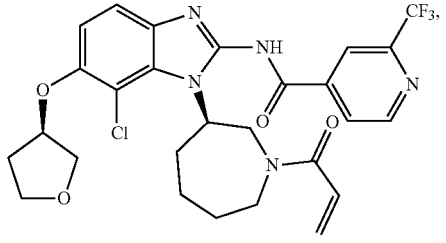
C8
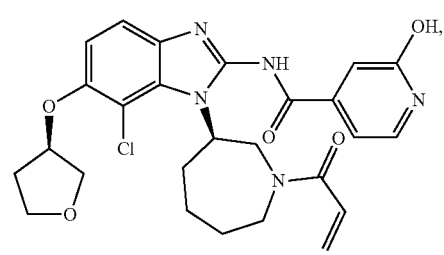
C14

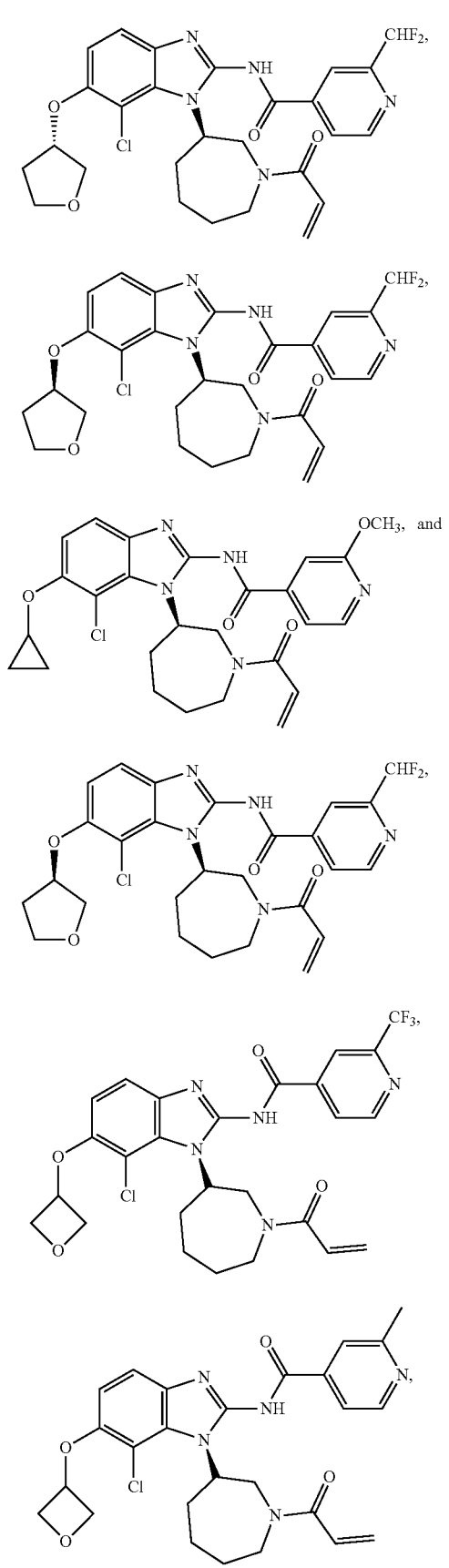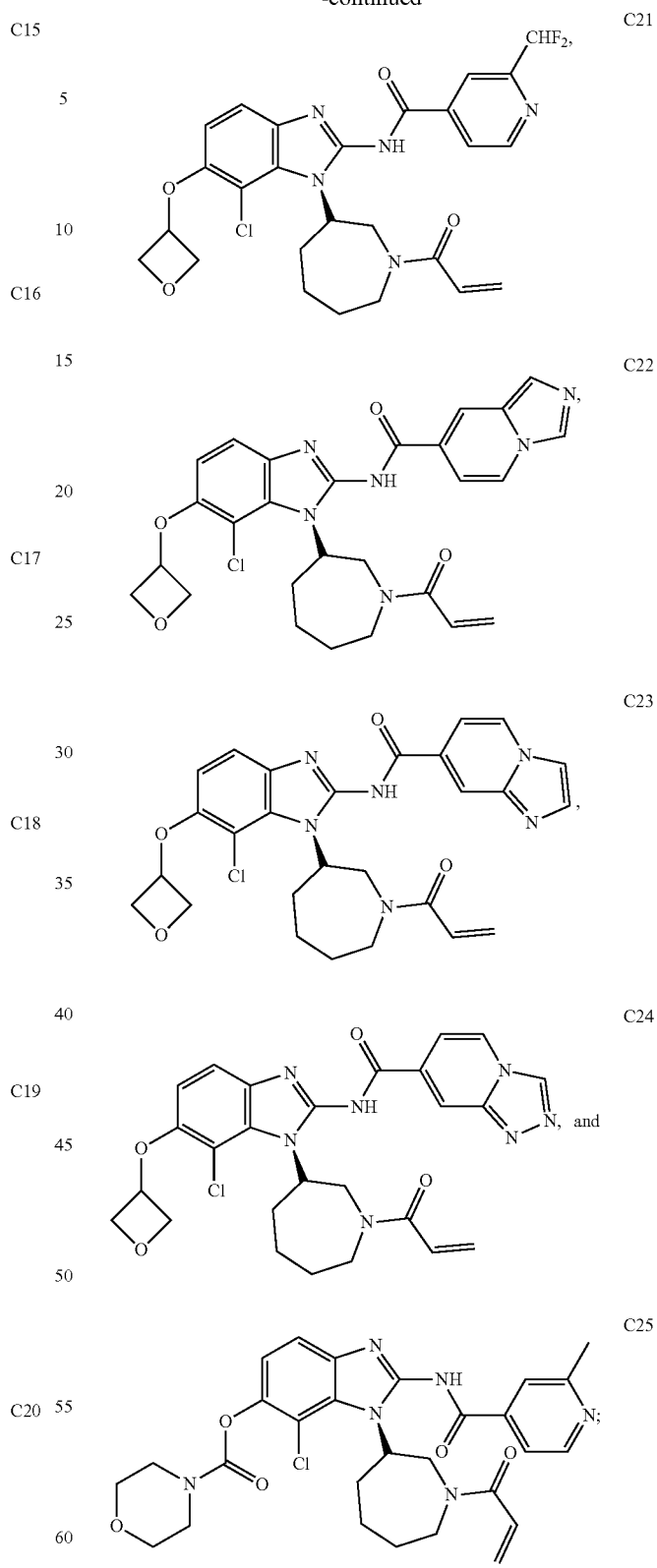
and isotopic variants thereof, and pharmaceutically acceptable salts, solvates, and prodrugs thereof.
In yet another embodiment, provided herein is a compound selected from the group consisting of:

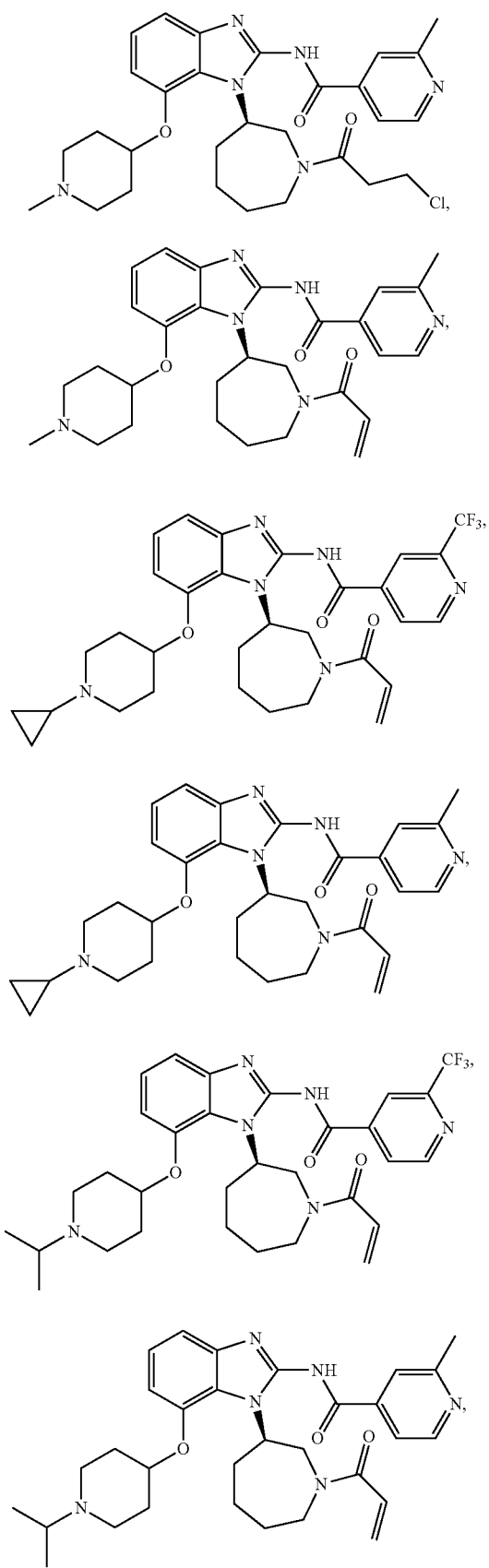
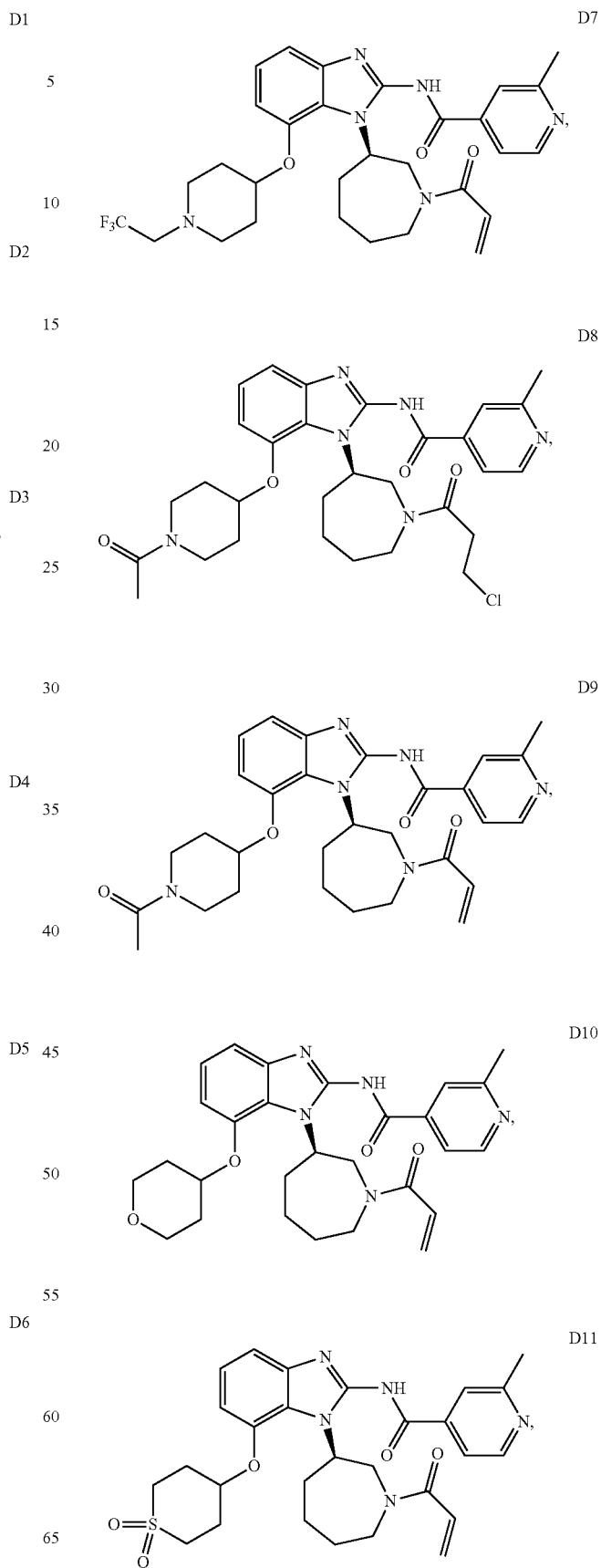

-continued
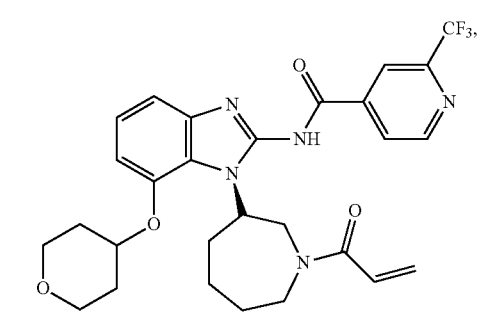
D12
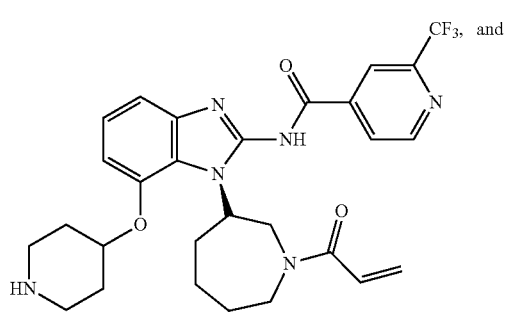
D13
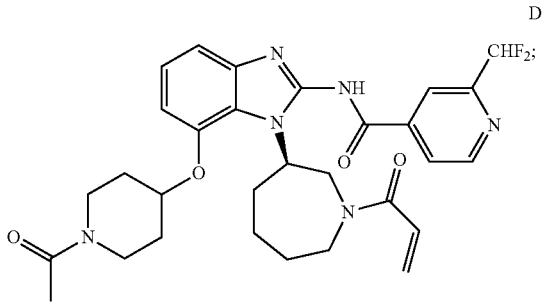
D14
and isotopic variants thereof; and pharmaceutically acceptable salts, solvates, and prodrugs thereof.
In one embodiment, provided herein is a compound selected from the group consisting of:
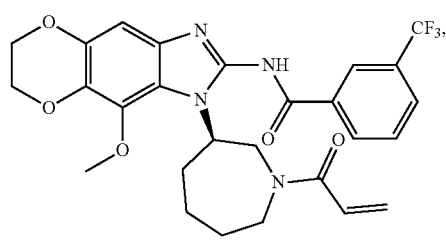
A1-A
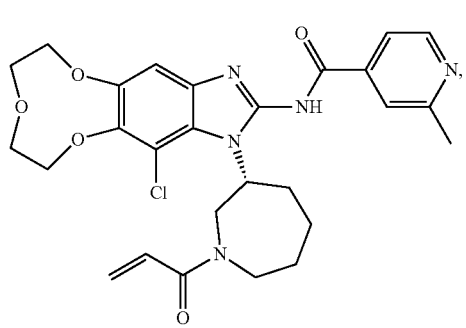
A2-A
-continued
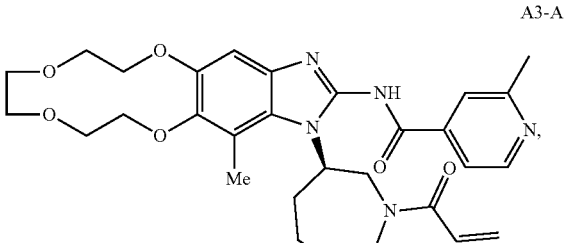
A3-A
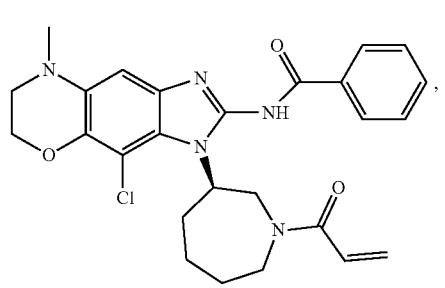
A4-A
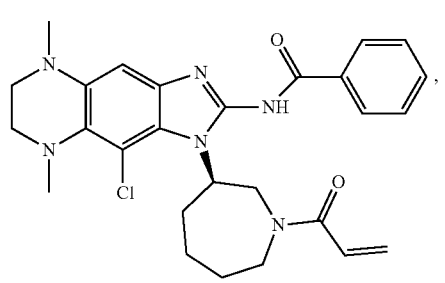
A5-A
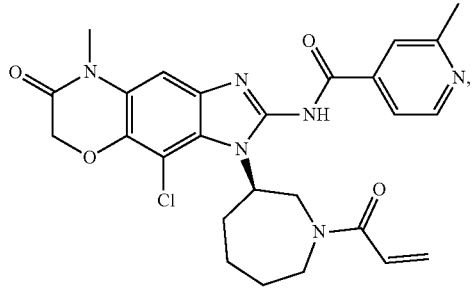
A6-A
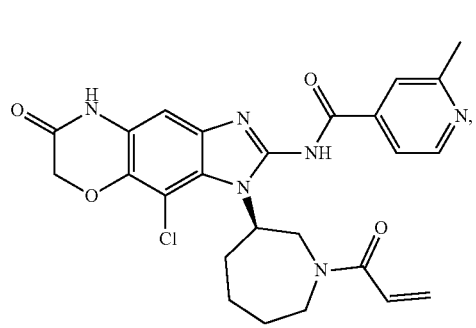
A7-A A8-A
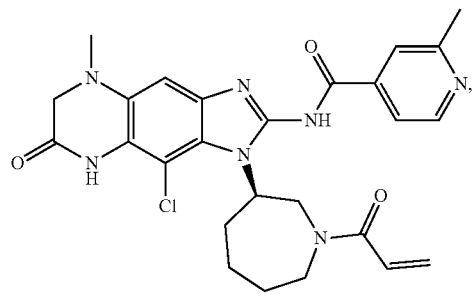
A9-A
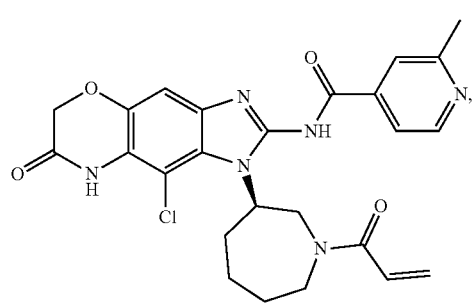
A10-A
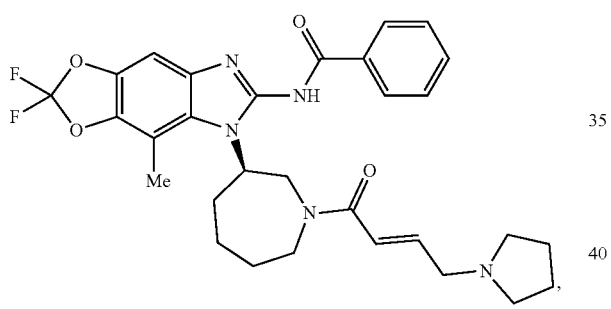
A11-A
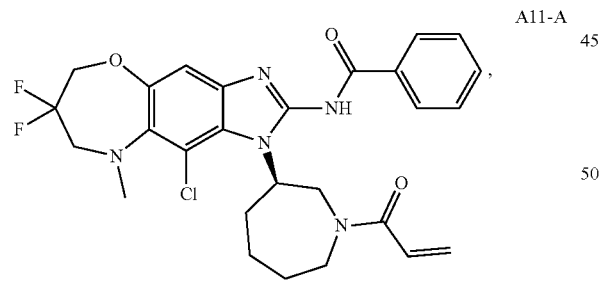
A12-A
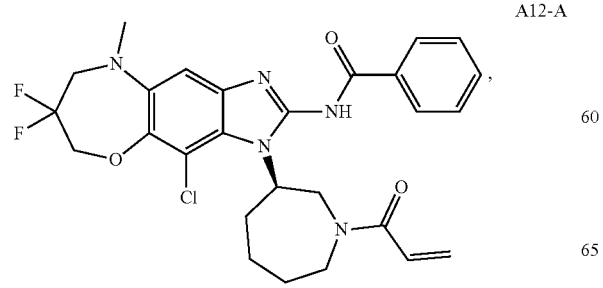
A13-A
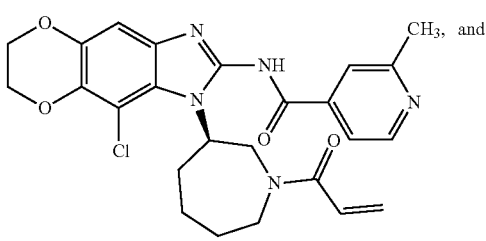
A14-A
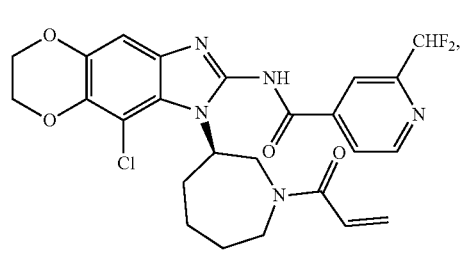
and isotopic variants thereof; and pharmaceutically acceptable salts, solvates, and prodrugs thereof.
In another embodiment, provided herein is a compound selected from the group consisting of:
B1-A
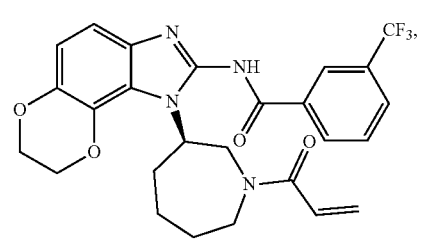
B2-A
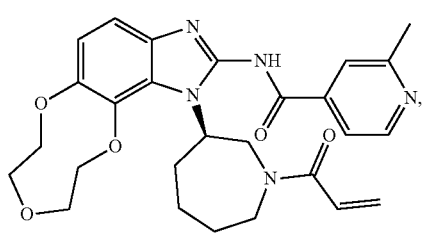
B3-A
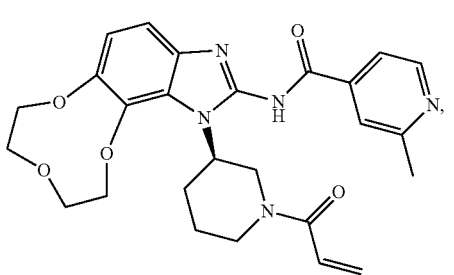

B4-A
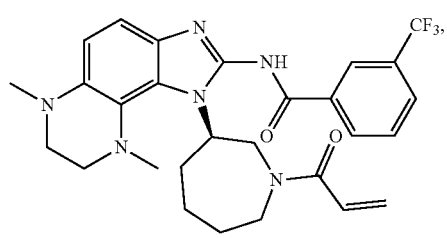
B5-A
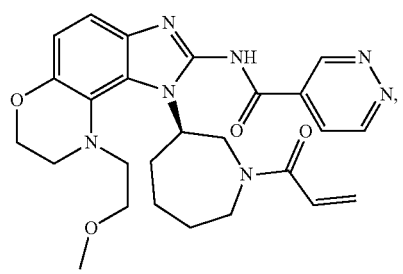
B6-A
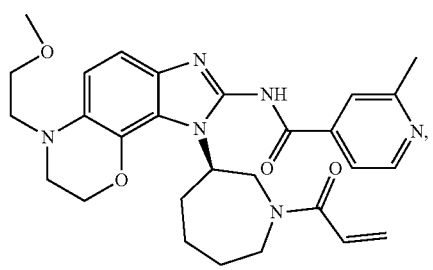
B7-A
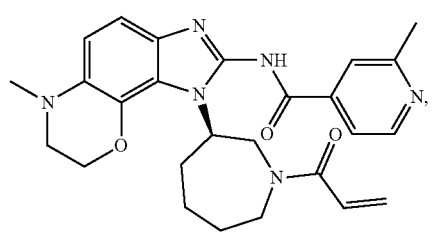
B8-A
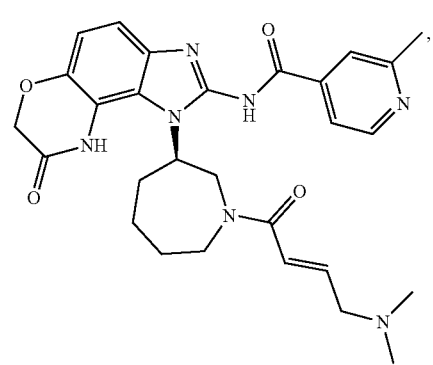
B9-A
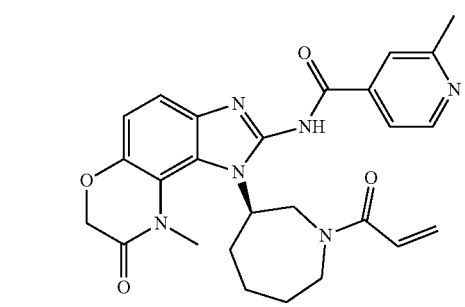
B10-A
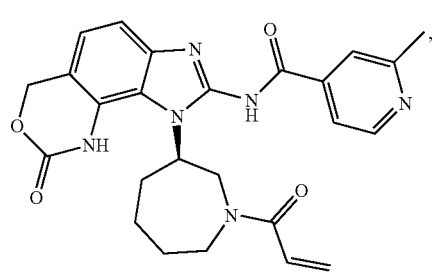
B11-A
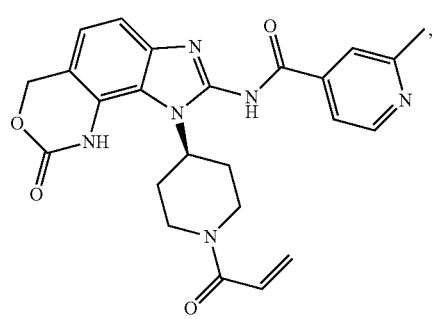
B12-A
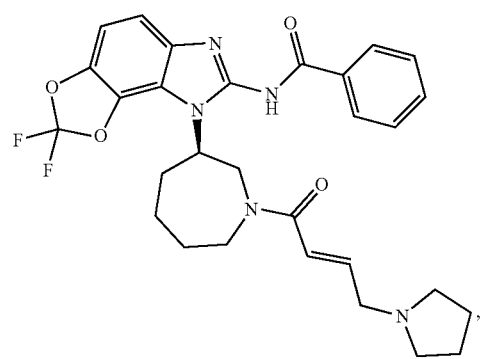
B13-A
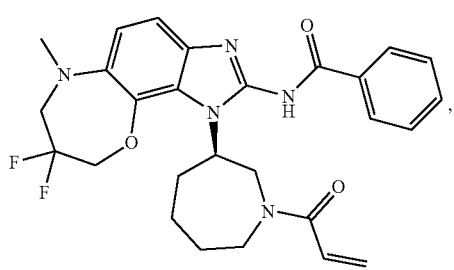

-continued
B14-A
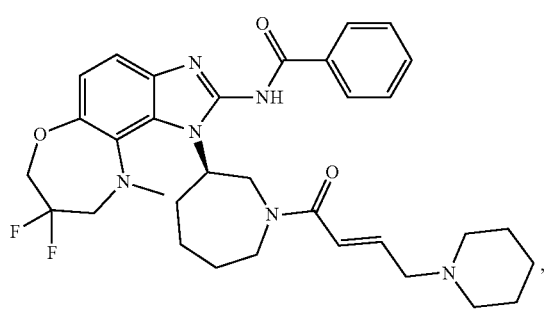
B15-A
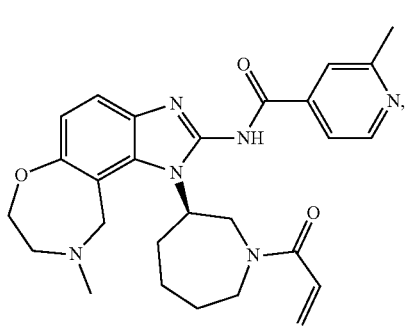
B16-A
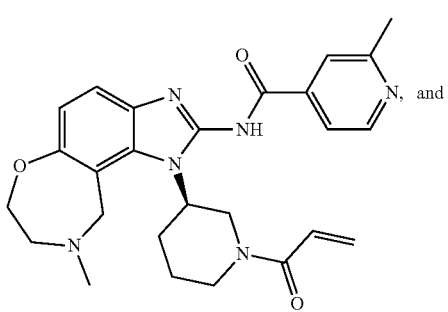, and
B17-A
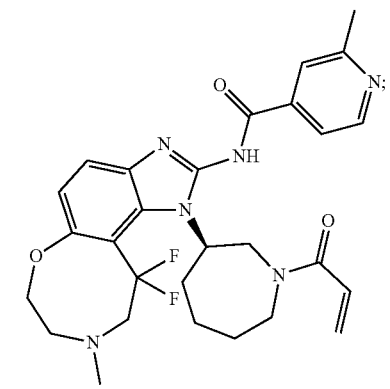
and isotopic variants thereof; and pharmaceutically acceptable salts, solvates, and prodrugs thereof.
In yet another embodiment, provided herein is a compound selected from the group consisting of:
C1-A
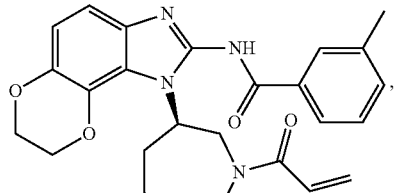
C2-A
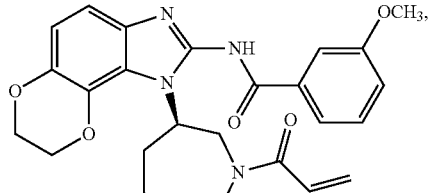
C3-A
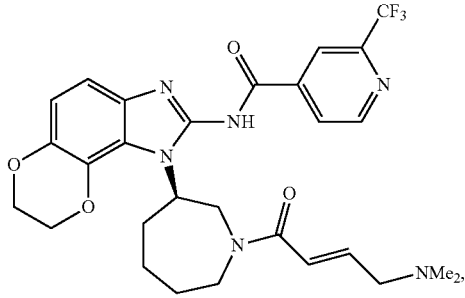
C4-A
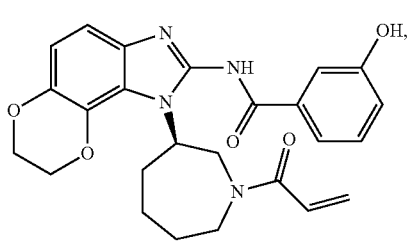
C5-A
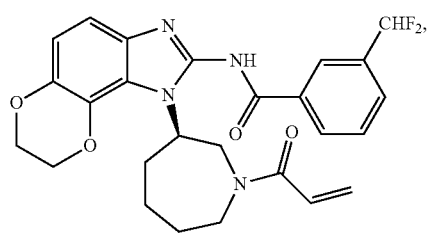
C6-A
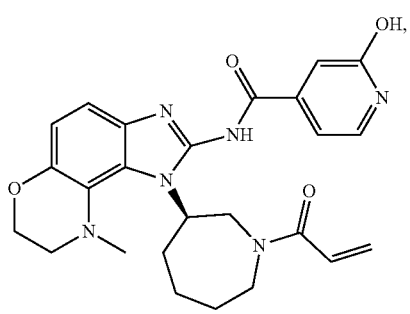

C7-A
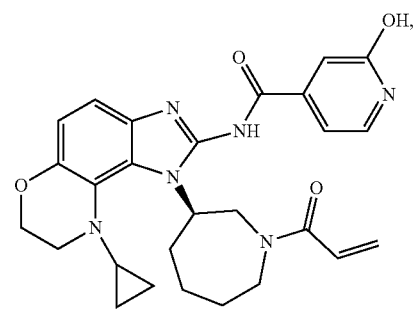
C8-A
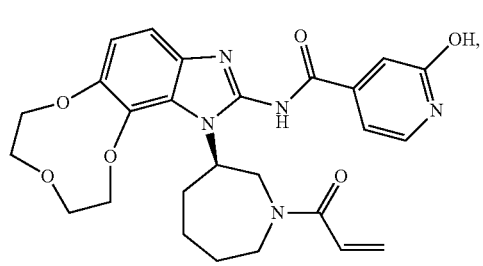
C9-A
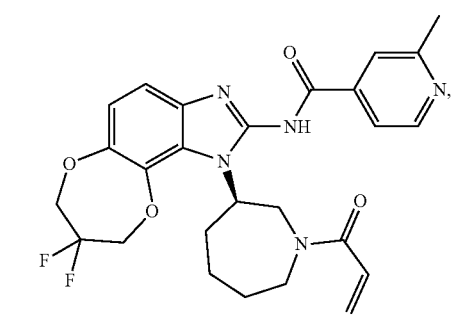
C10-A
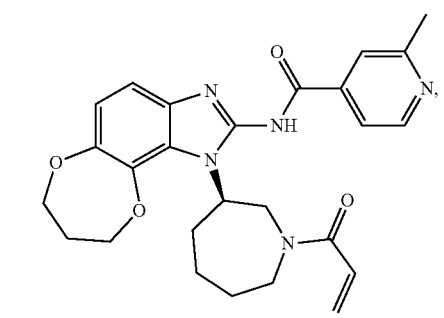
C11-A
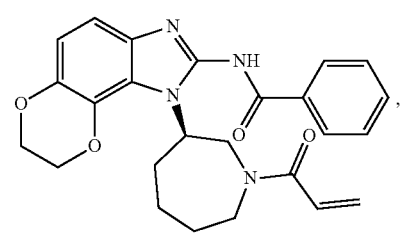
C12-A
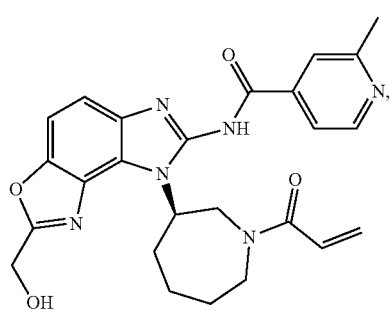
C13-A
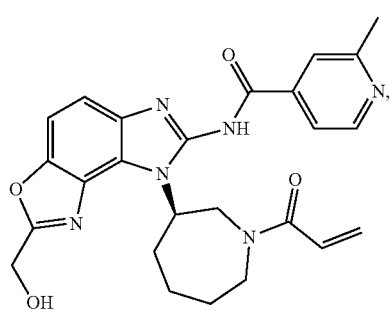
C14-A
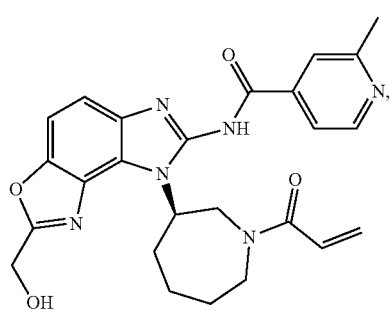
C15-A
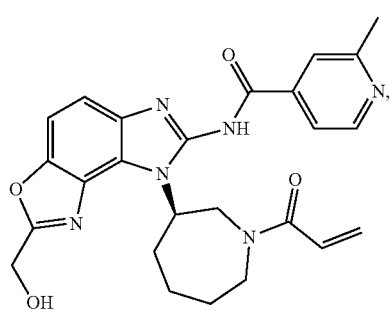
C16-A
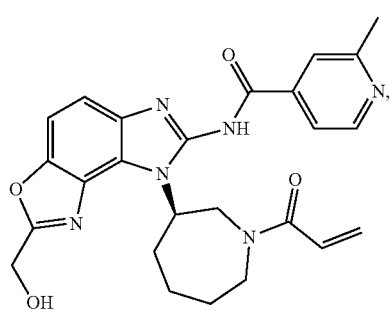

C17-A

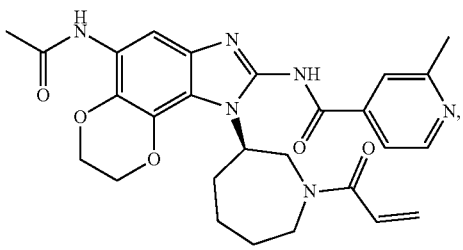

C18-A

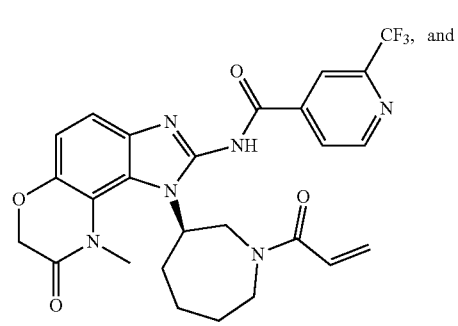

C19-A

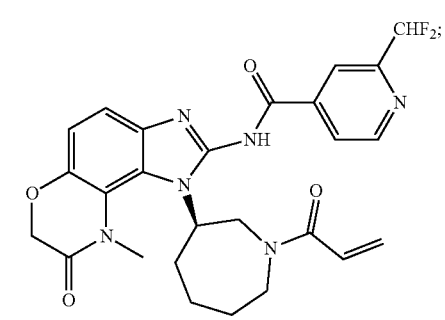

and isotopic variants thereof; and pharmaceutically acceptable salts, solvates, and prodrugs thereof.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

For example, the compound of Formula I, when $R^{24}$ is hydrogen, may exist in any of the following tautomeric forms as shown below.

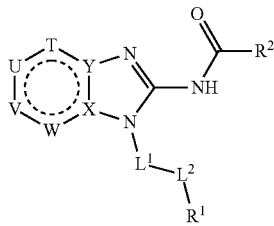

(i)

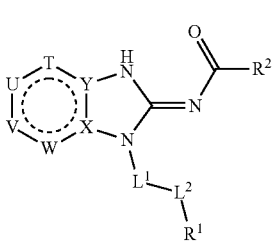

(ii)

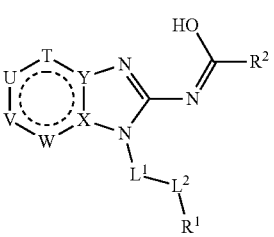

(iii)

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt. See, Berge et al., *J. Pharm. Sci.* 1977, 66, 1-19; and *Handbook of Pharmaceutical Salts, Properties, and Use*; Stahl and Wermuth, Ed.; Wiley-VCH and VHCA: Zurich, Switzerland, 2002.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I, and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, Harper, *Progress in Drug Research* 1962, 4, 221-294; Morozowich et al. in *Design of Biopharmaceutical Properties through Prodrugs and Analogs*; Roche Ed., APHA Acad. Pharm. Sci.: 1977; Gangwar et al., *Des. Biopharm. Prop. Prodrugs Analogs,* 1977, 409-421; Bundgaard, *Arch. Pharm. Chem.* 1979, 86, 1-39; Farquhar et al., *J. Pharm. Sci.* 1983, 72, 324-325; Wernuth in *Drug Design: Fact or Fantasy*; Jolles et al. Eds.; Academic Press: London, 1984; pp 47-72; *Design of Prodrugs*; Bundgaard et al. Eds.; Elsevier: 1985; Fleisher et al., *Methods Enzymol.* 1985, 112, 360-381; Stella et al., *Drugs* 1985, 29, 455-473; *Bioreversible Carriers in Drug in Drug Design, Theory and Application*; Roche Ed.; APHA Acad. Pharm. Sci.: 1987; Bundgaard, *Controlled Drug Delivery* 1987, 17, 179-96; Waller et al., *Br. J. Clin. Pharmac.* 1989, 28, 497-507; Balant et al., *Eur. J Drug Metab. Pharmacokinet.* 1990, 15, 143-53; Freeman et al., *J. Chem. Soc., Chem. Commun.* 1991, 875-877; Bundgaard, *Adv. Drug Delivery Rev.* 1992, 8, 1-38; Nathwani and Wood, *Drugs* 1993, 45, 866-94; Friis and Bundgaard, *Eur. J. Pharm. Sci.* 1996, 4, 49-59; Fleisher et al., *Adv. Drug Delivery Rev.* 1996, 19, 115-130; Sinhababu and Thakker, *Adv. Drug Delivery Rev.* 1996, 19, 241-273; Taylor, *Adv. Drug Delivery Rev.* 1996, 19, 131-148; Gaignault et al., *Pract. Med. Chem.* 1996, 671-696; Browne, *Clin. Neuropharmacol.* 1997, 20, 1-12; Valentino and Borchardt, *Drug Discovery Today* 1997, 2, 148-155; Pauletti et al., *Adv. Drug. Delivery Rev.* 1997, 27, 235-256; Mizen et al., *Pharm. Biotech.* 1998, 11, 345-365; Wiebe and Knaus, *Adv. Drug Delivery Rev.* 1999, 39, 63-80; Tan et al., *Adv. Drug Delivery Rev.* 1999, 39, 117-151; Balimane and Sinko, *Adv. Drug Delivery Rev.* 1999, 39, 183-209; Wang et al., *Curr. Pharm. Design* 1999, 5, 265-287; Han et al., *AAPS Pharmsci.* 2000, 2, 1-11; Asgharnejad in *Transport Processes in Pharmaceutical Systems*; Amidon et al., Eds.; Marcell Dekker: 2000; pp 185-218; Sinha et al., *Pharm. Res.* 2001, 18, 557-564; Anand et al., *Expert Opin. Biol. Ther.* 2002, 2, 607-620; Rao, *Resonace* 2003, 19-27; Sloan et al., *Med. Res. Rev.* 2003, 23, 763-793; Patterson et al., *Curr. Pharm. Des.* 2003, 9, 2131-2154; Hu, *IDrugs* 2004, 7, 736-742; Robinson et al., *Proc. Natl. Acad. Sci. U.S.A.* 2004, 101, 14527-14532; Erion et al., *J. Pharmacol. Exp. Ther.* 2005, 312, 554-560; Fang et al., *Curr. Drug Discov. Technol.* 2006, 3, 211-224; Stanczak et al., *Pharmacol. Rep.* 2006, 58, 599-613; Sloan et al., *Pharm. Res.* 2006, 23, 2729-2747; Stella et al., *Adv. Drug Deliv. Rev.* 2007, 59, 677-694; Gomes et al., *Molecules* 2007, 12, 2484-2506; Krafz et al., *Chem Med Chem* 2008, 3, 20-53; Rautio et al., *AAPS J.* 2008, 10, 92-102; Rautio et al., *Nat. Rev. Drug. Discov.* 2008, 7, 255-270; Pavan et al., *Molecules,* 2008, 13, 1035-1065; Sandros et al., *Molecules* 2008, 13, 1156-1178; Singh et al., *Curr. Med. Chem.* 2008, 15, 1802-1826; Onishi et al., *Molecules,* 2008, 13, 2136-2155; Huttunen et al., *Curr. Med. Chem.* 2008, 15, 2346-2365; and Serafin et al., *Mini Rev. Med. Chem.* 2009, 9, 481-497.

Methods of Synthesis

The compounds provided herein can be prepared, isolated, or obtained by any method known to one of skill in the art. For an example, a compound of Formula I can be prepared as shown in Scheme I.

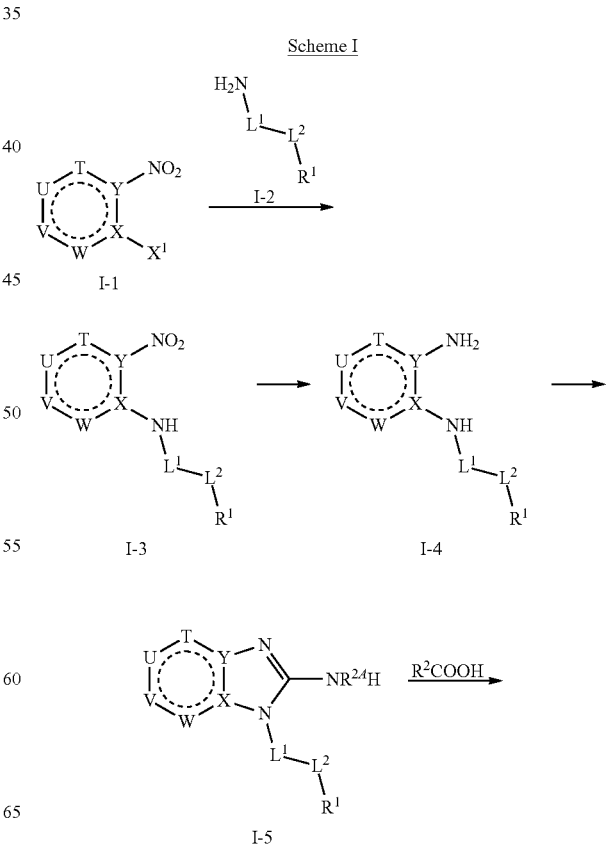

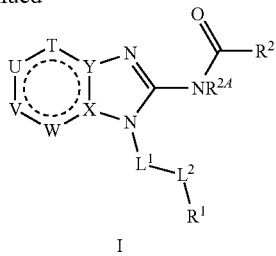

I

Compound I-1 is treated with nucleophilic amine I-2 to form compound I-3, wherein $X^1$ is a leaving group, including, but not limited to fluoro, chloro, bromo, methoxy, ethoxy, and nitro. The nitro group of compound I-3 is reduced with a reducing agent, e.g., zinc, $FeCl_2$, $NiCl_2$, or $Na_2S_2O_3$, to form compound I-4. The reduction can also be accomplished via hydrogenation using, e.g., ammonium formate or hydrogen in the presence of Pd/C. Compound I-5 is then cyclized to form compound I-5 with the Z group installed simultaneously. When Z is NH, compound I-5 is then coupled with an acid ($R^2COOH$) using a coupling reagent, e.g., HATU, HBTU, PyBroP, PyBOP, or EDCI, to form compound of Formula I.

Pharmaceutical Compositions

Provided herein are pharmaceutical compositions comprising a compound provided herein, e.g., a compound of Formula I, II, XIXa, XXII, XXV, XXVI, XXVII, VIII-A, IX-A, or X-A, as an active ingredient, including a single enantiomer, a racemic mixture, a mixture of diastereomers, or an isotopic variant thereof; or a pharmaceutically acceptable salt, solvate, or prodrug thereof; and a pharmaceutically acceptable vehicle, carrier, diluent, or excipient, or a mixture thereof.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose, or other mono- or di-saccharides. As used herein, the term "lactose-free" means that the amount of lactose present, if any, is insufficient to substantially increase the degradation rate of an active ingredient.

The compound provided herein may be administered alone, or in combination with one or more other compounds provided herein. The pharmaceutical compositions that comprise a compound provided herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Delivery Technology*, 2nd ed.; Rathbone et al., Eds.; Marcel Dekker, Inc.: New York, N.Y., 2008).

In one embodiment, the pharmaceutical compositions are provided in a dosage form for oral administration, which comprise a compound provided herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof; and a pharmaceutically acceptable salt, solvate, or prodrug thereof.

In another embodiment, the pharmaceutical compositions are provided in a dosage form for parenteral administration, which comprise a compound provided herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof; and a pharmaceutically acceptable salt, solvate, or prodrug thereof.

In yet another embodiment, the pharmaceutical compositions are provided in a dosage form for topical administration, which comprise a compound provided herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof; and a pharmaceutically acceptable salt, solvate, or prodrug thereof.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including ca-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy,* supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy,* supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated- and fast-, targeted, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,958,458; 5,972,891; 5,980,945; 5,993,855; 6,045,830; 6,087,324; 6,113,943; 6,197,350; 6,248,363; 6,264,970; 6,267,981; 6,270,798; 6,375,987; 6,376,461; 6,419,961; 6,589,548; 6,613,358; 6,623,756; 6,699,500; 6,793,936; 6,827,947; 6,902,742; 6,958,161; 7,255,876; 7,416,738; 7,427,414; 7,485,322; Bussemer et al., *Crit. Rev. Ther. Drug Carrier Syst.* 2001, 18, 433-458; *Modified-Release Drug Delivery Technology*, 2nd ed.; Rathbone et al., Eds.; Marcel Dekker AG: 2005; Maroni et al., *Expert. Opin. Drug Deliv.* 2005, 2, 855-871; Shi et al., *Expert Opin. Drug Deliv.* 2005, 2, 1039-1058; *Polymers in Drug Delivery*; Ijeoma et al., Eds.; CRC Press LLC: Boca Raton, Fla., 2006; Badawy et al., *J. Pharm. Sci.* 2007, 9, 948-959; *Modified-Release Drug Delivery Technology*, supra; Conway, *Recent Pat. Drug Deliv. Formul.* 2008, 2, 1-8; Gazzaniga et al., *Eur. J. Pharm. Biopharm.* 2008, 68, 11-18; Nagarwal et al., *Curr. Drug Deliv.* 2008, 5, 282-289; Gallardo et al., *Pharm. Dev. Technol.* 2008, 13, 413-423; Chrzanowski, *AAPS PharmSciTech.* 2008, 9, 635-638; Chrzanowski, *AAPS Pharm Sci Tech.* 2008, 9, 639-645; Kalantzi et al., *Recent Pat. Drug Deliv. Formul.* 2009, 3, 49-63; Saigal et al., *Recent Pat. Drug Deliv. Formul.* 2009, 3, 64-70; and Roy et al., *J. Control Release* 2009, 134, 74-80.

1. Matrix Controlled Release Devices

The pharmaceutical compositions provided herein in a modified release dosage form can be fabricated using a matrix controlled release device known to those skilled in the art. See, Takada et al. in *Encyclopedia of Controlled Drug Delivery*; Mathiowitz Ed.; Wiley: 1999; Vol 2.

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art. See, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; and Verma et al., *J. Controlled Release* 2002, 79, 7-27.

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and International Pat. Appl. Publ. No. WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 µm to about 3 mm, about 50 µm to about 2.5 mm, or from about 100 µm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Ghebre-Sellassie Ed.; Marcel Dekker: 1994; and *Pharmaceutical Pelletization Technology*; Ghebre-Sellassie Ed.; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 5,709,874; 5,759,542; 5,840,674; 5,900,252; 5,972,366; 5,985,307; 6,004,534; 6,039,975; 6,048,736; 6,060,082; 6,071,495; 6,120,751; 6,131,570; 6,139,865; 6,253,872; 6,271,359; 6,274,552; 6,316,652; and 7,169,410.

Methods of Use

In one embodiment, provided herein is a method for treating, preventing, or ameliorating one or more symptoms of a condition, disorder, or disease mediated by a lipid kinase or a protein kinase in a subject, comprising administering to the subject a compound disclosed herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In certain embodiments, the condition, disorder, or disease is mediated by a lipid kinase. In certain embodiments, the condition, disorder, or disease is mediated by a protein kinase. In certain embodiments, the condition, disorder, or disease is mediated by a tyrosine protein kinase. In certain embodiments, the condition, disorder, or disease is mediated by a serine/threonine protein kinase.

In certain embodiments, the condition, disorder, or disease is mediated by ABL1, BLK, BMX, BTK, CLK1, CLK2, CLK3, CLK4, CK1 epsilon, CK1 gamma 1, CK1 gamma 2, CK1 gamma 3, EPHB2, FLT4 (VEGFR3), GSK3A, GSK3B, ITK, JAK3, MAP4K4 (HGK), MINK1, PAK4, PAK7, PIK3CD/PIK3R1 (p110 delta/p85 alpha), RET, RET V804L, RET Y791F, RIPK3, STK16, TEC, TNIK, or TXK. In certain embodiments, the condition, disorder, or disease is mediated by BLK, BMX, BTK, CSNK1E (CK1 epsilon), GSK3 beta, JAK3, ITK, MAP4K4 (HGK), MINK1, PIK3C, PIK3D, TEC, TNIK, or TXK. In certain embodiments, the condition, disorder, or disease is mediated by BLK, BMX, BTK, PIK3C, PIK3D, ITK, TEC, or TXK. In certain embodiments, the condition, disorder, or disease is mediated by BMX, BTK, PIK3C, PIK3D, ITK, TEC, or TXK.

In one embodiment, provided herein is a method for treating, preventing, or ameliorating one or more symptoms of a Bmx kinase-mediated condition, disorder, or disease in a subject, comprising administering to the subject a compound disclosed herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In certain embodiments, the Bmx kinase-mediated condition, disorder, or disease is a proliferative disease. In certain embodiments, the Bmx kinase-mediated condition, disorder, or disease is cancer. In certain embodiments, the Bmx kinase-mediated condition, disorder, or disease is glioblastoma, prostate cancer, breast cancer, or lung cancer.

In yet another embodiment, provided herein is a method for treating, preventing, or ameliorating one or more symptoms of a BTK kinase-mediated condition, disorder, or disease in a subject, comprising administering to the subject a compound disclosed herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In certain embodiments, the BTK kinase-mediated condition, disorder, or disease is a proliferative disease. In certain embodiments, the BTK kinase-mediated condition, disorder, or disease is an inflammatory disease. In certain embodiments, the BTK kinase-mediated condition, disorder, or disease is rheumatoid arthritis.

In certain embodiments, the BTK kinase-mediated condition, disorder, or disease is cancer. In certain embodiments, the BTK kinase-mediated condition, disorder, or disease is a blood cancer.

In certain embodiments, the BTK kinase-mediated condition, disorder, or disease is leukemia. In certain embodiments, the BTK kinase-mediated condition, disorder, or disease is chronic lymphocytic leukemia (CLL), prolymphocytic leukemia, or Richter's transformation. In certain embodiments, the BTK kinase-mediated condition, disorder, or disease is high-risk CLL. In certain embodiments, the BTK kinase-mediated condition, disorder, or disease is B-cell CLL.

In certain embodiments, the BTK kinase-mediated condition, disorder, or disease is lymphoma. In certain embodiments, the BTK kinase-mediated condition, disorder, or disease is B-cell lymphoma. In certain embodiments, the BTK kinase-mediated condition, disorder, or disease is Hodgkin's lymphoma.

In certain embodiments, the BTK kinase-mediated condition, disorder, or disease is diffuse large B cell lymphoma (DLBCL), follicular lymphoma, marginal zone lymphoma (MZL), mucosa-associated lymphatic tissue lymphoma (MALT), small lymphocytic lymphoma, or Mantle cell lymphoma (MCL).

In certain embodiments, the BTK kinase-mediated condition, disorder, or disease is non-Hodgkin's lymphoma (NHL). In certain embodiments, the BTK kinase-mediated condition, disorder, or disease is indolent NHL. In certain embodiments, the BTK kinase-mediated condition, disorder, or disease is Burkitt lymphoma, follicular lymphoma, or Waldenstrom's macroglobulinemia.

In certain embodiments, the BTK kinase-mediated condition, disorder, or disease is refractory follicular lymphoma. In certain embodiments, the BTK kinase-mediated condition, disorder, or disease is relapsed DLBCL. In certain embodiments, the BTK kinase-mediated condition, disorder, or disease is relapsed MCL.

In certain embodiments, the BTK kinase-mediated condition, disorder, or disease is a mature B-cell neoplasm. In certain embodiments, the BTK kinase-mediated condition, disorder, or disease is a recurrent mature B-cell neoplasm.

In yet another embodiment, provided herein is a method for treating, preventing, or ameliorating one or more symptoms of a PIK3C/D kinase-mediated condition, disorder, or disease in a subject, comprising administering to the subject a compound disclosed herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In certain embodiments, the PIK3C/D kinase-mediated condition, disorder, or disease is a proliferative disease. In certain embodiments, the PIK3C/D kinase-mediated condition, disorder, or disease is cancer. In certain embodiments, the PIK3C/D kinase-mediated condition, disorder, or disease is a blood cancer. In certain embodiments, the PIK3C/D kinase-mediated condition, disorder, or disease is leukemia. In certain embodiments, the PIK3C/D kinase-mediated condition, disorder, or disease is CLL.

In certain embodiments, the PIK3C/D kinase-mediated condition, disorder, or disease is lymphoma. In certain embodiments, the PIK3C/D kinase-mediated condition, disorder, or disease is B-cell lymphoma. In certain embodiments, the PIK3C/D kinase-mediated condition, disorder, or disease is Hodgkin's lymphoma. In certain embodiments, the PIK3C/D kinase-mediated condition, disorder, or disease is non-Hodgkin's lymphoma (NHL). In certain embodiments, the PIK3C/D kinase-mediated condition, disorder, or disease is small lymphocytic lymphoma.

In yet another embodiment, provided herein is a method for treating, preventing, or ameliorating one or more symptoms of an ITK kinase-mediated condition, disorder, or disease in a subject, comprising administering to the subject a compound disclosed herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In certain embodiments, the ITK kinase-mediated condition, disorder, or disease is a proliferative disease. In certain embodiments, the ITK kinase-mediated condition, disorder, or disease is an infectious disease. In certain embodiments, the ITK kinase-mediated condition, disorder, or disease is a parasitic infection. In certain embodiments, the ITK kinase-mediated condition, disorder, or disease is *Listeria monocytogenes*.

In certain embodiments, the ITK kinase-mediated condition, disorder, or disease is cancer. In certain embodiments, the ITK kinase-mediated condition, disorder, or disease is a blood cancer.

In certain embodiments, the ITK kinase-mediated condition, disorder, or disease is breast cancer. In certain embodiments, the ITK kinase-mediated condition, disorder, or disease is triple negative breast cancer. In certain embodiments, the ITK kinase-mediated condition, disorder, or disease is colon cancer.

In yet another embodiment, provided herein is a method for treating, preventing, or ameliorating one or more symptoms of a TEC kinase-mediated condition, disorder, or disease in a subject, comprising administering to the subject a compound disclosed herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In certain embodiments, the TEC kinase-mediated condition, disorder, or disease is a proliferative disease. In certain embodiments, the TEC kinase-mediated condition, disorder, or disease is an inflammatory disease. In certain embodiments, the TEC kinase-mediated condition, disorder, or disease is rheumatoid arthritis, psoriasis, inflammatory bowel disease, or organ transplant rejection.

In yet another embodiment, provided herein is a method for treating, preventing, or ameliorating one or more symptoms of a TXK kinase-mediated condition, disorder, or disease in a subject, comprising administering to the subject a compound disclosed herein, e.g., a compound of Formula I, II, XIXa, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In certain embodiments, the TXK kinase-mediated condition, disorder, or disease is a proliferative disease. In certain embodiments, the TXK kinase-mediated condition, disorder, or disease is an inflammatory disease. In certain embodiments, the TXK kinase-mediated condition, disorder, or disease is rheumatoid arthritis, psoriasis, inflammatory bowel disease, or organ transplant rejection.

In still another embodiment, provided herein is a method for treating, preventing, or ameliorating one or more symptoms of an ERBB-mediated condition, disorder, or disease in a subject, comprising administering to the subject a compound disclosed herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In certain embodiments, the ERBB is a wild-type ERBB. In certain embodiments, the ERBB is an ERBB variant.

In certain embodiments, the ERBB is an EGFR. In certain embodiments, the ERBB is a wild-type EGFR. In certain embodiments, the ERBB is an EGFR variant. In certain embodiments, the EGFR variant contains a deletion, insertion, or substitution. In certain embodiments, the EGFR variant contains one or more deletions, insertions, or substitutions at the amino acid positions of 689, 700, 709, 715, 719, 720, 746-759, 761-765, 767-775, 783, 784, 790, 796, 826, 839, 846, 858, 861, and 863. In certain embodiments, the EGFR variant contains one, two, or more deletions, insertions, and/or substitutions, each independently selected from V689M, N700D, E709K, E709Q, E709V, E709A, E709G, I715S, G719C, G719S, G719A, S720P, ΔE746-A750, ΔE746-T751, ΔE746-A750 (ins RP), ΔE746-T751 (ins A/I), ΔE746-T751 (ins VA), ΔE746-S752 (ins A/V), L747S, ΔL747-E749 (A750P), ΔL747-A750 (ins P), ΔL747-T751, ΔL747-T751 (ins P/S), ΔL747-S752, ΔL747-752 (E746V), ΔL747-752 (P753 S), ΔL747-S752 (ins Q), ΔL747-P753, ΔL747-P753 (ins S), ΔS752-I759, D761Y, ΔD761-E762 (ins EAFQ), ΔA763-Y764 (ins FQEA), V765A, ΔM766-A767 (ins AI), ΔA767-S768 (ins TLA), ΔA767-S768 (ins SVA), S7681, ΔS768-D770 (dup SVD), V769L, ΔV769-D770 (ins ASV), ΔD770-N771 (ins NPG), ΔD770-N771 (ins SVQ), ΔD770-N771 (ins SVD), ΔD770-N771 (ins G), ΔD770-P772 (ins ASV), N771T, ΔP772-H773 (ins PR), ΔP772-H773 (ins YNP), ΔH773-V774 (ins NPH), ΔH773-V774 (ins NP), ΔH773-V774 (ins H), ΔH773-V774 (ins PH), ΔH773-V774 (ins GNPH), ΔV774-C775 (ins HV), H775Y, P782R, T783A, T784A, T790M, G796A, N826S, A839T, K846R, L858R, L861Q, and G863D, provided that there is only one deletion and/or insertion, or substitution at a given amino acid position in the EGFR variant. In certain embodiments, the EGFR variant contains one, two, or more deletions, insertions, and/or substitutions, each independently selected from G719C, G719S. G719A, ΔE746-A750, ΔE746-T751, ΔE746-A750 (ins RP), T790M, and L858R. In certain embodiments, the EGFR variant contains T790M and/or L858R. In certain embodiments, the EGFR variant contains one, two, or more deletions, insertions, and/or substitutions, each independently selected from ΔD761-E762 (ins EAFQ), ΔS768-D770 (dup SVD), ΔV769-D770 (ins ASV), ΔD770-N771 (ins SVQ), ΔP772-H773 (ins PR), ΔH773-V774 (ins NPH), ΔH773-V774 (ins H), ΔH773-V774 (ins PH), and ΔH773-V774 (ins GNPH). In certain embodiments, the EGFR variant contains a deletion, insertion, or substitution in exon 19. In certain embodiments, the EGFR variant contains a deletion, insertion, or substitution in exon 20.

In certain embodiments, the ERBB is a HER2. In certain embodiments, the ERBB is a wild-type HER2. In certain embodiments, the ERBB is a HER2 variant. In certain embodiments, the HER2 variant contains a deletion, insertion, or substitution. In certain embodiments, the HER2 variant contains one or more deletions, insertions, or substitutions at the amino acid positions of 309, 310, 630, 717, 719, 726, 733, 755-759, 767, 769, 775-778, 780, 781, 783, 785, 798, 803, 812, 821, 835, 839, 842, 896, and 915. In certain embodiments, the HER2 variant contains one, two, or more deletions, insertions, and/or substitutions, each independently selected from G309A, G309E, S310F, C630Y, E717K, E719G, E719K, L726F, T733I, L755S, L755W, ΔL755-T759, I767M, D769H, D769Y, ΔA775-G776 (ins YVMA), G776VC, G776LC, ΔV777-G778 (ins CG), V777L, P780L, ΔP780-Y781 (ins GSP), S783P, L785F, T798I, Y803N, E812K, D821N, Y835F, V839G, V842I, R896C, and L915M, provided that there is only one deletion and/or insertion, or substitution at a given amino acid position in the HER2 variant. In certain embodiments, the HER2 variant contains one, two, or more deletions, insertions, and/or substitutions, each independently selected from G309A, L755S, ΔL755-T759, ΔA775-G776 (ins YVMA), V777L, ΔP780-Y781 (ins GSP), V842I, and R896C.

In certain embodiments, the ERBB is a HER3. In certain embodiments, the ERBB is a wild-type HER3. In certain embodiments, the ERBB is a HER3 variant. In certain embodiments, the HER3 variant contains a deletion, insertion, or substitution.

In certain embodiments, the ERBB is a HER4. In certain embodiments, the ERBB is a wild-type HER4. In certain embodiments, the ERBB is a HER4 variant. In certain embodiments, the HER4 variant contains a deletion, insertion, or substitution.

In certain embodiments, the ERBB is a dimer. In certain embodiments, the ERBB is a homodimer. In certain embodiments, the ERBB is a heterodimer. In certain embodiments, the ERBB is a heterodimer of EGFR, HER2, HER3, HER4, and variants thereof.

In certain embodiments, the compound provided herein is a selective inhibitor of a mutant ERBB. In certain embodiments, the compound provided herein has a selectivity against a mutant ERBB over a wild-type ERBB ranging from about 2 fold, about 4 fold, about 8 fold, about 20 fold, about 50 fold, about 100 fold, about 200 fold, about 500 fold, or about 1000 fold.

In certain embodiments, the compound provided herein is a selective inhibitor of a mutant EGFR. In certain embodiments, the compound provided herein has a selectivity against a mutant EGFR over a wild-type EGFR ranging from about 2 fold, about 4 fold, about 8 fold, about 20 fold, about 50 fold, about 100 fold, about 200 fold, about 500 fold, or about 1000 fold.

In certain embodiments, the compound provided herein is a selective inhibitor of a mutant HER2. In certain embodiments, the compound provided herein has a selectivity against a mutant HER2 over a wild-type HER2 ranging from about 2 fold, about 4 fold, about 8 fold, about 20 fold, about 50 fold, about 100 fold, about 200 fold, about 500 fold, or about 1000 fold.

In certain embodiments, the compound provided herein is a selective inhibitor of a mutant HER3. In certain embodiments, the compound provided herein has a selectivity against a mutant HER3 over a wild-type HER3 ranging from about 2 fold, about 4 fold, about 8 fold, about 20 fold, about 50 fold, about 100 fold, about 200 fold, about 500 fold, or about 1000 fold.

In certain embodiments, the compound provided herein is a selective inhibitor of a mutant HER4. In certain embodiments, the compound provided herein has a selectivity against a mutant HER4 over a wild-type HER4 ranging from about 2 fold, about 4 fold, about 8 fold, about 20 fold, about 50 fold, about 100 fold, about 200 fold, about 500 fold, or about 1000 fold.

In yet another embodiments, provided herein is a method for treating, preventing, or ameliorating one or more symptoms of a proliferative disease in a subject, comprising administering to the subject a therapeutically effective amount of a compound disclosed herein, e.g., a compound of Formula I, II, XIXa, XXII, XXV, XXVI, XXVII, VIII-A, IX-A, or X-A, or an enantiomer, a mixture of enantiomers, a mixture of two or more diastereomers, or an isotopic variant thereof; or a pharmaceutically acceptable salt, solvate, hydrate, or prodrug thereof.

In certain embodiments, the subject is a mammal. In certain embodiments, the subject is a human. In certain embodiments, the subject is a primate other than a human, a farm animal such as cattle, a sport animal, or a pet such as a horse, dog, or cat.

In certain embodiments, the ERBB-mediated condition, disorder, or disease is a proliferative disease. In certain embodiments, the ERBB-mediated condition, disorder, or disease is cancer. In certain embodiments, the ERBB-mediated condition, disorder, or disease is a drug-resistant cancer. In certain embodiments, the ERBB-mediated condition, disorder, or disease is multidrug-resistant cancer. In certain embodiments, the ERBB-mediated condition, disorder, or disease is relapsed multidrug-resistant cancer. In certain embodiments, the ERBB-mediated condition, disorder, or disease is an inflammatory disease. In certain embodiments, the ERBB-mediated condition, disorder, or disease is an immune disorder.

In certain embodiments, the proliferative disease is cancer. In certain embodiments, the cancer is relapsed cancer. In certain embodiments, the cancer is drug-resistant cancer. In certain embodiments, the cancer is relapsed drug-resistant cancer. In certain embodiments, the cancer is multidrug-resistant cancer. In certain embodiments, the cancer is relapsed multidrug-resistant cancer.

In certain embodiments, the cancer is ERBB inhibitor-resistant cancer. In certain embodiments, the cancer is reversible ERBB inhibitor-resistant cancer. In certain embodiments, the cancer is irreversible ERBB inhibitor-resistant cancer. In certain embodiments, the cancer is relapsed ERBB inhibitor-resistant cancer. In certain embodiments, the cancer is relapsed reversible ERBB inhibitor-resistant cancer. In certain embodiments, the cancer is relapsed irreversible ERBB inhibitor-resistant cancer. In certain embodiments, the cancer is resistant to afatinib, canertinib, dacomitinib, erlotinib, gefitinib, icotinib, lapatinib, neratinib, pelitinib, varlitinib, or a combination thereof.

In certain embodiments, the cancer is EGFR inhibitor-resistant cancer. In certain embodiments, the cancer is reversible EGFR inhibitor-resistant cancer. In certain embodiments, the cancer is irreversible EGFR inhibitor-resistant cancer. In certain embodiments, the cancer is relapsed EGFR inhibitor-resistant cancer. In certain embodiments, the cancer is relapsed reversible EGFR inhibitor-resistant cancer. In certain embodiments, the cancer is relapsed irreversible EGFR inhibitor-resistant cancer.

In certain embodiments, the cancer is HER2 inhibitor-resistant cancer. In certain embodiments, the cancer is reversible HER2 inhibitor-resistant cancer. In certain embodiments, the cancer is irreversible HER2 inhibitor-resistant cancer. In certain embodiments, the cancer is relapsed HER2 inhibitor-resistant cancer. In certain embodiments, the cancer is relapsed reversible HER2 inhibitor-resistant cancer. In certain embodiments, the cancer is relapsed irreversible HER2 inhibitor-resistant cancer.

In certain embodiments, the cancer is HER3 inhibitor-resistant cancer. In certain embodiments, the cancer is reversible HER3 inhibitor-resistant cancer. In certain embodiments, the cancer is irreversible HER3 inhibitor-resistant cancer. In certain embodiments, the cancer is relapsed HER3 inhibitor-resistant cancer. In certain embodiments, the cancer is relapsed reversible HER3 inhibitor-resistant cancer. In certain embodiments, the cancer is relapsed irreversible HER3 inhibitor-resistant cancer.

In certain embodiments, the cancer is HER4 inhibitor-resistant cancer. In certain embodiments, the cancer is reversible HER4 inhibitor-resistant cancer. In certain embodiments, the cancer is irreversible HER4 inhibitor-resistant cancer. In certain embodiments, the cancer is relapsed HER4 inhibitor-resistant cancer. In certain embodiments, the cancer is relapsed reversible HER4 inhibitor-resistant cancer. In certain embodiments, the cancer is relapsed irreversible HER4 inhibitor-resistant cancer.

In certain embodiments, the proliferative disease is an inflammatory disease. In certain embodiments, the proliferative disease is an immune disorder.

The conditions, disorders, or diseases treatable with a compound provided herein include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the cancer treatable with a compound provided herein includes, but is not limited to, (1) leukemias, including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML), (2) chronic leukemias, including, but not limited to, chronic myelocytic (granulocytic) leukemia, chronic lymphocytic leukemia, and hairy cell leukemia; (3) polycythemia vera; (4) lymphomas, including, but not limited to, Hodgkin's disease and non-Hodgkin's disease; (5) multiple myelomas, including, but not limited to, smoldering multiple myeloma, nonsecretory myeloma, osteosclerotic myeloma, plasma cell leukemia, solitary plasmacytoma, and extramedullary plasmacytoma; (6) Waldenstrom's macroglobulinemia; (7) monoclonal gammopathy of undetermined significance; (8) benign monoclonal gammopathy; (9) heavy chain disease; (10) bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma; (11) brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; (12) breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; (13) adrenal cancer, including, but not limited to, pheochromocytom and adrenocortical carcinoma; (14) thyroid cancer, including, but not limited to, papillary or follicular thyroid cancer, medullary thyroid cancer, and anaplastic thyroid cancer; (15) pancreatic cancer, including, but not limited to, insulinoma, gastrinoma, glucagonoma, vipoma, somatostatin-secreting tumor, and carcinoid or islet cell tumor; (16) pituitary cancer, including, but limited to, Cushing's disease, prolactin-secreting tumor, acromegaly, and diabetes insipius; (17) eye cancer, including, but not limited, to ocular melanoma such as iris melanoma, choroidal melanoma, and cilliary body melanoma, and retinoblastoma; (18) vaginal cancer, including, but not limited to, squamous cell carcinoma, adenocarcinoma, and melanoma; (19) vulvar cancer, including, but not limited to, squamous cell carcinoma, melanoma, adenocarcinoma, basal cell carcinoma, sarcoma, and Paget's disease; (20) cervical cancers, including, but not limited to, squamous cell carcinoma, and adenocarcinoma; (21) uterine cancer, including, but not limited to, endometrial carcinoma and uterine sarcoma; (22) ovarian cancer, including, but not limited to, ovarian epithelial carcinoma, borderline tumor, germ cell tumor, and stromal tumor; (23) esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; (24) stomach cancer, including, but not limited to, adenocarcinoma, fungating (polypoid), ulcerating, superficial spreading, diffusely spreading, malignant lymphoma, liposarcoma, fibrosarcoma, and carcinosarcoma; (25) colon cancer; (26) rectal cancer; (27) liver cancer, including, but not limited to, hepatocellular carcinoma and hepatoblastoma; (28) gallbladder cancer, including, but not limited to, adenocarcinoma; (29) cholangiocarcinomas, including, but not limited to, pappillary, nodular, and diffuse; (30) lung cancer, including, but not limited to, non-small cell lung cancer, squamous cell carcinoma (epidermoid carcinoma), adenocarcinoma, large-cell carcinoma, and small-cell lung cancer; (31) testicular cancer, including, but not limited to, germinal tumor, seminoma, anaplastic, classic (typical), spermatocytic, non-seminoma, embryonal carcinoma, teratoma carcinoma, and choriocarcinoma (yolk-sac tumor); (32) prostate cancer, including, but not limited to, adenocarcinoma, leiomyosarcoma, and rhabdomyosarcoma; (33) penal cancer; (34) oral cancer, including, but not limited to, squamous cell carcinoma; (35) basal cancer; (36) salivary gland cancer, including, but not limited to, adenocarcinoma, mucoepidermoid carcinoma, and adenoidcystic carcinoma; (37) pharynx cancer, including, but not limited to, squamous cell cancer and verrucous; (38) skin cancer, including, but not limited to, basal cell carcinoma, squamous cell carcinoma and melanoma, superficial spreading melanoma, nodular melanoma, lentigo malignant melanoma, and acral lentiginous melanoma; (39) kidney cancer, including, but not limited to, renal cell cancer, adenocarcinoma, hypernephroma, fibrosarcoma, and transitional cell cancer (renal pelvis and/or uterer); (40) Wilms' tumor; (41) bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas (See Fishman et al., 1985, *Medicine*, 2d Ed., J. B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

In certain embodiments, the proliferative disease is bladder cancer, brain tumor, breast cancer, cancer of the mouth and throat, colorectal cancer, lung cancer, or pancreatic cancer, prostate cancer, stomach cancer, or uterine cancer.

In certain embodiments, the proliferative disease is lung cancer. In certain embodiments, the proliferative disease is drug-resistant lung cancer. In certain embodiments, the proliferative disease is multidrug-resistant lung cancer. In certain embodiments, the proliferative disease is relapsed lung cancer. In certain embodiments, the proliferative disease is relapsed drug-resistant lung cancer. In certain embodiments, the proliferative disease is relapsed multidrug-resistant lung cancer. In certain embodiments, the proliferative disease is non-small cell lung cancer. In certain embodiments, the proliferative disease is drug resistant non-small cell lung cancer. In certain embodiments, the proliferative disease is multidrug resistant non-small cell lung cancer. In certain embodiments, the proliferative disease is relapsed non-small cell lung cancer. In certain embodiments, the proliferative disease is relapsed drug resistant non-small cell lung cancer. In certain embodiments, the proliferative disease is relapsed multidrug resistant non-small cell lung cancer.

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period.

In the treatment, prevention, or amelioration of one or more symptoms of the disorders, diseases, or conditions described herein, an appropriate dosage level generally is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day.

For oral administration, the pharmaceutical compositions provided herein can be formulated in the form of tablets containing from about 1.0 to about 1,000 mg of the active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The pharmaceutical compositions can be administered on a regimen of 1 to 4 times per day, including once, twice, three times, and four times per day.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

In one embodiment, provided herein is a method of inhibiting the growth of a cell, comprising contacting the cell with a compound provided herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In another embodiment, provided herein is a method of inhibiting the growth of a cell in a subject, comprising administering to the subject a compound disclosed herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In certain embodiments, the cell is a cancer cell. In certain embodiments, the cell contains an ERBB variant.

In one embodiment, provided herein is a method for modulating the activity of a tyrosine kinase, in one embodiment, an ERBB kinase, comprising contacting the ERBB kinase with a compound disclosed herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In another embodiment, provided herein is a method for modulating the activity of a tyrosine kinase, in one embodiment, an ERBB kinase, in a subject, comprising administering to the subject a compound disclosed herein, e.g., a compound of Formula I, II, XIXa, XXII, XXV, XXVI, XXVII, VIII-A, IX-A, or X-A, or a single enantiomer, a racemic mixture, a mixture of diastereomers, or an isotopic variant thereof; or a pharmaceutically acceptable salt, solvate, or prodrug thereof.

In certain embodiments, the ERBB is a wild-type ERBB. In certain embodiments, the ERBB is an ERBB variant. In certain embodiments, the ERBB is an EGFR. In certain embodiments, the ERBB is a wild-type EGFR. In certain embodiments, the ERBB is an EGFR variant. In certain embodiments, the ERBB is a HER2. In certain embodiments, the ERBB is a wild-type HER2. In certain embodiments, the ERBB is a HER2 variant. In certain embodiments, the ERBB is a HER3. In certain embodiments, the ERBB is a wild-type HER3. In certain embodiments, the ERBB is a HER3 variant. In certain embodiments, the ERBB is a HER4. In certain embodiments, the ERBB is a wild-type HER4. In certain embodiments, the ERBB is a HER4 variant.

The compound provided herein, e.g., a compound of Formula I, II, XIXa, XXII, XXV, XXVI, XXVII, VIII-A, IX-A, or X-A, or an enantiomer, a mixture of enantiomers, a mixture of two or more diastereomers, or an isotopic variant thereof; or a pharmaceutically acceptable salt, solvate, hydrate, or prodrug thereof; can also be combined or used in combination with other agents or therapies useful in the treatment, prevention, or amelioration of one or more symptoms of the conditions, disorders, or diseases for which the compounds provided herein are useful.

Suitable other therapeutic agents can also include, but are not limited to, (1) alpha-adrenergic agents; (2) antiarrhythmic agents; (3) anti-atherosclerotic agents, such as ACAT inhibitors; (4) antibiotics, such as anthracyclines, bleomycins, mitomycin, dactinomycin, and plicamycin; (5) anticancer agents and cytotoxic agents, e.g., alkylating agents, such as nitrogen mustards, alkyl sulfonates, nitrosoureas, ethylenimines, and triazenes; (6) anticoagulants, such as acenocoumarol, argatroban, bivalirudin, lepirudin, fondaparinux, heparin, phenindione, warfarin, and ximelagatran; (7) antidiabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; (8) antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; (9) antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; (10) antimetabolites, such as folate antagonists, purine analogues, and pyrimidine analogues; (11) anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; (12) antiproliferatives, such as methotrexate, FK506 (tacrolimus), and mycophenolate mofetil; (13) anti-TNF antibodies or soluble TNF receptor, such as etanercept, rapamycin, and leflunimide; (14) aP2 inhibitors; (15) beta-adrenergic agents, such as carvedilol and metoprolol; (16) bile acid sequestrants, such as questran; (17) calcium channel blockers, such as amlodipine besylate; (18) chemotherapeutic agents; (19) cyclooxygenase-2 (COX-2) inhibitors, such as celecoxib and rofecoxib; (20) cyclosporins; (21) cytotoxic drugs, such as azathioprine and cyclophosphamide; (22) diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; (23) endothelin converting enzyme (ECE) inhibitors, such as phosphoramidon; (24) enzymes, such as L-asparaginase; (25) Factor VIIa Inhibitors and Factor Xa Inhibitors; (26) farnesyl-protein transferase inhibitors; (27) fibrates; (28) growth factor inhibitors, such as modulators of PDGF activity; (29) growth hormone secretagogues; (30) HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; (31) hormonal agents, such as glucocorticoids (e.g., cortisone), estrogens/antiestrogens, androgens/antiandrogens, progestins, and luteinizing hormone-releasing hormone antagonists, and octreotide acetate; (32) immunosuppressants; (33) mineralocorticoid receptor antagonists, such as spironolactone and eplerenone; (34) microtubule-disruptor agents, such as ecteinascidins; (35) microtubule-stabilizing agents, such as pacitaxel, docetaxel, and epothilones A-F; (36) MTP Inhibitors; (37) niacin; (38) phosphodiesterase inhibitors, such as PDE III inhibitors (e.g., cilostazol) and PDE V inhibitors (e.g., sildenafil, tadalafil, and vardenafil); (39) plant-derived products, such as vinca alkaloids, epipodophyllotoxins, and taxanes; (40) platelet activating factor (PAF) antagonists; (41) platinum coordination complexes, such as cisplatin, satraplatin, and carboplatin; (42) potassium channel openers; (43) prenyl-protein transferase inhibitors; (44) protein tyrosine kinase inhibitors; (45) renin inhibitors; (46) squalene synthetase inhibitors; (47) steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; (48) TNF-alpha inhibitors, such as tenidap; (49) thrombin inhibitors, such as hirudin; (50) thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); (51) thromboxane receptor antagonists, such as ifetroban; (52) topoisomerase inhibitors; (53) vasopeptidase inhibitors (dual NEP-ACE inhibitors), such as omapatrilat and gemopatrilat; and (54) other miscellaneous agents, such as, hydroxyurea, procarbazine, mitotane, hexamethylmelamine, and gold compounds.

In certain embodiments, the other therapies that may be used in combination with the compounds provided herein include, but are not limited to, surgery, endocrine therapy, biologic response modifiers (e.g., interferons, interleukins, and tumor necrosis factor (TNF)), hyperthermia and cryotherapy, and agents to attenuate any adverse effects (e.g., antiemetics).

In certain embodiments, the other therapeutic agents that may be used in combination with the compounds provided herein include, but are not limited to, alkylating drugs (mechlorethamine, chlorambucil, cyclophosphamide, melphalan, and ifosfamide), antimetabolites (cytarabine (also known as cytosine arabinoside or Ara-C), HDAC (high dose cytarabine), and methotrexate), purine antagonists and pyrimidine antagonists (6-mercaptopurine, 5-fluorouracil, cytarbine, and gemcitabine), spindle poisons (vinblastine, vincristine, and vinorelbine), podophyllotoxins (etoposide, irinotecan, and topotecan), antibiotics (daunorubicin, doxorubicin, bleomycin, and mitomycin), nitrosoureas (carmustine and lomustine), enzymes (asparaginase), and hormones (tamoxifen, leuprolide, flutamide, and megestrol), imatinib, adriamycin, dexamethasone, and cyclophosphamide. For a more comprehensive discussion of updated cancer therapies; See, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In another embodiment, the method provided herein comprises administration of a compound provided herein, e.g., a compound of Formula I, II, XIXa, XXII, XXV, XXVI, XXVII, VIII-A, IX-A, or X-A, or an enantiomer, a mixture of enantiomers, a mixture of two or more diastereomers, or an isotopic variant thereof, or a pharmaceutically acceptable salt, solvate, hydrate, or prodrug thereof, together with administering one or more chemotherapeutic agents and/or therapies selected from: alkylation agents (e.g., cisplatin, carboplatin); antimetabolites (e.g., methotrexate and 5-FU); antitumour antibiotics (e.g., adriamymycin and bleomycin); antitumour vegetable alkaloids (e.g., taxol and etoposide); antitumor hormones (e.g., dexamethasone and tamoxifen); antitumour immunological agents (e.g., interferon α, β, and γ); radiation therapy; and surgery. In certain embodiments, the one or more chemotherapeutic agents and/or therapies are administered to the subject before, during, or after the administration of the compound provided herein.

Such other agents, or drugs, can be administered, by a route and in an amount commonly used therefor, simultaneously or sequentially with the compound provided herein, e.g., a compound of Formula I, II, XIXa, XXII, XXV, XXVI, XXVII, VIII-A, IX-A, or X-A, or an enantiomer, a mixture of enantiomers, a mixture of two or more diastereomers, or an isotopic variant thereof; or a pharmaceutically acceptable salt, solvate, hydrate, or prodrug thereof. When a compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to a compound provided herein.

The weight ratio of a compound provided herein to the second active ingredient can be varied, and will depend upon the effective dose of each ingredient. Generally, an effective dose of each will be used. Thus, for example, when a compound provided herein is combined with a NSAID, the weight ratio of the compound to the NSAID can range from about 1,000:1 to about 1:1,000, or about 200:1 to about 1:200. Combinations of a compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, e.g., a compound of Formula I, II, XIXa, XXII, XXV, XXVI, XXVII, VIII-A, IX-A, or X-A, or an enantiomer, a mixture of enantiomers, a mixture of two or more diastereomers, or an isotopic variant thereof; or a pharmaceutically acceptable salt, solvate, hydrate, or prodrug thereof.

In certain embodiments, the kit includes a container comprising a dosage form of the compound provided herein, e.g., a compound of Formula I, II, XIXa, XXII, XXV, XXVI, XXVII, VIII-A, IX-A, or X-A, or an enantiomer, a mixture of enantiomers, a mixture of two or more diastereomers, or an isotopic variant thereof; or a pharmaceutically acceptable salt, solvate, hydrate, or prodrug thereof; in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); L, (liter); mM (millimolar); μM (micromolar); Hz (Hertz); MHz (megahertz); mmol (millimoles); eq. (equivalent); hr or hrs (hours); min (minutes); MS (mass spectrometry); NMR (nuclear magnetic resonance); ESI (electrospray ionization); HPLC (high-performance liquid chromatography or high pressure liquid chromatography); ACN, (acetonitrile); $CDCl_3$ (deuterated chloroform); DCM (dichloromethane); DMA (N,N-dimethylacetamide); DME (dimethoxyethane); DMF (N,N-dimethylformamide); DMSO (dimethylsulfoxide); DMSO-$d_6$ (deuterated dimethylsulfoxide); EtOAc (ethyl acetate); $Et_2O$ (diethyl ether); EtOH (ethanol); MeOH (methanol); PE (petroleum ether); THF (tetrahydrofuran); DIPEA (N,N-diisopropylethylamine); TEA (triethylamine); TFA (trifluoroacetic acid); BOP (benzotriazole-1-yl-oxytris-(dimethylamino)-phosphonium hexafluorophosphate); HATU (2-(7-aza-1H-benzotriazole-1-yl)-1,1,3,3-tetramethyluronium hexafluorophosphate); TBTU (O-(benzotriazol-1-yl)-N,N,N',N'-tetramethyluronium tetrafluoroborate); DIPC (1,3-diisopropylcarbodiimide); $Ms_2O$ (methanesulfonic anhydride); Me (methyl); Et (ethyl); iPr, (isopropyl); tBu (tert-butyl); Boc (tert-butoxylcarbony); Bn (benzyl); Ph (phenyl); Ms (mesylate); and AcO (acetate).

HPLC-MS analyses were performed on Waters HPLC 2790 coupled with Waters micromass ZQ 4000 (Model MAA050) as a mass detector and with Waters 2487 UV as a UV-visible detector, using a KINETEX™ reversed phase column (5 μM XB-C18-100 Å, 50×4.6 mm; Phenomenex, 00B-4605-E0). The mobile phase was eluent A (water, 0.05% TFA) and eluent B ($CH_3OH$, 0.05% TFA). The HPLC was run at 1 mL/min with a linear gradient from 10% B to 90% B for 8 min, followed by 90% B isocratic for 2 min, with the total run time of 10 min.

For all of the following examples, standard work-up and purification methods known to those skilled in the art can be utilized. Unless otherwise indicated, all temperatures are expressed in ° C. (degrees Centigrade). All reactions conducted at room temperature unless otherwise noted. Synthetic methodologies herein are intended to exemplify the applicable chemistry through the use of specific examples and are not indicative of the scope of the disclosure.

Example 1A

Cell Proliferation Assay

The biological activity of a test compound was determined using cell proliferation assays. The activity against wild-type ERBB1 was determined using A431 human epidermoid carcinoma cells (ATCC) and human epidermal keratinocytes, neonatal, or HEKn cells (ATCC). The activity against mutant ERBB1 was determined using HCC827 human NSCLC adenocarcinoma cells (ATCC), which has a deletion of E746-A759 in exon 19. The activity against a drug-resistant mutant ERBB1 was determined using H1975 human NSCLC adenocarcinoma cells (ATCC), which has the T790M mutation in-cis with the L858R mutation.

A431 cells were grown in DMEM (Invitrogen) supplemented with 10% FBS (Lonza), 1% penicillin-streptomycin, and 2 mM glutamine (Invitrogen). HEKn cells were grown in EPILIFE® (Invitrogen) supplemented with HKGS (Invitrogen). HCC827 and H1975 were cultured in RPMI1640 supplemented with 10% FBS (Lonza), 1% penicillin-streptomycin, and 2 mM glutamine (Invitrogen). Cells were maintained and propagated at 37° C. and 5% $CO_2$ in a humidified cell culture incubator. Aliquots of cells from early passages were preserved for liquid nitrogen storage. Frozen vials of cells were thawed at 37° C. water bath. Cells were spun to remove freezing medium. The newly revived frozen cells were adapted in culture for 10 days before used for compound testing. Cells used in the assay were less than 20 subculture passages or 3 months in culture.

The test compounds were dissolved in dimethylsulfoxide (DMSO) and stored at −20° C. before testing. For the cell proliferation assays, cells were seeded in 96-well plates (Costar, 3917) at various numbers: A431 cells at 2,000 cells per well, HEKn, HCC827, and H1975 at 1,000 cells per well. The cells were placed in a culture incubator overnight. Next day, test compounds in DMSO were added to the cells and placed back in the culture incubator for 72 hrs. In the meantime, the cell numbers at time zero of the compound treatment (TO) was measured by ENERCOUNT® (Codex BioSolutions). At the end of the compound treatment, the cell numbers were again measured by EnerCount as T72 values. The untreated controls (Ctrl) were cell numbers recorded from the 0.1% DMSO treatment. The percent growth inhibition by the test compound was calculated by the formula: (1-(T72-TO)/(Ctrl-TO))×100. The $GI_{50}$, the compound concentration at which 50% of cell growth is inhibited, was determined from the 10-point dose-response growth inhibition using non-linear sigmoidal curve fitting using GraphPad Prism.

The results are summarized in Tables 1 and 2, wherein A represents a value no greater than 500 nM, B represents a value greater than 500 nM but no greater than 1 μM, C represents a value greater than 1 μM but no greater than 5 μM, and D represents a value greater than 5 μM; and wherein A' represents a ratio of greater than 10, B' represents a ratio of no greater than 10 but no less than 5, C' represents a ratio of no greater than 5 but no less than 2, and D' represents a ratio of no greater than 2.

Example 2A

Z'-LYTE® FRET Kinase Assay

The Z'-LYTE® biochemical assay is a fluorescence-based, coupled-enzyme assay based on the differential sensitivity of phosphorylated and non-phosphorylated peptides to proteolytic cleavage. A peptide substrate for a kinase is labeled with two fluorophores, one at each end, to form a FRET pair.

TABLE 1

Inhibition of Cell Proliferation

| Cmpd. | GI$_{50}$ | | | | |
|---|---|---|---|---|---|
| | HCC827 | H1975 | HEKn | A431 | Calu3 |
| A1 | A | A | C | A | |
| A2 | A | A | D | B | |
| A3 | A | A | C | D | |
| A4 | A | A | C | C | |
| A5 | A | A | C | C | |
| C16 | A | A | | A | A |
| C19 | A | A | | B | A |
| C20 | A | A | | A | A |
| D12 | A | A | | C | B |
| D14 | A | A | | C | A |
| A13-A | A | A | | B | A |
| B1-A | A | A | D | C | |
| C1-A | A | A | C | C | |
| C2-A | A | A | C | C | |
| C11-A | A | A | | D | C |
| Erlotinib | 7.0 | 4381 | 2200 | | |
| Afatinib | 1.0 | 120 | 21 | 1.4 | |
| CO-1686 | 32 | 109 | 2500 | | |

In the primary reaction, the kinase transfers the gamma-phosphate of ATP to a single tyrosine, serine, or threonine residue in the synthetic FRET-peptide substrate. In the secondary reaction, a site-specific protease recognizes and cleaves non-phosphorylated FRET-peptides. Cleavage disrupts FRET between the donor and acceptor fluorophores on the FRET-peptide, whereas uncleaved, phosphorylated FRET-peptides maintain FRET. An inhibitory activity of a compound is thus determined from its effect on the cleavage of the synthetic FRET-peptide substrate.

Inhibition of BMX, BTK, ITK, and TXK kinases by a test compound is determined in 50 mM HEPES, pH 7.5, 0.01% BRIJ-35, 10 mM MgCl$_2$, and 1 mM EGTA in the presence of 1% DMSO by volume.

TABLE 2

Selectivity

| | Ratio (Wild-type ERBB1/Mutant ERBB1) | | | |
|---|---|---|---|---|
| Cmpd. | HEKn/ HCC827 | A431/ HCC827 | HEKn/ H1975 | A431/ H1975 |
| A1 | A' | A' | A' | A' |
| A2 | A' | A' | A' | B' |
| A3 | A' | A' | A' | B' |
| A4 | A' | A' | C' | C' |
| A5 | A' | A' | A' | C' |
| Erlotinib | A' | | D' | |
| Afatinib | A' | D' | D' | D' |
| CO-1686 | A' | | A' | |

Example 3A

LANTHASCREEN® Eu Kinase Assay

Binding of an ALEXA FLUOR® conjugate or "tracer" to a kinase is detected by addition of a Eu-labeled anti-tag antibody. Binding of the tracer and antibody to a kinase results in a high degree of FRET, whereas displacement of the tracer with a kinase inhibitor results in a loss of FRET. An inhibitory activity of a compound is thus determined from the extent of the FRET signal loss. Inhibition of ITK and TEC kinases by a test compound is determined in the presence of 1% DMSO.

Example 4A

Inhibition of BMX, BTK, PIK3C-D, ITK, TEC, and TXK Kinases

Inhibition of BMX, BTK, PIK3C-D, ITK, TEC, and TXK kinases by compound A2 was measured using one of the assays described in Examples 2A and 3A. The results are summarized in Table 3 below, wherein A represents a value no greater than 10 nM or no less than 90% inhibition.

TABLE 3

Inhibition of BMX, BTK, PIK3C-D, ITK, TEC, and TXK kinases

| Kinase | Inhibition | IC$_{50}$ |
|---|---|---|
| BMX | A | A |
| BTK | A | A |
| PIK3C-D | A | A |
| ITK | A | A |
| TEC | A | A |
| TXK | A | A |

Example 1

Synthesis of benzyl 4-(2-fluoro-3-nitrophenoxy) piperidine-1-carboxylate 8

The synthesis of benzyl 4-(2-fluoro-3-nitrophenoxy)piperidine-1-carboxylate 8 is shown in Scheme 1.

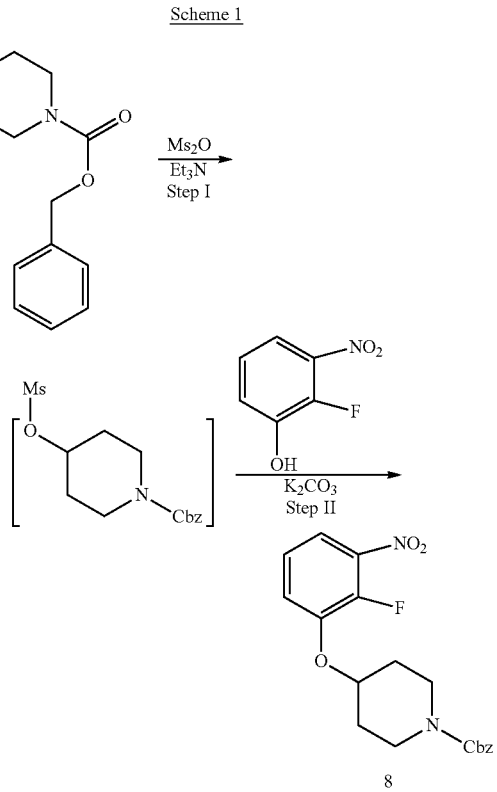

Scheme 1

Step I: Dry benzyl 4-hydroxypiperidine-1-carboxylate (50 mmol, 11.8 g) was dissolved in dry DCM (100 mL) at 0° C. Methanesulfonic anhydride (50 mmol, 8.74 g) was added, followed by addition of triethylamine (62.5 mmol, 8.70 mL). The reaction was stirred for 30 min at room temperature. DCM was stripped. The residue obtained was dried under high vacuum for 5 min to afford benzyl 4-((methylsulfonyl)oxy)piperidine-1-carboxylate 8, which was directly used in the next step without further treatment.

Step II: Benzyl 4-((methylsulfonyl)oxy)piperidine-1-carboxylate (estimated to be 25 mmol) in DMF (25 mL) was added to a suspension of 2-fluoro-3-nitrophenol (25 mmol, 4.33 g) and K₂CO₃ (100 mmol, 13.8 g) in DMF (50 mL). The reaction was heated and stirred at 80° C. for 4 hrs, then another equivalent of benzyl 4-((methylsulfonyl)oxy)-piperidine-1-carboxylate (25 mmol estimated) in DMF (25 mL) was added. The mixture was stirred at 70° C. overnight. DMF was stripped under reduced pressure. The residue obtained was diluted with 250 mL of EtOAc. The EtOAc solution was washed with saturated NaHCO₃ (40 mL), water (40 mL), and brine (40 mL), dried with Na₂SO₄, and concentrated. The residue obtained was subjected to silica gel chromatography purification (0-40% EtOAc) to afford benzyl 4-(2-fluoro-3-nitrophenoxy)piperidine-1-carboxylate 8 as brownish foam in 40% yield (3.8 g).

Example 2

Synthesis of tert-butyl (R)-3-(7-((1-((benzyloxy)carbonyl)piperidin-4-yl)oxy)-2-(2-methylisonicotinamido)-1H-benzo[d]imidazol-1-yl)azepane-1-carboxylate 4

The synthesis of tert-butyl (R)-3-(7-((1-((benzyloxy)carbonyl)piperidin-4-yl)oxy)-2-(2-methylisonicotinamido)-1H-benzo[d]imidazol-1-yl)azepane-1-carboxylate 4 is shown in Scheme 2.

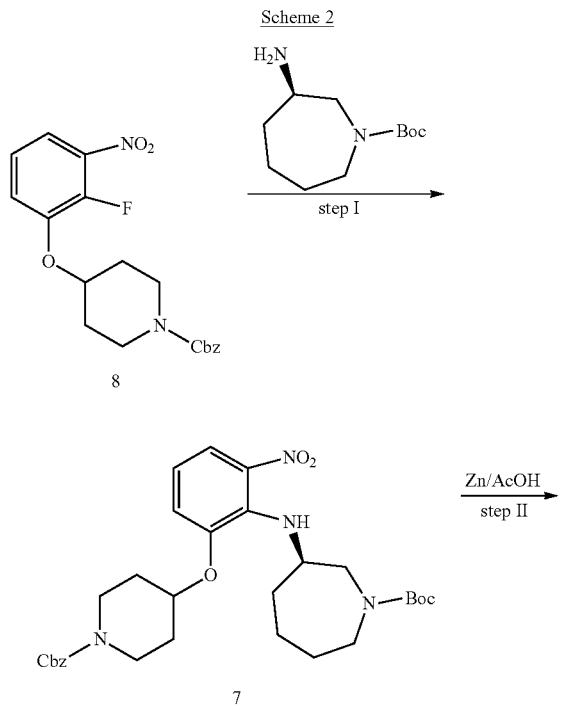

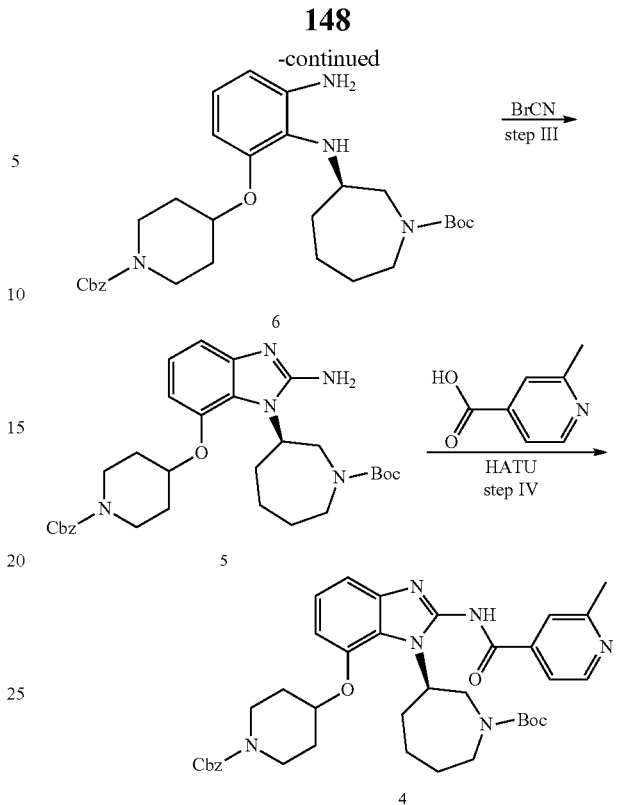

Step I: To benzyl 4-(2-fluoro-3-nitrophenoxy)piperidine-1-carboxylate 8 (10.1 mmol, 3.80 g) in DMF (20 mL) was added DIPEA (11.1 mmol, 1.94 mL) and tert-butyl (R)-3-aminoazepane-1-carboxylate (10.1 mmol, 2.16 g). The reaction was stirred at 100° C. for 4 hrs, then dissolved in 150 mL of EtOAc, washed with water (20 mL), 0.1N HCl aq. (20 mL), brine (20 mL), saturated NaHCO₃ (30 mL), and water, and dried over Na₂SO₄. Then, the solvent was stripped off under reduced pressure. The residue obtained was purified by silica gel flash-chromatography (25% to 40% EtOAc in hexane) to afford tert-butyl (R)-3-((2-((1-((benzyloxy)carbonyl)piperidin-4-yl)oxy)-6-nitrophenyl)amino)azepane-1-carboxylate 7 as yellow solid in 57.9% yield (3.3 g).

Step II: To a mixture of tert-butyl (R)-3-((2-((1-((benzyloxy)carbonyl)-piperidin-4-yl)oxy)-6-nitrophenyl)amino)azepane-1-carboxylate 7 (3.30 g, 5.80 mmol) in acetic acid (20 mL) was added zinc powder (5.57 g, 87 mmol) in batches under nitrogen at 0° C. The reaction was stirred at 25° C. for 20 min. Then the reaction was filtered and the cake was washed with DCM. The combined organic solution was stripped off solvents. The residue obtained was stirred in 16 mL of 0.2 N NaOH aq. (130 mL) for 3 min, and then extracted with EtOAc (200 mL×3). The combined organic phase was washed with sodium potassium tartrate solution (1 g in 30 mL of water), and brine, dried with Na₂SO₄ and concentrated. The residue obtained, containing tert-butyl (R)-3-((2-amino-6-((1-((benzyloxy)carbonyl)piperidin-4-yl)oxy)phenyl)amino)azepane-1-carboxylate 6, was directly used in the next step of reaction without further purification.

Step III: A mixture of tert-butyl (R)-3-((2-amino-6-((1-((benzyloxy)-carbonyl)piperidin-4-yl)oxy)phenyl)amino)azepane-1-carboxylate 6 (3.12 g, 5.8 mmol) and cyanogen bromide (9.7 mmol, 3.2 mL of 3M DCM solution) dissolved in MeOH (30 mL) and water (10 mL) was stirred at 52° C. for 2.5 hrs in a sealed tube. The solvents were stripped and the residue obtained was basified with saturated sodium carbonate solution. The reaction was then extracted with EtOAc (80 mL×3). The combined organic layers were washed with brine and water, dried over sodium sulfate, and evaporated to dryness. The residue obtained was purified by silica gel chromatography (Et₃N/EtOAc, 5 to 20%), yielding tert-butyl (R)-3-(2-amino-7-((1-((benzyloxy)carbonyl)piperidin-4-yl)oxy)-1H-benzo[d]imidazol-1-yl)azepane-1-carboxylate 5 as tanish powder in 76% yield (2.50 g).

Step IV: 2-Methylisonicotinic acid (0.392 g, 2.858 mmol) and HATU (1.09 g, 2.858 mmol) were dissolved in a DCM/DMF mixture (total 10 mL, 1:1). DIPEA (0.671 mL, 4.083 mmol) was added and the reaction was stirred for 10 min before adding to a solution of tert-butyl (R)-3-(2-amino-7-((1-((benzyloxy)carbonyl)piperidin-4-yl)oxy)-1H-benzo[d]imidazol-1-yl)azepane-1-carboxylate (1.15 g, 2.04 mmol) in DCM/DMF (10 mL, 1:1). After one hour of stirring, the reaction was stripped off solvents. The residue was dissolved in EtOAc (200 mL). The organic solution was washed with NaOH aq. (1N, 40 mL×3), brine (40 mL), dried ((1-acetylpiperidin-4-yl)oxy)-2-(2-methylisonicotinamido)-1H-benzo[d]imidazol-1-yl)azepane-1-carboxylate 2' is shown in Scheme 3.

Step I: Tert-butyl (R)-3-(7-((1-((benzyloxy)carbonyl)piperidin-4-yl)oxy)-2-(2-methylisonicotinamido)-1H-benzo[d]imidazol-1-yl)azepane-1-carboxylate 4 (1.2 g, 1.757 mmol) and Pd/C (0.1 g, 10% Pd on carbon) were stirred in EtOAc/methanol mixture (1:1, 20 mL) under hydrogen atmosphere for 3 hrs. The reaction was filtered through celite and the filtrate was concentrated to afford tert-butyl (R)-3-(2-(2-methylisonicotinamido)-7-(piperidin-4-yloxy)-1H-benzo[d]imidazol-1-yl)azepane-1-carboxylate 3 in 78% yield (0.96 g).

Scheme 3

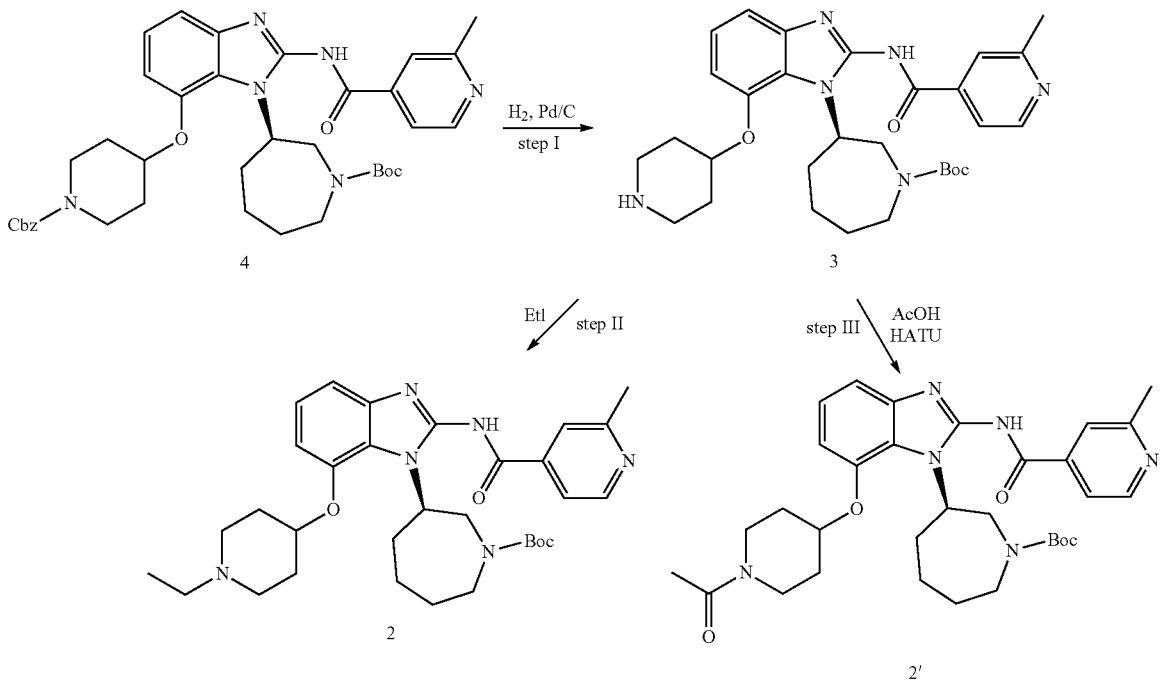

with Na₂SO₄, and concentrated. The residue obtained was purified on a silica gel column (0-2% methanol in DCM) to afford 1.2 g (86%) of tert-butyl (R)-3-(7-((1-((benzyloxy)carbonyl)piperidin-4-yl)oxy)-2-(2-methylisonicotinamido)-1H-benzo[d]imidazol-1-yl)azepane-1-carboxylate 4.

Example 3

Synthesis of tert-butyl (R)-3-(7-((1-ethylpiperidin-4-yl)oxy)-2-(2-methylisonicotinamido)-1H-benzo[d]imidazol-1-yl)azepane-1-carboxylate 2 and tert-butyl (R)-3-(7-((1-acetylpiperidin-4-yl)oxy)-2-(2-methylisonicotinamido)-1H-benzo[d]imidazol-1-yl)azepane-1-carboxylate 2'

The synthesis of tert-butyl (R)-3-(7-((1-ethylpiperidin-4-yl)oxy)-2-(2-methylisonicotinamido)-1H-benzo[d]imidazol-1-yl)azepane-1-carboxylate 2 and tert-butyl (R)-3-(7-

Step II: Ethyl iodide (30.66 μL) was dissolved in 1 mL of DMA and 0.1 mL of this solution was added to a suspension of tert-butyl (R)-3-(2-(2-methylisonicotinamido)-7-(piperidin-4-yloxy)-1H-benzo[d]imidazol-1-yl)azepane-1-carboxylate 3 (20 mg, 0.0365 mmol) and Na₂CO₃ (6.8 mg, 0.064 mmol) in 1 mL of DMA. The reaction was stirred at room temperature for 2 days, filtered through celite, and washed with ethanol. Then the filtrate was stripped off solvents to afford tert-butyl (R)-3-(7-((1-ethylpiperidin-4-yl)oxy)-2-(2-methylisonicotinamido)-1H-benzo[d]imidazol-1-yl)azepane-1-carboxylate 2 (21 mg). LC/MS showed retention time of 0.43 min (HPLC column: 2.1×30 mm, 1.7 μm c18; Eluent: 1-99% ACN in water with 5 mM HCl; 1 min run; solvent flow rate: 12 mL/min) and correct mass (M+1 calculated for Chemical Formula $C_{32}H_{44}N_6O_4$ is 577.34, observed 577.6). The compound was directly used in the next step of reaction without purification.

Step III: Acetic acid (0.185 mmol, 11.1 mg) and HATU (0.185 mmol, 70.3 mg) were mixed in DMA (1 mL), followed by addition of DIPEA (47.7 mg, 0.37 mmol). After five minutes of stirring, the reaction was transferred to a solution of tert-butyl (R)-3-(2-(2-methylisonicotinamido)-7-(piperidin-4-yloxy)-1H-benzo[d]imidazol-1-yl)azepane-1-carboxylate 3 (94.2 mg, 0.1718 mmol) in DMA (1 mL). The reaction was further stirred for 1 hr, then filtered, and purified by HPLC (column 75×30 mm, 5 μm c18, 1-99% ACN in water with 5 mM HCl, mass triggered collection) to yield tert-butyl (R)-3-(7-((1-acetylpiperidin-4-yl)oxy)-2-(2-methylisonicotinamido)-1H-benzo[d]imidazol-1-yl) azepane-1-carboxylate 2' in 51 mg.

Example 4

Synthesis of (R)—N-(1-(azepan-3-yl)-7-(piperidin-4-yloxy)-1H-benzo[d]imidazol-2-yl)-2-methylisonicotinamide 1"

The synthesis of (R)—N-(1-(azepan-3-yl)-7-(piperidin-4-yloxy)-1H-benzo[d]imidazol-2-yl)-2-methylisonicotinamide 1" is shown in Scheme 4.

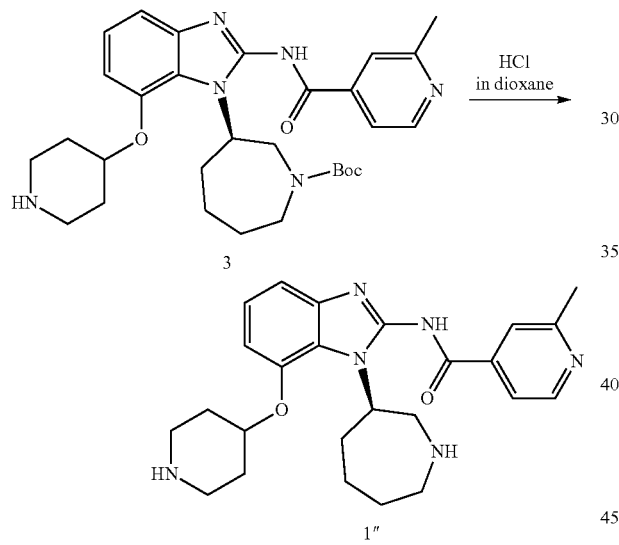

Tert-butyl (R)-3-(2-(2-methylisonicotinamido)-7-(piperidin-4-yloxy)-1H-benzo[d]imidazol-1-yl)azepane-1-carboxylate (50 mg, 0.091 mmol) was dissolved in 1 mL of MeOH. A solution of 4M HCl in dioxane (3 mL, 12 mmol) was added. The reaction was stirred at room temperature for 5 hrs and then HCl and solvents were stripped. The residue obtained, a HCl salt of (R)—N-(1-(azepan-3-yl)-7-((1-ethylpiperidin-4-yl)oxy)-1H-benzo[d]imidazol-2-yl)-2-methylisonicotinamide, was directly used in the next step of reaction without further treatment.

Example 5

Synthesis of (R)—N-(7-((1-acetylpiperidin-4-yl) oxy)-1-(azepan-3-yl)-1H-benzo[d]imidazol-2-yl)-2-methylisonicotinamide 1'

The synthesis of (R)—N-(7-((1-acetylpiperidin-4-yl) oxy)-1-(azepan-3-yl)-1H-benzo[d]imidazol-2-yl)-2-methylisonicotinamide 1' is shown in Scheme 5.

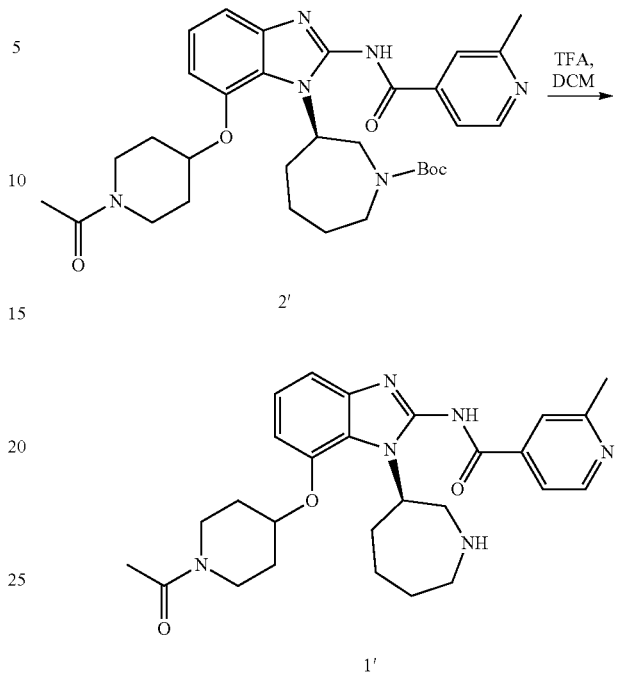

Tert-butyl (R)-3-(7-((1-acetylpiperidin-4-yl)oxy)-2-(2-methylisonicotinamido)-1H-benzo[d]imidazol-1-yl) azepane-1-carboxylate 2' (51 mg, 0.086 mmol) was dissolved in DCM. Trifluoroacetic acid (0.5 mL) was added and the reaction was stirred at room temperature for 1 hr. The solvents were stripped. The residue obtained was dissolved in 150 mL of a solvent (1:2 volume ratio of IPA:DCM) and washed with aq. NaHCO₃ (15 mL), brine (20 mL), dried with Na₂SO₄, filtered, and concentrated to yield (R)—N-(7-((1-acetylpiperidin-4-yl)oxy)-1-(azepan-3-yl)-1H-benzo[d] imidazol-2-yl)-2-methylisonicotinamide 1' in 52 mg.

Example 6

Synthesis of (R)—N-(1-(azepan-3-yl)-7-((1-ethylpiperidin-4-yl)oxy)-1H-benzo[d]imidazol-2-yl)-2-methylisonicotinamide 1

The synthesis of (R)—N-(1-(azepan-3-yl)-7-((1-ethylpiperidin-4-yl)oxy)-1H-benzo[d]imidazol-2-yl)-2-methylisonicotinamide 1 is shown in Scheme 6.

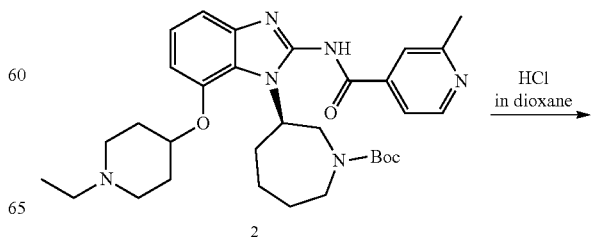

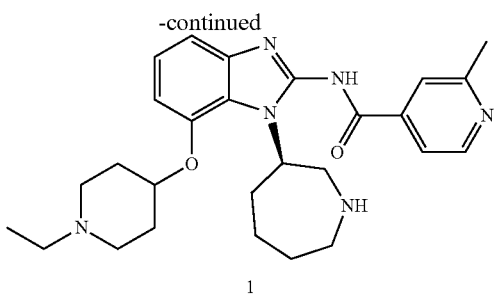

1

A HCl salt of (R)—N-(1-(azepan-3-yl)-7-((1-ethylpiperidin-4-yl)oxy)-1H-benzo[d]imidazol-2-yl)-2-methylisonicotinamide 1 (23 mg) was prepared from compound 2, following the synthetic procedures of compound 1". LC/MS showed retention time of 0.45 min (HPLC column: 2.1×30 mm, 1.7 μm c18; Eluent: 1-99% ACN in water with 5 mM HCl; 1 min run; solvent flow rate: 12 mL/min) and correct mass (M+1 expected: 477.29, observed 477.6).

Example 7

Synthesis of (R)—N-(7-((1-acetylpiperidin-4-yl)oxy)-1-(1-acryloylazepan-3-yl)-1H-benzo[d]imidazol-2-yl)-2-methylisonicotinamide A2

The synthesis of (R)—N-(7-((1-acetylpiperidin-4-yl)oxy)-1-(1-acryloylazepan-3-yl)-1H-benzo[d]imidazol-2-yl)-2-methylisonicotinamide A2 is shown in Scheme 7.

Scheme 7

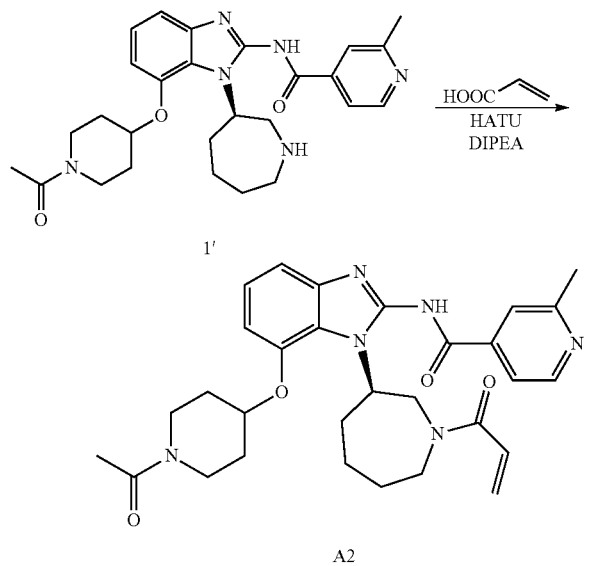

Acrylic acid (0.127 mmol, 9.1 mg) and HATU (48.4 mg, 0.127 mmol) were mixed in DMA (1 mL), followed by addition of DIPEA (0.212 mmol, 27.4 mg). After 5 minutes of stirring, the mixture was transferred into a solution of (R)—N-(7-((1-acetyl-piperidin-4-yl)oxy)-1-(azepan-3-yl)-1H-benzo[d]imidazol-2-yl)-2-methylisonicotinamide 1' (52 mg, 0.106 mmol) in DMA (1 mL). The reaction was further stirred for 1 hr and then was stripped off DMA, directly dry-loaded onto a silica gel column, and eluted with 1-10% MeOH in DCM. The expected product was isolated in 33 mg. LC/MS showed the correct mass of M+1=545.5 (calculated to be 545.28 for $C_{30}H_{36}N_6O_4$) with Rt=0.42 min (HPLC column: 2.1×30 mm, 1.7 m c18; Eluent: 1-99% ACN in water with 5 mM HCl; 1 min run; solvent flow rate: 12 mL/min). $^1$H NMR (400 MHz, chloroform-d) δ 12.59 (s, 1H), 8.68 (dd, J=15.1, 4.7 Hz, 1H), 7.96 (d, J=13.2 Hz, 1H), 7.88 (dd, J=12.1, 5.3 Hz, 1H), 7.27-7.11 (m, 1H), 6.99 (dd, J=19.6, 8.1 Hz, 1H), 6.93-6.74 (m, 1H), 6.65 (dt, J=16.5, 11.4 Hz, 1H), 6.53-6.21 (m, 1H), 5.83-5.64 (m, 1H), 5.55 (q, J=10.6, 8.5 Hz, 1H), 4.81 (d, J=7.4 Hz, 2H), 4.63-4.33 (m, 2H), 4.04 (t, J=15.4 Hz, 1H), 3.91 (h, J=8.6, 7.8 Hz, 2H), 3.85-3.59 (m, 3H), 3.59-3.10 (m, 5H), 2.69 (d, J=3.7 Hz, 5H), 2.35-1.68 (m, 13H), 1.37 (t, J=13.0 Hz, 1H).

Example 8

Synthesis of (R)—N-(1-(1-acryloylazepan-3-yl)-7-((1-acryloylpiperidin-4-yl)oxy)-1H-benzo[d]imidazol-2-yl)-2-methylisonicotinamide A3

The synthesis of (R)—N-(1-(1-acryloylazepan-3-yl)-7-((1-acryloylpiperidin-4-yl)oxy)-1H-benzo[d]imidazol-2-yl)-2-methylisonicotinamide A3 is shown in Scheme 8.

Scheme 8

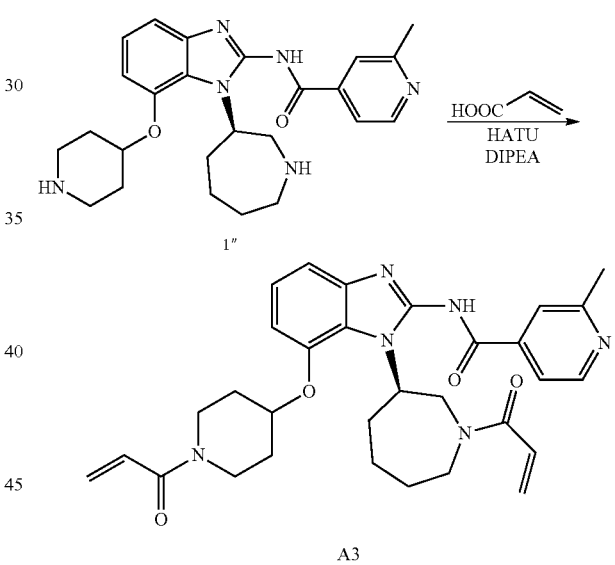

Acrylic acid (0.2 mmol, 14.4 mg) and HATU (76.1 mg, 0.20 mmol) were mixed in DMA (1 mL), followed by addition of DIPEA (0.575 mmol, 74.2 mg). After 5 minutes of stirring, the mixture was transferred into a solution of (R)—N-(1-(azepan-3-yl)-7-(piperidin-4-yloxy)-1H-benzo[d]imidazol-2-yl)-2-methylisonicotinamide (0.091 mmol) in DMA (1 mL). The reaction was further stirred for 1 hr and then was stripped off DMA, directly dry-loaded onto silica gel column, and eluted with 1-10% MeOH in DCM. The expected product was isolated in 17 mg. LC/MS showed the correct mass of M+1=557.5 (calculated to be 557.28 for $C_{31}H_{36}N_6O_4$) with Rt=0.45 min (HPLC column: 2.1×30 mm, 1.7 mm c18; Eluent: 1-99% ACN in water with 5 mM HCl; 1 min run; solvent flow rate: 12 mL/min). $^1$H NMR (400 MHz, chloroform-d), δ 12.57 (s, 1H), 8.70 (t, J=4.9 Hz, 1H), 8.66 (dd, J=4.4, 1.4 Hz, 1H), 8.31 (dd, J=8.4, 1.4 Hz, 1H), 8.10-7.91 (m, 1H), 7.33 (dd, J=8.4, 4.4 Hz, 1H), 7.27-7.15 (m, 1H), 7.03 (m, 0.3H), 6.99 (d, J=8.0 Hz, 0.7H), 6.88-6.82 (m, 03H), 6.78 (d, J=8.4 Hz, 0.7H), 6.69-6.58 (m, 1H), 6.47-6.19 (m, 1H), 5.84-5.63 (m, 2H), 5.62-5.45 (m, 1H), 4.80 (br s, 1H), 4.60-4.33 (m, 1H), 4.29-3.29 (m, 7H), 3.18 (q, J=7.4 Hz, 1H), 2.75 (s, 2.1H), 2.73 (, 0.9H), 1.57-1.09 (m, 7H).

Example 9

Synthesis of (R)—N-(1-(1-Acryloylazepan-3-yl)-7-chloro-5-(trifluoromethoxy)-1H-benzo[d]imidazol-2-yl)-2-methylisonicotinamide A4

The synthesis of (R)—N-(1-(1-Acryloylazepan-3-yl)-7-chloro-5-(trifluoromethoxy)-1H-benzo[d]imidazol-2-yl)-2-methylisonicotinamide A4 is shown in Scheme 9.

A solution of 2-nitro-4-trifluoromethoxy-aniline 21 (40.0 g, 0.180 mol) and N-chlorosuccinimide (30.0 g, 0.225 mol) in ACN (300 mL) was heated at 70° C. for 4 hrs. The mixture was then cooled down to room temperature and diluted with saturated NH$_4$Cl solution (600 mL) and ethyl acetate (600 mL). The organic layer was washed with water (200 mL) and dried over Na$_2$SO$_4$. Evaporation of solvent under reduced pressure gave a dark orange solid, which on trituration with hexane gave 2-chloro-6-nitro-4-(trifluoromethoxy)-aniline 22 as an orange solid in 50% yield (23.0 g). $^1$H NMR (400 MHz, chloroform-d) δ 8.03 (dq, J=2.7, 0.9 Hz, 1H), 7.52-7.46 (m, 1H), 6.60 (s, 2H).

To a suspension of copper (II) chloride (12.6 g, 93.5 mmol) and t-butyl nitrite (13.9 mL, 117 mmol) in anhydrous ACN (100 mL) at 61° C. was added a solution of 2-chloro-6-nitro-4-(trifluoromethoxy)aniline 22 (20.0 g, 78.0 mmol) in acetonitrile (100 mL) dropwise. The mixture was stirred at 61° C. for 1 hr after the addition. The solvent was removed, and the residue was treated with 4N HCl (350 mL) and extracted with EtOAc (150 mL×3). The extracts were combined, dried over Na$_2$SO$_4$, and purified by silica gel chromatography (hexane: EtOAc from 20:1 to 10:1) to afford compound 23 in 67% yield (14.5 g) as orange oil. $^1$H NMR (400 MHz, Chloroform-d) 7.61 (dq, J=1.7, 0.8 Hz, 1H), 7.60 (dq, J=2.7, 0.9 Hz, 1H).

Compound 24 was prepared following the procedures in step I of Example 2. $^1$H NMR (400 MHz, chloroform-d) δ 7.98-7.77 (m, 1H), 7.46 (d, J=21.0 Hz, 1H), 7.11 (d, J=9.6 Hz, 0.5H), 6.61 (d, J=10.3 Hz, 0.5H), 4.28 (m, 0.5H), 4.08 (br s, 0.5H), 3.85-3.42 (m, 2.7H), 3.26-3.00 (m, 1.3H), 2.01-1.76 (m, 1.7H), 1.78-1.59 (m, 2.8H), 1.54-1.30 (m, 1.54H), 1.45 (s, 5.3H), 1.39 (s, 3.7H).

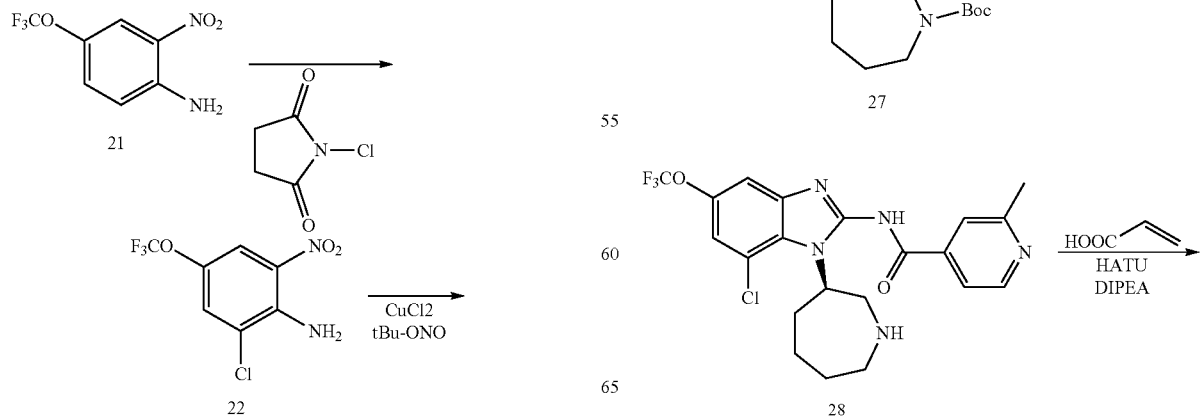

Scheme 9

-continued

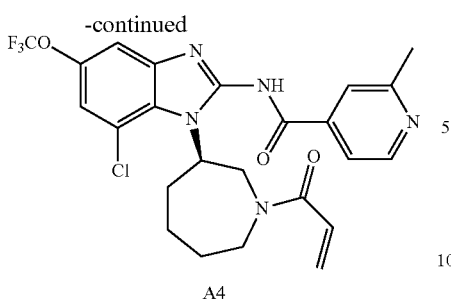

A4

Compound 25 was prepared following the procedures in step II of Example 2.

Compound 26 was prepared following the procedures in step III of Example 2. MS calculated for titled compound (M+1+) 449.15; observed 449.4 with HPLC retention time 0.59 min.

Compound 27 was prepared following the procedures in step IV of Example 2.

Compound 28 was prepared following the procedures in Example 5.

(R)—N-(1-(1-Acryloylazepan-3-yl)-7-chloro-5-(trifluoromethoxy)-1H-benzo[d]imidazol-2-yl)-2-methylisonicotinamide A4 was prepared following the procedures in Example 7 or 8. MS observed for $C_{24}H_{23}ClF_3N_5O_3$ (M+H+): 522.3; HPLC retention time: 0.55 min. $^1$H NMR (400 MHz, acetonitrile-$d_3$) 312.65 (s, 1H), 8.62 (t, J=5.8 Hz, 1H), 8.49-8.42 (m, 1H), 8.40-8.33 (m, 1H), 7.60-7.49 (m, 1H), 7.38-7.28 (m, 1H), 6.78 (ddd, J=16.7, 13.2, 10.4 Hz, 1H), 6.27 (ddd, J=16.7, 10.0, 2.3 Hz, 1H), 5.78-5.47 (m, 2H), 4.65 (ddd, J=19.1, 14.0, 10.4 Hz, 1H), 4.29-3.89 (m, 2H), 3.84-3.67 (m, 1H), 2.95 (two singlets, total 3H), 2.73-2.60 (m, 2H), 2.19-2.00 (m, 2H), 1.55-1.46 (m, 2H).

Example 10

Synthesis of Compounds A1 and A5

Compounds A1 and A5 were prepared following the procedures as described in Examples 7 and 8.

(R)—N-(1-(1-Acryloylazepan-3-yl)-7-((1-ethylpiperidin-4-yl)oxy)-1H-benzo[d]imidazol-2-yl)-2-methylisonicotinamide A1

MS observed for $C_{30}H_{38}N_6O_3$ (M+H+): 531.4; HPLC retention time: 0.33 min.

(R,E)-N-(7-Chloro-1-(1-(4-(dimethylamino)but-2-enoyl)azepan-3-yl)-5-(trifluoromethoxy)-1H-benzo[d]imidazol-2-yl)-2-methylisonicotinamide A5

MS observed for $C_{27}H_{30}ClF_3N_6O_3$ (M+H+): 579.3; HPLC retention time: 0.44 min. $^1$H NMR (400 MHz, methanol-$d_4$) 38.85 (dd, J=6.1, 2.0 Hz, 1H), 8.56-8.43 (m, 2H), 7.60-7.51 (m, 1H), 7.43-7.35 (m, 1H), 7.12-6.99 (m, 1H), 6.80 (dtd, J=14.8, 7.2, 3.2 Hz, 1H), 5.78-5.51 (m, 1H), 4.79-4.68 (m, 1H), 4.38-4.15 (m, 2H), 4.02 (d, J=7.2 Hz, 2H), 3.97-3.77 (m, 2H), 2.96 and 2.91 (two singlets, total 9H), 2.28-1.94 (m, 5H), 1.59-1.46 (m, 1H).

Example 11

Synthesis of N-(1-((R)-1-acryloylazepan-3-yl)-7-chloro-6-((2-oxopyrrolidin-3-yl)oxy)-1H-benzo[d]imidazol-2-yl)-2-methylisonicotinamide C1

The synthesis of N-(1-((R)-1-acryloylazepan-3-yl)-7-chloro-6-((2-oxopyrrolidin-3-yl)oxy)-1H-benzo[d]imidazol-2-yl)-2-methylisonicotinamide C1 is shown in Scheme 10.

Step I: A mixture of tert-butyl (R)-3-(6-(benzyloxy)-7-chloro-2-(2-methylisonicotinamido)-1H-benzo[d]imidazol-1-yl)azepane-1-carboxylate 31 (1.1 g) and 10% Pd/C (0.194 g) in MeOH (5 mL) was purged by vacuume and then filled with hydrogen from a balloon. The reaction mixture was stirred under hydrogen at room temperature for 4 hrs. The catalyst Pd/C was filtered through a pad of celite and the pad was washed with MeOH. The combined solution was concentrated to afford compound 32 in a quantitative yield (932 mg).

Step II: To a solution of 3-hydroxy-pyrrolidin-2-one (200 mg, 1.97 mmol) in DCM (5 mL) was added Ms$_2$O (539 mg, 3.1 mmol) and pyridine (2 mL) at 0° C. The reaction mixture was stirred at 0° C. for 20 min and then overnight at room temperature. The reaction mixture was concentrated under reduced pressure. The residue was dissolved in isopropanol/CHCl$_3$ (1:3; 40 mL), washed with saturated NaHCO$_3$, dried over anhydrous Na$_2$SO$_4$, and evaporated to dryness under reduced pressure to afford 2-oxopyrrolidin-3-yl methanesulfonate 33 in 38% yield (137 mg).

Scheme 10

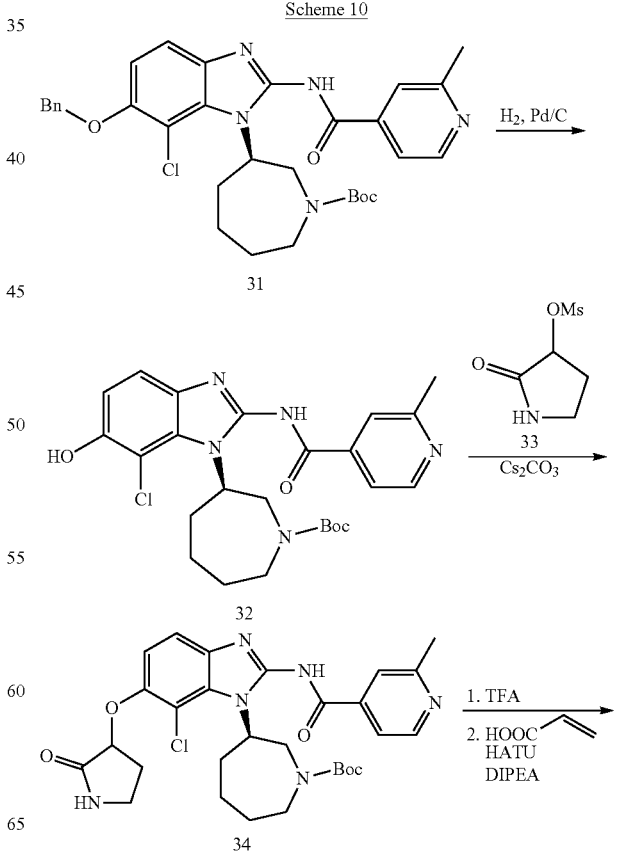

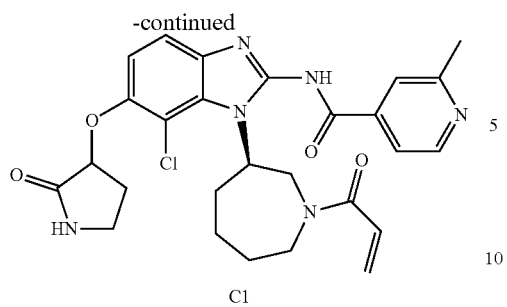

C1

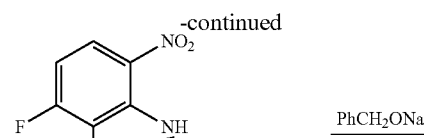

To a solution of compound 32 (200 mg, 0.4 mmol) in DMF (2 mL) under N$_2$ was added Cs$_2$CO$_3$ (98 mg, 0.6 mmol) and compound 33 (108 mg, 0.6 mmol). The reaction mixture was stirred at 55° C. overnight. After the mixture was cooled down to room temperature, saturated NH$_4$Cl (10 mL) was added. The reaction mixture was extracted with isopropanol/CHCl$_3$ (1:3; 3×30 mL). The organic phase was washed with brine, dried over anhydrous Na$_2$SO$_4$, concentrated under reduced pressure, and purified by column chromatography on silica gel with DCM:MeOH (100:0 to 90:10) to afford tert-butyl (3R)-3-(7-chloro-2-(2-methylisonicotinamido)-6-((2-oxopyrrolidin-3-yl)oxy)-1H-benzo[d]imidazol-1-yl)azepane-1-carboxylate 34. MS observed for C$_{29}$H$_{35}$ClN$_6$O$_5$: 583.2 (M+H$^+$); HPLC retention time: 7.72 min.

Step III: To a solution of acrylic acid (20.4 mg, 0.28 mmol) in DMA (1 mL) under N$_2$ at −20° C. was added HATU (107 mg, 0.28 mmol) and DIPEA (61 mg, 0.47 mmol). After stirred at 0° C. for 20 min, the mixture was added to a solution of compound 34 (120 mg, 0.25 mmol) in DMA (1 mL). After stirred at room temperature for 2 hrs, the reaction mixture was diluted with isopropanol/CHCl$_3$ (1:3; 60 mL), washed with 1N NaOH (2×20 mL), dried over anhydrous Na$_2$SO$_4$, concentrated under reduced pressure, and purified by column chromatography on silica gel with DCM; MeOH (100:0 to 90:10) to afford N-(1-((R)-1-acryloylazepan-3-yl)-7-chloro-6-((2-oxopyrrolidin-3-yl)oxy)-1H-benzo[d]imidazol-2-yl)-2-methylisonicotinamide C1 in 15.5% yield (20 mg) for the last 2 steps. $^1$H NMR (400 MHz, CDCl$_3$): δ 12.7 (bs, 1H), 8.64 (m, 1H), 7.90-7.93 (m, 1H), 7.81-7.84 (m, 1H), 7.34-7.40 (m, 1H), 7.17-7.23 (m, 1H), 6.64 (m, 1H), 6.37-6.43 (m, 1H), 5.96 (s, 1H), 5.67-5.75 (m, 1H), 4.74-4.88 (m, 2H), 4.41-4.58 (m, 1H), 3.83-4.23 (m, 2H), 3.40-3.64 (m, 4H), 1.45-2.79 (m, 10H); MS observed for C$_{27}$H$_{29}$ClN$_6$O$_4$: 537.7 (M+H$^+$); HPLC retention time: 4.92 min.

Compounds 31 was prepared according to Scheme 11 and Example 17.

Scheme 11

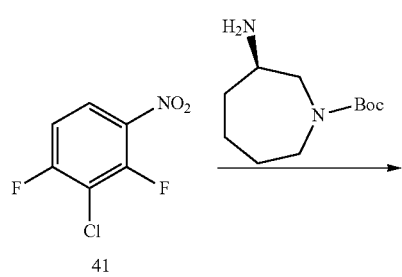

41

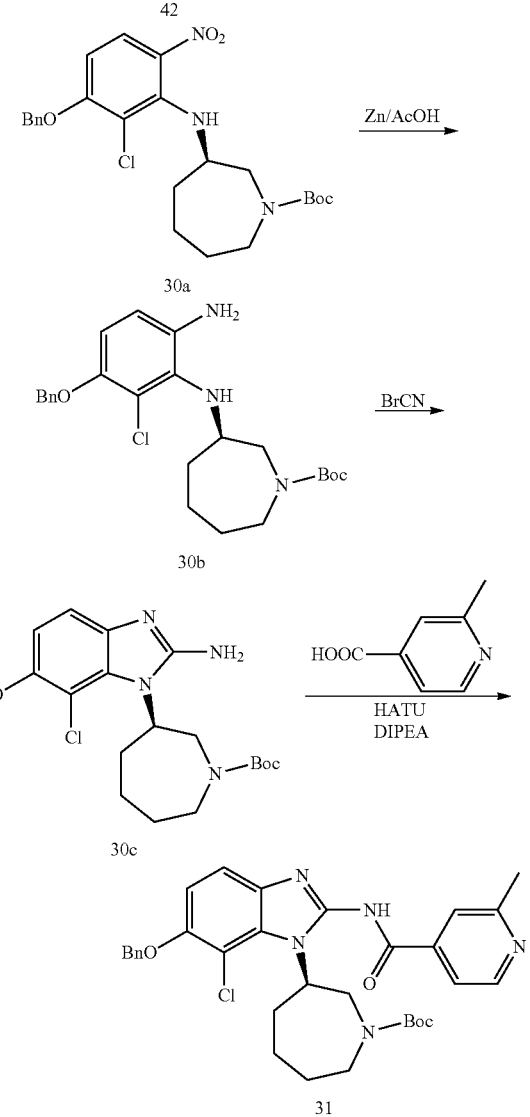

Example 12

Synthesis of N-(1-((R)-1-acryloylazepan-3-yl)-7-chloro-6-(((tetrahydrofuran-3-yl)oxy)-1H-benzo[d]imidazol-2-yl)-2-methylisonicotinamide C2

The synthesis of N-(1-((R)-1-acryloylazepan-3-yl)-7-chloro-6-(((tetrahydrofuran-3-yl)oxy)-1H-benzo[d]imidazol-2-yl)-2-methylisonicotinamide C2 is shown in Scheme 12.

Step I: To a solution of 3-hydroxytetrahydrofuran (200 mg, 1.55 mmol) in DCM (5 mL) was added Ms$_2$O (539 mg, 3.10 mmol) and pyridine (367 mg, 4.65 mmol) at −10° C. After stirred at room temperature overnight, the reaction mixture was diluted with DCM (10 mL), washed with saturated NaHCO$_3$, dried over anhydrous Na$_2$SO$_4$, and evaporated to dryness under reduced pressure to afford tetrahydrofuran-3-yl methanesulfonate 35 in 89% yield (285 mg).

Scheme 12

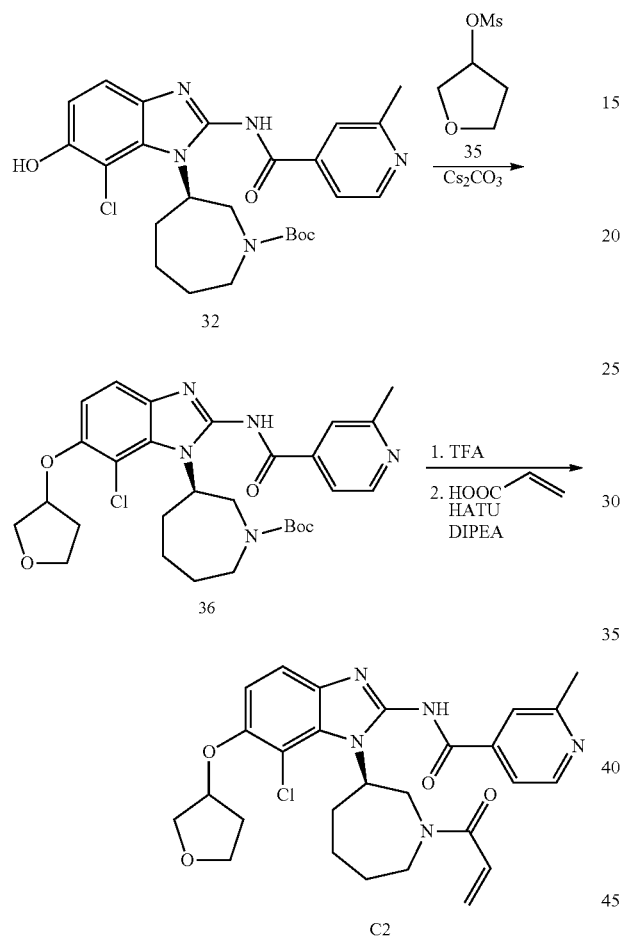

The conversion from compound 32 to compound 36 was performed according to the procedures as described in Example 11. (3R)-Tert-butyl 3-(7-chloro-2-(2-methylisonicotinamido)-6-((tetrahydrofuran-3-yl)oxy)-1H-benzo[d]imidazol-1-yl)azepane-1-carboxylate 36: MS calculated for C$_{29}$H$_{36}$ClN$_5$O$_5$: 570.6 (M+H$^+$); HPLC retention time: 8.39 min.

Step II: The coversion from compound 36 to compound C2 was performed according to the procedures as described in Example 11. N-(1-((R)-1-Acryloylazepan-3-yl)-7-chloro-6-(((tetrahydrofuran-3-yl)oxy)-1H-benzo[d]imidazol-2-yl)-2-methylisonicotinamide C2: $^1$H NMR (400 MHz, CDCl$_3$): δ 12.7 (m, 1H), 8.64 (m, 1H), 7.90-7.93 (m, 1H), 7.81-7.83 (m, 1H), 7.14-7.21 (m, 1H), 6.60-6.66 (m, 1H), 6.36-6.43 (m, 1H), 5.60-5.88 (m, 2H), 4.96-4.99 (m, 1H), 4.41-4.58 (m, 1H), 3.84-4.08 (m, 6H), 3.42-3.68 (m, 1H), 1.49-2.79 (m, (m, 13H); MS observed for C$_{27}$H$_{30}$ClN$_5$O$_4$: 524.1 (M+H$^+$); HPLC retention time: 7.14 min.

Example 13

Synthesis of (R)—N-(1-(1-acryloylazepan-3-yl)-7-chloro-6-((tetrahydro-2H-pyran-4-yl)oxy)-1H-benzo[d]imidazol-2-yl)-2-methylisonicotinamide C3

Compound C3 was prepared according to the procedures as described in Example 12. MS observed for C$_{28}$H$_{32}$ClN$_5$O$_4$: 538.6 (M+H$^+$); HPLC retention time: 2.09 min.

Example 14

Synthesis of (R)—N-(1-(1-acryloylazepan-3-yl)-7-chloro-6-((tetrahydro-2H-pyran-4-yl)oxy)-1H-benzo[d]imidazol-2-yl)-2-(trifluoromethyl)isonicotinamide C4

Compound C4 was prepared according to the procedures as described in Example 12. MS observed for C$_{28}$H$_{29}$ClF$_3$N$_5$O$_4$: 592.1 (M+H$^+$); HPLC retention time: 2.14 min.

Example 15

Synthesis of (R)—N-(1-(1-acryloylazepan-3-yl)-7-chloro-6-((1,1-dioxidotetrahydro-2H-thiopyran-4-yl)oxy)-1H-benzo[d]imidazol-2-yl)-2-methylisonicotinamide C5

Compound C5 was prepared according to the procedures as described in Example 12. MS observed for C$_{28}$H$_{32}$ClN$_5$O$_5$S: 586.0 (M+H$^+$); HPLC retention time: 1.94 min.

Example 16

Synthesis of (R)—N-(1-(1-acryloylazepan-3-yl)-7-chloro-6-(pyrimidin-4-yloxy)-1H-benzo[d]imidazol-2-yl)-2-methylisonicotinamide C6

The synthesis of (R)—N-(1-(1-acryloylazepan-3-yl)-7-chloro-6-(pyrimidin-4-yloxy)-1H-benzo[d]imidazol-2-yl)-2-methylisonicotinamide C6 is shown in Scheme 13.

Scheme 13

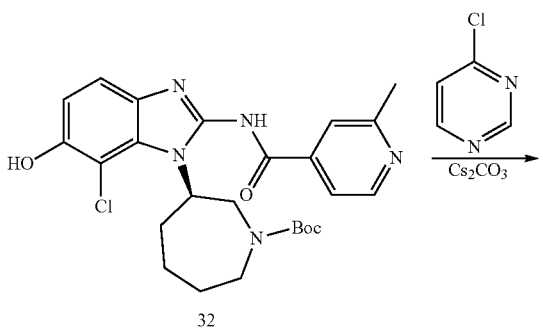

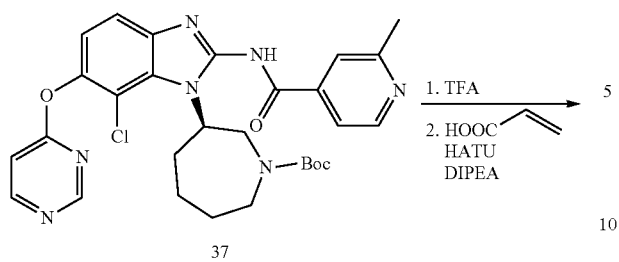

37

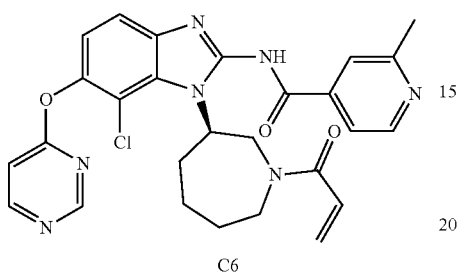

C6

Step I: To a solution of compound 32 (200 mg, 0.4 mmol) in DMF (2 mL) was added Cs$_2$CO$_3$ (99 mg, 0.6 mmol) and 2-chloropyrazine (90 mg, 0.6 mmol). After stirred at 55° C. overnight, the reaction mixture was cooled down to room temperature and saturated NH$_4$Cl (10 mL) was added. The mixture was extracted with isopropanol/CHCl$_3$ (1:3; 3×30 mL). The organic phase was washed with brine, dried over anhydrous Na$_2$SO$_4$, concentrated under reduced pressure, and purified by column chromatography on silica gel using DCM:MeOH (100:0 to 90:10) to afford compound 37 in 30% yield (70 mg) HPLC retention time: 8.15 min.

Step II: The conversion from compound 37 to compound C6 was performed according to the procedures as described in Example 11. MS observed for C$_{27}$H$_{26}$ClN$_7$O$_3$: 532.27 (M+H$^+$); HPLC retention time: 7.01 min.

Example 17

Synthesis of (R)-tert-butyl 3-(2-amino-7-chloro-6-(((R)-tetrahydrofuran-3-yl)oxy)-1H-benzo[d]imidazol-1-yl)azepane-1-carboxylate 45

The synthesis of ((R)-tert-butyl 3-(2-amino-7-chloro-6-(((R)-tetrahydrofuran-3-yl)oxy)-1H-benzo[d]imidazol-1-yl) azepane-1-carboxylate 45 is shown in Scheme 14

Scheme 14

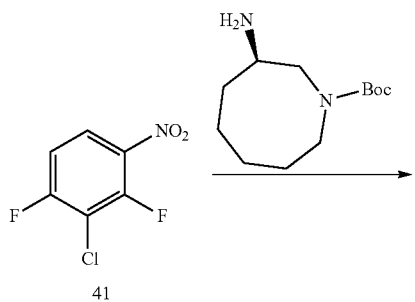

41

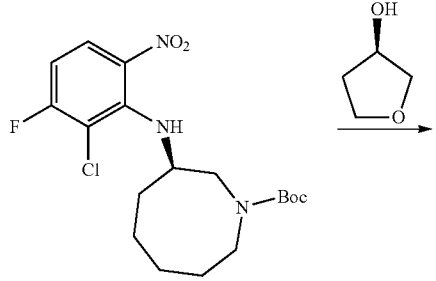

42

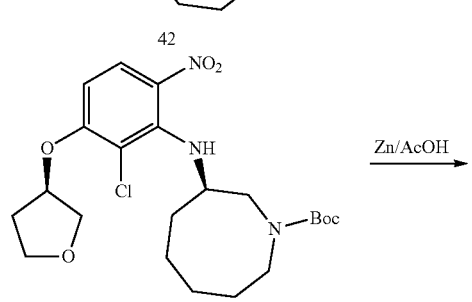

43

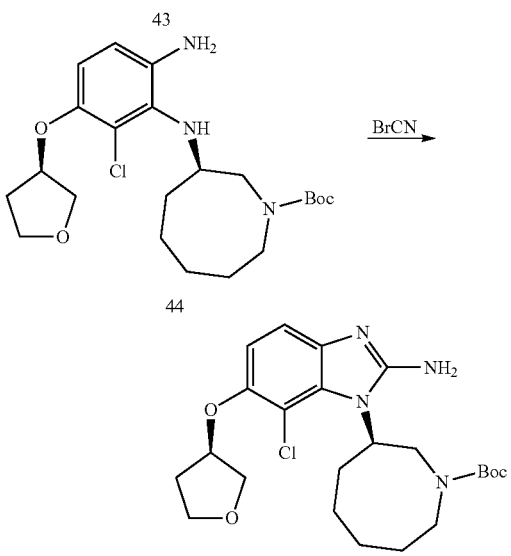

Step I: A solution of 2-chloro-1,3-difluoro-4-nitrobenzene 41 (3.29 g, 16.99 mmol) and tert-butyl (R)-3-aminoazepane-1-carboxylate (4.0 g, 18.69 mmol) in DME (80 mL) was stirred at 85° C. for 4 hrs. The reaction was quenched with water (100 mL) and extracted with EtOAc (3×100 mL). The organic layers were combined and dried over anhydrous Na$_2$SO$_4$. The solvent was removed under reduced pressure and the residue was purified by flash chromatography on silica (eluent PE/EtOAc=10:1-5:1) to afford compound 42 in 85% yield (5.6 g). TLC R$_f$=0.5 (PE/EtOAc=5:1, UV 254 nm).

Step II: To a solution of (R)-3-hydroxyltetrahedrofuran (1.82 g, 20.63 mmol) in DME (100 mL) at 0° C. was added NaHMDS (10.83 mL, 2 M in THF, 21.66 mmol) dropwise. After stirred at 0° C. for 15 min, the mixture was then added dropwise to a solution of tert-butyl (R)-3-((2-chloro-3-fluoro-6-nitrophenyl)amino)azepane-1-carboxylate 42 (4.0 g, 10.31 mmol) in DME (50 mL) at 0° C. The reaction mixture was heated at 50° C. for 2 hrs. After the mixture was cooled to 0° C., ice water (100 mL) was added and extracted with EtOAc (3×200 mL). The organic layers were combined and dried over anhydrous $Na_2SO_4$. The solvent was removed under reduced pressure and the residue was purified by flash chromatography on silica (eluent PE/EtOAc=10:1-2:1) to afford tert-butyl (R)-3-((2-chloro-6-nitro-3-(((R)-tetrahydrofuran-3-yl)oxy)phenyl)amino)azepane-1-carboxylate 43 in 61% yield (2.88 g). TLC $R_f$=0.35 (PE/EtOAc=2:1, UV 254 nm).

Step III: The conversion from compound 43 to compound 45 was carried out according to the procedures as described in Example 2 and Scheme 2.

Example 18

Synthesis of N-(1-((R)-1-acryloylazepan-3-yl)-7-chloro-6-(((R)-tetrahydrofuran-3-yl)oxy)-1H-benzo[d]imidazol-2-yl)-2-methylisonicotinamide C7

The synthesis of N-(1-((R)-1-acryloylazepan-3-yl)-7-chloro-6-(((R)-tetrahydrofuran-3-yl)oxy)-1H-benzo[d]imidazol-2-yl)-2-methylisonicotinamide C7 is shown in Scheme 15.

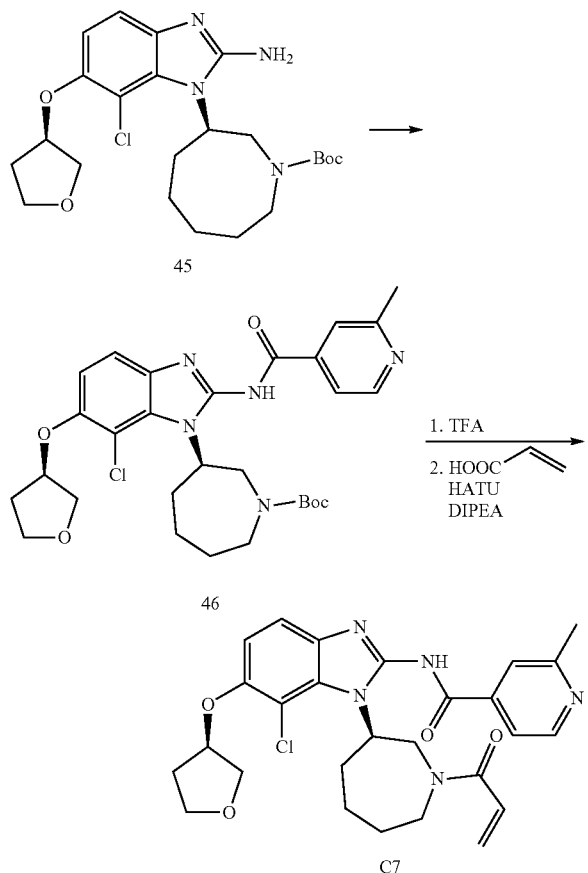

The conversion from compound 45 to compound 46 was performed according to the procedures as described Example 2 and Scheme 2. The conversion from compound 46 to compound C7 were performed according to the procedures as described in Example 11. N-(1-((R)-1-Acryloylazepan-3-yl)-7-chloro-6-(((R)-tetrahydrofuran-3-yl)oxy)-1H-benzo[d]imidazol-2-yl)-2-methylisonicotinamide C7. MS observed for $C_{27}H_{30}ClN_5O_4$: 524.6 (M+H$^+$); HPLC retention time: 2.14 min.

Example 19

Synthesis of N-(1-((R)-1-acryloylazepan-3-yl)-7-chloro-6-(((R)-tetrahydrofuran-3-yl)oxy)-1H-benzo[d]imidazol-2-yl)-2-(trifluoromethyl)isonicotinamide C8

N-(1-((R)-1-Acryloylazepan-3-yl)-7-chloro-6-(((R)-tetrahydrofuran-3-yl)oxy)-1H-benzo[d]imidazol-2-yl)-2-(trifluoromethyl)isonicotinamide C8 was synthesized according to the procedures as described in Example 18. MS observed for $C_{27}H_{27}ClF_3N_5O_4$: 576.4 (M+H$^-$), 578.2 (M+H$^+$); HPLC retention time: 1.85 min.

Example 20

Synthesis of N-(1-((R)-1-acryloylazepan-3-yl)-7-chloro-6-(((S)-tetrahydrofuran-3-yl)oxy)-1H-benzo[d]imidazol-2-yl)-2-methylisonicotinamide C9

N-(1-((R)-1-Acryloylazepan-3-yl)-7-chloro-6-(((S)-tetrahydrofuran-3-yl)oxy)-1H-benzo[d]imidazol-2-yl)-2-methylisonicotinamide C9 was synthesized according to the procedures as described in Example 18. MS observed for $C_{27}H_{30}ClN_5O_4$: 522.5 (M−H$^-$); HPLC retention time: 2.05 min.

Example 21

Synthesis of N-(1-((R)-1-acryloylazepan-3-yl)-7-chloro-6-(((S)-tetrahydrofuran-3-yl)oxy)-1H-benzo[d]imidazol-2-yl)-2-(trifluoromethyl)isonicotinamide C10

N-(1-((R)-1-Acryloylazepan-3-yl)-7-chloro-6-(((S)-tetrahydrofuran-3-yl)oxy)-1H-benzo[d]imidazol-2-yl)-2-(trifluoromethyl)isonicotinamide C10 was synthesized according to the procedures as described in Example 18. MS observed for $C_{27}H_{27}ClF_3N_5O_4$: 576.5 (M−H$^-$); HPLC retention time: 1.85 min.

Example 22

Synthesis of (R)—N-(1-(1-(3-chloropropanoyl)azepan-3-yl)-7-((1-methylpiperidin-4-yl)oxy)-1H-benzo[d]imidazol-2-yl)-2-methylisonicotinamide D1 and (R)—N-(1-(1-acryloylazepan-3-yl)-7-((1-methylpiperidin-4-yl)oxy)-1H-benzo[d]imidazol-2-yl)-2-methylisonicotinamide D2

The synthesis of (R)—N-(1-(1-(3-chloropropanoyl)azepan-3-yl)-7-((1-methylpiperidin-4-yl)oxy)-1H-benzo[d]imidazol-2-yl)-2-methylisonicotinamide D1 and (R)—N-(1-(1-acryloylazepan-3-yl)-7-((1-methylpiperidin-4-yl)oxy)-1H-benzo[d]imidazol-2-yl)-2-methylisonicotinamide D2 is shown in Scheme 16.

Step I: To a solution of compound 3 (510 mg, 0.929 mmol) in 1,2-dichloroethane (3 mL) at 0° C. was added HCOOH (120 mg, 1.39 mmol) and $NaBH(OAc)_3$ (256 mg). After the reaction mixture was stirred at room temperature for 3 hrs, water (10 mL) was added and the mixture was extracted with $CHCl_3$/isoporpanol (3:1, 30 mL×3). The organic phase was dried with anhydrous $Na_2SO_4$ and concentrated under reduced pressure. The resulting residue was used directly in the next step without further purification.

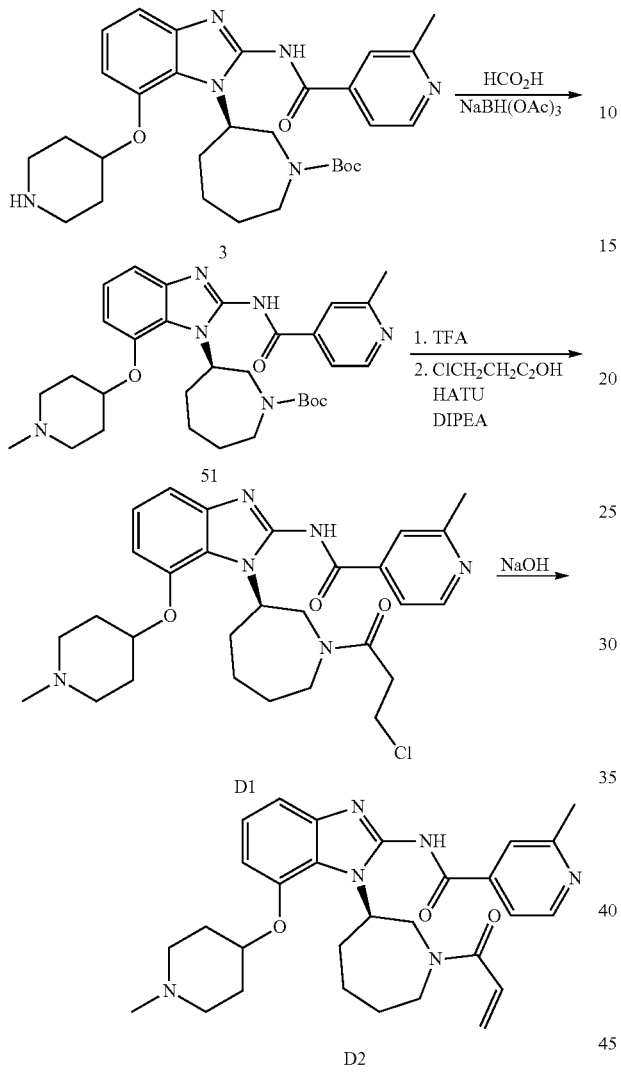

Step II: The conversion from compound 51 to compound D1 was performed according to the procedures as described in Example 11. First, compound 51 was treated with TFA to form a free amine. To a solution of the free amine (400 mg, 0.865 mmol) in anhydrous THF under $N_2$ at −30° C. was added 3-chloropropanyl acid (113 mg), DIPEA (223 mg), and HATU (390 mg). The reaction mixture was allowed to slowly warm up to room temperature. After stirred at room temperature for 1 hr, the LC-MS showed no starting material left. Isopropanol/CHCl$_3$ (1:3; 60 mL) and H$_2$O (30 mL) was added. The organic phase was washed with NaHCO$_3$, dried over anhydrous Na$_2$SO$_4$, concentrated under reduced pressure, and purified via Combi-Flash (1-10% MeOH in DCM) to afford compound D1. MS observed for $C_{29}H_{37}ClN_6O_3$: 553.1 (M+H$^+$); HPLC retention time: 6.81 min.

Step III: To a solution of compound D1 (514 mg) in dioxane (5 mL) was added NaOH (104 mg) in H$_2$O (2 mL). After the reaction mixture was stirred at 50° C. for 1 hr, LC-MS showed no starting material left. The reaction mixture was extracted with isopropanol and CHCl$_3$ (1:3) (60 mL). The organic phase was concentrated and purified via Combi-Flash (1-10% MeOH in DCM) to afford compound D2 in 31% yield (149 mg) for the last three steps. MS observed for $C_{29}H_{36}N_6O_3$: 517.6 (M+H$^+$); HPLC retention time: 6.92 min.

Example 23

Synthesis of (R)—N-(1-(1-acryloylazepan-3-yl)-7-((1-cyclopropylpiperidin-4-yl)oxy)-1H-benzo[d]imidazol-2-yl)-2-(trifluoromethyl)isonicotinamide D3

(R)—N-(1-(1-Acryloylazepan-3-yl)-7-((1-cyclopropylpiperidin-4-yl)oxy)-1H-benzo[d]imidazol-2-yl)-2-(trifluoromethyl)isonicotinamide D3 was synthesized according to the procedures as described in Example 22. MS observed for $C_{31}H_{35}F_3N_6O_3$: 597.5 (M+H$^+$); HPLC retention time: 2.10 min.

Example 24

Synthesis of (R)—N-(1-(1-acryloylazepan-3-yl)-7-((1-cyclopropylpiperidin-4-yl)oxy)-1H-benzo[d]imidazol-2-yl)-2-methylisonicotinamide D4

(R)—N-(1-(1-Acryloylazepan-3-yl)-7-((1-cyclopropylpiperidin-4-yl)oxy)-1H-benzo[d]imidazol-2-yl)-2-methylisonicotinamide D4 was synthesized according to the procedures as described in Example 22. MS observed for $C_{31}H_{38}N_6O_3$: 543.6 (M+H$^+$); HPLC retention time: 1.99 min.

Example 25

Synthesis of (R)—N-(1-(1-acryloylazepan-3-yl)-7-((1-isopropylpiperidin-4-yl)oxy)-1H-benzo[d]imidazol-2-yl)-2-(trifluoromethyl)isonicotinamide D5

(R)—N-(1-(1-Acryloylazepan-3-yl)-7-((1-isopropylpiperidin-4-yl)oxy)-1H-benzo[d]imidazol-2-yl)-2-(trifluoromethyl)isonicotinamide D5 was synthesized according to the procedures as described in Example 22. MS observed for $C_{31}H_{37}F_3N_6O_3$: 599.5 (M+H$^+$); HPLC retention time: 2.11 min.

Example 26

Synthesis of (R)—N-(1-(1-acryloylazepan-3-yl)-7-((1-isopropylpiperidin-4-yl)oxy)-1H-benzo[d]imidazol-2-yl)-2-methylisonicotinamide D6

(R)—N-(1-(1-Acryloylazepan-3-yl)-7-((1-isopropylpiperidin-4-yl)oxy)-1H-benzo[d]imidazol-2-yl)-2-methylisonicotinamide D6 was synthesized according to the procedures as described in Example 22. MS observed for $C_{31}H_{40}N_6O_3$: 545.5 (M+H$^+$); HPLC retention time: 1.98 min.

Example 27

Synthesis of (R)—N-(1-(1-acryloylazepan-3-yl)-7-((1-(2,2,2-trifluoroethyl)piperidin-4-yl)oxy)-1H-benzo[d]imidazol-2-yl)-2-methylisonicotinamide D7

The synthesis of (R)—N-(1-(1-acryloylazepan-3-yl)-7-((1-(2,2,2-trifluoroethyl)piperidin-4-yl)oxy)-1H-benzo[d]imidazol-2-yl)-2-methylisonicotinamide D7 is shown in Scheme 17.

Step I: To a solution of compound 3 (120 mg, 0.2 mmol) in DME (2 mL) at 0° C. was added $CF_3CH_2OSO_2CF_3$ (95 mg) and DIPEA (103 mg). After the reaction mixture was stirred at room temperature overnight, a second batch of $CF_3CH_2OSO_2CF_3$ (95 mg) and $K_2CO_3$ (30 mg) were added. The reaction mixture was stirred at room temperature for 3 days and then purified with flash column chromatograph with 0-30% EtOAc in hexanes to afford compound 52 in 53% yield (66 mg). MS: 531.7 (M+H$^+$).

Scheme 17

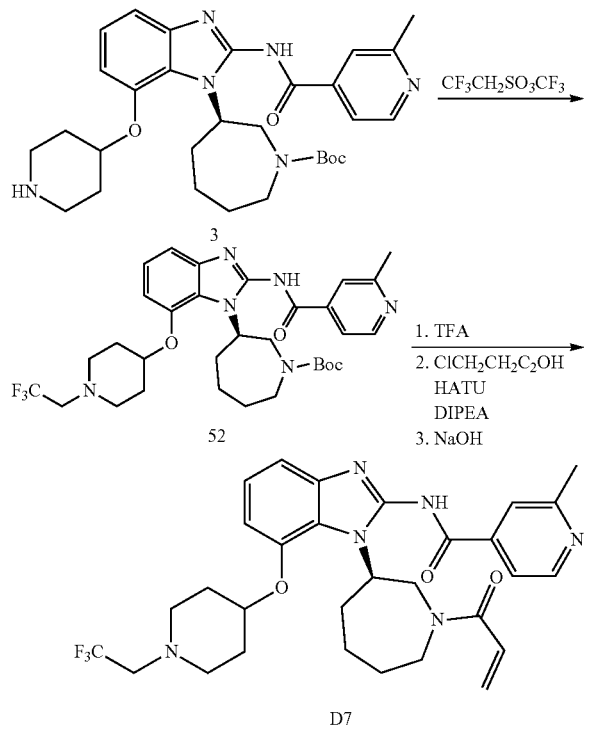

Step II: The conversion from compound 52 to compound D7 was performed according to the procedures as described in Example 22. MS observed for $C_{30}H_{35}F_3N_6O_3$: 585.7 (M+H$^+$); HPLC retention time: 7.01 min.

Example 28

Synthesis of (R)—N-(7-((1-acetylpiperidin-4-yl)oxy)-1-(1-(3-chloropropanoyl)azepan-3-yl)-1H-benzo[d]imidazol-2-yl)-2-(trifluoromethyl)isonicotinamide D8 and (R)—N-(7-((1-acetylpiperidin-4-yl)oxy)-1-(1-acryloylazepan-3-yl)-1H-benzo[d]imidazol-2-yl)-2-(trifluoromethyl)isonicotinamide D9

The synthesis of (R)—N-(7-((1-acetylpiperidin-4-yl)oxy)-1-(1-(3-chloropropanoyl)azepan-3-yl)-1H-benzo[d]imidazol-2-yl)-2-(trifluoromethyl)isonicotinamide D8 and (R)—N-(7-((1-acetylpiperidin-4-yl)oxy)-1-(1-acryloylazepan-3-yl)-1H-benzo[d]imidazol-2-yl)-2-(trifluoromethyl)isonicotinamide D9 is shown in Scheme 18, and was synthesized according to the procedures as described in Example 22.

(R)—N-(7-((1-Acetylpiperidin-4-yl)oxy)-1-(1-(3-chloropropanoyl)azepan-3-yl)-1H-benzo[d]imidazol-2-yl)-2-(trifluoromethyl)isonicotinamide D8

MS observed for $C_{30}H_{37}ClN_6O_4$: 635.1 (M+H$^+$); HPLC retention time: 2.03 min.

(R)—N-(7-((1-Acetylpiperidin-4-yl)oxy)-1-(1-acryloylazepan-3-yl)-1H-benzo[d]imidazol-2-yl)-2-(trifluoromethyl)isonicotinamide D9

MS observed for $C_{30}H_{36}N_6O_4$: 599.1 (M+H$^+$); HPLC retention time: 2.09 min.

Scheme 18

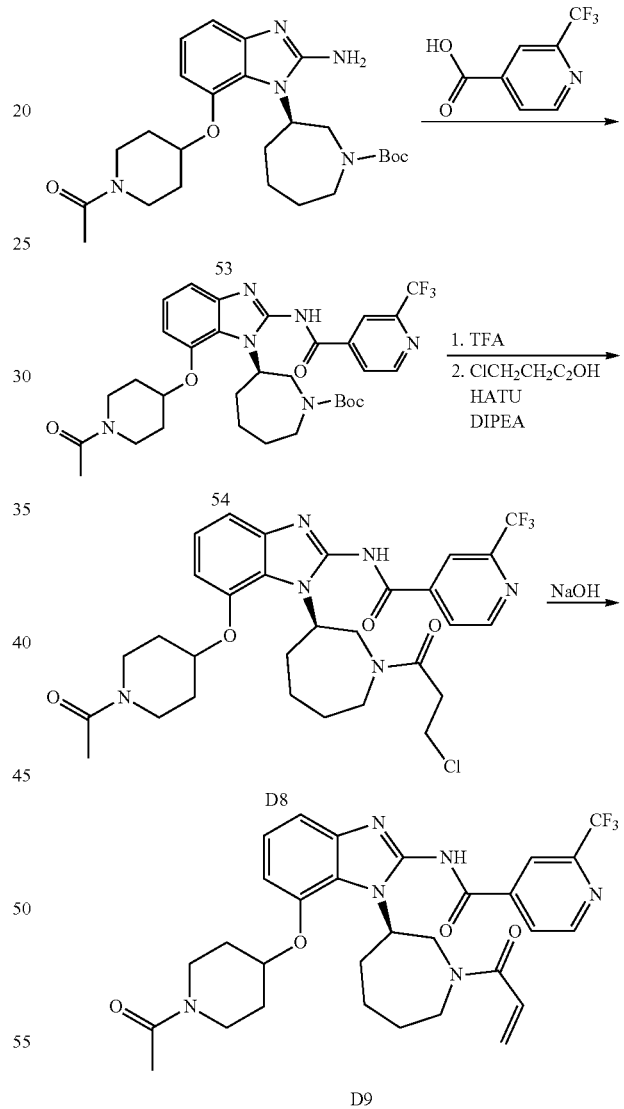

Example 29

Synthesis of (R)—N-(1-(1-acryloylazepan-3-yl)-7-((tetrahydro-2H-pyran-4-yl)oxy)-1H-benzo[d]imidazol-2-yl)-2-methylisonicotinamide D10

(R)—N-(1-(1-Acryloylazepan-3-yl)-7-((tetrahydro-2H-pyran-4-yl)oxy)-1H-benzo[d]imidazol-2-yl)-2-methylisonicotinamide D10 was synthesized according to the procedures as described in Examples 2, 3, and 18. MS observed for $C_{28}H_{33}N_5O_4$: 504.10 (M+H$^+$); HPLC retention time: 2.21 min.

Example 30

Synthesis of (R)—N-(1-(1-acryloylazepan-3-yl)-7-((1,1-dioxidotetrahydro-2H-thiopyran-4-yl)oxy)-1H-benzo[d]imidazol-2-yl)-2-methylisonicotinamide D11

(R)—N-(1-(1-Acryloylazepan-3-yl)-7-((1,1-dioxidotetrahydro-2H-thiopyran-4-yl)oxy)-1H-benzo[d]imidazol-2-yl)-2-methylisonicotinamide D11 was synthesized according to the procedures as described in Examples 2, 3, and 18. MS observed for $C_{28}H_{33}N_5O_5S$: 552.5 (M+H$^+$); HPLC retention time: 2.11 min.

Example 31

Synthesis and Characterization of Compounds A14 to A17, A20, C19 to C24, and D12 to D14

Compounds A14 to A17, A20, C19 to C24, and D12 to D14 were synthesized according to one of the methods described in Examples 1 to 30. The analytical data are summarized in Table 4 below.

TABLE 4

MS Analyses

| Cmpd. | Chemical Formula (M + H)$^+$ | Calcd. | Observed. |
|---|---|---|---|
| A14 | $C_{26}H_{26}ClF_3N_5O_4$ | 564.2 | 564.2 |
| A15 | $C_{26}H_{29}ClN_5O_4$ | 510.2 | 510.2 |
| A16 | $C_{26}H_{27}ClF_2N_5O_4$ | 546.2 | 546.2 |
| A17 | $C_{28}H_{30}ClF_3N_5O_4$ | 592.2 | 592.2 |
| A20 | $C_{30}H_{33}ClF_3N_6O_4$ | 633.2 | 633.2 |
| C19 | $C_{26}H_{26}ClF_3N_5O_4$ | 564.1 | 564.2 |
| C20 | $C_{26}H_{29}ClN_5O_4$ | 510.2 | 510.2 |
| C21 | $C_{26}H_{27}ClF_2N_5O_4$ | 546.2 | 546.2 |
| C22 | $C_{27}H_{28}ClN_6O_4$ | 535.2 | 535.2 |
| C23 | $C_{27}H_{28}ClN_6O_4$ | 535.2 | 535.2 |
| C24 | $C_{26}H_{27}ClN_7O_4$ | 536.2 | 536.2 |
| D12 | $C_{28}H_{31}F_3N_5O_4$ | 558.2 | 558.2 |
| D13 | $C_{28}H_{32}F_3N_6O_3$ | 557.2 | 557.2 |
| D14 | $C_{30}H_{35}F_2N_6O_4$ | 581.3 | 581.3 |

Example 32

Synthesis of (R)-1-(1-acryloylazepan-3-yl)-7-chloro-2-(2-methylisonicotinamido)-1H-benzo[d]imidazol-6-yl morpholine-4-carboxylate C25

The synthesis of (R)-1-(1-acryloylazepan-3-yl)-7-chloro-2-(2-methylisonicotinamido)-1H-benzo[d]imidazol-6-yl morpholine-4-carboxylate C25 is shown in Scheme 19.

Scheme 19

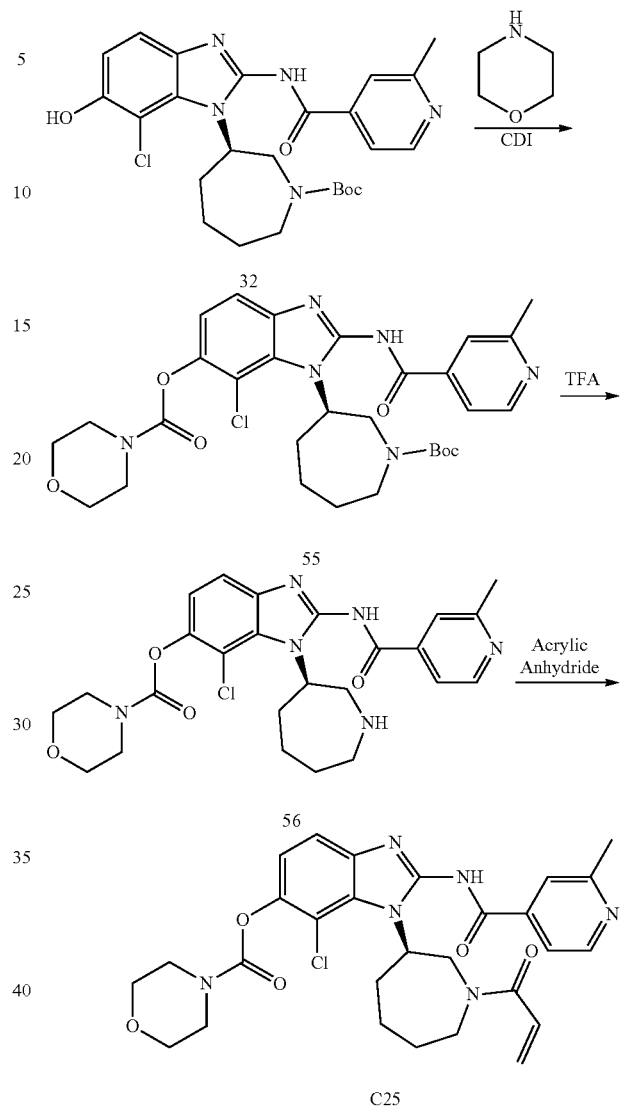

Step I. To a solution of morpholine (0.15 mmol) in THF (1 mL) was added K$_2$CO$_3$ (0.2 mmol) and CDI (0.15 mmol) at 0° C. The mixture was stirred at room temperature for 60 min. Compound 32 was added. After the reaction mixture was stirred at room temperature for 1 hr and then refluxed for 2 hrs, LC/MS showed completion f reaction. The reaction mixture was concentrated and the residue obtained was purified by silica gel chromatography (MeOH/DCM, 3%) to afford compound 55 in 80% yield (49 mg).

Step II. To a solution of compound 55 (0.1 mmol) in DCM (1 mL) was added TFA (1 mL). After the reaction mixture was stirred at room temperature for 30 min, LC/MS showed completion f reaction. The reaction mixture was concentrated and dried under vacuum over night to afford compound 56 in a quantitative yield.

Step III. To a solution of compound 56 (51 mg, 0.1 mmol) in DCM (2 mL) at −78° C. was added acrylic anhydride (25 mg, 0.2 mmol), followed by addition of DIPEA (52 mg, 0.4 mmol). After the reaction was slowly warmed up to room temperature, LC/MS showed completion of reaction. The reaction mixture was diluted with DCM (35 mL) and IPA (15 mL). The mixture was washed with water, brine, and sodium bicarbonate solution, dried over Na$_2$SO$_4$, and concentration. The residue obtained was purified by silica gel chromatography (MeOH/DCM, 5%) to afford compound 55 in 45% yield (25.7 mg). MS observed for C$_{28}$H$_{32}$ClN$_6$O$_5$: 567.2 (M+H$^+$); HPLC retention time: 1.67 min.

Example 33

Synthesis of (R)-tert-butyl 3-(7-chloro-5-hydroxy-2-(2-methylisonicotinamido)-1H-benzo[d]imidazol-1-yl)azepane-1-carboxylate 70

The synthesis of (R)-tert-butyl 3-(7-chloro-5-hydroxy-2-(2-methylisonicotinamido)-1H-benzo[d]imidazol-1-yl)azepane-1-carboxylate 70 is shown in Scheme 20.

Step I: To a solution of 1-chloro-2-fluoro-3-nitrobenzene 61 (3 g, 17.09 mmol) in concentrated sulfuric acid (20 mL) was added N-bromosuccinimide (NBS) (4.26 g, 23.9 mmol) at 25° C. After the reaction mixture was heated to 65° C. and stirred for 3 hrs, TLC (PE:EtOAc=10:1) showed completion of the reaction. The reaction mixture was cooled down to 25° C., then poured into ice water, extracted with DCM, dried over Na$_2$SO$_4$, and concentrated to yield 5-bromo-1-chloro-2-fluoro-3-nitrobenzene 62, which was used directly in the next step without further purification.

Scheme 20

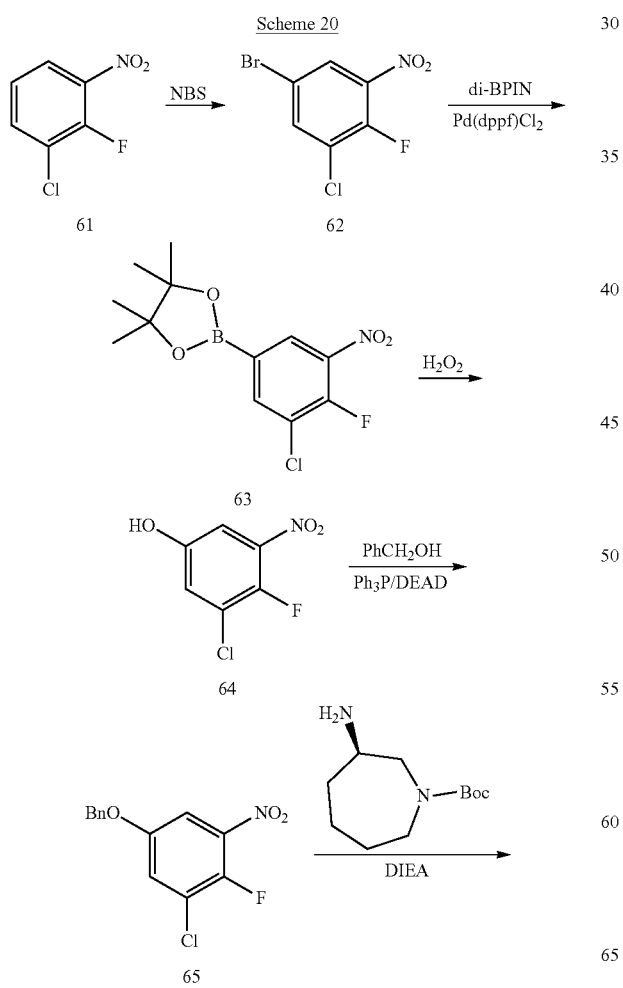

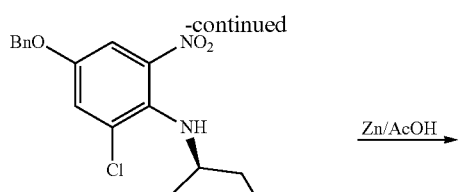

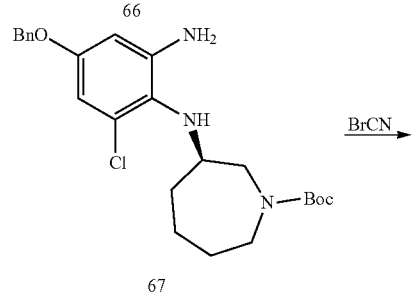

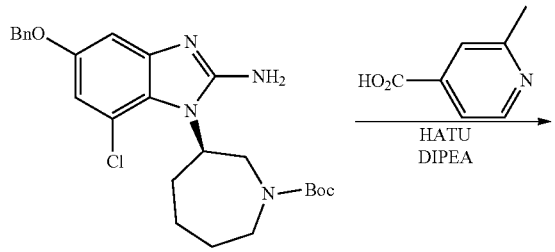

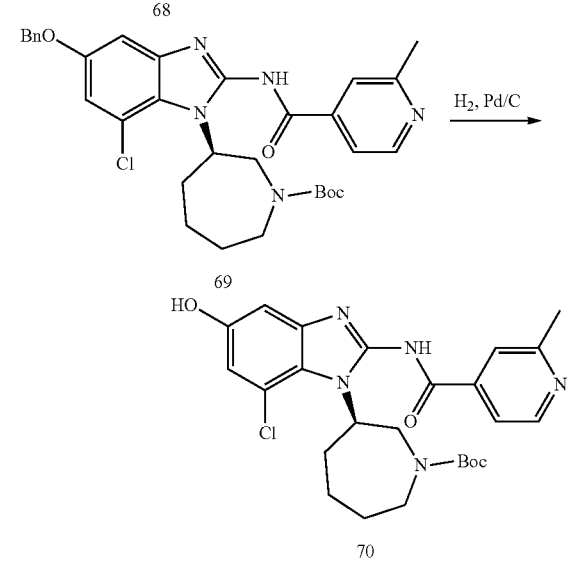

Step II: To a mixture of 5-bromo-1-chloro-2-fluoro-3-nitrobenzene 62 (510 mg, 2 mmol), KOAc (589 mg, 6 mmol), and bis(pinacolato)diboron (Di-BPIN) (559 mg, 2.2 mmol) in dioxane (5 mL) was added Pd(dppf)Cl$_2$ (73 mg, 0.10 mmol) under nitrogen. After the reaction mixture was stirred at 100° C. for 4 hrs, LC-MS showed no starting material 62 left. The reaction mixture was cooled down to 25° C. and then ice water was added. The reaction mixture was extracted with EtOAc (2×30 mL). The combined organic phase was filtered through a SiO$_2$ bed and then the filtrate was concentrated to yield a dark oil residue. The residue obtained was purified by silica gel chromatography (MeOH/DCM, 10 to 20%) to yield compound 63 (604 mg) as a brownish solid, which was used directly in the next step without further purification.

Step III: To a mixture of compound 63 (604 mg) and HOAc (144 mg, 2.4 mmol) in dioxane (5 mL) was added $H_2O_2$ (35%, 273 mg, 2.4 mmol) dropwise at 0° C. After the reaction mixture was stirred at 0° C. for 10 min and at room temperature for 3 hrs, LC-MS showed no starting material 63 left. The reaction mixture was cooled down to 0° C., and saturated $NaHSO_3$ was then added until no starch-iodine paper changed color. The reaction mixture was adjusted with HCl (4N) to pH 5-6 and extracted with EtOAc (3×30 mL). The combined organic phase was concentrated and the residue obtained was purified by silica gel chromatography (EtOAc/hexanes, 0 to 10%) to yield 3-chloro-4-fluoro-5-nitrophenol 64 (284 mg, 70% purity), which was directly in the next step without further purification.

Step IV: To a mixture of 3-chloro-4-fluoro-5-nitrophenol 64 (279 mg, 1.36 mmol) and benzyl alcohol in THF (10 mL) was added $Ph_3P$ (572 mg, 2.18 mmol) at 0° C. under nitrogen, followed by addition of DEAD (383 mg, 2.18 mmol) dropwise at 0° C. over 10 min. After the reaction mixture was stirred at 0° C. for 20 min and at room temperature for 2 hrs, LC-MS showed no starting material 64 left. The reaction mixture was concentrated and EtOAc (30 mL) was added. The reaction mixture was washed with $NH_4Cl$ and then concentrated to yield an oil. To the oil obtained was added $Et_2O$ and the solid formed was filtered. The filtrate was concentrated to afford an oil, which was purified by silica gel chromatography (EtOAc/hexanes, 0 to 10%) to yield 5-(benzyloxy)-1-chloro-2-fluoro-3-nitrobenzene 65 (323 mg, 70% purity), which was directly in the next step without further purification.

Step V: A mixture of 5-(benzyloxy)-1-chloro-2-fluoro-3-nitrobenzene 65 (110 mg, 0.39 mmol), tert-butyl (R)-3-aminoazepane-1-carboxylate (92 mg, 0.43 mmol), and DIEA (66 mg, 0.51 mmol) in THF (2 mL) was refluxed in a high pressure resistant tube for 8 hrs. LC-MS showed less than 3% of starting material 65 left. The reaction mixture was concentrated. The residue obtained was purified by silica gel chromatography (EtOAc/hexanes, 0 to 10%) to yield (R)-tert-butyl 3-((4-(benzyloxy)-2-chloro-6-nitrophenyl)amino)azepane-1-carboxylate 66 (130 mg).

(R)-Tert-butyl 3-(5-(benzyloxy)-7-chloro-2-(2-methylisonicotinamido)-1H-benzo[d]imidazol-1-yl)azepane-1-carboxylate 69 was prepared from (R)-tert-butyl 3-((4-(benzyloxy)-2-chloro-6-nitrophenyl)amino)azepane-1-carboxylate 66 according to the procedures as described in Example 12 for the preparation of compound 31 from compound 30a. MS observed for $C_{32}H_{37}ClN_5O_4$: 591.5 (M+H$^+$); HPLC retention time: 7.04 min.

(R)-Tert-butyl 3-(7-chloro-5-hydroxy-2-(2-methylisonicotinamido)-1H-benzo[d]imidazol-1-yl)azepane-1-carboxylate 70 was prepared from (R)-tert-butyl 3-(5-(benzyloxy)-7-chloro-2-(2-methylisonicotinamido)-1H-benzo[d]imidazol-1-yl)azepane-1-carboxylate 69 according to the procedure as described in Example 11 for the preparation of compound 32 from compound 31. MS observed for $C_{25}H_{31}ClN_5O_4$: 500.0 (M+H$^+$).

Example 34

Synthesis of (R)-1-(1-acryloylazepan-3-yl)-7-chloro-2-(2-methylisonicotinamido)-1H-benzo[d]imidazol-5-yl morpholine-4-carboxylate A23

The synthesis of (R)-1-(1-acryloylazepan-3-yl)-7-chloro-2-(2-methylisonicotinamido)-1H-benzo[d]imidazol-5-yl morpholine-4-carboxylate A23 is shown in Scheme 21. MS observed for $C_{28}H_{32}ClN_6O_5$: 567.4 (M+H$^+$) for compound A23.

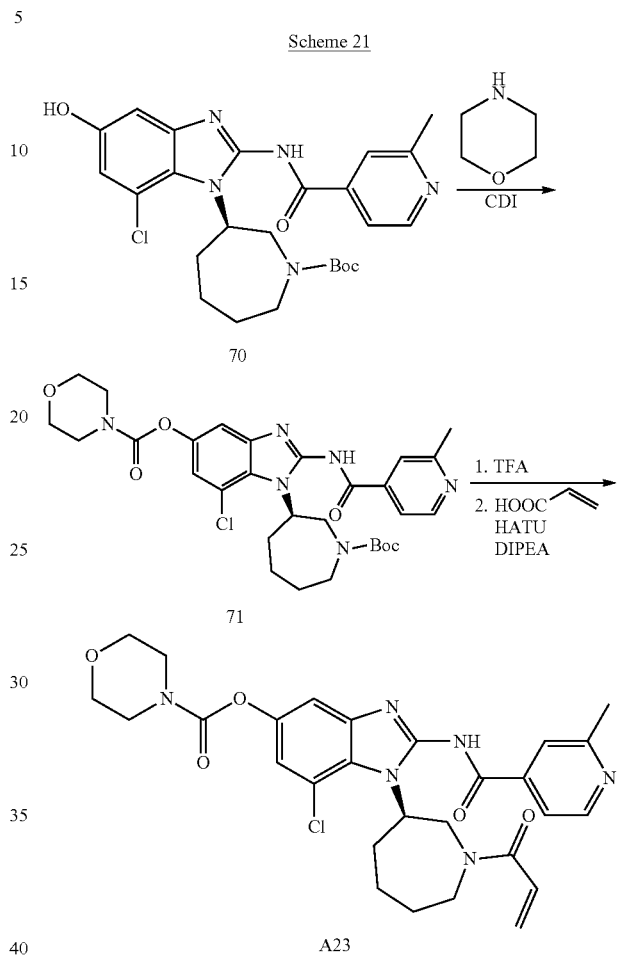

Scheme 21

Example 35

Synthesis of (R)-1-(1-acryloylazepan-3-yl)-7-chloro-2-(2-methylisonicotinamido)-1H-benzo[d]imidazol-5-yl azetidine-1-carboxylate A24

The synthesis of (R)-1-(1-acryloylazepan-3-yl)-7-chloro-2-(2-methylisonicotinamido)-1H-benzo[d]imidazol-5-yl azetidine-1-carboxylate A24 is shown in Scheme 22.

Example 1-A

Synthesis of (R)-tert-butyl 3-(2-amino-7,8-dihydro-1H-[1,4]dioxino[2',3':3,4]benzo[1,2-d]imidazol-1-yl) azepane-1-carboxylate 5-A The synthesis of (R)-tert-butyl 3-(2-amino-7,8-dihydro-1H-[1,4]dioxino[2',3':3,4]benzo[1,2-d]imidazol-1-yl) azepane-1-carboxylate 5-A is shown in Scheme 1-A.

5-Fluoro-2,3-dihydrobenzo[b][1,4]dioxine 1-A

To a mixture of 3-fluorobenzene-1,2-diol (25.0 g, 195 mmol) and $K_2CO_3$ (81.0 g, 585 mmol) in DMF (150 mL) was added 1,2-dibromoethane (33.6 ml, 390 mmol). After stirred at 110° C. temperature overnight, the reaction mixture was poured into water (500 mL), extracted with EtOAc (3×500 mL). The combined extracts were washed with water, brine, dried over anhydrous $Na_2SO_4$, and concentrated under reduced pressure, and purified by silica gel column chromatography with PE/EtOAc (40:1) to afford compound 1-A.

Scheme 22

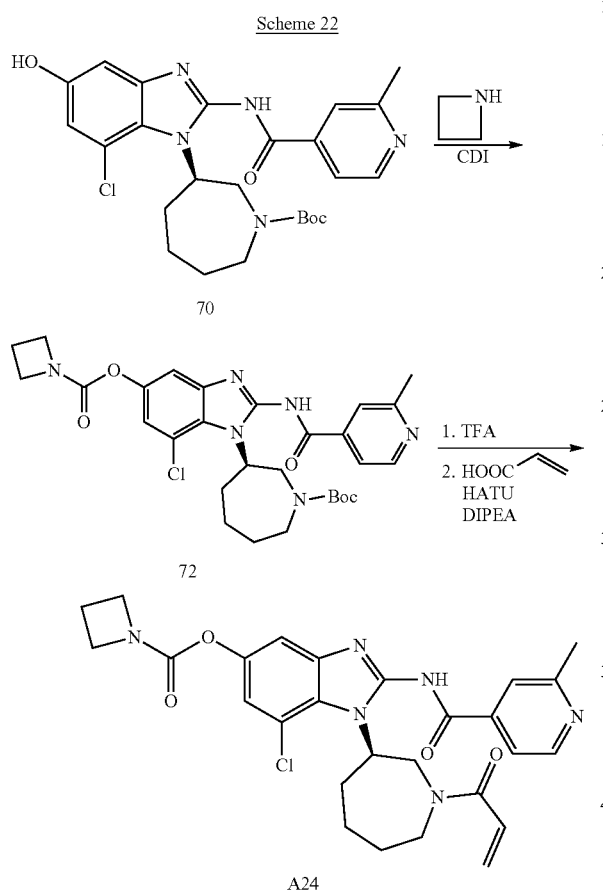

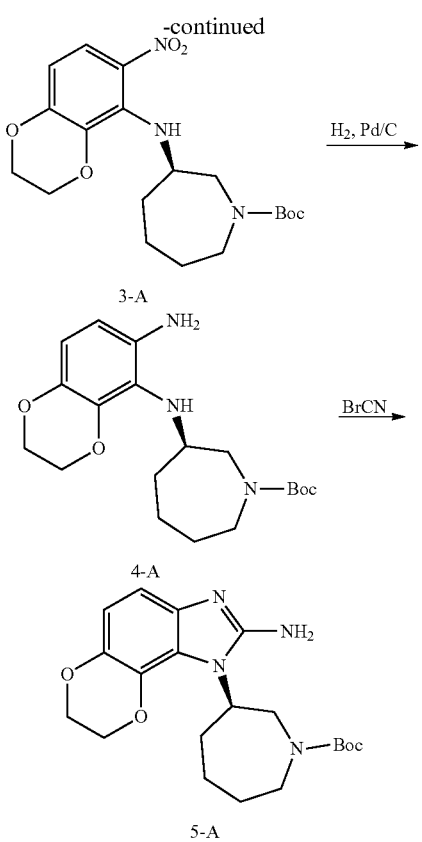

5-Fluoro-6-nitro-2,3-dihydrobenzo[b][1,4]dioxine 2-A

To a solution of 85% $HNO_3$ (100 mL) at 0° C. was added 5-fluoro-2,3-dihydrobenzo[b][1,4]dioxine 1-A (20.0 g, 130 mmol) in portions. After stirred at 0° C. for 30 min, the reaction mixture was poured over ice water (800 mL), extracted with EtOAc (3×500 mL). The combined organic extracts were washed with brine, dried over anhydrous $Na_2SO_4$, and evaporated under reduced pressure, and purified by silica gel column chromatography with PE/DCM (4:1) to afford compound 2-A in 18.9% yield (4.88 g).

(R)-Tert-butyl 3-((6-nitro-2,3-dihydrobenzo[b][1,4]dioxin-5-yl)amino)azepane-1-carboxylate 3-A To a solution of 5-fluoro-6-nitro-2,3-dihydrobenzo[b][1,4]dioxine 2-A (1.2 g, 6.03 mmol) in dry N-methyl-2-pyrrolidone (NMP) (15 mL) were added (R)-tert-butyl 3-aminoazepane-1-carboxylate (1.35 g, 6.33 mmol) and DIPEA (1.5 mL). After stirred at 120° C. overnight, the reaction mixture was cooled to room temperature and water (200 mL) was added. The reaction mixture was extracted with EtOAc (200 mL×3). The combined organic extracts were washed with brine, dried over anhydrous $Na_2SO_4$, evaporated under reduced pressure, and purified on a silica gel column with PE/EtOAc (5:1) to afford compound 3-A in 97% yield (2.3 g).

(R)-Tert-butyl 3-((6-amino-2,3-dihydrobenzo[b][1,4]dioxin-5-yl)amino)azepane-1-carboxylate 4-A To a solution of (R)-tert-butyl 3-(6-nitro-2,3-dihydrobenzo[b][1,4]dioxin-5-ylamino)azepane-1-carboxylate Scheme 1-A

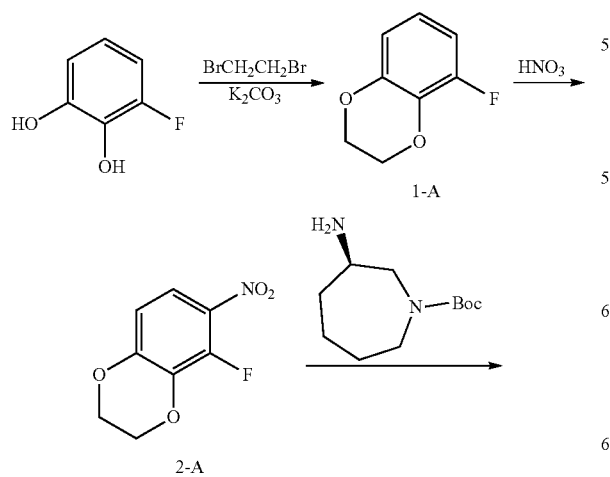

3-A (2.3 g, 5.85 mmol) in MeOH (100 mL) under nitrogen atmosphere was added 10% Pd/c (400 mg). The reaction mixture was stirred at room temperature under hydrogen atmosphere overnight. The catalyst was filtrated off through a pad of celite and the filtrate was concentrated in vacuo to provide compound 4-A in 94.3% yield ((2.0 g), which was used directly in the next step without further purification.

(R)-Tert-butyl 3-(2-amino-7,8-dihydro-1H-[1,4]dioxino[2',3':3,4]benzo[1,2-d]imidazol-1-yl)azepane-1-carboxylate 5-A To a solution of (R)-tert-butyl 3-(6-amino-2,3-dihydrobenzo[b][1,4]dioxin-5-ylamino)azepane-1-carboxylate 4-A (2.1 g, 5.78 mmol) in 50 mL of MeOH/ACN/H$_2$O (3:1:1) was added BrCN (1.05 g). After stirred at 50° C. overnight, the reaction mixture was concentrated in vacuo and the residue was purified on a silica gel column with DCM/MeOH (45:1) to furnish compound 5-A in 93.5% yield (2.1 g). MS observed (M+H$^+$) for C$_{20}$H$_{28}$N$_4$O$_4$: 389.30; HPLC retention time: 3.59 min.

Example 2-A

Synthesis of (R)—N-(1-(1-acryloylazepan-3-yl)-7,8-dihydro-1H-[1,4]dioxino[2',3':3,4]benzo[1,2-d]imidazol-2-yl)-2-methylisonicotinamide C1-A The synthesis of (R)—N-(1-(1-acryloylazepan-3-yl)-7,8-dihydro-1H-[1,4]dioxino[2',3':3,4]benzo[1,2-d]imidazol-2-yl)-2-methylisonicotinamide C1-A is shown in Scheme 2-A.

(R)-Tert-butyl 3-(2-(2-methylisonicotinamido)-7,8-dihydro-1H-[1,4]dioxino[2',3':3,4]benzo[1,2-d]imidazol-1-yl)azepane-1-carboxylate 6-A 2-Methylisonicotinic acid (0.050 g, 0.036 mmol) and HATU (0.150 g, 0.040 mmol) were dissolved in a DMF mixture (4 mL), followed by addition of 10 molar percent of 4-simethylaminopyridine (DMAP) and DIPEA (0.18 mL, 1 mmol). The reaction mixture was stirred for 10 min before adding to a solution of (R)-tert-butyl 3-(2-amino-7,8-dihydro-1H-[1,4]dioxino[2',3':3,4]benzo[1,2-d]imidazol-1-yl)azepane-1-carboxylate 5-A (0.130 g, 0.033 mmol) in DMF (1 mL). After one hour of stirring, the reaction was stripped off solvents. The residue was dissolved in EtOAc (200 mL). The organic solution was washed with saturated NaHCO$_3$ (10 mL), brine (40 mL), dried with anhydrous Na$_2$SO$_4$, and concentrated under vacuum. The residue obtained was purified on a silica gel column (0-2% methanol in DCM) to afford (R)-Tert-butyl 3-(2-(2-methylisonicotinamido)-7,8-dihydro-1H-[1,4]dioxino[2',3':3,4]benzo[1,2-d]imidazol-1-yl)azepane-1-carboxylate 6-A in 83% yield (0.139 g).

Scheme 2-A

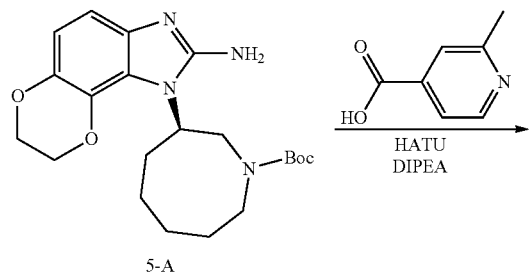

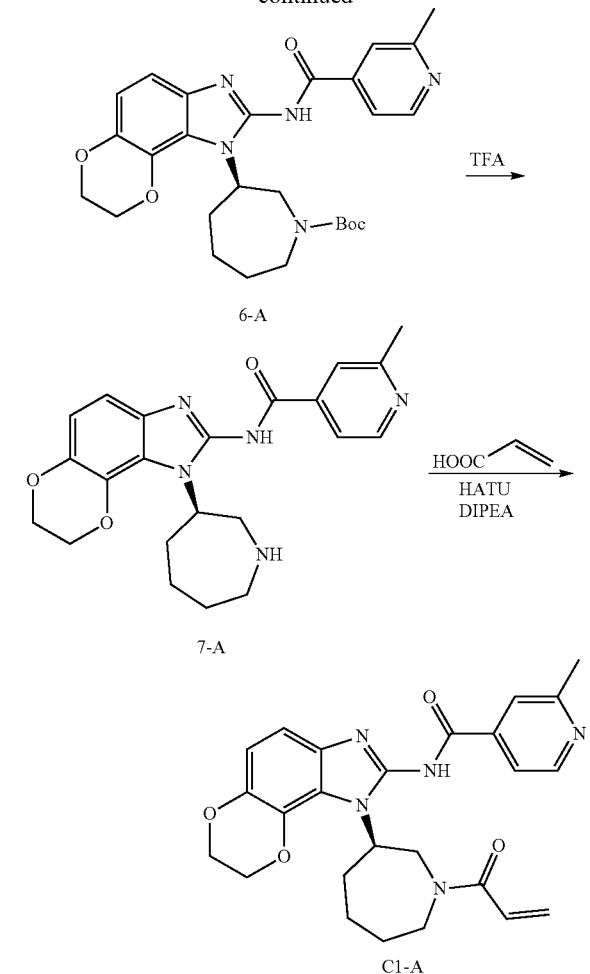

(R)—N-(1-(Azepan-3-yl)-7,8-dihydro-1H-[1,4]dioxino[2',3':3,4]benzo[1,2-d]imidazol-2-yl)-2-methylisonicotinamide 7-A (R)-Tert-butyl 3-(2-(2-methylisonicotinamido)-7,8-dihydro-1H-[1,4]dioxino[2',3':3,4]benzo[1,2-d]imidazol-1-yl)azepane-1-carboxylate 6-A (139 mg, 0.027 mmol) was dissolved in DCM (2 mL). Trifluoroacetic acid (1.0 mL) was added and the reaction mixture was stirred at room temperature for 1 hr. The solvents were stripped off. The residue obtained was dissolved in 50 mL of DCM and washed with saturated NaHCO$_3$ (15 mL), brine (20 mL), dried with anhydrous Na$_2$SO$_4$, and concentrated to yield (R)—N-(1-(azepan-3-yl)-7,8-dihydro-1H-[1,4]dioxino[2',3':3,4]benzo[1,2-d]imidazol-2-yl)-2-methylisonicotinamide 7-A in 91% yield (100 mg).

(R)—N-(1-(1-acryloylazepan-3-yl)-7,8-dihydro-1H-[1,4]dioxino[2',3':3,4]benzo[1,2-d]imidazol-2-yl)-2-methylisonicotinamide C1-A Acrylic acid (0.25 mmol, 24 mg) and HATU (94 mg, 0.25 mmol) were mixed in DMF (8 mL), followed by addition of DMAP (0.022 mmol, 4 mg) and DIPEA (0.6 mmol, 0.1 mL). After 5 minutes of stirring, the mixture was added to a solution of (R)—N-(1-(azepan-3-yl)-7,8-dihydro-1H-[1,4]dioxino[2',3':3,4]benzo[1,2-d]imidazol-2-yl)-2-methylisonicotinamide 7 (91 mg, 0.22 mmol) in DMF (1 mL). The reaction mixture was further stirred overnight and then was diluted with DCM (60 mL), washed with saturated sodium bicarbonate solution (10 mL) and water (10 mL), dried with anhydrous sodium sulfate, and concentrated. The residue obtained was purified on a silica gel column with 1-10% MeOH in DCM to yield (R)—N-(1-(1-acryloylazepan-3-yl)-7,8-dihydro-1H-[1,4]dioxino[2',3':3,4]benzo[1,2-d]imidazol-2-yl)-2-methylisonicotinamide C1-A in 27% yield (25 mg). MS calculated for $C_{25}H_{27}N_5O_4$: 460.7 (M−H$^-$); HPLC retention time: 2.34 min.

Example 3-A

Synthesis of (R)—N-(1-(1-acryloylazepan-3-yl)-7,8-dihydro-1H-[1,4]dioxino[2',3':3,4]benzo[1,2-d]imidazol-2-yl)-2-(trifluoromethyl)isonicotinamide B1-A (R)—N-(1-(1-Acryloylazepan-3-yl)-7,8-dihydro-1H-[1,4]dioxino[2',3':3,4]benzo[1,2-d]imidazol-2-yl)-2-(trifluoromethyl)isonicotinamide B1-A was synthesized according to the procedures as described in Example 2-A. MS calculated for $C_{25}H_{24}F_3N_5O_4$: 514.8 (M−H$^-$); HPLC retention time: 2.55 min.

Example 4-A

Synthesis of (R)—N-(1-(1-acryloylazepan-3-yl)-7,8-dihydro-1H-[1,4]dioxino[2',3':3,4]benzo[1,2-d]imidazol-2-yl)-2-methoxyisonicotinamide C2-A (R)—N-(1-(1-Acryloylazepan-3-yl)-7,8-dihydro-1H-[1,4]dioxino[2',3':3,4]benzo[1,2-d]imidazol-2-yl)-2-methoxyisonicotinamide C2-A was synthesized according to the procedures as described in Example 2-A. MS calculated for $C_{25}H_{27}N_5O_5$: 476.6 (M−H$^-$); HPLC retention time: 2.78 min.

Example 5-A

Synthesis of (R,E)-N-(1-(1-(4-(dimethylamino)but-2-enoyl)azepan-3-yl)-7,8-dihydro-1H-[1,4]dioxino[2',3':3,4]benzo[1,2-d]imidazol-2-yl)-2-(trifluoromethyl)isonicotinamide C3-A (R,E)-N-(1-(1-(4-(Dimethylamino)but-2-enoyl)azepan-3-yl)-7,8-dihydro-1H-[1,4]dioxino[2',3':3,4]benzo[1,2-d]imidazol-2-yl)-2-(trifluoromethyl)isonicotinamide C3-A was synthesized according to the procedures as described in Example 2-A. MS calculated for $C_{28}H_{31}F_3N_6O_4$: 571.5 (M−H$^-$); HPLC retention time: 2.10 min.

Example 6-A

Synthesis and Characterization of Compounds A13-A, A14-A, and C11-A to C19-A

Compounds A13-A, A14-A, and C11-A to C19-A were synthesized according to one of the methods described in Examples 1-A to 5-A. The analytical data are summarized in Table 3-A below.

TABLE 3-A

MS Analyses

| Cmpd. | Chemical Formula (M + H)$^+$ | Calcd. | Observed. |
|---|---|---|---|
| A13-A | $C_{25}H_{24}ClF_3N_5O_4$ | 550.1 | 550.1 |
| A14-A | $C_{25}H_{25}ClF_2N_5O_4$ | 532.2 | 532.1 |
| C11-A | $C_{25}H_{27}N_4O_4$ | 447.2 | 447.2 |
| C12-A | $C_{25}H_{27}N_6O_4$ | 475.2 | 475.2 |
| C13-A | $C_{25}H_{24}F_3N_6O_4$ | 529.2 | 529.2 |
| C14-A | $C_{25}H_{27}N_6O_4$ | 475.2 | 475.2 |
| C15-A | $C_{27}H_{28}F_3N_6O_5$ | 573.2 | 573.2 |
| C16-A | $C_{27}H_{29}F_2N_6O_5$ | 555.2 | 555.2 |
| C17-A | $C_{27}H_{30}N_6O_5$ | 519.2 | 519.2 |
| C18-A | $C_{26}H_{26}F_3N_6O_4$ | 543.2 | 543.2 |
| C19-A | $C_{26}H_{27}F_2N_6O_4$ | 525.2 | 525.2 |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:
1. A compound selected from:
 (R)—N-(1-(1-acryloylazepan-3-yl)-7-chloro-5-(oxetan-3-yloxy)-1H-benzo[d]imidazol-2-yl)-2-(trifluoromethyl)isonicotinamide A14;
 (R)—N-(1-(1-acryloylazepan-3-yl)-7-chloro-5-(oxetan-3-yloxy)-1H-benzo[d]imidazol-2-yl)-2-methylisonicotinamide A15;
 (R)—N-(1-(1-acryloylazepan-3-yl)-7-chloro-5-(oxetan-3-yloxy)-1H-benzo[d]imidazol-2-yl)-2-(difluoromethyl)isonicotinamide A16;
 (R)—N-(1-(1-acryloylazepan-3-yl)-7-chloro-5-((tetrahydro-2H-pyran-4-yl)oxy)-1H-benzo[d]imidazol-2-yl)-2-(trifluoromethyl)isonicotinamide A17;
 (R)—N-(1-(1-acryloylazepan-3-yl)-7-chloro-5-((tetrahydro-2H-pyran-4-yl)oxy)-1H-benzo[d]imidazol-2-yl)-2-(difluoromethyl)isonicotinamide A18;
 (S)—N-(1-(1-acryloylazepan-3-yl)-7-chloro-5-((tetrahydro-2H-pyran-4-yl)oxy)-1H-benzo[d]imidazol-2-yl)-2-methylisonicotinamide A19;
 (R)—N-(5-((1-acetylpiperidin-4-yl)oxy)-1-(1-acryloylazepan-3-yl)-7-chloro-1H-benzo[d]imidazol-2-yl)-2-(trifluoromethyl)isonicotinamide A20;
 (R)—N-(5-((1-acetylpiperidin-4-yl)oxy)-1-(1-acryloylazepan-3-yl)-7-chloro-1H-benzo[d]imidazol-2-yl)-2-(difluoromethyl)isonicotinamide A21;
 (R)—N-(5-((1-acetylpiperidin-4-yl)oxy)-1-(1-acryloylazepan-3-yl)-7-chloro-1H-benzo[d]imidazol-2-yl)-2-methylisonicotinamide A22;
 (R)-1-(1-acryloylazepan-3-yl)-7-chloro-2-(2-methylisonicotinamido)-1H-benzo[d]imidazol-5-yl morpholine-4-carboxylate A23;
 (R)-1-(1-acryloylazepan-3-yl)-7-chloro-2-(2-methylisonicotinamido)-1H-benzo[d]imidazol-5-yl azetidine-1-carboxylate A24;
 (R)—N-(1-(1-acryloylazepan-3-yl)-7-chloro-6-(oxetan-3-yloxy)-1H-benzo[d]imidazol-2-yl)-2-(trifluoromethyl)isonicotinamide C19;

(R)—N-(1-(1-acryloylazepan-3-yl)-7-chloro-6-(oxetan-3-yloxy)-1H-benzo[d]imidazol-2-yl)-2-methylisonicotinamide C20;

(R)—N-(1-(1-acryloylazepan-3-yl)-7-chloro-6-(oxetan-3-yloxy)-1H-benzo[d]imidazol-2-yl)-2-(difluoromethyl)isonicotinamide C21;

(R)—N-(1-(1-acryloylazepan-3-yl)-7-chloro-6-(oxetan-3-yloxy)-1H-benzo[d]imidazol-2-yl)imidazo[1,5-a]pyridine-7-carboxamide C22;

(R)—N-(1-(1-acryloylazepan-3-yl)-7-chloro-6-(oxetan-3-yloxy)-1H-benzo[d]imidazol-2-yl)imidazo[1,2-a]pyridine-7-carboxamide C23;

(R)—N-(1-(1-acryloylazepan-3-yl)-7-chloro-6-(oxetan-3-yloxy)-1H-benzo[d]imidazol-2-yl)-[1,2,4]triazolo[4,3-a]pyridine-7-carboxamide C24;

(R)-1-(1-acryloylazepan-3-yl)-7-chloro-2-(2-methyl-isonicotinamido)-1H-benzo[d]imidazol-6-yl morpholine-4-carboxylate C25;

(R)—N-(1-(1-acryloylazepan-3-yl)-7-((tetrahydro-2H-pyran-4-yl)oxy)-1H-benzo[d]imidazol-2-yl)-2-(trifluoromethyl)isonicotinamide D12;

(R)—N-(1-(1-acryloylazepan-3-yl)-7-(piperidin-4-yloxy)-1H-benzo[d]imidazol-2-yl)-2-(trifluoromethyl)isonicotinamide D13; and (R)—N-(7-((1-acetylpiperidin-4-yl)oxy)-1-(1-acryloylazepan-3-yl)-1H-benzo[d]imidazol-2-yl)-2-(difluoromethyl)isonicotinamide D14;

and single enantiomers, racemic mixtures, mixtures of diastereomers, and isotopic variants thereof; and pharmaceutically acceptable salts, solvates, and prodrugs thereof.

2. A compound of Formula XIXa:

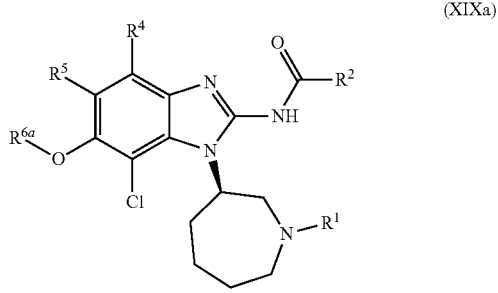

(XIXa)

or a single enantiomer, a racemic mixture, a mixture of diastereomers, or an isotopic variant thereof; or a pharmaceutically acceptable salt, solvate, or prodrug thereof; wherein:

$R^1$ is selected from:

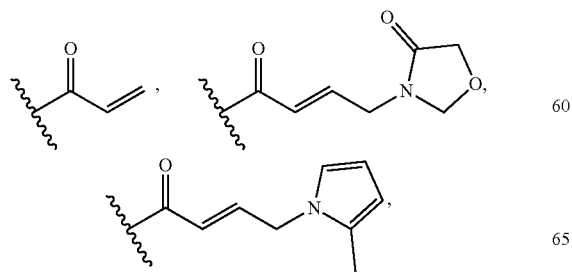

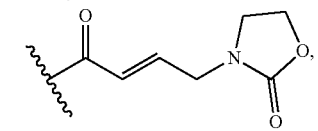

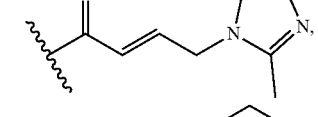

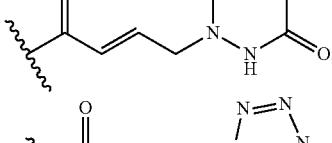

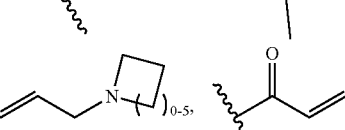

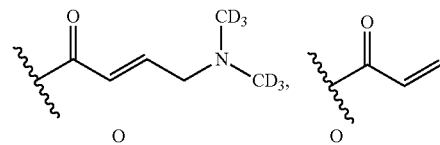

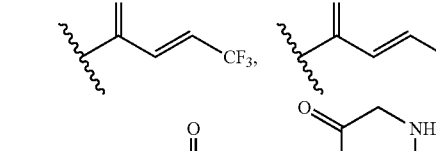

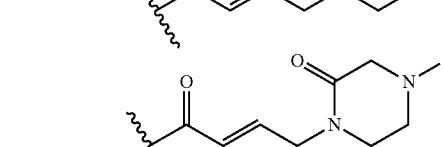

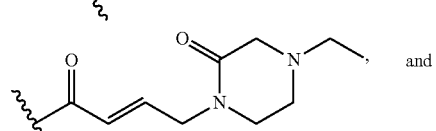

and

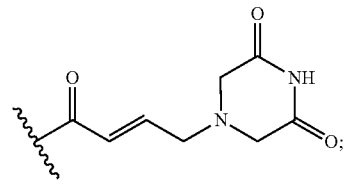

$R^2$ is $C_{3-10}$ cycloalkyl, $C_{6-14}$ aryl, heteroaryl, or heterocyclyl;

$R^4$ and $R^5$ are each independently (a) hydrogen, cyano, halo, or nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$ NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$;

R$^{6a}$ is —C(O)OR$^{1a}$ or —C(O)NR$^{1b}$R$^{1c}$; and each R$^{1a}$, R$^{1b}$, R$^{1c}$, and R$^{1d}$ is independently hydrogen, $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more substituents Q, where each Q is independently selected from (a) oxo, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OP(O)(OR$^a$)$_2$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each of which is optionally substituted with one or more substituents Q$^a$; or (iii) R$^b$ and R$^c$ together with the N atom to which they are attached form heterocyclyl, optionally substituted with one or more substituents Q$^a$;

wherein each Q$^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^f$, —C(O)OR$^f$, —C(O)NR$^g$R$^h$, —C(NR$^f$)NR$^g$R$^h$, —OR$^f$, —OC(O)R$^f$, —OC(O)OR$^f$, —OC(O)NR$^g$R$^h$, —OC(=NR$^f$)NR$^g$R$^h$, —OP(O)(OR$^f$)$_2$, —OS(O)R$^f$, —OS(O)$_2$R$^f$, —OS(O)NR$^g$R$^h$, —OS(O)$_2$NR$^g$R$^h$, —NR$^g$R$^h$, —NR$^f$C(O)R$^k$, —NR$^f$C(O)OR$^k$, —NR$^f$C(O)NR$^g$R$^h$, —NR$^f$C(=NR$^k$)NR$^g$R$^h$, —NR$^f$S(O)R$^k$, —NR$^f$S(O)$_2$R$^k$, —NR$^f$S(O)NR$^g$R$^h$, —NR$^f$S(O)$_2$ NR$^g$R$^h$, —SR$^f$, —S(O)R$^f$, —S(O)$_2$R$^f$, —S(O)NR$^g$R$^h$, and —S(O)$_2$NR$^g$R$^h$; wherein each R$^f$, R$^g$, R$^h$, and R$^k$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^g$ and R$^h$ together with the N atom to which they are attached form heterocyclyl.

3. The compound of claim 2, wherein R$^{6a}$ is —C(O)OR$^{1a}$.

4. The compound of claim 3, wherein R$^{1a}$ is $C_{1-6}$ alkyl, $C_{3-10}$ cycloalkyl, or heterocyclyl, each of which is optionally substituted with one or more substituents Q.

5. The compound of claim 4, wherein R$^{1a}$ is methyl, isopropyl, cyclobutyl, cyclopentyl, cyclohexyl, oxetanyl, tetrahydrofuryl, or tetrahydro-2H-pyranyl, each of which is optionally substituted with one or more substituents Q.

6. The compound of claim 2, wherein R$^{6a}$ is —C(O)NR$^{1b}$R$^{1c}$.

7. The compound of claim 6, wherein R$^{1b}$ and R$^{1c}$ are each independently $C_{1-6}$ alkyl, optionally substituted with one or more substituents Q; or R$^{1b}$ and R$^{1c}$ together with the N atom to which they are attached form heterocyclyl, optionally substituted with one or more substituents Q.

8. The compound of claim 2, wherein R$^{6a}$ is methoxycarbonyl, isopropoxycarbonyl, cyclobutoxycarbonyl, cyclopentoxycarbonyl, cyclohexoxycarbonyl, oxetan-3-oxycarbonyl, tetrahydrofuran-3-oxycarbonyl, tetrahydro-2H-pyran-4-oxycarbonyl, N,N-dimethylaminecarbonyl, N-methyl-N-isopropylaminecarbonyl, aziridin-1-ylcarbonyl, azetidin-1-ylcarbonyl, pyrrolidin-1-ylcarbonyl, 3-fluoro-pyrrolidin-1-ylcarbonyl, 3-methoxy-pyrrolidin-1-ylcarbonyl, 3,3-difluoro-pyrrolidin-1-ylcarbonyl, morpholin-4-ylcarbonyl, 4-isopropyl-piperazin-1-ylcarbonyl, 4-cyclopropyl-piperazin-1-ylcarbonyl, 4-acetyl-piperazin-1-ylcarbonyl, or 1,1-dioxo-thiomorpholin-4-ylcarbonyl.

9. The compound of claim 2, wherein R$^4$ is hydrogen.

10. The compound of claim 2, wherein R$^5$ is hydrogen.

11. The compound of claim 2, having the structure of Formula XXI:

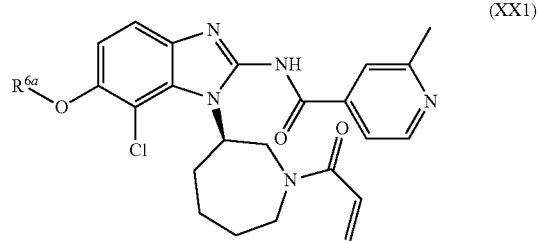

(XXI)

or a single enantiomer, a racemic mixture, a mixture of diastereomers, or an isotopic variant thereof; or a pharmaceutically acceptable salt, solvate, or prodrug thereof; wherein R$^{6a}$ is methoxycarbonyl, isopropoxycarbonyl, cyclobutoxycarbonyl, cyclopentoxycarbonyl, cyclohexoxycarbonyl, oxetan-3-oxycarbonyl, tetrahydrofuran-3-oxycarbonyl, tetrahydro-2H-pyran-4-oxycarbonyl, N,N-dimethylaminecarbonyl, N-methyl-N-isopropylaminecarbonyl, aziridin-1-ylcarbonyl, azetidin-1-ylcarbonyl, pyrrolidin-1-ylcarbonyl, 3-fluoro-pyrrolidin-1-ylcarbonyl, 3-methoxy-pyrrolidin-1-ylcarbonyl, 3,3-difluoro-pyrrolidin-1-ylcarbonyl, morpholin-4-ylcarbonyl, 4-isopropyl-piperazin-1-ylcarbonyl, 4-cyclopropyl-piperazin-1-ylcarbonyl, 4-acetyl-piperazin-1-ylcarbonyl, or 1,1-dioxo-thiomorpholin-4-ylcarbonyl.

12. A compound of Formula XXV:

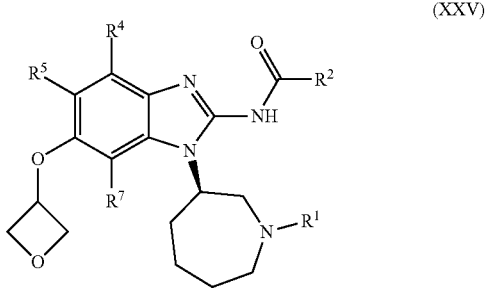

(XXV)

or a single enantiomer, a racemic mixture, a mixture of diastereomers, or an isotopic variant thereof; or a pharmaceutically acceptable salt, solvate, or prodrug thereof;
wherein:
R$^1$ is selected from:

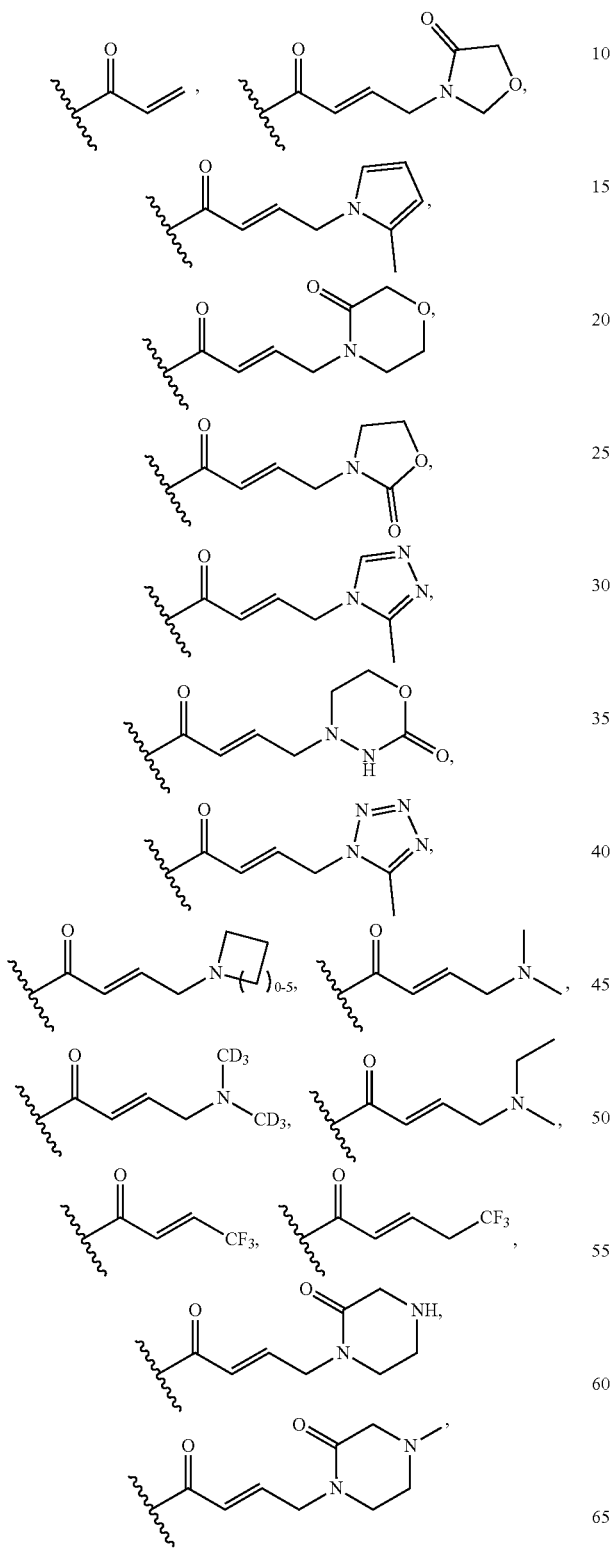

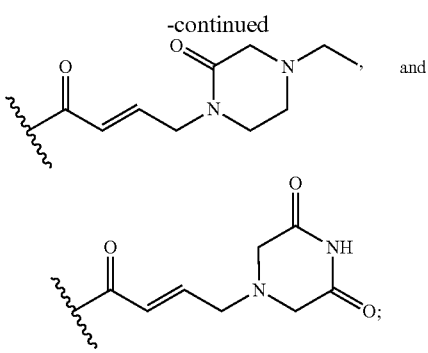

R$^2$ is C$_{3-10}$ cycloalkyl, C$_{6-14}$ aryl, heteroaryl, or heterocyclyl;

R$^4$, R$^5$, and R$^7$ are each independently (a) hydrogen, cyano, halo, or nitro; (b) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (c) —C(O)R$^{1a}$, —C(O)OR$^{1a}$, —C(O)NR$^{1b}$R$^{1c}$, —C(NR$^{1a}$)NR$^{1b}$R$^{1c}$, —OR$^{1a}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)NR$^{1b}$R$^{1c}$, —NR$^{1a}$S(O)$_2$NR$^{1b}$R$^{1c}$, —SR$^{1a}$, —S(O)R$^{1a}$, —S(O)$_2$R$^{1a}$, —S(O)NR$^{1b}$R$^{1c}$, or —S(O)$_2$NR$^{1b}$R$^{1c}$; and each R$^{1a}$, R$^{1b}$, R$^{1c}$, and R$^{1d}$ is independently hydrogen, C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl; or R$^{1a}$ and R$^{1c}$ together with the C and N atoms to which they are attached form heterocyclyl; or R$^{1b}$ and R$^{1c}$ together with the N atom to which they are attached form heterocyclyl;

wherein each alkyl, alkenyl, alkynyl, cycloalkyl, aryl, aralkyl, heteroaryl, and heterocyclyl is optionally substituted with one or more substituents Q, where each Q is independently selected from (a) oxo, cyano, halo, and nitro; (b) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, and heterocyclyl, each of which is further optionally substituted with one or more substituents Q$^a$; and (c) —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OP(O)(OR$^a$)$_2$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) C$_{1-6}$ alkyl, C$_{2-6}$ alkenyl, C$_{2-6}$ alkynyl, C$_{3-7}$ cycloalkyl, C$_{6-14}$ aryl, C$_{7-15}$ aralkyl, heteroaryl, or heterocyclyl, each of which is optionally substituted with one or more substituents Q$^a$; or (iii) R$^b$ and R$^c$ together with the N atom to which they are attached form heterocyclyl, optionally substituted with one or more substituents Q$^a$;

wherein each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^f$, —C(O)OR$^f$, —C(O)NR$^g$R$^h$, —C(NR$^f$)NR$^g$R$^h$, —OR$^f$, —OC(O)R$^f$, —OC(O)OR$^f$, —OC(O)NR$^g$R$^h$, —OC(=NR$^f$)NR$^g$R$^h$, —OP(O)(OR$^f$)$_2$, —OS(O)R$^f$, —OS(O)$_2$R$^f$, —OS(O)NR$^g$R$^h$, —OS(O)$_2$NR$^g$R$^h$, —NR$^g$R$^h$, —NR$^f$C(O)R$^k$, —NR$^f$C(O)OR$^k$, —NR$^f$C(O)NR$^g$R$^h$, —NR$^f$C(=NR$^k$)NR$^g$R$^h$, —NR$^f$S(O)R$^k$, —NR$^f$S(O)$_2$R$^k$, —NR$^f$S(O)NR$^g$R$^h$, —NR$^f$S(O)$_2$NR$^g$R$^h$, —SR$^f$, —S(O)R$^f$, —S(O)$_2$R$^f$, —S(O)NR$^g$R$^h$, and —S(O)$_2$NR$^g$R$^h$; wherein each R$^f$, R$^g$, R$^h$, and R$^k$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^g$ and R$^h$ together with the N atom to which they are attached form heterocyclyl.

13. The compound of claim 12, wherein R$^7$ is halo.
14. The compound of claim 12, wherein R$^7$ is chloro.
15. The compound of claim 12, wherein R$^4$ is hydrogen.
16. The compound of claim 12, wherein R$^5$ is hydrogen.
17. The compound of claim 12, wherein the compound is

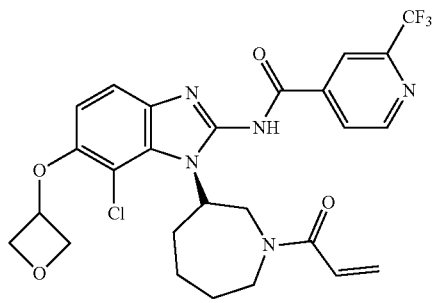

or a pharmaceutically acceptable salt thereof.

18. The compound of claim 12, wherein the compound is

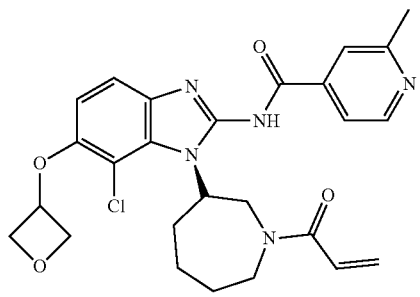

or a pharmaceutically acceptable salt thereof.

19. The compound of claim 12, wherein the compound is

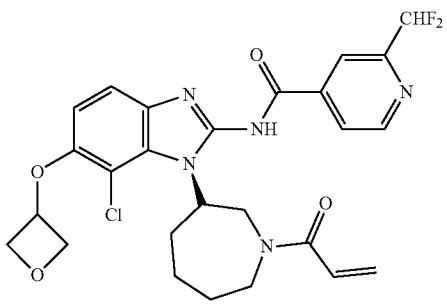

or a pharmaceutically acceptable salt thereof.

20. The compound of claim 12, wherein the compound is

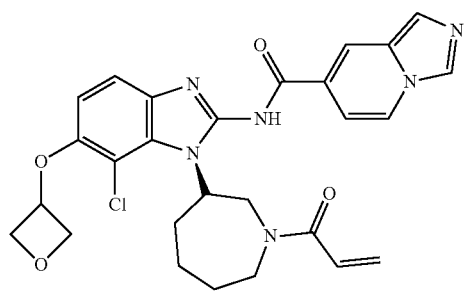

or a pharmaceutically acceptable salt thereof.

21. The compound of claim 12, wherein the compound is

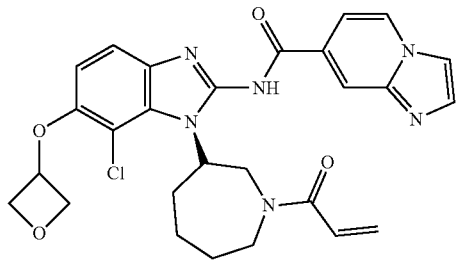

or a pharmaceutically acceptable salt thereof.

22. The compound of claim 12, wherein the compound is

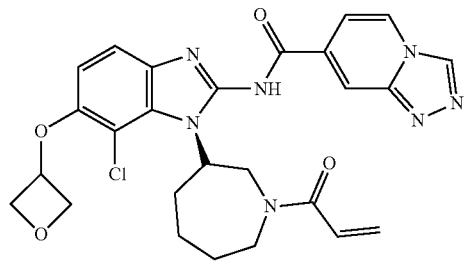

or a pharmaceutically acceptable salt thereof.

* * * * *